(12) United States Patent
Kamioka et al.

(10) Patent No.: US 11,564,920 B2
(45) Date of Patent: Jan. 31, 2023

(54) 5-HETEROARYL-1H-PYRAZOL-3-AMINE DERIVATIVE

(71) Applicant: Sumitomo Pharma Co., Ltd., Osaka (JP)

(72) Inventors: Seiji Kamioka, Osaka (JP); Hitoshi Ban, Osaka (JP); Makoto Matsuoka, Osaka (JP); Wataru Hirose, Tokyo (JP); Naoaki Shimada, Osaka (JP); Kento Hayashi, Osaka (JP); Hiroki Umehara, Osaka (JP)

(73) Assignee: Sumitomo Pharma Co., Ltd., Osaka (JP)

( * ) Notice: Subject to any disclaimer, the term of this patent is extended or adjusted under 35 U.S.C. 154(b) by 0 days.

(21) Appl. No.: 17/731,163

(22) Filed: Apr. 27, 2022

(65) Prior Publication Data

US 2022/0273649 A1    Sep. 1, 2022

Related U.S. Application Data

(63) Continuation of application No. 17/772,093, filed as application No. PCT/JP2021/043666 on Nov. 29, 2021.

(30) Foreign Application Priority Data

Nov. 30, 2020 (JP) .................. 2020-198648

(51) Int. Cl.
*A61K 31/497* (2006.01)
*A61K 31/506* (2006.01)
*A61K 31/513* (2006.01)
*A61K 31/519* (2006.01)
*A61K 31/704* (2006.01)
*A61K 31/7068* (2006.01)
(Continued)

(52) U.S. Cl.
CPC ............ *A61K 31/497* (2013.01); *A61K 9/127* (2013.01); *A61K 31/282* (2013.01); *A61K 31/337* (2013.01); *A61K 31/454* (2013.01); *A61K 31/4745* (2013.01); *A61K 31/506* (2013.01); *A61K 31/513* (2013.01); *A61K 31/519* (2013.01); *A61K 31/5377* (2013.01); *A61K 31/704* (2013.01); *A61K 31/7048* (2013.01); *A61K 31/7068* (2013.01); *A61K 33/243* (2019.01); *A61K 39/3955* (2013.01); *A61K 47/24* (2013.01); *A61K 47/28* (2013.01); *A61P 35/00* (2018.01)

(58) Field of Classification Search
CPC ......... A61P 35/00; A61K 9/127; A61K 47/24; A61K 47/28; A61K 33/243; A61K 39/3955; A61K 31/497; A61K 31/506; A61K 31/519; A61K 31/513; A61K 31/282; A61K 31/337; A61K 31/454; A61K 31/5377; A61K 31/4745; A61K 31/704; A61K 31/7068; A61K 31/7048

See application file for complete search history.

(56) References Cited

U.S. PATENT DOCUMENTS

2011/0144126 A1*  6/2011  Farouz ................. C07D 403/12
                                                      544/405
2013/0190262 A1   7/2013  Joseph et al.
(Continued)

FOREIGN PATENT DOCUMENTS

JP      2017-508787 A    3/2017
WO   WO 2010/077758 A1   7/2010
(Continued)

OTHER PUBLICATIONS

International Search Report dated Jan. 11, 2022, in PCT/JP2021/043666 filed Nov. 29, 2021, (with English translation of categories), 6 pages.
C.G. Wermuth, Saishin Souyakukagaku (Latest Drug Discovery Chemistry), vol. 1, Technomics, Inc., The Practice of Medicinal Chemistry, 1998, (with partial English translation), 45 pages total.
M. Nozaki, et al., Souyakukagaku (Medicinal Chemistry), Kagakudojin, 1995, (with partial English translation), 4 pages total.
(Continued)

*Primary Examiner* — Erich A Leeser
(74) *Attorney, Agent, or Firm* — Oblon, McClelland, Maier & Neustadt, L.L.P.

(57) ABSTRACT

The present disclosure provides a compound that exerts an anticancer action based on CHK1 inhibition. The present disclosure was completed by finding that a compound represented by formula (1) or a pharmaceutically acceptable salt thereof exhibits an excellent antitumor action by having a potent inhibitory action against CHK1:

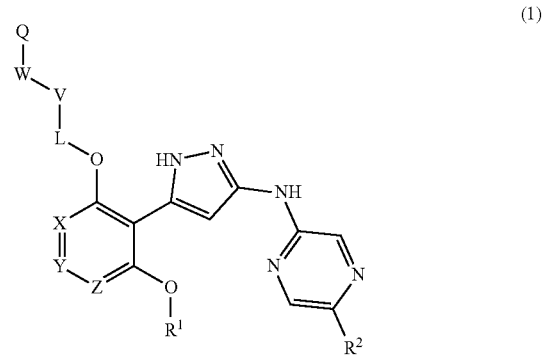

(1)

wherein $R^1$, $R^2$, L, V, W, and Q are as defined herein, X, Y, and Z each independently represent $CR^8$ or a nitrogen atom, wherein X, Y, and Z are not simultaneously $CR^8$, and $R^8$ is as defined herein.

18 Claims, 5 Drawing Sheets

(51) Int. Cl.

| | |
|---|---|
| *A61K 31/7048* | (2006.01) |
| *A61K 31/4745* | (2006.01) |
| *A61K 31/282* | (2006.01) |
| *A61K 31/337* | (2006.01) |
| *A61K 31/454* | (2006.01) |
| *A61K 31/5377* | (2006.01) |
| *A61K 39/395* | (2006.01) |
| *A61K 47/24* | (2006.01) |
| *A61K 47/28* | (2006.01) |
| *A61K 9/127* | (2006.01) |
| *A61K 33/243* | (2019.01) |
| *A61P 35/00* | (2006.01) |

(56) References Cited

U.S. PATENT DOCUMENTS

2016/0361310 A1   12/2016   Boyle et al.
2021/0137918 A1   5/2021    Cai et al.

FOREIGN PATENT DOCUMENTS

| WO | WO 2012/064548 A1 | 5/2012 |
| WO | WO 2015/120390 A1 | 8/2015 |
| WO | WO 2017/132928 A1 | 8/2017 |
| WO | WO 2021/104461 A1 | 6/2021 |

OTHER PUBLICATIONS

Y. Dai, et al.. "New Insights into Checkpoint Kinase 1 in the DNA Damage Response Signaling Network", Molecular Pathways, Clinical Cancer Research, vol. 16, No. 2, 2010, 9 pages.

J. Benada, et al., "Targeting the Checkpoint to Kill Cancer Cells", Biomolecuies, vol. 5, 2015, pp. 1912-1937.

C. King, et al., "LY2606368 Causes Replication Catastrophe and Antitumor Effects through CHK1-Dependent Mechanisms", Molecular Cancer Therapeutics, vol. 14, No. 9, 2015, 11 pages.

P. Dent, "Investigational CHK1 inhibitors in early phase clinical trials for the treatment of cancer", Expert Opinion on investigational Drugs, vol. 28, No. 12, 2019, 7 pages.

G. Evangelisti, et al., "Prexasertib: an investigational checkpoint kinase inhibitor for the treatment of high-grade serous ovarian cancer", Expert Opinion on Investigational Drugs, vol. 29, No. 8, 2020, 15 pages.

D. Hong, et al., "Phase I Study of LY2606368, a Checkpoint Kinase 1 Inhibitor, in Patients With Advanced Cancer", Journal of Clinical Oncology, vol. 34, No. 15, 2016, 14 pages.

\* cited by examiner

5-HETEROARYL-1H-PYRAZOL-3-AMINE DERIVATIVE

This application is a Continuation of U.S. Ser. No. 17/772,093 filed Apr. 26, 2022, pending, which is a 371 application of PCT/JP2021/043666 filed Nov. 29, 2021. The contents of each of these applications are incorporated herein by reference in their entirety.

TECHNICAL FIELD

The present disclosure relates to a 5-heteroaryl-1H-pyrazol-3-amine derivative that is useful as a drug for inhibiting Checkpoint Kinase 1 (CHK1) to treat or prevent cancer characterized by a malfunction in deoxyribonucleic acid (DNA) replication, chromosome segregation, or cell division, and a pharmaceutically acceptable salt thereof, a pharmaceutical composition comprising the same, a liposome comprising the same, and a therapeutic agent or a prophylactic agent for a pathological condition associated with CHK1 comprising the composition or the liposome.

BACKGROUND ART

CHK1 is a serine/threonine protein kinase downstream of ATR in a checkpoint signaling pathway of DNA damage during a cell cycle. In mammals, CHK1 is ATR dependently phosphorylated in response to a DNA damage induced by ionizing radiation or the like, or DNA replication stress due to excessive cell growth or genome instability in cancer cells or the like (Non Patent Literatures 1 to 5). Through such phosphorylation that activates CHK1, CHK1 phosphorylates CDC25A, and dephosphorylation of cyclin E/CDK2 by CDC25A is inhibited, and progression from the S phase is discontinued. CHK1 also phosphorylates CDC25C, and dephosphorylation of cyclin B/CDK1 by CDC25C is inhibited, and progression from the G2M phase is discontinued. In either case, regulation of CDK activity induces discontinuation of the cell cycle and obstruction of cell division in the presence of a DNA damage to promote repair of the DNA damage. In a cancer cell, inhibition of CHK1 suppresses a checkpoint function of a DNA damage in a cell cycle induces DNA repair deficiency, uncontrollable DNA synthesis, etc. in the presence of a DNA damage, resulting in induction of a DNA fragmentation, replication catastrophe, and cell death (Patent Literatures 1 to 2).

Various CHK1 inhibitors (Patent Literatures 1 to 3) have been reported.

CITATION LIST

Patent Literature

[PTL 1] International Publication No. WO 2010/077758
[PTL 2] International Publication No. WO 2012/064548
[PTL 3] International Publication No. WO 2017/132928

Non Patent Literature

[NPL 1] Dai Y and Grant S, Clin Cancer Res, 16(2): 376-383 (2010)
[NPL 2] Benada J and Macurek L, Biomolecules, 5: 1912-1937 (2015)
[NPL 3] King C, Mol Cancer Ther, 14(9): 2004-2013 (2015)
[NPL 4] Dent P, Expert Opinion on Investigational drugs, 28 (12) 1095-1100 (2019)
[NPL 5] Evangelisti G. et al, Expert Opinion on Investigational Drugs, 29(8): 779-792 (2020)
[NPL 6] David H. et al. J Clin Oncol, 34: 1764-1771 (2016)

SUMMARY OF INVENTION

Solution to Problem

The present disclosure provides a compound that exerts an anticancer action based on CHK1 inhibition. Preferably, the present disclosure provides a compound having a divergence between a concentration of a compound that suppresses CHK1 inhibitory activity and a concentration of a compound that suppresses hERG current, a compound that does not exhibit CYP inhibition based on MBI, which induces a severe side effect such as hepatotoxicity, a compound having divergence between a concentration of a compound that suppresses CHK1 inhibitory activity and a concentration of a compound that induces toxicity to hemocytes, and/or a compound, which is encapsulated in a liposome and is sustainably released from the liposome. Specifically, an antitumor agent with a high therapeutic effect while reducing side effects is provided.

As a result of a diligent study, the inventors completed the present disclosure by finding that a compound represented by formula (1) or a pharmaceutically acceptable salt thereof (also referred to as the "compound of the present disclosure" hereinafter) exhibits an excellent antitumor action by having a potent inhibitory action against CHK1.

Specifically, the present disclosure is the following.

[Item 1]

A compound represented by

[Chemical Formula 7]

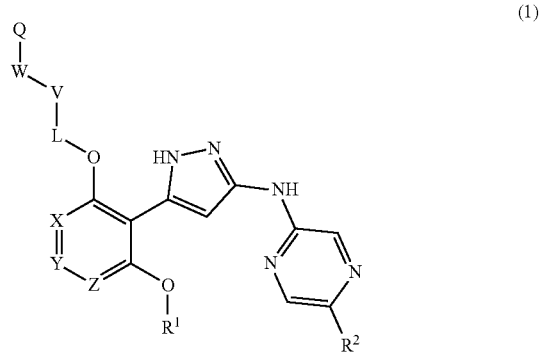

(1)

or a pharmaceutically acceptable salt thereof, wherein
$R^1$ represents a hydrogen atom, optionally substituted $C_{1-6}$ alkyl, optionally substituted $C_{3-10}$ cycloalkyl, an optionally substituted 3- to 10-membered saturated heterocyclic group, optionally substituted $C_{6-10}$ aryl, or optionally substituted 5- to 12-membered heteroaryl, $R^2$ represents a hydrogen atom, a halogen atom, cyano, nitro, carboxyl, sulfonic acid, phosphoric acid, —$OR^3$, —$SR^3$, —$COR^4$, —$CO_2R^4$, —$CONR^5R^6$, —$SO_2R^4$, —$SO_2NR^5R^6$, —$OCOR^4$, —$OCO_2R^4$, —$OCONR^5R^6$, —$NR^5R^6$, —$NR^7COR^4$, —$NR^7CO_2R^4$, —$NR^7CONR^5R^6$, —$NR^7SO_2R^4$, —$NR^7SO_2NR^5R^6$, optionally substituted $C_{1-6}$ alkyl, optionally substituted $C_{2-6}$ alkenyl, optionally substituted $C_{2-6}$ alkynyl, optionally substituted $C_{3-10}$ cycloalkyl, an optionally substituted 3- to 10-membered saturated heterocyclic group, optionally substituted $C^{6-10}$ aryl, or optionally substituted 5- to 12-membered heteroaryl, $R^3$ represents a hydrogen atom or $C_{1-6}$ alkyl, $R^4$ represents $C_{1-6}$ alkyl, $R^5$, $R^6$, and $R^7$ each independently represent a hydrogen atom or $C_{1-6}$ alkyl, wherein $R^5$ and $R^6$ that attach to the same nitrogen atom, when both are $C_{1-6}$ alkyl, together with the nitrogen atom to which each is attached, may form a 3- to 8-membered nitrogen-containing saturated heterocycle, X, Y, and Z each independently represent $CR^8$ or a nitrogen atom, wherein X, Y, and Z are not simultaneously $CR^8$, $R^8$, if there are multiple instances, each independently represent a hydrogen atom, a halogen atom, cyano, nitro, carboxyl, sulfonic acid, phosphoric acid, —$OR^9$, —$SR^9$, —$COR^{10}$, —$CO_2R^{10}$, —$CONR^{11}R^{12}$, —$SO_2R^{10}$, —$SO_2NR^{11}R^{10}$, —$OCOR^{10}$, —$OCO_2R^{10}$, —$OCONR^{11}R^{12}$, —$NR^{11}R^{12}$, —$NR^{13}COR^{10}$, —$NR^{13}CO_2R^{10}$, —$NR^{13}CONR^{11}R^{12}$, —$NR^{13}SO_2R^{10}$, —$NR^{13}SO_2NR^{11}R^{12}$, optionally substituted $C_{1-6}$ alkyl, optionally substituted $C_{2-6}$ alkenyl, optionally substituted $C_{2-6}$ alkynyl, optionally substituted $C_{3-10}$ cycloalkyl, an optionally substituted 3- to 10-membered saturated heterocyclic group, optionally substituted $C_{6-10}$ aryl, or optionally substituted 5- to 12-membered heteroaryl, $R^9$ represents a hydrogen atom or $C_{1-6}$ alkyl, $R^{10}$ represents $C_{1-6}$ alkyl, $R^{11}$, $R^{12}$, and $R^{13}$ each independently represent a hydrogen atom or $C_{1-6}$ alkyl, wherein $R^{11}$ and $R^{12}$ that attach to the same nitrogen atom, when both are $C_{1-6}$ alkyl, together with the nitrogen atom to which each is attached, may form a 3- to 8-membered nitrogen-containing saturated heterocycle, L represents a single bond or optionally substituted $C_{1-6}$ alkylene, V represents a single bond, optionally substituted $C_{3-10}$ cycloalkylene, or an optionally substituted 3- to 10-membered divalent saturated heterocyclic group, W represents a single bond or optionally substituted $C_{1-6}$ alkylene, Q represents a hydrogen atom or $NHR^{14}$, and $R^{14}$ represents a hydrogen atom, optionally substituted $C_{1-6}$ alkyl, optionally substituted $C_{3-10}$ cycloalkyl, or an optionally substituted 3- to 10-membered saturated heterocyclic group.

[Item 2]

The compound or pharmaceutically acceptable salt thereof of item 1, wherein optionally substituted $C_{1-6}$ alkyl, optionally substituted $C_{2-6}$ alkenyl, optionally substituted $C_{2-6}$ alkynyl, optionally substituted $C_{3-10}$ cycloalkyl, an optionally substituted 3- to 10-membered saturated heterocyclic group, optionally substituted $C^{6-10}$ aryl, optionally substituted 5- to 12-membered heteroaryl, optionally substituted $C_{1-6}$ alkylene, optionally substituted $C_{3-10}$ cycloalkylene, or an optionally substituted 3- to 10-membered divalent saturated heterocyclic group in $R^1$, $R^2$, $R^8$, $R^{14}$, L, V, and W is, each independently, optionally substituted with 1 to 5 of the same or different substituents selected from the group consisting of (1) a halogen atom,
(2) a hydroxyl group,
(3) CE-10 aryl,
(4) 5- to 12-membered heteroaryl,
(5) $C_{1-6}$ alkyl,
(6) $C_{2-t}$ alkenyl,
(7) $C_{2-6}$ alkynyl,
(8) $C_{1-6}$ alkoxy,
(9) $C_{1-6}$ alkylthio
(10) $C_{3-10}$ cycloalkyl,
(11) a 3- to 10-membered saturated heterocyclic group,
(12) carboxyl,
(13) —$COR^{15}$,
(14) —$CO_2R^{15}$,
(15) —$CONR^{16}R^{17}$,
(16) —$NR^{16}R^{17}$,
(17) —$NR^{18}COR^{15}$,
(18) —$NR^{18}CO_2R^{15}$,
(19) —$NR^{18}SO_2R^{15}$,
(20) —$NR^{18}CONR^{16}R^{17}$,
(21) —$NR^{18}SO_2NR^{16}R^{17}$,
(22) —$SO_2R^{15}$,
(23) —$SO_2NR^{16}R^{17}$,
(24) —$OCOR^{15}$,
(25) —$OCO_2R^{15}$,
(26) —$OCONR^{16}R^{17}$,
(27) sulfonic acid,
(28) phosphoric acid,
(29) cyano, and
(30) nitro, wherein the groups represented by (3) $C_{6-10}$ aryl, (4) 5- to 12-membered heteroaryl, (5) $C_{1-6}$ alkyl, (6) $C_{2-6}$ alkenyl, (7) $C_{2-6}$ alkynyl, (8) $C_{1-6}$ alkoxy, (9) $C_{1-6}$ alkylthio, (9) $C_{3-10}$ cycloalkyl, and (10) a 3- to 10-membered saturated heterocyclic group are optionally substituted with 1 to 5 of the same or different substituents selected from the group consisting of (a) a halogen atom,
(b) a hydroxyl group,
(c) $C_{6-10}$ aryl,
(d) 5- to 12-membered heteroaryl,
(e) $C_{1-6}$ alkyl,
(f) $C_{2-6}$ alkenyl,
(g) $C_{2-6}$ alkynyl,
(h) $C_{1-6}$ alkoxy,
(i) $C_{3-10}$ cycloalkyl,
(j) a 3- to 10-membered saturated heterocyclic group,
(k) carboxyl,
(l) —$COR^{15}$,
(m) —$CO_2R^{15}$,
(n) —$CONR^{16}R^{17}$,
(o) —$NR^{16}R^{17}$,
(p) —$NR^{18}COR^{15}$,
(q) —$NR^{18}SO_2R^{15}$,
(r) —$SO_2R^{15}$,
(s) —$SO_2NR^{16}R^{17}$,
(t) sulfonic acid,
(u) phosphoric acid,
(v) cyano, and
(w) nitro, $R^{15}$, if there are multiple instances, are each independently $C_{1-6}$ alkyl, $R^{16}$ and $R^{17}$ are each independently a hydrogen atom or $C_{1-6}$ alkyl, and if there are multiple instances of $R^{16}$ or $R^{17}$, each of $R^{16}$ or $R^{17}$ may be the same or different, wherein $R^{16}$ and $R^{17}$ that attach to the same nitrogen atom, when both are $C_{1-6}$ alkyl, together with the nitrogen atom to which each is attached, may form a 3- to 8-membered nitrogen-containing saturated heterocycle, and $R^{18}$ is a hydrogen atom or $C_{1-6}$ alkyl.

[Item 3]

The compound or pharmaceutically acceptable salt thereof of item 1 or 2, wherein optionally substituted $C_{1-6}$ alkyl, optionally substituted $C_{2-6}$ alkenyl, optionally substituted $C_{2-6}$ alkynyl, optionally substituted $C_{3-10}$ cycloalkyl, an optionally substituted 3- to 10-membered saturated heterocyclic group, optionally substituted $C_{6-10}$ aryl, optionally substituted 5- to 12-membered heteroaryl, optionally substituted $C_{1-6}$ alkylene, optionally substituted $C_{3-10}$ cycloalkylene, or an optionally substituted 3- to 10-membered divalent saturated heterocyclic group in $R^1$, $R^2$, $R^8$, $R^{14}$, L, V, and W is, each independently, optionally substituted with 1 to 5 of the same or different substituents selected from the group consisting of
(1) a halogen atom,
(2) a hydroxyl group,
(3) $C_{6-10}$ aryl,
(4) 5- to 12-membered heteroaryl,
(5) $C_{1-6}$ alkyl optionally substituted with 1 to 3 substituents selected from the group consisting of a halogen atom and a hydroxyl group,
(6) $C_{2-6}$ alkenyl,
(7) $C_{2-6}$ alkynyl,
(8) $C_{1-6}$ alkoxy,
(9) $C_{3-10}$ cycloalkyl,
(10) a 3- to 10-membered saturated heterocyclic group,
(11) carboxyl,
(12) —$COR^{15}$,
(13) —$CO_2R^{15}$,
(14) —$CONR^{16}R^{17}$,
(15) —$NR^{16}R^{17}$,
(16) —$SO_2R^{15}$,
(17) —$SO_2NR^{16}R^{17}$,
(18) sulfonic acid,
(19) phosphoric acid,
(20) cyano, and
(21) nitro, $R^{15}$, if there are multiple instances, are each independently $C_{1-6}$ alkyl, $R^6$ and $R^{17}$ each independently represent a hydrogen atom or $C_{1-6}$ alkyl, and if there are multiple instances of $R^{16}$ or $R^{17}$, each of $R^{16}$ or $R^{17}$ may be the same or different, wherein $R^{16}$ and $R^{17}$ that attach to the same nitrogen atom, when both are $C_{1-6}$ alkyl, together with the nitrogen atom to which each is attached, may form a 3- to 8-membered nitrogen-containing saturated heterocycle.

[Item 4]

The compound or pharmaceutically acceptable salt thereof of any one of items 1 to 3, wherein
optionally substituted $C_{1-6}$ alkyl, optionally substituted $C_{2-6}$ alkenyl, optionally substituted $C_{2-6}$ alkynyl, optionally substituted $C_{3-10}$ cycloalkyl, an optionally substituted 3- to 10-membered saturated heterocyclic group, optionally substituted $C_{6-10}$ aryl, optionally substituted 5- to 12-membered heteroaryl, optionally substituted $C_{1-6}$ alkylene, optionally substituted $C_{3-10}$ cycloalkylene, or an optionally substituted 3- to 10-membered divalent saturated heterocyclic group in $R^1$, $R^2$, $R^3$, L, V, and W is, each independently, optionally substituted with 1 to 5 of the same or different substituents selected from the group consisting of
(1) a halogen atom,
(2) a hydroxyl group,
(3) phenyl,
(4) 5- to 6-membered heteroaryl,
(5) $C_{1-6}$ alkyl optionally substituted with 1 to 3 substituents selected from the group consisting of a halogen atom and a hydroxyl group,
(6) $C_{1-6}$ alkoxy,
(7) $C_{3-7}$ cycloalkyl,
(8) a 3- to 7-membered saturated heterocyclic group,
(9) —$COR^{15}$,
(10) —$CO_2R^{15}$,
(11) —$CONR^{16}R^{17}$,
(12) —$NR^{16}R^{17}$,
(13) —$SO_2R^{15}$,
(14) —$SO_2NR^{16}R^{17}$, and
(15) cyano, $R^{15}$, if there are multiple instances, are each independently $C_{1-6}$ alkyl, $R^{16}$ and $R^{17}$ are each independently a hydrogen atom or $C_{1-6}$ alkyl, and if there are multiple instances of $R^{16}$ or $R^{17}$, each of $R^{16}$ or $R^{17}$ may be the same or different, wherein $R^{16}$ and $R^{17}$ that attach to the same nitrogen atom, when both are $C_{1-6}$ alkyl, together with the nitrogen atom to which each is attached, may form a 3- to 8-membered nitrogen-containing saturated heterocycle.

[Item 5]

The compound or pharmaceutically acceptable salt thereof of any one of items 1 to 4, wherein $R^1$ is a hydrogen atom or $C_{1-6}$ alkyl optionally substituted with 1 to 3 fluorine atoms.

[Item 6]

The compound or pharmaceutically acceptable salt thereof of any one of items 1 to 4, wherein $R^1$ is an ethyl group or a methyl group optionally substituted with 1 to 3 fluorine atoms.

[Item 7]

The compound or pharmaceutically acceptable salt thereof of anyone of items 1 to 4, wherein $R^1$ is a methyl group optionally substituted with 1 to 3 fluorine atoms.

[Item 8]

The compound or pharmaceutically acceptable salt thereof of any one of items 1 to 4, wherein $R^1$ is a methyl group.

[Item 9]

The compound or pharmaceutically acceptable salt thereof of any one of items 1 to 8, wherein $R^2$ is a hydrogen atom, a halogen atom, cyano, —$OR^3$, $C_{1-6}$ alkyl, $C_{3-10}$ cycloalkyl, or a 3- to 10-membered saturated heterocyclic group.

[Item 10]

The compound or pharmaceutically acceptable salt thereof of any one of items 1 to 8, wherein $R^2$ is a halogen atom, cyano, or $C_{1-6}$ alkyl optionally substituted with 1 to 3 halogen atoms.

[Item 11]

The compound or pharmaceutically acceptable salt thereof of any one of items 1 to 8, wherein $R^2$ is cyano.

[Item 12]

The compound or pharmaceutically acceptable salt thereof of any one of items 1 to 11, wherein $R^8$, if there are multiple instances, are each independently a hydrogen atom, a halogen atom, cyano, —$OR^9$, —$CO_2R^{10}$, —$CONR^{11}R^{12}$, —$NR^{11}R^{12}$, —$NR^{13}COR^{10}$, $C_{1-6}$ alkyl (wherein the alkyl is optionally substituted with 1 to 3 of the same or different substituents selected from the group consisting of a fluorine atom, a chlorine atom, a bromine atom, a hydroxyl group, phenyl, 5- to 6-membered heteroaryl, $C_{1-6}$ alkoxy, $C_{3-7}$ cycloalkyl, a 3- to 7-membered saturated heterocyclic group, —$CONR^{16}R^{17}$, —$NR^{16}R^{17}$, and cyano), $C_{3-10}$ cycloalkyl (wherein the cycloalkyl is optionally substituted with 1 to 3 of the same or different substituents selected from the group consisting of a fluorine atom, a chlorine atom, a bromine atom, a hydroxyl group, phenyl, 5- to 6-membered heteroaryl, $C_{1-6}$ alkyl, $C_{1-6}$ alkoxy, $C_{3-7}$ cycloalkyl, a 3- to 7-membered saturated heterocyclic group, —$CONR^{16}R^{17}$, —$NR^{16}R^{17}$, and cyano), a 3- to 10-membered saturated heterocyclic group (wherein the saturated heterocyclic group is optionally substituted with 1 to 3 of the same or different substituents selected from the group consisting of a fluorine atom, a chlorine atom, a bromine atom, a hydroxyl group, phenyl, 5- to 6-membered heteroaryl, $C_{1-6}$ alkyl, $C_{1-6}$ alkoxy, $C_{3-7}$ cycloalkyl, a 3- to 7-membered saturated heterocyclic group, —$CONR^{16}R^{17}$, —$NR^{16}R^{17}$, and cyano), phenyl (wherein the phenyl is optionally substituted with 1 to 3 of the same or different substituents selected from the group consisting of a fluorine atom, a chlorine atom, a bromine atom, a hydroxyl group, phenyl, 5- to 6-membered heteroaryl, $C_{1-6}$ alkyl, $C_{1-6}$ alkoxy, $C_{3-7}$ cycloalkyl, a 3- to 7-membered saturated heterocyclic group, —$CONR^{16}R^{17}$, —$NR^{16}R^{17}$, and cyano), or 5- to 6-membered heteroaryl (wherein the heteroaryl is optionally substituted with 1 to 3 of the same or different substituents selected from the group consisting of a fluorine atom, a chlorine atom, a bromine atom, a hydroxyl group, phenyl, 5- to 6-membered heteroaryl, $C_{1-6}$ alkyl, $C_{1-6}$ alkoxy, $C_{3-7}$ cycloalkyl, a 3- to 7-membered saturated heterocyclic group, —$CONR^{16}R^{17}$, —$NR^{16}R^{17}$, and cyano).

[Item 13]

The compound or pharmaceutically acceptable salt thereof of any one of items 1 to 11, wherein $R^8$, if there are multiple instances, are each independently
  a hydrogen atom,
  a halogen atom
  —$OR^9$,
  $C_{1-6}$ alkyl (wherein the alkyl is optionally substituted with 1 to 3 of the same or different substituents selected from the group consisting of a fluorine atom, a hydroxyl group, $C_{1-3}$ alkoxy, —$NR^{16}R^{17}$, and cyano),
  $C_{3-7}$ cycloalkyl (wherein the cycloalkyl is optionally substituted with 1 to 3 of the same or different substituents selected from the group consisting of a fluorine atom, a hydroxyl group, $C_{1-3}$ alkyl, $C_{1-3}$ alkoxy, —$NR^{16}R^{17}$, and cyano),
  a 3- to 7-membered saturated heterocyclic group (wherein the saturated heterocyclic group is optionally substituted with 1 to 3 of the same or different substituents selected from the group consisting of a fluorine atom, a hydroxyl group, $C_{1-3}$ alkyl, $C_{1-3}$ alkoxy, —$NR^{16}R^{17}$, and cyano),
  phenyl (wherein the phenyl is optionally substituted with 1 to 3 of the same or different substituents selected from the group consisting of a fluorine atom, a hydroxyl group, $C_{1-3}$ alkyl, $C_{1-3}$ alkoxy, —$NR^{16}R^{17}$, and cyano), or
  5- to 6-membered heteroaryl (wherein the heteroaryl is optionally substituted with 1 to 3 of the same or different substituents selected from the group consisting of a fluorine atom, a hydroxyl group, $C_{1-3}$ alkyl, $C_{1-3}$ alkoxy, —$NR^{16}R^{17}$, and cyano).

[Item 14]

The compound or pharmaceutically acceptable salt thereof of any one of items 1 to 11, wherein $R^8$, if there are multiple instances, are each independently
  a hydrogen atom,
  a fluorine atom,
  a chlorine atom,
  a bromine atom,
  $C_{1-6}$ alkyl (wherein the alkyl is optionally substituted with 1 to 2 of the same or different substituents selected from the group consisting of a fluorine atom, a hydroxyl group, $C_{1-3}$ alkoxy, —$NR^{16}R^{17}$, and cyano), or
  5- to 6-membered heteroaryl (wherein the heteroaryl is optionally substituted with 1 to 2 of the same or different substituents selected from the group consisting of a fluorine atom, a hydroxyl group, $C_{1-3}$ alkyl, $C_{1-3}$ alkoxy, —$NR^{16}R^{17}$, and cyano).

[Item 15]

The compound or pharmaceutically acceptable salt thereof of any one of items 1 to 14, wherein L is
  a single bond, or
  $C_{1-6}$ alkylene (wherein the alkylene is optionally substituted with 1 to 3 of the same or different substituents selected from the group consisting of a fluorine atom, a hydroxyl group, $C_{1-3}$ alkoxy, —$NR^{16}R^{17}$, and cyano).

[Item 16]

The compound or pharmaceutically acceptable salt thereof of any one of items 1 to 15, wherein V is
  a single bond,
  $C_{3-10}$ cycloalkylene (wherein the cycloalkylene is optionally substituted with 1 to 3 of the same or different substituents selected from the group consisting of a fluorine atom, a hydroxyl group, $C_{1-3}$ alkyl, $C_{1-3}$ alkoxy, —$NR^{16}R^{17}$, and cyano), or
  a 3- to 10-membered divalent saturated heterocyclic group (wherein the saturated heterocyclic group is optionally substituted with 1 to 3 of the same or different substituents selected from the group consisting of a fluorine atom, a hydroxyl group, $C_{1-3}$ alkyl optionally substituted with 1 to 2 hydroxyl groups or fluorine atoms, $C_{1-3}$ alkoxy, —$NR^{16}R^{17}$, and cyano).

[Item 17]

The compound or pharmaceutically acceptable salt thereof of any one of items 1 to 16, wherein W is
  a single bond, or
  $C_{1-6}$ alkylene (wherein the alkylene is optionally substituted with 1 to 3 of the same or different substituents selected from the group consisting of a fluorine atom, a hydroxyl group, $C_{1-3}$ alkoxy, —$NR^{16}R^{17}$, and cyano).

[Item 18]

The compound or pharmaceutically acceptable salt thereof of any one of items 1 to 17, wherein $R^{14}$ is
  a hydrogen atom,
  $C_{1-6}$ alkyl (wherein the alkyl is optionally substituted with 1 to 3 of the same or different substituents selected from the group consisting of a fluorine atom, a hydroxyl group, $C_{1-3}$ alkoxy, —$NR^{16}R^{17}$, and cyano),
  $C_{3-10}$ cycloalkyl (wherein the cycloalkyl is optionally substituted with 1 to 3 of the same or different substituents selected from the group consisting of a fluorine atom, a hydroxyl group, $C_{1-3}$ alkyl, $C_{1-3}$ alkoxy, —$NR^{16}R^{17}$, and cyano), or
  a 3- to 10-membered saturated heterocyclic group (wherein the saturated heterocyclic group is optionally substituted with 1 to 3 of the same or different substituents selected from the group consisting of a fluorine atom, a hydroxyl group, $C_{1-3}$ alkyl, $C_{1-3}$ alkoxy, —$NR^{16}R^{17}$, and cyano).

[Item 19]

The compound or pharmaceutically acceptable salt thereof of item 1, wherein
  $R^1$ is $C_{1-6}$ alkyl optionally substituted with 1 to 3 fluorine atoms,
  $R^2$ is
  a halogen atom,
  cyano, or
  $C_{1-6}$ alkyl optionally substituted with 1 to 3 fluorine atoms,
  X, Y, and Z are each independently $CR^8$ or a nitrogen atom, wherein X, Y, and Z are not simultaneously $CR^8$,
  $R^8$, if there are multiple instances, are each independently
  a hydrogen atom,
  a fluorine atom,
  a chlorine atom,
  a bromine atom, $C_{1-6}$ alkyl (wherein the alkyl is optionally substituted with 1 to 2 of the same or different substituents selected from the group consisting of a fluorine atom, a hydroxyl group, $C_{1-3}$ alkoxy, —NR$^{16}$R$^{17}$, and cyano), or 5- to 6-membered heteroaryl (wherein the heteroaryl is optionally substituted with 1 to 2 of the same or different substituents selected from the group consisting of a fluorine atom, a hydroxyl group, $C_{1-3}$ alkyl, $C_{1-3}$ alkoxy, —NR$^{16}$R$^{17}$, and cyano), L is a single bond, or $C_{3-10}$ alkylene (wherein the alkylene is optionally substituted with 1 to 3 of the same or different substituents selected from the group consisting of a fluorine atom, a hydroxyl group, $C_{1-3}$ alkoxy, —NR$^{16}$R$^{17}$, and cyano), V is a single bond, $C_{3-10}$ cycloalkylene (wherein the cycloalkylene is optionally substituted with 1 to 3 of the same or different substituents selected from the group consisting of a fluorine atom, a hydroxyl group, $C_{1-3}$ alkyl, $C_{1-3}$ alkoxy, —NR$^{16}$R$^{17}$, and cyano), or a 3- to 10-membered divalent saturated heterocyclic group (wherein the saturated heterocyclic group is optionally substituted with 1 to 3 of the same or different substituents selected from the group consisting of a fluorine atom, a hydroxyl group, $C_{1-3}$ alkyl optionally substituted with 1 to 2 hydroxyl groups or fluorine atoms, $C_{1-3}$ alkoxy, —NR$^{16}$R$^{17}$, and cyano), W is a single bond, or $C_{1-6}$ alkylene (wherein the alkylene is optionally substituted with 1 to 3 of the same or different substituents selected from the group consisting of a fluorine atom, a hydroxyl group, $C_{1-3}$ alkoxy, —NR$^{16}$R$^{17}$, and cyano), Q is a hydrogen atom or NHR$^{14}$, R$^{14}$ is a hydrogen atom, $C_{1-6}$ alkyl (wherein the alkyl is optionally substituted with 1 to 3 of the same or different substituents selected from the group consisting of a fluorine atom, a hydroxyl group, $C_{1-3}$ alkoxy, —NR$^{16}$R$^{17}$, and cyano), $C_{3-10}$ cycloalkyl (wherein the cycloalkyl is optionally substituted with 1 to 3 of the same or different substituents selected from the group consisting of a fluorine atom, a hydroxyl group, $C_{1-3}$ alkyl, $C_{1-3}$ alkoxy, —NR$^{16}$R$^{17}$, and cyano), or a 3- to 10-membered saturated heterocyclic group (wherein the saturated heterocyclic group is optionally substituted with 1 to 3 of the same or different substituents selected from the group consisting of a fluorine atom, a hydroxyl group, $C_{1-3}$ alkyl, $C_{1-3}$ alkoxy, —NR$^{16}$R$^{17}$, and cyano), and R$^{16}$ and R$^{17}$ are each independently a hydrogen atom or $C_{1-6}$ alkyl, and if there are multiple instances of R$^{16}$ or R$^{17}$, each of R$^{16}$ or R$^{17}$ may be the same or different, wherein R$^{16}$ and R$^{17}$ that attach to the same nitrogen atom, when both are $C_{1-6}$ alkyl, together with the nitrogen atom to which each is attached, may form a 3- to 8-membered nitrogen-containing saturated heterocycle.

[Item 20]

The compound or pharmaceutically acceptable salt thereof of item 1, wherein formula (1) is represented by formula (2):

[Chemical Formula 8]

(2)

wherein

X, Y, and Z each independently represent CR$^8$ or a nitrogen atom, wherein X, Y, and Z are not simultaneously CR$^8$, R$^8$, if there are multiple instances, each independently represent a hydrogen atom, a fluorine atom, a chlorine atom, a bromine atom, $C_{1-6}$ alkyl (wherein the alkyl is optionally substituted with 1 to 2 of the same or different substituents selected from the group consisting of a fluorine atom, a hydroxyl group, $C_{1-3}$ alkoxy, —NR$^{16}$R$^{17}$, and cyano), or 5- to 6-membered heteroaryl (wherein the heteroaryl is optionally substituted with 1 to 2 of the same or different substituents selected from the group consisting of a fluorine atom, a hydroxyl group, $C_{1-3}$ alkyl, $C_{1-3}$ alkoxy, —NR$^{16}$R$^{17}$, and cyano), L represents a single bond, or $C_{1-6}$ alkylene (wherein the alkylene is optionally substituted with 1 to 3 of the same or different substituents selected from the group consisting of a fluorine atom, a hydroxyl group, $C_{1-3}$ alkoxy, —NR$^{16}$R$^{17}$, and cyano), V represents a single bond, $C_{3-10}$ cycloalkylene (wherein the cycloalkylene is optionally substituted with 1 to 3 of the same or different substituents selected from the group consisting of a fluorine atom, a hydroxyl group, $C_{1-3}$ alkyl, $C_{1-3}$ alkoxy, —NR$^{16}$R$^{17}$, and cyano), or a 3- to 10-membered divalent saturated heterocyclic group (wherein the saturated heterocyclic group is optionally substituted with 1 to 3 of the same or different substituents selected from the group consisting of a fluorine atom, a hydroxyl group, $C_{1-3}$ alkyl optionally substituted with 1 to 2 hydroxyl groups or fluorine atoms, $C_{1-3}$ alkoxy, —NR$^{16}$R$^{17}$, and cyano), W represents a single bond, or $C_{1-6}$ alkylene (wherein the alkylene is optionally substituted with 1 to 3 of the same or different substituents selected from the group consisting of a fluorine atom, a hydroxyl group, $C_{1-3}$ alkoxy, —NR$^{16}$R$^{17}$, and cyano), Q represents a hydrogen atom or NHR$^{14}$, R$^{14}$ represents a hydrogen atom, $C_{1-6}$ alkyl (wherein the alkyl is optionally substituted with 1 to 3 of the same or different substituents selected from the group consisting of a fluorine atom, a hydroxyl group, $C_{1-3}$ alkoxy, —$NR^{16}R^{17}$, and cyano), $C_{3-10}$ cycloalkyl (wherein the cycloalkyl is optionally substituted with 1 to 3 of the same or different substituents selected from the group consisting of a fluorine atom, a hydroxyl group, $C_{1-3}$ alkyl, $C_{1-3}$ alkoxy, —$NR^{16}R^{17}$, and cyano), or a 3- to 10-membered saturated heterocyclic group (wherein the saturated heterocyclic group is optionally substituted with 1 to 3 of the same or different substituents selected from the group consisting of a fluorine atom, a hydroxyl group, $C_{1-3}$ alkyl, $C_{1-3}$ alkoxy, —$NR^{16}R^{17}$, and cyano), and $R^{16}$ and $R^{17}$ each independently represent a hydrogen atom or $C_{1-6}$ alkyl, and if there are multiple instances of $R^{16}$ or $R^{17}$, each of $R^{16}$ or $R^{17}$ may be the same or different, wherein $R^{16}$ and $R^{17}$ that attach to the same nitrogen atom, when both are $C_{1-6}$ alkyl, together with the nitrogen atom to which each is attached, may form a 3- to 8-membered nitrogen-containing saturated heterocycle.

[Item 21]
The compound or pharmaceutically acceptable salt thereof of any one of items 1 to 20, wherein one or two of X, Y, and Z represents a nitrogen atom.

[Item 22]
The compound or pharmaceutically acceptable salt thereof of any one of items 1 to 21, wherein
X is a nitrogen atom, and
Y and Z are $CR^8$.

[Item 23]
The compound or pharmaceutically acceptable salt thereof of any one of items 1 to 21, wherein
Y is a nitrogen atom, and
X and Z are $CR^8$.

[Item 24]
The compound or pharmaceutically acceptable salt thereof of any one of items 1 to 21, wherein
Z is a nitrogen atom, and
X and Y are $CR^8$.

[Item 25]
The compound or pharmaceutically acceptable salt thereof of any one of items 1 to 24, wherein $R^8$, if there are multiple instances, are each independently
a hydrogen atom,
a fluorine atom,
a chlorine atom,
a bromine atom, or
$C_{1-6}$ alkyl (wherein the alkyl is optionally substituted with 1 to 2 of the same or different substituents selected from the group consisting of a fluorine atom, a hydroxyl group, and $C_{1-3}$ alkoxy).

[Item 26]
The compound or pharmaceutically acceptable salt thereof of any one of items 1 to 24, wherein $R^E$, if there are multiple instances, are each independently a hydrogen atom, a fluorine atom, a chlorine atom, a bromine atom, or $C_{1-3}$ alkyl.

[Item 27]
The compound or pharmaceutically acceptable salt thereof of any one of items 1 to 26, wherein L is
a single bond, or
$C_{1-6}$ alkylene (wherein the alkylene is optionally substituted with 1 to 2 of the same or different substituents selected from the group consisting of a fluorine atom, a hydroxyl group, and cyano).

[Item 28]
The compound or pharmaceutically acceptable salt thereof of any one of items 1 to 26, wherein L is
a single bond, or
$C_{1-6}$ alkylene (wherein the alkylene is optionally substituted with 1 substituent selected from the group consisting of a fluorine atom, a hydroxyl group, and cyano).

[Item 29]
The compound or pharmaceutically acceptable salt thereof of any one of items 1 to 26, wherein L is
a single bond, or
$C_{1-6}$ alkylene optionally substituted with 1 hydroxyl group or fluorine atom.

[Item 30]
The compound or pharmaceutically acceptable salt thereof of any one of items 1 to 29, wherein V is
a single bond,
$C_{3-7}$ cycloalkylene (wherein the cycloalkylene is optionally substituted with 1 to 2 of the same or different substituents selected from the group consisting of a fluorine atom, a hydroxyl group, $C_{1-3}$ alkyl optionally substituted with 1 to 2 hydroxyl groups, and cyano), or
a 3- to 7-membered divalent saturated heterocyclic group (wherein the saturated heterocyclic group is optionally substituted with 1 to 2 of the same or different substituents selected from the group consisting of a fluorine atom, a hydroxyl group, $C_{1-3}$ alkyl optionally substituted with 1 to 2 hydroxyl groups or fluorine atoms, and cyano).

[Item 31]
The compound or pharmaceutically acceptable salt thereof of any one of items 1 to 29, wherein V is
a single bond,
$C_{3-7}$ cycloalkylene (wherein the cycloalkylene is optionally substituted with 1 substituent selected from the group consisting of a fluorine atom, a hydroxyl group, $C_{1-3}$ alkyl optionally substituted with 1 to 2 hydroxyl groups, and cyano), or
a 3- to 7-membered divalent saturated heterocyclic group (wherein the saturated heterocyclic group is optionally substituted with 1 substituent selected from the group consisting of a fluorine atom, a hydroxyl group, $C_{1-3}$ alkyl optionally substituted with 1 to 2 hydroxyl groups or fluorine atoms, and cyano).

[Item 32]
The compound or pharmaceutically acceptable salt thereof of any one of items 1 to 29, wherein V is
a single bond,
$C_{3-7}$ cycloalkylene (wherein the cycloalkylene is optionally substituted with 1 substituent selected from the group consisting of a hydroxyl group and $C_{1-3}$ alkyl), or
a 3- to 7-membered divalent saturated heterocyclic group (wherein the saturated heterocyclic group is optionally substituted with 1 substituent selected from the group consisting of a fluorine atom, a hydroxyl group, and $C_{1-3}$ alkyl optionally substituted with 1 to 2 hydroxyl groups or fluorine atoms).

[Item 33]
The compound or pharmaceutically acceptable salt thereof of any one of items 1 to 32, wherein W is
a single bond, or
$C_{1-6}$ alkylene (wherein the alkylene is optionally substituted with 1 to 2 of the same or different substituents selected from the group consisting of a fluorine atom, a hydroxyl group, and cyano).

[Item 34]
The compound or pharmaceutically acceptable salt thereof of any one of items 1 to 32, wherein W is a single bond, or C$_{1-3}$ alkylene (wherein the alkylene is optionally substituted with 1 substituent selected from the group consisting of a fluorine atom, a hydroxyl group, and cyano).

[Item 35]

The compound or pharmaceutically acceptable salt thereof of any one of items 1 to 32, wherein W is a single bond, or C$_{1-3}$ alkylene optionally substituted with 1 hydroxyl group.

[Item 36]

The compound or pharmaceutically acceptable salt thereof of any one of items 1 to 35, wherein R$^{14}$ is a hydrogen atom, or C$_{1-6}$ alkyl (wherein the alkyl is optionally substituted with 1 to 2 of the same or different substituents selected from the group consisting of a fluorine atom, a hydroxyl group, and cyano).

[Item 37]

The compound or pharmaceutically acceptable salt thereof of any one of items 1 to 35, wherein R$^{14}$ is a hydrogen atom, or C$_{1-3}$ alkyl (wherein the alkyl is optionally substituted with 1 substituent selected from the group consisting of a fluorine atom, a hydroxyl group, and cyano).

[Item 38]

The compound or pharmaceutically acceptable salt thereof of any one of items 1 to 37, wherein Q is a hydrogen atom, NH$_2$, or NHMe.

[Item 39]

The compound or pharmaceutically acceptable salt thereof of item 1, wherein formula (1) is represented by formula (3):

[Chemical Formula 9]

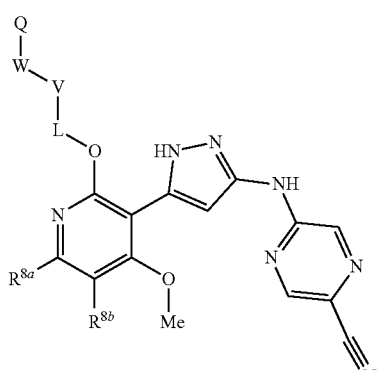

(3)

wherein,

R$^{8a}$ and R$^{8b}$ each independently represent a hydrogen atom, a fluorine atom, a chlorine atom, a bromine atom, or C$_{1-3}$ alkyl, L represents a single bond or C$_{1-6}$ alkylene optionally substituted with 1 hydroxyl group, V represents a single bond, C$_{3-7}$ cycloalkylene (wherein the cycloalkylene is optionally substituted with 1 substituent selected from the group consisting of a hydroxyl group and C$_{1-3}$ alkyl), or a 3- to 7-membered divalent saturated heterocyclic group (wherein the saturated heterocyclic group is optionally substituted with 1 substituent selected from the group consisting of a fluorine atom, cyano, a hydroxyl group, and C$_{1-3}$ alkyl), W represents a single bond, or C$_{1-3}$ alkylene optionally substituted with 1 hydroxyl group, and Q is a hydrogen atom or NH$_2$.

[Item 40]

The compound or pharmaceutically acceptable salt thereof of item 39, wherein R$^{8a}$ and R$^{8b}$ are each independently a hydrogen atom, a fluorine atom, or a chlorine atom.

[Item 41]

The compound or pharmaceutically acceptable salt thereof of item 39, wherein R$^{8a}$ and R$^{8b}$ are each independently a hydrogen atom or a chlorine atom.

[Item 42]

The compound or pharmaceutically acceptable salt thereof of any one of items 39 to 41, wherein L is C$_{1-3}$ alkylene.

[Item 43]

The compound or pharmaceutically acceptable salt thereof of any one of items 39 to 42, wherein V is a single bond.

[Item 44]

The compound or pharmaceutically acceptable salt thereof of any one of items 39 to 42, wherein V is C$_{3-7}$ cycloalkylene.

[Item 45]

The compound or pharmaceutically acceptable salt thereof of any one of items 39 to 44, wherein W is a single bond.

[Item 46]

The compound or pharmaceutically acceptable salt thereof of any one of items 36 to 44, wherein W is C$_{1-3}$ alkylene.

[Item 47]

The compound or pharmaceutically acceptable salt thereof of any one of items 36 to 46, wherein Q is NH$_2$.

[Item 48]

The compound or pharmaceutically acceptable salt thereof of item 1, wherein formula (1) is represented by formula (4):

[Chemical Formula 10]

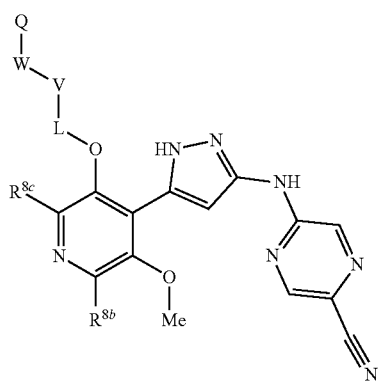

(4)

wherein $R^{8b}$ and $R^{8c}$ each independently represent a hydrogen atom, a fluorine atom, a chlorine atom, a bromine atom, or $C_{1-3}$ alkyl, L represents a single bond, or $C_{1-6}$ alkylene (wherein the alkylene is optionally substituted with 1 substituent selected from the group consisting of a fluorine atom, a hydroxyl group, and cyano), V represents a single bond, $C_{3-7}$ cycloalkylene (wherein the cycloalkylene is optionally substituted with 1 substituent selected from the group consisting of a hydroxyl group and $C_{1-3}$ alkyl), or a 3- to 7-membered divalent saturated heterocyclic group (wherein the saturated heterocyclic group is optionally substituted with 1 substituent selected from the group consisting of a fluorine atom, cyano, a hydroxyl group, and $C_{1-3}$ alkyl optionally substituted with 1 to 3 hydroxyl groups and fluorine atoms), W represents a single bond, or $C_{1-3}$ alkylene optionally substituted with 1 hydroxyl group, and Q is a hydrogen atom, $NH_2$, or NHMe.

[Item 49]

The compound or pharmaceutically acceptable salt thereof of item 48, wherein $R^{8b}$ and $R^{8c}$ are hydrogen atoms.

[Item 50]

The compound or pharmaceutically acceptable salt thereof of item 48 or 49, wherein L is a single bond, or $C_{1-6}$ alkylene optionally substituted with 1 hydroxyl group or 1 fluorine atom.

[Item 51]

The compound or pharmaceutically acceptable salt thereof of item 48 or 49, wherein L is $C_{1-4}$ alkylene optionally substituted with a hydroxyl group or a fluorine atom.

[Item 52]

The compound or pharmaceutically acceptable salt thereof of item 48 or 49, wherein L is a single bond.

[Item 53]

The compound or pharmaceutically acceptable salt thereof of any one of items 48 to 52, wherein V is a single bond, $C_{3-7}$ cycloalkylene, or a 3- to 7-membered divalent saturated heterocyclic group (wherein the saturated heterocyclic group is optionally substituted with 1 substituent selected from the group consisting of a fluorine atom, a hydroxyl group, and $C_{1-3}$ alkyl).

[Item 54]

The compound or pharmaceutically acceptable salt thereof of any one of items 48 to 53, wherein W is a single bond, or $C_{1-3}$ alkylene.

[Item 55]

The compound or pharmaceutically acceptable salt thereof of any one of items 48 to 53, wherein W is a single bond.

[Item 56]

The compound or pharmaceutically acceptable salt thereof of any one of items 48 to 53, wherein W is $C_{1-3}$ alkylene.

[Item 57]

The compound or pharmaceutically acceptable salt thereof of any one of items 48 to 56, wherein Q is a hydrogen atom.

[Item 58]

The compound or pharmaceutically acceptable salt thereof of any one of items 48 to 56, wherein Q is $NH_2$.

[Item 59]

The compound or pharmaceutically acceptable salt thereof of any one of items 48 to 56, wherein Q is NHMe.

[Item 60]

The compound or pharmaceutically acceptable salt thereof of item 1, wherein formula (1) is represented by formula (5):

[Chemical Formula 11]

$$(5)$$

wherein $R^{8a}$ and $R^{8c}$ each independently represent a hydrogen atom, a fluorine atom, a chlorine atom, a bromine atom, or $C_{1-3}$ alkyl, L represents a single bond or $C_{1-6}$ alkylene optionally substituted with 1 hydroxyl group, V represents a single bond, $C_{3-7}$ cycloalkylene (wherein the cycloalkylene is optionally substituted with 1 substituent selected from the group consisting of a hydroxyl group and $C_{1-3}$ alkyl), or a 3- to 7-membered divalent saturated heterocyclic group (wherein the saturated heterocyclic group is optionally substituted with 1 substituent selected from the group consisting of a fluorine atom, cyano, a hydroxyl group, and $C_{1-3}$ alkyl optionally substituted with 1 hydroxyl group), W represents a single bond, or $C_{1-3}$ alkylene optionally substituted with 1 hydroxyl group, and Q is a hydrogen atom or $NH_2$.

[Item 61]

The compound or pharmaceutically acceptable salt thereof of item 60, wherein $R^{8a}$ and $R^{8c}$ are hydrogen atoms.

[Item 62]

The compound or pharmaceutically acceptable salt thereof of item 60 or 61, wherein L is $C_{1-6}$ alkylene optionally substituted with 1 hydroxyl group.

[Item 63]

The compound or pharmaceutically acceptable salt thereof of any one of items 60 to 62, wherein V is a single bond, C$_{3-7}$ cycloalkylene, or a 3- to 7-membered divalent saturated heterocyclic group (wherein the saturated heterocyclic group is optionally substituted with 1 substituent selected from the group consisting of a hydroxyl group and C$_{1-3}$ alkyl optionally substituted with 1 hydroxyl group).

[Item 64]

The compound or pharmaceutically acceptable salt thereof of any one of items 60 to 62, wherein V is a single bond.

[Item 65]

The compound or pharmaceutically acceptable salt thereof of any one of items 60 to 62, wherein V is C$_{3-7}$ cycloalkylene.

[Item 66]

The compound or pharmaceutically acceptable salt thereof of any one of items 60 to 62, wherein V is a 3- to 7-membered divalent saturated heterocyclic group (wherein the saturated heterocyclic group is optionally substituted with 1 substituent selected from the group consisting of a hydroxyl group and C$_{1-3}$ alkyl).

[Item 67]

The compound or pharmaceutically acceptable salt thereof of any one of items 60 to 66, wherein W is a single bond, or C$_{1-3}$ alkylene.

[Item 68]

The compound or pharmaceutically acceptable salt thereof of any one of items 60 to 66, wherein W is a single bond.

[Item 69]

The compound or pharmaceutically acceptable salt thereof of any one of items 60 to 66, wherein W is C$_{1-3}$ alkylene.

[Item 70]

The compound or pharmaceutically acceptable salt thereof of any one of items 60 to 69, wherein Q is a hydrogen atom.

[Item 71]

The compound or pharmaceutically acceptable salt thereof of any one of items 60 to 69, wherein Q is NH$_2$.

[Item 72]

The compound or pharmaceutically acceptable salt thereof of item 1, wherein formula (1) is represented by formula (6):

[Chemical Formula 12]

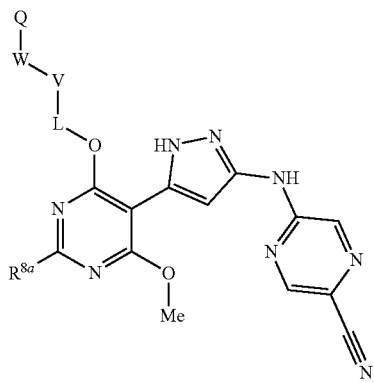

(6)

wherein

R$^{8a}$ represents a hydrogen atom, a fluorine atom, a chlorine atom, a bromine atom, or C$_{1-3}$ alkyl, L represents a single bond, or C$_{1-6}$ alkylene (wherein the alkylene is optionally substituted with 1 substituent selected from the group consisting of a fluorine atom, a hydroxyl group, and cyano), V represents a single bond, C$_{3-7}$ cycloalkylene (wherein the cycloalkylene is optionally substituted with 1 substituent selected from the group consisting of a hydroxyl group and C$_{1-3}$ alkyl), or a 3- to 7-membered divalent saturated heterocyclic group (wherein the saturated heterocyclic group is optionally substituted with 1 substituent selected from the group consisting of a fluorine atom, cyano, a hydroxyl group, and C$_{1-3}$ alkyl optionally substituted with 1 to 3 fluorine atoms), W represents a single bond, or C$_{1-3}$ alkylene optionally substituted with 1 hydroxyl group, and Q is a hydrogen atom, NH$_2$, or NHMe.

[Item 73]

The compound or pharmaceutically acceptable salt thereof of item 72, wherein R$^{8a}$ is a hydrogen atom.

[Item 74]

The compound or pharmaceutically acceptable salt thereof of item 72 or 73, wherein L is C$_{1-4}$ alkylene.

[Item 75]

The compound or pharmaceutically acceptable salt thereof of any one of items 72 to 74, wherein V is a single bond, or C$_{3-7}$ cycloalkylene.

[Item 76]

The compound or pharmaceutically acceptable salt thereof of any one of items 72 to 74, wherein V is a single bond.

[Item 77]

The compound or pharmaceutically acceptable salt thereof of any one of items 72 to 74, wherein V is C$_{3-7}$ cycloalkylene.

[Item 78]

The compound or pharmaceutically acceptable salt thereof of any one of items 72 to 77, wherein W is a single bond, or C$_{1-3}$ alkylene.

[Item 79]

The compound or pharmaceutically acceptable salt thereof of any one of items 72 to 77, wherein W is a single bond.

[Item 80]

The compound or pharmaceutically acceptable salt thereof of any one of items 72 to 77, wherein W is C$_{1-3}$ alkylene.

[Item 81]

The compound or pharmaceutically acceptable salt thereof of any one of items 72 to 80, wherein Q is NH$_2$.

[Item 82]

The compound or pharmaceutically acceptable salt thereof of item 1, selected from the following compounds:

5-({5-[2-(3-aminopropoxy)-4-methoxypyridin-3-yl]-1H-pyrazol-3-yl}amino)pyrazine-2-carbonitrile (Example 1), 5-({5-[2-(3-aminopropoxy)-6-chloro-4-methoxypyridin-3-yl]-1H-pyrazol-3-yl}amino)pyrazine-2-carbonitrile (Example 2), 5-({5-[3-(3-aminopropoxy)-5-methoxypyridin-4-yl]-1H-pyrazol-3-yl}amino)pyrazine-2-carbonitrile (Example 3), 5-({5-[4-(3-aminopropoxy)-2-methoxypyridin-3-yl]-1H-pyrazol-3-yl}amino)pyrazine-2-carbonitrile (Example 4), 5-[(5-{3-[(3-fluoroazetidin-3-yl)methoxy]-5-methoxypyridin-4-yl}-1H-pyrazol-3-yl)amino]pyrazine-2-carbonitrile (Example 5), 5-[(5-{2-methoxy-4-[(3-methylazetidin-3-yl)methoxy]pyridin-3-yl}-1H-pyrazol-3-yl)amino]pyrazine-2-carbonitrile (Example 6), 5-[(5-{4-[(3-hydroxyazetidin-3-yl)methoxy]-2-methoxypyridin-3-yl}-1H-pyrazol-3-yl)amino]pyrazine-2-carbonitrile (Example 7), 5-{[5-(4-{[3-(hydroxymethyl)azetidin-3-yl]methoxy}-2-methoxypyridin-3-yl)-1H-pyrazol-3-yl]amino}pyrazine-2-carbonitrile (Example 8), 5-[(5-{3-[(3R)-3-aminobutoxy]-5-methoxypyridin-4-yl}-1H-pyrazol-3-yl)amino]pyrazine-2-carbonitrile (Example 9), 5-[(5-{3-[(3S)-3-aminobutoxy]-5-methoxypyridin-4-yl}-1H-pyrazol-3-yl)amino]pyrazine-2-carbonitrile (Example 10), 5-{[5-(3-{[1-(aminomethyl)cyclopropyl]methoxy}-5-methoxypyridin-4-yl)-1H-pyrazol-3-yl]amino}pyrazine-2-carbonitrile (Example 11), 5-[(5-{3-methoxy-5-[(morpholin-2-yl)methoxy]pyridin-4-yl}-1H-pyrazol-3-yl)amino]pyrazine-2-carbonitrile (Example 12), 5-[(5-{3-methoxy-5-[(morpholin-2-yl)methoxy]pyridin-4-yl}-1H-pyrazol-3-yl)amino]pyrazine-2-carbonitrile (Example 13), 5-[(5-{3-[(2S)-3-amino-2-hydroxypropoxy]-5-methoxypyridin-4-yl}-1H-pyrazol-3-yl)amino]pyrazine-2-carbonitrile (Example 14), N-{5-[2-(3-aminopropoxy)-4-methoxypyridin-3-yl]-1H-pyrazol-3-yl}-5-chloropyrazin-2-amine (Example 15), N-{5-[2-(3-aminopropoxy)-4-methoxypyridin-3-yl]-1H-pyrazol-3-yl}-5-(trifluoromethyl)pyrazin-2-amine (Example 16), 5-({5-[4-(3-aminopropoxy)-6-methoxypyrimidin-5-yl]-1H-pyrazol-3-yl}amino)pyrazine-2-carbonitrile (Example 17), 5-({5-[3-(azetidin-3-yl)methoxy-5-methoxypyridin-4-yl]-1H-pyrazol-3-yl}amino)pyrazine-2-carbonitrile (Example 18), 5-{[5-(3-{[(1R,3S)-3-aminocyclohexyl]oxy}-5-methoxypyridin-4-yl)-1H-pyrazol-3-yl]amino}pyrazine-2-carbonitrile (Example 19), (S)-5-[(5-{3-[(3-fluoropyrrolidin-3-yl)methoxy]-5-methoxypyridin-4-yl}-1H-pyrazol-3-yl)amino]pyrazine-2-carbonitrile (Example 20), (S)-5-[(5-{3-methoxy-5-[(pyrrolidin-3-yl)methoxy]pyridin-4-yl}-1H-pyrazol-3-yl)amino]pyrazine-2-carbonitrile (Example 21), (R)-5-[(5-{3-[(3-fluoropyrrolidin-3-yl)methoxy]-5-methoxypyridin-4-yl}-1H-pyrazol-3-yl)amino]pyrazine-2-carbonitrile (Example 22), 5-{[5-(4-{[1-(aminomethyl)cyclopropyl]methoxy}-6-methoxypyrimidin-yl)-1H-pyrazol-3-yl]amino}pyrazine-2-carbonitrile (Example 23), 5-({5-[3-(3-aminopropoxy)-5-(fluoromethoxy)pyridin-4-yl]-1H-pyrazol-3-yl}amino)pyrazine-2-carbonitrile (Example 24), 5-[(5-{3-methoxy-5-[(3-methylazetidin-3-yl)methoxy]pyridin-4-yl}-1H-pyrazol-3-yl)amino]pyrazine-2-carbonitrile (Example 25), 5-{[5-(3-{[3-(difluoromethyl)azetidin-3-yl]methoxy}-5-methoxypyridin-4-yl)-1H-pyrazol-3-yl]amino}pyrazine-2-carbo nitrile (Example 26), 5-[(5-{3-[(2S)-3-amino-2-methoxypropoxy]-5-methoxypyridin-4-yl}-1H-pyrazol-3-yl)amino]pyrazine-2-carbonitrile (Example 27), 5-[(5-{3-[(2R)-3-amino-2-methoxypropoxy]-5-methoxypyridin-4-yl}-1H-pyrazol-3-yl)amino]pyrazine-2-carbonitrile (Example 28), 5-[(5-{3-[(2S)-3-amino-2-fluoropropoxy]-5-methoxypyridin-4-yl}-1H-pyrazol-3-yl)amino]pyrazine-2-carbonitrile (Example 29), 5-[(5-{3-[(2R)-3-amino-2-fluoropropoxy]-5-methoxypyridin-4-yl}-1H-pyrazol-3-yl)amino]pyrazine-2-carbonitrile (Example 30), 5-[(5-{3-methoxy-5-[3-(methylamino)propoxy]pyridin-4-yl}-1H-pyrazol-3-yl)amino]pyrazine-2-carbonitrile (Example 31), 5-{[5-(3-{[(1R,3R)-3-aminocyclopentyl]oxy}-5-methoxypyridin-4-yl)-1H-pyrazol-3-yl]amino}pyrazine-2-carbonitrile (Example 32), 5-[(5-{3-[(1R)-1-(azetidin-3-yl)ethoxy]-5-methoxypyridin-4-yl}-1H-pyrazol-3-yl)amino]pyrazine-2-carbonitrile (Example 33), 5-[(5-{3-[(1R)-1-(3-hydroxyazetidin-3-yl)ethoxy]-5-methoxypyridin-4-yl}-1H-pyrazol-3-yl)amino]pyrazine-2-carbonitrile (Example 34), 5-{[5-(3-methoxy-5-{[(1R,3R)-3-(methylamino)cyclopentyl]oxy}pyridin-4-yl)-1H-pyrazol-3-yl]amino}pyrazine-2-carbonitrile (Example 35), 5-{[5-(3-{[(1R,2S,4S,5S)-4-aminobicyclo[3.1.0]hexan-2-yl]oxy}-5-methoxypyridin-4-yl)-1H-pyrazol-3-yl]amino}pyrazine-2-carbonitrile (Example 36), 5-{[5-(2-{[1-(aminomethyl)cyclopropyl]methoxy}-4-methoxypyridin-3-yl)-1H-pyrazol-3-yl]amino}pyrazine-2-carbonitrile (Example 37), and 5-{[5-(4-{[1-(aminomethyl)cyclopropyl]methoxy}-2-methoxypyridin-3-yl)-1H-pyrazol-3-yl]amino}pyrazine-2-carbonitrile (Example 38).

[Item 83]

The compound or pharmaceutically acceptable salt thereof of item 1, selected from the following compounds:

5-({5-[2-(3-aminopropoxy)-4-methoxypyridin-3-yl]-1H-pyrazol-3-yl}amino)pyrazine-2-carbonitrile (Example 1), 5-({5-[3-(3-aminopropoxy)-5-methoxypyridin-4-yl]-1H-pyrazol-3-yl}amino)pyrazine-2-carbonitrile (Example 3), and 5-({5-[4-(3-aminopropoxy)-2-methoxypyridin-3-yl]-1H-pyrazol-3-yl}amino)pyrazine-2-carbonitrile (Example 4).

[Item 84]

The compound or pharmaceutically acceptable salt thereof of item 1, selected from the following compounds:

5-({5-[4-(3-aminopropoxy)-2-methoxypyridin-3-yl]-1H-pyrazol-3-yl}amino)pyrazine-2-carbonitrile (Example 4).

[Item 85]

The following compound or pharmaceutically acceptable salt thereof of item 1:

5-({5-[2-(3-aminopropoxy)-4-methoxypyridin-3-yl]-1H-pyrazol-3-yl}amino)pyrazine-2-carbonitrile (Example 1).

[Item 86]

The following compound or pharmaceutically acceptable salt thereof of item 1:

5-({5-[3-(3-aminopropoxy)-5-methoxypyridin-4-yl]-1H-pyrazol-3-yl}amino)pyrazine-2-carbonitrile (Example 3).

[Item 87]

A liposome comprising the compound of any one of items 1 to 86, prexasertib, or a pharmaceutically acceptable salt thereof.

[Item 88]

A liposome comprising the compound or pharmaceutically acceptable salt thereof of any one of items 1 to 86.

[Item 89]

A pharmaceutical composition comprising the compound or pharmaceutically acceptable salt thereof of any one of items 1 to 86 as an active ingredient.

[Item 90]

A pharmaceutical composition comprising a liposome encapsulating the compound of any one of items 1 to 86, prexasertib, or pharmaceutically acceptable salt thereof.

[Item 91]

A pharmaceutical composition comprising a liposome encapsulating the compound or pharmaceutically acceptable salt thereof of any one of items 1 to 86.

[Item 92]

The pharmaceutical composition of item 90 or 91, wherein the liposome further comprises a phospholipid.

[Item 93]

The pharmaceutical composition of item 90 or 91, wherein the liposome comprises
(1) the compound or pharmaceutically acceptable salt thereof of any one of items 1 to 86, and
(2) a phospholipid.

[Item 94]

The pharmaceutical composition of item 92 or 93, wherein the phospholipid is one selected from the group consisting of phosphatidylcholine, phosphatidylglycerol, phosphatidic acid, phosphatidylethanolamine, phosphatidylserine, phosphatidylinositol, sphingomyelin, soybean lecithin, egg yolk lecithin, hydrogenated egg yolk lecithin, and hydrogenated soybean lecithin or a combination of two or more thereof.

[Item 95]

The pharmaceutical composition of any one of items 90 to 94, wherein the liposome further comprises sterol.

[Item 96]

The pharmaceutical composition of item 95, wherein the sterol is cholesterol.

[Item 97]

The pharmaceutical composition of any one of items 90 to 96, wherein the liposome further comprises a polymer-modified lipid.

[Item 98]

The pharmaceutical composition of item 97, wherein a polymer moiety of the polymer-modified lipid is polyethylene glycol, polypropylene glycol, polyvinyl alcohol, polyvinyl pyrrolidone, methoxypolyethylene glycol, methoxypolypropylene glycol, methoxypolyvinyl alcohol, methoxypolyvinyl pyrrolidone, ethoxypolyethylene glycol, ethoxypolypropylene glycol, ethoxypolyvinyl alcohol, ethoxypolyvinyl pyrrolidone, propoxypolyethylene glycol, propoxypolypropylene glycol, propoxypolyvinyl alcohol, or propoxypolyvinyl pyrrolidone.

[Item 99]

The pharmaceutical composition of item 97 or 98, wherein a lipid moiety of the polymer-modified lipid is phosphatidylethanolamine or diacylglycerol.

[Item 100]

The pharmaceutical composition of item 97 or 98, wherein the polymer-modified lipid comprises polyethylene glycol, polypropylene glycol, polyvinyl alcohol, polyvinyl pyrrolidone, methoxypolyethylene glycol, methoxypropylene glycol, methoxypolyvinyl alcohol, methoxypolyvinyl pyrrolidone, ethoxypolyethylene glycol, ethoxypolypropylene glycol, ethoxypolyvinyl alcohol, ethoxypolyvinyl pyrrolidone, propoxypolyethylene glycol, propoxypolypropylene glycol, propoxypolyvinyl alcohol, or propoxypolyvinyl pyrrolidone as a polymer moiety, and phosphatidylethanolamine or diacylglycerol as a lipid moiety.

[Item 101]

The pharmaceutical composition of item 91 or 92, wherein the liposome comprises
(1) the compound or pharmaceutically acceptable salt thereof of any one of items 1 to 86,
(2) 40 to 70 mol % of phospholipid,
(3) 30 to 50 mol % of cholesterol, and
(4) 1 to 10 mol % of polymer-modified lipid.

[Item 102]

The pharmaceutical composition of any one of items 91 to 101, wherein the liposome further comprises an additive selected from the group consisting of inorganic acids, inorganic acid salts, organic acids, organic acid salts, saccharides, buffer, antioxidants, and polymers.

[Item 103]

A therapeutic agent and/or prophylactic agent for cancer, comprising the compound or pharmaceutically acceptable salt thereof of any one of items 1 to 86 as an active ingredient.

[Item 104]

The therapeutic agent and/or prophylactic agent of item 103, wherein the cancer is at least one type of cancer selected from the group consisting of acute leukemia, chronic lymphocytic leukemia, chronic myelogenous leukemia, myelodysplastic syndrome, polycythemia vera, malignant lymphoma, plasma cell tumor, multiple myeloma, brain tumor, head and neck cancer, esophageal cancer, thyroid cancer, small cell lung cancer, non-small cell lung cancer, thymoma/thymic carcinoma, breast cancer, gastric cancer, gallbladder/bile duct cancer, liver cancer, hepatocellular carcinoma, pancreatic cancer, colon cancer, rectal cancer, anal cancer, gastrointestinal stromal tumor, choriocarcinoma, endometrial cancer, cervical cancer, ovarian cancer, bladder cancer, urothelial cancer, renal cancer, renal cell cancer, prostate cancer, testicular tumor, testicular germ cell tumor, ovarian germ cell tumor, Wilms tumor, malignant melanoma, neuroblastoma, osteosarcoma, Ewing sarcoma, chondrosarcoma, soft tissue sarcoma, and skin cancer.

[Item 105]

A method of treating and/or preventing cancer, comprising administering, to a patient in need thereof, a therapeutically and/or prophylactically effective amount of the compound or pharmaceutically acceptable salt thereof of any one of items 1 to 86, the liposome of item 87 or 88, the pharmaceutical composition of items 89 to 102, or the therapeutic agent and/or prophylactic agent of item 103 or 104.

[Item 106]

The method of treating and/or preventing of item 105, wherein the cancer is at least one type of cancer selected from the group consisting of acute leukemia, chronic lymphocytic leukemia, chronic myelogenous leukemia, myelodysplastic syndrome, polycythemia vera, malignant lymphoma, plasma cell tumor, multiple myeloma, brain tumor, head and neck cancer, esophageal cancer, thyroid cancer, small cell lung cancer, non-small cell lung cancer, thymoma/thymic carcinoma, breast cancer, gastric cancer, gallbladder/bile duct cancer, liver cancer, hepatocellular carcinoma, pancreatic cancer, colon cancer, rectal cancer, anal cancer, gastrointestinal stromal tumor, choriocarcinoma, endometrial cancer, cervical cancer, ovarian cancer, bladder cancer, urothelial cancer, renal cancer, renal cell cancer, prostate cancer, testicular tumor, testicular germ cell tumor, ovarian germ cell tumor, Wilms tumor, malignant melanoma, neuroblastoma, osteosarcoma, Ewing sarcoma, chondrosarcoma, soft tissue sarcoma, and skin cancer.

[Item 107]

Use of the compound or pharmaceutically acceptable salt thereof of any one of items 1 to 86, the liposome of item 87 or 88, the pharmaceutical composition of items 89 to 102, or the therapeutic agent and/or prophylactic agent of item 103 or 104, for the manufacture of a therapeutic agent and/or prophylactic agent for cancer.

[Item 108]

The use of the compound or pharmaceutically acceptable salt thereof of any one of items 1 to 86, a pharmaceutical composition, a liposome, or a therapeutic agent and/or prophylactic agent, wherein the cancer is at least one type of cancer selected from the group consisting of acute leukemia, chronic lymphocytic leukemia, chronic myelogenous leukemia, myelodysplastic syndrome, polycythemia vera, malignant lymphoma, plasma cell tumor, multiple myeloma, brain tumor, head and neck cancer, esophageal cancer, thyroid cancer, small cell lung cancer, non-small cell lung cancer, thymoma/thymic carcinoma, breast cancer, gastric cancer, gallbladder/bile duct cancer, liver cancer, hepatocellular carcinoma, pancreatic cancer, colon cancer, rectal cancer, anal cancer, gastrointestinal stromal tumor, choriocarcinoma, endometrial cancer, cervical cancer, ovarian cancer, bladder cancer, urothelial cancer, renal cancer, renal cell cancer, prostate cancer, testicular tumor, testicular germ cell tumor, ovarian germ cell tumor, Wilms tumor, malignant melanoma, neuroblastoma, osteosarcoma, Ewing sarcoma, chondrosarcoma, soft tissue sarcoma, and skin cancer.

[Item 109]

The compound or pharmaceutically acceptable salt thereof of any one of items 1 to 86, the liposome of item 87 or 88, the pharmaceutical composition of items 89 to 102, or the therapeutic agent and/or prophylactic agent of item 103 or 104, for use in the treatment and/or prophylaxis of cancer.

[Item 110]

The compound or pharmaceutically acceptable salt thereof of any one of items 1 to 86, a pharmaceutical composition, a liposome, or a therapeutic agent and/or prophylactic agent, wherein the cancer is at least one type of cancer selected from the group consisting of acute leukemia, chronic lymphocytic leukemia, chronic myelogenous leukemia, myelodysplastic syndrome, polycythemia vera, malignant lymphoma, plasma cell tumor, multiple myeloma, brain tumor, head and neck cancer, esophageal cancer, thyroid cancer, small cell lung cancer, non-small cell lung cancer, thymoma/thymic carcinoma, breast cancer, gastric cancer, gallbladder/bile duct cancer, liver cancer, hepatocellular carcinoma, pancreatic cancer, colon cancer, rectal cancer, anal cancer, gastrointestinal stromal tumor, choriocarcinoma, endometrial cancer, cervical cancer, ovarian cancer, bladder cancer, urothelial cancer, renal cancer, renal cell cancer, prostate cancer, testicular tumor, testicular germ cell tumor, ovarian germ cell tumor, Wilms tumor, malignant melanoma, neuroblastoma, osteosarcoma, Ewing sarcoma, chondrosarcoma, soft tissue sarcoma, and skin cancer.

[Item 111]

The compound or pharmaceutically acceptable salt thereof of any one of items 1 to 86, or the liposome of item 87 or 88 for treating cancer by concomitantly using a concomitantly used drug or a pharmaceutically acceptable salt thereof, wherein the concomitantly used drug is at least one selected from the group consisting of a hormonal therapy agent, a chemotherapeutic agent, an immunotherapeutic agent, and an agent inhibiting a cell growth factor and a receptor action thereof.

[Item 112]

The compound or pharmaceutically acceptable salt thereof of any one of items 1 to 86, or the liposome of item 87 or 88 for treating cancer by concomitantly using a concomitantly used drug or a pharmaceutically acceptable salt thereof, wherein the concomitantly used drug is at least one selected from the group consisting of a 5-FU agent, cytarabine, doxorubicin hydrochloride, gemcitabine, methotrexate, pemetrexed, etoposide, irinotecan, topotecan, cisplatin, carboplatin, oxaliplatin, paclitaxel, docetaxel, ionizing radiation, bevacizumab, liposomal doxorubicin, rucaparib, olaparib, niraparib, trabectedin, pazopanib, pembrolizumab, nivolumab, ipilimumab, durvalumab, avelumab, atezolizumab, larotrectinib, entrectinib, nab paclitaxel, erlotinib, liposomal irinotecan, leucovorin, cetuximab, eribulin, ifosfamide, and dacarbazine.

[Item 113]

The compound or pharmaceutically acceptable salt thereof of any one of items 1 to 86, or the liposome of item 87 or 88 for treating cancer by concomitantly using a concomitantly used drug or a pharmaceutically acceptable salt thereof, wherein the concomitantly used drug is at least one selected from the group consisting of a5-FU agent, irinotecan, gemcitabine, cisplatin, carboplatin, oxaliplatin, paclitaxel, ionizing radiation, rucaparib, olaparib, niraparib, pembrolizumab, and nivolumab.

[Item 114]

(a) The compound or pharmaceutically acceptable salt thereof of any one of items 1 to 86, or the liposome of item 87 or 88 for treating cancer by concomitantly using a concomitantly used drug or a pharmaceutically acceptable salt thereof, wherein (b) the concomitantly used drug is at least one selected from the group consisting of a hormonal therapy agent, a chemotherapeutic agent, an immunotherapeutic agent, and an agent inhibiting a cell growth factor and a receptor action thereof, characterized in that:

(1) (a) and (b) are simultaneously administered;

(2) (a) is administered after administration of (b); or (3) (b) is administered after administration of (a).

[Item 115]

The compound or pharmaceutically acceptable salt thereof, or the liposome of item 114, wherein the concomitantly used drug (b) is a chemotherapeutic agent or an immunotherapeutic agent.

[Item 116]

The compound or pharmaceutically acceptable salt thereof, or the liposome of item 114 or 115, wherein the concomitantly used drug (b) is gemcitabine.

[Item 117]

The compound or pharmaceutically acceptable salt thereof, or the liposome of item 116, wherein the (a) compound or pharmaceutically acceptable salt thereof, or the liposome is simultaneously administered with the (b) gemcitabine.

[Item 118]

The compound or pharmaceutically acceptable salt thereof, or the liposome of item 116, wherein the (a) compound or pharmaceutically acceptable salt thereof, or the liposome is administered within about 24 to 48 hours after administration of the (b) gemcitabine.

[Item 119]

The compound or pharmaceutically acceptable salt thereof, or the liposome of item 116, wherein the (b)

gemcitabine is administered within about 24 to 48 hours after administration of the (a) compound or pharmaceutically acceptable salt thereof, or the liposome.

[Item 120]

The compound or pharmaceutically acceptable salt thereof, or the liposome of item 114 or 115, wherein the concomitantly used drug (b) is an anti-PD-1 antibody.

[Item 121]

The compound or pharmaceutically acceptable salt thereof, or the liposome of item 120, wherein the (a) compound or pharmaceutically acceptable salt thereof, or the liposome is simultaneously administered with the (b) anti-PD-1 antibody.

[Item 122]

The compound or pharmaceutically acceptable salt thereof, or the liposome of item 120, wherein the (b) anti-PD-1 antibody is administered within about 72 to 96 hours after administration of the (a) compound or pharmaceutically acceptable salt thereof, or the liposome.

[Item 123]

The compound or pharmaceutically acceptable salt thereof, or the liposome of item 116, wherein the (a) compound or pharmaceutically acceptable salt thereof, or the liposome is administered within about 72 to 96 hours after administration of the (b) anti-PD-1 antibody.

[Item 124]

A pharmaceutical composition comprising the compound or pharmaceutically acceptable salt thereof of any one of items 1 to 86, or the pharmaceutical composition of any one of items 89 to 102, comprised as a combination with a concomitantly used drug, wherein the concomitantly used drug is at least one selected from the group consisting of a hormonal therapy agent, a chemotherapeutic agent, an immunotherapeutic agent, and an agent inhibiting a cell growth factor and a receptor action thereof.

[Item 125]

A pharmaceutical composition comprising the compound or pharmaceutically acceptable salt thereof of any one of items 1 to 86, or the pharmaceutical composition of any one of items 89 to 102, comprised as a combination with a concomitantly used drug, wherein the concomitantly used drug is at least one selected from the group consisting of a 5-FU agent, cytarabine, doxorubicin hydrochloride, gemcitabine, methotrexate, pemetrexed, etoposide, irinotecan, topotecan, cisplatin, carboplatin, oxaliplatin, paclitaxel, docetaxel, ionizing radiation, bevacizumab, liposomal doxorubicin, rucaparib, olaparib, niraparib, trabectedin, pazopanib, pembrolizumab, nivolumab, ipilimumab, durvalumab, avelumab, atezolizumab, larotrectinib, entrectinib, nab paclitaxel, erlotinib, liposomal irinotecan, leucovorin, cetuximab, eribulin, ifosfamide, and dacarbazine.

[Item 126]

A pharmaceutical composition comprising the compound or pharmaceutically acceptable salt thereof of any one of items 1 to 86, or the pharmaceutical composition of any one of items 89 to 102, comprised as a combination with a concomitantly used drug, wherein the concomitantly used drug is at least one selected from the group consisting of a 5-FU agent, irinotecan, gemcitabine, cisplatin, carboplatin, oxaliplatin, paclitaxel, ionizing radiation, rucaparib, olaparib, niraparib, pembrolizumab, and nivolumab.

[Item 127]

5-({5-[2-(3-aminopropoxy)-4-methoxypyridin-3-yl]-1H-pyrazol-3-yl}amino)pyrazine-2-carbonitrile hydrochloride of a crystalline form of form I, having diffraction angle (2θ°) peaks at 7.2°±0.2° and 8.8°±0.2° in X-ray powder diffraction.

[Item 128]

5-({5-[2-(3-aminopropoxy)-4-methoxypyridin-3-yl]-1H-pyrazol-3-yl}amino)pyrazine-2-carbonitrile hydrochloride of a crystalline form of form I, having four or more diffraction angle (2θ°) peaks selected from 7.2°±0.2°, 8.8°±0.2°, 9.8°±0.2°, 10.2°±0.2°, 10.7°±0.2°, 16.7°±0.2°, 18.5°±0.2°, 26.2°±0.2°, 27.0°±0.2°, and 26.4°±0.2° in X-ray powder diffraction.

[Item 129]

5-({5-[2-(3-aminopropoxy)-4-methoxypyridin-3-yl]-1H-pyrazol-3-yl}amino)pyrazine-2-carbonitrile phosphate of a crystalline form of form II, having diffraction angle (2θ°) peaks at 6.8°±0.2° and 13.0°±0.2° in X-ray powder diffraction.

[Item 130]

5-({5-[2-(3-aminopropoxy)-4-methoxypyridin-3-yl]-1H-pyrazol-3-yl}amino)pyrazine-2-carbonitrile phosphate of a crystalline form of form II, having four or more diffraction angle (2θ°) peaks selected from 6.8°±0.2°, 7.5°±0.2°, 11.7°±0.2°, 11.9°±0.2°, 13.0°±0.2°, 16.4°±0.2°, 19.3°±0.2°, 20.4°±0.2°, 22.7°±0.2°, and 24.3°±0.2° in X-ray powder diffraction.

[Item 131]

5-({5-[2-(3-aminopropoxy)-4-methoxypyridin-3-yl]-1H-pyrazol-3-yl}amino)pyrazine-2-carbonitrile tosylate of a crystalline form of form III, having diffraction angle (2θ°) peaks at 6.0°±0.2° and 17.0°±0.2° in X-ray powder diffraction.

[Item 132]

5-({5-[2-(3-aminopropoxy)-4-methoxypyridin-3-yl]-1H-pyrazol-3-yl}amino)pyrazine-2-carbonitrile tosylate of a crystalline form of form III, having four or more diffraction angle (2θ°) peaks selected from 6.0°±0.2°, 9.0°±0.2°, 12.1°±0.2°, 14.4°±0.2°, 16.2°±0.2°, 17.0°±0.2°, 22.8°±0.2°, and 26.3°±0.2° in X-ray powder diffraction.

[Item 133]

5-({5-[2-(3-aminopropoxy)-4-methoxypyridin-3-yl]-1H-pyrazol-3-yl}amino)pyrazine-2-carbonitrile of a crystalline form of form IV, having diffraction angle (2θ°) peaks at 9.3°±0.2° and 10.2°±0.2° in X-ray powder diffraction.

[Item 134]

5-({5-[2-(3-aminopropoxy)-4-methoxypyridin-3-yl]-1H-pyrazol-3-yl}amino)pyrazine-2-carbonitrile of a crystalline form of form IV, having four or more diffraction angle (2θ°) peaks selected from 9.3°±0.2°, 10.2°±0.2°, 10.7°±0.2°, 13.6°±0.2°, 16.7°±0.2°, 17.1°±0.2°, 17.8°±0.2°, 18.6°±0.2°, 26.1°±0.2°, and 26.4°±0.2° in X-ray powder diffraction.

[Item 135]

5-({5-[2-(3-aminopropoxy)-4-methoxypyridin-3-yl]-1H-pyrazol-3-yl}amino)pyrazine-2-carbonitrile of a crystalline form of form V, having diffraction angle (2θ°) peaks at 7.9°±0.2° and 8.7°±0.2° in X-ray powder diffraction.

[Item 136]

5-({5-[2-(3-aminopropoxy)-4-methoxypyridin-3-yl]-1H-pyrazol-3-yl}amino)pyrazine-2-carbonitrile of a crystalline form of form V, having four or more diffraction angle (2θ°) peaks selected from 7.9°±0.2°, 8.7°±0.2°, 12.2°±0.2°, 13.1°±0.2°, 15.9°±0.2°, 17.6°±0.2°, 19.9°±0.2°, 21.9°±0.2°, 22.8°±0.2°, and 26.6°±0.2° in X-ray powder diffraction.

[Item 137]

5-({5-[2-(3-aminopropoxy)-4-methoxypyridin-3-yl]-1H-pyrazol-3-yl}amino)pyrazine-2-carbonitrile of a crystalline form of form VI, having diffraction angle (2θ°) peaks at 5.3°±0.2° and 5.7°±0.2° in X-ray powder diffraction.

[Item 138]

5-({5-[2-(3-aminopropoxy)-4-methoxypyridin-3-yl]-1H-pyrazol-3-yl}amino)pyrazine-2-carbonitrile of a crystalline form of form VI, having four or more diffraction angle (2θ°) peaks selected from 5.3°±0.2°, 5.7°±0.2°, 7.0°±0.2°, 7.3°±0.2°, 7.8°±0.2°, 8.4°±0.2°, 9.3°±0.2°, 10.5°±0.2°, 11.5°±0.2°, and 14.1°±0.2° in X-ray powder diffraction.

Advantageous Effects of Invention

The present disclosure provides a CHK1 inhibitor comprising a 5-heteroaryl-1H-pyrazol-3-amine derivative or a pharmaceutically acceptable salt thereof. The compound of the present disclosure has both an excellent CHK1 inhibitory activity as well as high safety. The compound is encapsulated in a liposome and is controllably released from the liposome to sustainably act on cancer to exhibit a potent antitumor effect. The compound of the present disclosure is useful as a therapeutic drug against CHK1-related diseases. Specifically, the compound can be applied to patients with pancreatic cancer, ovarian cancer, osteosarcoma, Ewing sarcoma, chondrosarcoma, soft tissue sarcoma, or the like.

The present disclosure elucidated that compounds which exhibited a pharmacological action on ovarian cancer patients in Phase 2 trials did not achieve maximization of efficacy from 72 hours of sustained exposure expected from a non-clinical trial relative to a 5-phenyl-1H-pyrazol-3-amine derivative prexasertib, whereas the compound of the present disclosure or a salt thereof can be a further improvement thereof. In comparison to prexasertib that results in a side effect due to a high maximum blood concentration, the compound of the present disclosure and a salt thereof did not have such a side effect in a single administration. While a side effect due to drug exposure for an extended period was observed, such a side effect was not observed with the compound of the present disclosure or a salt thereof in 3-day continuous administration (Non Patent Literature 3, Non Patent Literature 6). In addition, the inventors have newly found that prexasertib has a hepatotoxic risk, while the compound of present application has a reduced hepatotoxic risk. In view of the above, the compound of the present disclosure has both an excellent CHK1 inhibitory activity and high safety.

In particular, a compound having a pyridine ring with a nitrogen atom at a specific position represented by formula (3) has a characteristic of having a high antitumor activity as well as safety while also having excellent pharmacokinetics.

In particular, the compound of Example 1 encompassed by formula (3) has characteristics of exhibiting a higher CHK1 inhibitory activity and having a more potent cell growth suppression effect as well as higher safety, compared to prexasertib. The compound of Example 1 also has characteristics of exhibiting excellent pharmacokinetics as well as efficient encapsulation in a liposome. A liposome formulation of the compound of Example 1 has an excellent antitumor effect as well as high safety, and exerts an even more significant antitumor effect when used concomitantly with an existing anticancer agent.

DESCRIPTION OF EMBODIMENTS

Figure 1:
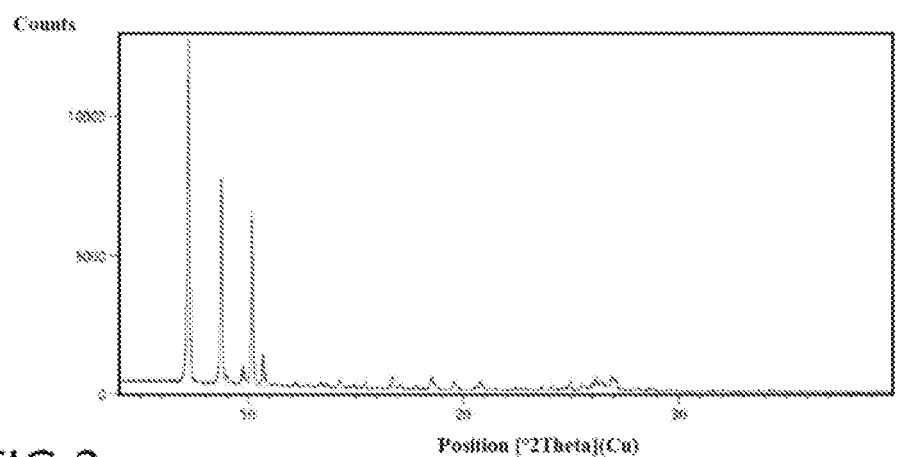
FIG. 1 shows the X ray powder diffraction pattern of form I of a compound of Example 39. The horizontal axis indicates diffraction angle 2θ(°), and the vertical axis indicates the count (the same applies to FIGS. 2 to 6 hereinafter).

The present disclosure is described hereinafter in more detail. Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. The terms used herein should also be understood as being used in the meaning that is commonly used in the art, unless specifically noted otherwise. Thus, unless defined otherwise, all terminologies and scientific technical terms that are used herein have the same meaning as the general understanding of those skilled in the art to which the present disclosure pertains. In case of a contradiction, the present specification (including the definitions) takes precedence.

The terms that are used herein are described hereinafter.

As used herein, the number of substituents in a group defined as "optionally substituted" is not particularly limited, as long as they are substitutable. The description of each group is also applicable when the group is a substituent or a part of another group, unless specifically noted otherwise.

Examples of a "halogen atom" include a fluorine atom, a chlorine atom, a bromine atom, an iodine atom, and the like. A halogen atom is preferably a fluorine atom or a chlorine atom.

"$C_{1-6}$ alkyl" refers to alkyl with 1 to 6 carbon atoms, and "Ce alkyl" refers to alkyl with 6 carbon atoms. The same applies to other numbers.

"$C_{1-6}$ alkyl" refers to a linear or branched saturated hydrocarbon group with 1 to 6 carbon atoms. $C_{1-6}$ alkyl is preferably "$C_{1-4}$ alkyl", and more preferably "$C_{1-3}$ alkyl". Specific examples of "$C_{1-3}$ alkyl" include methyl, ethyl, propyl, 1-methylethyl, and the like. Specific examples of "$C_{1-4}$ alkyl" include, in addition to the specific examples for the "$C_{1-3}$ alkyl" described above, butyl, 1,1-dimethylethyl, 1-methylpropyl, 2-methylpropyl, and the like. Specific examples of "$C_{1-6}$ alkyl" include, in addition to the specific examples for the "$C_{1-4}$ alkyl" described above, pentyl, 1,1-dimethylpropyl, 1,2-dimethylpropyl, 1-methylbutyl, 2-methylbutyl, 4-methylpentyl, 3-methylpentyl, 2-methylpentyl, 1-methylpentyl, hexyl, and the like.

"$C_{2-6}$ alkenyl" refers to a linear or branched unsaturated hydrocarbon group with 2 to 6 carbon atoms, comprising 1 to 3 double bonds. Preferred examples of "$C_{2-6}$ alkenyl" include "$C_{2-4}$ alkenyl". Specific examples of "$C_{2-4}$ alkenyl" include vinyl, propenyl, methylpropenyl, butenyl, and the like. Specific examples of "$C_{2-6}$ alkenyl" include, in addition to the specific examples for the "$C_{2-4}$ alkenyl" described above, pentenyl, hexenyl, and the like.

"$C_{2-6}$ alkynyl" refers to a linear or branched unsaturated hydrocarbon group with 2 to 6 carbon atoms, comprising one triple bonds. Preferred examples of "$C_{2-6}$ alkynyl" include "$C_{2-4}$ alkynyl". Specific examples of "$C_{2-4}$ alkynyl" include, in addition to the specific examples for the "$C_{2-4}$ alkynyl" described above, propynyl, methylpropynyl, butynyl, and the like. Specific examples of "$C_{2-4}$ alkynyl" include methylbutynyl, pentynyl, hexynyl, and the like.

"$C_{1-3}$ alkoxy" is "$C_{1-6}$ alkyloxy", and the "$C_{1-6}$ alkyl" moiety is defined the same as the "$C_{1-6}$ alkyl". "$C_{1-6}$ alkoxy" is preferably "$C_{1-4}$ alkoxy", and more preferably "$C_{1-3}$ alkoxy". Specific examples of "$C_{1-3}$ alkoxy" include methoxy, ethoxy, propoxy, 1-methylethoxy, and the like. Specific examples of "$C_{1-4}$ alkoxy" include, in addition to the specific examples for the "$C_{1-3}$ alkoxy" described above, butoxy, 1,1-dimethylethoxy, 1-methylpropoxy, 2-methylpropoxy, and the like. Specific examples of "$C_{1-6}$ alkoxy" include, in addition to the specific examples for the "$C_{1-4}$ alkoxy" described above, pentyloxy, 1,1-dimethylpropoxy, 1,2-dimethylpropoxy, 1-methylbutoxy, 2-methylbutoxy, 4-methylpentyloxy, 3-methylpentyloxy, 2-methylpentyloxy, 1-methylpentyloxy, hexyloxy, and the like.

The "$C_{1-6}$ alkyl" moiety of "$C_{1-6}$ alkylthio" is defined by the same as the "$C_{1-6}$ alkyl". "$C_{1-6}$ alkylthio" is preferably "$C_{1-4}$ alkylthio", and more preferably "$C_{1-3}$ alkylthio". Specific examples of "$C_{1-3}$ alkylthio" include methylthio, ethylthio, propylthio, 1-methylethylthio, and the like. Specific examples of "$C_{1-4}$ alkylthio" include, in addition to the specific examples for the "$C_{1-3}$ alkylthio" described above, butylthio, 1,1-dimethylethylthio, 1-methylpropylthio, 2-methylpropylthio, and the like. Specific examples of "$C_{1-6}$ alkylthio" include, in addition to the specific examples for the "$C_{1-4}$ alkylthio" described above, pentylthio, 1,1-dimethylpropylthio, 1,2-dimethylpropylthio, 1-methylbutylthio, 2-methylbutylthio, 4-methylpentylthio, 3-methylpentylthio, 2-methylpentylthio, 1-methylpentylthio, hexylthio, and the like.

"$C_{1-6}$ alkylene" refers to a linear or branched divalent saturated hydrocarbon group with 1 to 6 carbon atoms. "$C_{1-6}$ alkylene" is preferably "$C_{1-4}$ alkylene", and more preferably "$C_{1-3}$ alkylene". Specific examples of "$C_{1-3}$ alkylene" include methylene, ethylene, propylene, trimethylene, and the like. Specific examples of "$C_{1-4}$ alkylene" include, in addition to the specific examples for the "$C_{1-3}$ alkylene" described above, butylene, 1,1-dimethylethylene, 1,2-dimethylethylene, 1-methyltrimethylene, 2-methyltrimethylene, and the like. Specific examples of "$C_{1-6}$ alkylene" include, in addition to the specific examples for the "$C_{1-4}$ alkylene" described above, pentylene, 1,1-dimethyltrimethylene, 1,2-dimethyltrimethylene, 1-methylbutylene, 2-methylbutylene, 1-methylpentylene, 2-methylpentylene, 3-methylpentylene, hexylene, and the like.

"$C_{3-10}$ cycloalkyl" refers to a cyclic saturated hydrocarbon group with 3 to 10 carbon atoms, including those with a partially unsaturated bond and those with a crosslinked structure. "$C_3-1$, cycloalkyl" is preferably "$C_{3-7}$ cycloalkyl". Specific examples of "$C_{3-7}$ cycloalkyl" include cyclopropyl, cyclobutyl, cyclopentyl, cyclohexyl, cycloheptyl, and the like. Specific examples of "$C_{3-10}$ cycloalkyl" include, in addition to the specific examples for the "$C_{3-7}$ cycloalkyl" described above, cyclooctyl, cyclononyl, cyclodecyl, adamantyl, and the like.

"$C_{3-10}$ cycloalkyl" encompasses those that are bicyclic from fusing the $C_{3-10}$ cycloalkyl described above with an aromatic hydrocarbon ring. Specific examples of such a fused compound include the structure represented below and the like.

[Chemical Formula 13]

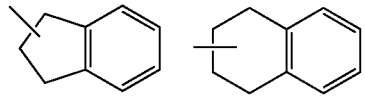

Specific examples of the crosslinked structure described above include the structure represented below and the like.

[Chemical Formula 14]

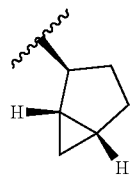

"$C_{3-10}$ cycloalkylene" refers to a cyclic divalent saturated hydrocarbon group with 3 to 10 carbon atoms, including those that have a partially unsaturated bond and those with a crosslinked structure. "$C_{3-10}$ cycloalkylene" is preferably "$C_{3-7}$ cycloalkylene". Specific examples of "$C_{3-7}$ cycloalkylene" include cyclopropylene, cyclobutylene, cyclopentylene, cyclohexylene, cycloheptylene, and the like. Specific examples of "$C_{3-10}$ cycloalkyl" include, in addition to the specific examples for the "$C_{3-7}$ cycloalkyl" described above, cyclooctylene, cyclononylene, cyclodecylene, adamantylene, and the like.

Specific examples of the crosslinked structure described above include the structure represented below and the like.

[Chemical Formula 15]

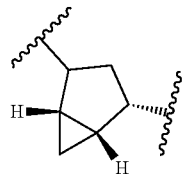

"3- to 10-membered saturated carbocyclic ring" refers to a cyclic saturated hydrocarbon with 3 to 10 carbon atoms. "3- to 10-membered saturated carbocyclic ring" is preferably "4- to 6-membered saturated carbocyclic ring". Specific examples of "4- to 6-membered saturated carbocyclic ring" include a cyclobutane ring, cyclopentane ring, cyclohexane ring, and the like. Specific examples of "3- to 10-membered saturated carbocyclic ring" include, in addition to the specific examples for the "4- to 6-membered saturated carbocyclic ring", a cyclopropane ring, cycloheptane ring, cyclooctane, cyclononane, cyclodecane, and the like.

"3- to 10-membered saturated heterocyclic group" refers to a monovalent saturated heterocyclic group comprised of 1 to 2 atoms independently selected from the group consisting of a nitrogen atom, an oxygen atom, and a sulfur atom, and 2 to 9 carbon atoms, including those having a partially unsaturated bond and those with a crosslinked structure. Atoms constituting a ring may include an atom that is oxidized such as —C(O)—, —S(O)—, or —SO$_2$—. "3- to 10-membered saturated heterocyclic group" is preferably "4- to 7-membered monocyclic saturated heterocyclic group". Specific examples of "4- to 7-membered monocyclic saturated heterocyclic group" include oxetanyl, azetidinyl, tetrahydrofuryl, pyrrolidinyl, imidazolidinyl, piperidinyl, morpholinyl, thiomorpholinyl, dioxothiomorpholinyl, hexamethyleniminyl, oxazolidinyl, thiazolidinyl, oxoimidazolidinyl, dioxoimidazolidinyl, oxooxazolidinyl, dioxooxazolidinyl, dioxothiazolidinyl, tetrahydrofuranyl, tetrahydropyranyl, and the like. Examples of "3- to 10-membered saturated heterocyclic group" include, in addition to the specific examples for the "4- to 7-membered monocyclic saturated heterocyclic group" described above, oxiranyl, aziridinyl, and the like.

"3- to 10-membered saturated heterocyclic group" encompasses those that are bicyclic forming a fused ring of the 3- to 10-membered saturated heterocyclic group and a 6-membered aromatic hydrocarbon ring or 6-membered aromatic heterocycle. Examples of the 6-membered aromatic hydrocarbon ring forming a fused ring include a benzene ring and the like. Examples of the 6-membered aromatic heterocycle forming a fused ring includes pyridine, pyrimidine, pyridazine, and the like. Specific examples of bicyclic "3- to 10-membered saturated heterocyclic group" forming a fused ring include dihydroindolyl, dihydroisoindolyl, dihydropurinyl, dihydrothiazolopyrimidinyl, dihydrobenzodioxanyl, isoindolyl, indazolyl, tetrahydroquinolinyl, tetrahydroisoquinolinyl, tetrahydronaphthyridinyl, and the like.

"3- to 8-membered nitrogen-containing saturated heterocycle" refers to a saturated heterocycle comprised of 1 nitrogen atom and 2 to 7 carbon atoms. "3- to 8-membered nitrogen-containing saturated heterocycle" is preferably "4- to 6-membered nitrogen-containing saturated heterocycle". Specific examples of "4- to 6-membered nitrogen-containing saturated heterocycle" include an azetidine ring, pyrrolidine ring, piperidine ring, and the like. Specific examples of "3- to 8-membered nitrogen-containing saturated heterocycle" include, in addition to the specific examples for the "4- to 6-membered nitrogen-containing saturated heterocycle" described above, an aziridine ring, azepane ring, azocane ring, and the like.

"3- to 10-membered divalent saturated heterocyclic group" refers to a divalent saturated heterocyclic group comprised of 1 to 2 atoms independently selected from the group consisting of a nitrogen atom, an oxygen atom, and a sulfur atom and 2 to 9 carbon atoms, including those having a partially unsaturated bond and those with a crosslinked structure. Atoms constituting a ring may include an atom that is oxidized such as —C(O)—, —S(O)—, or —SO$_2$—. "3- to 10-membered saturated heterocyclic group" is preferably "4- to 7-membered monocyclic saturated heterocyclic group". Specific examples of "4- to 7-membered monocyclic saturated heterocyclic group" include oxetanylene, azetidinylene, tetrahydrofurylene, pyrrolidinylene, imidazolidinylene, piperidinylene, morpholinylene, thiomorpholinylene, dioxothiomorpholinylene, hexamethyleniminylene, oxazolidinylene, thiazolidinylene, oxoimidazolidinylene, dioxooimidazolidinylene, oxooxazolidinylene, dioxooxazolidinylene, dioxothiazolidinylene, tetrahydrofuranylene, tetrahydropyranylene, and the like. Examples of "3- to 10-membered saturated heterocyclic group" include, in addition to the specific examples for the "4- to 7-membered monocyclic saturated heterocyclic group" described above, oxiranylene, aziridinylene, and the like.

"3- to 10-membered saturated heterocyclic group" encompasses those that are bicyclic forming a fused ring of the 3- to 10-membered saturated heterocyclic group and a 6-membered aromatic hydrocarbon ring or 6-membered aromatic heterocycle. Examples of the 6-membered aromatic hydrocarbon ring forming a fused ring include a benzene ring and the like. Examples of the 6-membered aromatic heterocycle forming a fused ring include pyridine, pyrimidine, pyridazine, and the like. Specific examples of bicyclic "3- to 10-membered saturated heterocyclic group" forming a fused ring include dihydroindolylene, dihydroisoindolylene, dihydropurinylene, dihydrothiazolopyrimidinylene, dihydrobenzodioxanylene, isoindolylene, indazolylene, tetrahydroquinolylene, tetrahydroisoquinolinylene, tetrahydronaphthylidinylene, and the like.

"C$_{6-10}$ aryl" refers to an aromatic hydrocarbon ring group with 6 to 10 carbon atoms. Specific examples of "C$_{6-10}$ aryl" include phenyl, 1-naphthyl, 2-naphthyl, and the like. Preferred examples thereof include phenyl.

"C$_{1-10}$ aryl" encompasses those that are bicyclic forming a fused ring of the C$_{6-10}$ aryl and C$_{4-6}$ cycloalkyl or 5- to 6-membered saturated heterocycle. Specific examples of bicyclic "C$_{6-10}$ aryl" forming a fused ring include the groups represented by the following and the like.

[Chemical Formula 16]

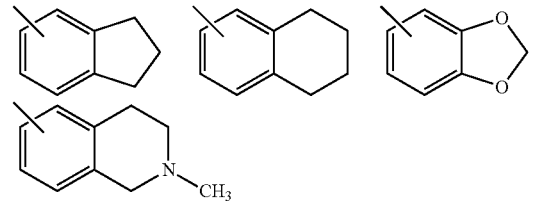

"Aromatic hydrocarbon ring" refers to the cyclic moiety of the "C$_{6-10}$ aryl" described above.

"5- to 12-membered heteroaryl" refers to a cyclic group of a monocyclic 5- to 7-membered aromatic heterocycle or a cyclic group of a bicyclic 8- to 12-membered aromatic heterocycle, comprising 1 to 4 atoms independently selected from the group consisting of a nitrogen atom, an oxygen atom, and a sulfur atom. This is preferably "5- to 7-membered monocyclic heteroaryl", more preferably pyridyl, pyrimidinyl, quinolyl, orisoquinolyl, and more preferably pyridyl. Specific examples of "5- to 7-membered monocyclic heteroaryl" include pyridyl, pyridazinyl, isothiazolyl, pyrrolyl, furyl, thienyl, thiazolyl, imidazolyl, pyrimidinyl, thiadiazolyl, pyrazolyl, oxazolyl, isooxazolyl, pyrazinyl, triazinyl, triazolyl, oxadiazolyl, triazolyl, tetrazolyl, and the like. Specific examples of "5- to 12-membered heteroaryl" include, in addition to the specific examples for the "5- to 7-membered monocyclic heteroaryl" described above, indolyl, indazolyl, chromenyl, quinolyl, isoquinolyl, benzofuranyl, benzothienyl, benzooxazolyl, benzothiazolyl, benzoisooxazolyl, benzoisothiazolyl, benzotriazolyl, benzoimidazolyl, and the like.

"Aromatic heterocycle" refers to a cyclic moiety of the "5- to 12-membered heteroaryl" described above.

"Cancer" and "tumor" are defined the same in the present disclosure, both referring to malignant tumor and encompassing cancer, sarcoma, and hematological malignancy. Specific examples of "cancer" and "tumor" include acute leukemia, chronic lymphocytic leukemia, chronic myelogenous leukemia, myelodysplastic syndrome, polycythemia vera, malignant lymphoma, plasma cell tumor, multiple myeloma, brain tumor, head and neck cancer, esophageal cancer, thyroid cancer, small cell lung cancer, non-small cell lung cancer, thymoma/thymic carcinoma, breast cancer, gastric cancer, gallbladder/bile duct cancer, liver cancer, hepatocellular carcinoma, pancreatic cancer, colon cancer, rectal cancer, anal cancer, gastrointestinal stromal tumor, choriocarcinoma, endometrial cancer, cervical cancer, ovarian cancer, bladder cancer, urothelial cancer, renal cancer, renal cell cancer, prostate cancer, testicular tumor, testicular germ cell tumor, ovarian germ cell tumor, Wilms tumor, malignant melanoma, neuroblastoma, osteosarcoma, Ewing sarcoma, chondrosarcoma, soft tissue sarcoma, skin cancer, and the like.

Prexasertib is a compound with the following structure.

[Chemical Formula 17]

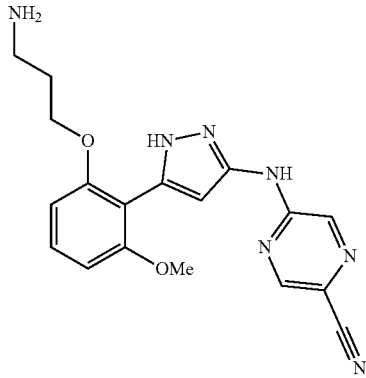

In the compound of the present disclosure represented by formula (1), (2), (3), (4), or (5), $R^1$, $R^2$, $R^3$, $R^4$, $R^5$, $R^6$, $R^7$, $R^8$, $R^{8a}$, $R^{8b}$, $R^{8c}$, $R^9$, $R^{10}$, $R^{11}$, $R^{12}$, $R^{13}$, $R^{14}$, $R^{15}$, $R^{16}$, $R^{17}$, $R^{18}$, X, Y, Z, L, V, W, Q, and Y are preferably the following, but the technical scope of the present disclosure is not limited to the scope of the compounds listed below.

Preferred embodiments of $R^1$ include $C_{1-6}$ alkyl optionally substituted with 1 to 3 fluorine atoms.

More preferred embodiments of $R^1$ include an ethyl group or methyl group optionally substituted with 1 to 3 fluorine atoms.

Still more preferred embodiments of $R^1$ include a methyl group optionally substituted with 1 to 3 fluorine atoms.

Yet still more preferred embodiments of $R^1$ include a methyl group.

Preferred embodiments of $R^2$ include a hydrogen atom, a halogen atom, cyano, —$OR^3$, $C_{1-6}$ alkyl optionally substituted with 1 to 3 halogen atoms, $C_{3-10}$ cycloalkyl, and a 3- to 10-membered saturated heterocyclic group.

More preferred embodiments of $R^2$ include a hydrogen atom, a halogen atom, cyano, and $C_{1-6}$ alkyl optionally substituted with 1 to 3 halogen atoms.

Still more preferred embodiments of $R^2$ include a halogen atom, cyano, and $C_{1-6}$ alkyl optionally substituted with 1 to 3 halogen atoms.

Yet still more preferred embodiments of $R^2$ include cyano.

Preferred embodiments of $R^3$ include a hydrogen atom and $C_{1-6}$ alkyl.

More preferred embodiments of $R^3$ include $C_{1-6}$ alkyl.

Still more preferred embodiments of $R^3$ include $C_{1-3}$ alkyl.

Yet still more preferred embodiments of $R^3$ include a methyl group.

Preferred embodiments of $R^4$ include $C_{1-3}$ alkyl.

More preferred embodiments of $R^4$ include a methyl group.

Preferred embodiments of $R^5$, $R^6$, and $R^7$ include a hydrogen atom and $C_{1-6}$ alkyl.

More preferred embodiments of $R^5$, $R^6$, and $R^7$ include $C_{1-6}$ alkyl.

Still more preferred embodiments of $R^5$, $R^6$, and $R^7$ include $C_{1-3}$ alkyl.

Yet still more preferred embodiments of $R^5$, $R^6$, and $R^7$ include a methyl group.

Preferred embodiments of $R^8$ include a hydrogen atom, a fluorine atom, a chlorine atom, a bromine atom, $C_{1-6}$ alkyl (wherein the alkyl is optionally substituted with 1 to 2 of the same or different substituents selected from the group consisting of a fluorine atom, a hydroxyl group, $C_{1-3}$ alkoxy, —$NR^{16}R^{17}$, and cyano), and 5- to 6-membered heteroaryl (wherein the heteroaryl is optionally substituted with 1 to 2 of the same or different substituents selected from the group consisting of a fluorine atom, a hydroxyl group, $C_{1-3}$ alkyl, $C_{1-3}$ alkoxy, —$NR^{16}R^{17}$, and cyano).

More preferred embodiments of $R^8$ include a hydrogen atom, a fluorine atom, a chlorine atom, a bromine atom, and $C_{1-6}$ alkyl (wherein the alkyl is optionally substituted with 1 to 2 of the same or different substituents selected from the group consisting of a fluorine atom, a hydroxyl group, $C_{1-3}$ alkoxy, —$NR^{16}R^{17}$, and cyano).

Still more preferred embodiments of $R^8$ include a hydrogen atom, a fluorine atom, a chlorine atom, a bromine atom, and $C_{1-3}$ alkyl.

Still more preferred embodiments of $R^3$ include a hydrogen atom and a chlorine atom.

Preferred embodiments of $R^{8a}$, $R^{8b}$, and $R^{8c}$ include a hydrogen atom, a fluorine atom, a chlorine atom, and a bromine atom.

More preferred embodiments of $R^{8a}$, $R^{8b}$, and $R^{8c}$ include a hydrogen atom and a chlorine atom.

Still more preferred embodiments of $R^{8a}$, $R^{8b}$, and $R^{8c}$ include a hydrogen atom.

Preferred embodiments of $R^9$ include a hydrogen atom and $C_{1-6}$ alkyl.

More preferred embodiments of $R^9$ include $C_{1-3}$ alkyl.

Still more preferred embodiments of $R^9$ include a methyl group.

Preferred embodiments of $R^{10}$ include $C_{1-3}$ alkyl.

Still more preferred embodiments of $R^{10}$ include a methyl group.

Preferred embodiments of $R^{11}$, $R^{12}$, and $R^{13}$ include a hydrogen atom and $C_{1-6}$ alkyl.

More preferred embodiments of $R^{11}$, $R^{12}$, and $R^{13}$ include $C_{1-3}$ alkyl.

Still more preferred embodiments of $R^{11}$, $R^{12}$, and $R^{13}$ include a methyl group.

Preferred embodiments of $R^{14}$ include a hydrogen atom, $C_{1-6}$ alkyl (wherein the alkyl is optionally substituted with 1 to 3 of the same or different substituents selected from the group consisting of a fluorine atom, a hydroxyl group, $C_{1-3}$ alkoxy, —$NR^{16}R^{17}$, and cyano), $C_{3-10}$ cycloalkyl (wherein the cycloalkylene is optionally substituted with 1 to 3 of the same or different substituents selected from the group consisting of a fluorine atom, a hydroxyl group, $C_{1-3}$ alkyl, $C_{1-3}$ alkoxy, —$NR^{16}R^{17}$, and cyano), and a 3- to 10-membered saturated heterocyclic group (wherein the saturated heterocyclic group is optionally substituted with 1 to 3 of the same or different substituents selected from the group consisting of a fluorine atom, a hydroxyl group, $C_{1-3}$ alkyl, $C_{1-3}$ alkoxy, —$NR^{16}R^{17}$, and cyano).

More preferred embodiments of $R^{14}$ include a hydrogen atom and $C_{1-6}$ alkyl (wherein the alkyl is optionally substituted with 1 to 3 of the same or different substituents selected from the group consisting of a fluorine atom, a hydroxyl group, $C_{1-3}$ alkoxy, —$NR^{16}R^{17}$, and cyano).

More preferred embodiments of $R^{14}$ include a hydrogen atom and $C_{1-3}$ alkyl (wherein the alkyl is optionally substituted with 1 substituent selected from the group consisting of a fluorine atom, a hydroxyl group, and cyano).

Still more preferred embodiments of $R^{14}$ include a hydrogen atom and a methyl group.

Preferred embodiments of $R^{15}$ include $C_{1-6}$ alkyl.

More preferred embodiments of $R^{15}$ include $C_{1-3}$ alkyl.

More preferred embodiments of $R^{15}$ include a methyl group.

Preferred embodiments of $R^{16}$ and $R^{17}$ include a hydrogen atom and $C_{1-6}$ alkyl.

More preferred embodiments of $R^{16}$ and $R^{17}$ include $C_{1-6}$ alkyl.

Still more preferred embodiments of $R^{16}$ and $R^{17}$ include $C_{1-3}$ alkyl.

Still more preferred embodiments of $R^{16}$ and $R^{17}$ include a methyl group.

Preferred embodiments of $R^{18}$ include a hydrogen atom and $C_{1-6}$ alkyl.

More preferred embodiments of $R^{18}$ include $C_{1-6}$ alkyl.

More preferred embodiments of $R^{18}$ include $C_{1-3}$ alkyl.

Still more preferred embodiments of $R^{18}$ include a methyl group.

Preferred embodiments of X, Y, and Z include $CR^8$ and a nitrogen atom. For the compound or pharmaceutically acceptable salt of the present disclosure, X, Y, and Z are not simultaneously $CR^8$ in the present disclosure.

In another preferred embodiment of X, Y, and Z, one or two of X, Y, and Z represents a nitrogen atom.

In another preferred embodiment of X, Y, and Z, X is $CR^8$, and Y and Z are nitrogen atoms.

In still another preferred embodiment of X, Y, and Z, Y is $CR^8$, and X and Z are nitrogen atoms.

In another different preferred embodiment of X, Y, and Z, Z is $CR^8$, and X and Y are nitrogen atoms.

Preferred embodiments of L include a single bond and $C_{1-6}$ alkylene (wherein the alkylene is optionally substituted with 1 to 3 of the same or different substituents selected from the group consisting of a fluorine atom, a hydroxyl group, $C_{1-3}$ alkoxy, —$NR^{16}R^{17}$, and cyano).

More preferred embodiments of L include a single bond, and $C_{1-6}$ alkylene (wherein the alkylene is optionally substituted with 1 substituent selected from the group consisting of a fluorine atom, a hydroxyl group, and cyano).

More preferred embodiments of L include a single bond, and $C_{1-6}$ alkylene (wherein the alkylene is optionally substituted with 1 substituent selected from the group consisting of a fluorine atom and a hydroxyl group).

Still more preferred embodiments of L include a single bond and $C_{1-6}$ alkylene optionally substituted with 1 hydroxyl group.

Preferred embodiments of V include a single bond, $C_{3-10}$ cycloalkylene (wherein the cycloalkylene is optionally substituted with 1 to 3 of the same or different substituents selected from the group consisting of a fluorine atom, a hydroxyl group, $C_{1-3}$ alkyl, $C_{1-3}$ alkoxy, —$NR^{16}R^{17}$, and cyano), and a 3- to 10-membered divalent saturated heterocyclic group (wherein the saturated heterocyclic group is optionally substituted with 1 to 3 of the same or different substituents selected from the group consisting of a fluorine atom, a hydroxyl group, $C_{1-3}$ alkyl optionally substituted with 1 to 2 hydroxyl groups or fluorine atoms, $C_{1-3}$ alkoxy, —$NR^{16}R^{17}$, and cyano).

More preferred embodiments of V include a single bond, $C_{3-7}$ cycloalkylene (wherein the cycloalkylene is optionally substituted with 1 to 2 of the same or different substituents selected from the group consisting of a fluorine atom, a hydroxyl group, $C_{1-3}$ alkyl optionally substituted with 1 to 2 hydroxyl groups, and cyano), and a 3- to 7-membered divalent saturated heterocyclic group (wherein the saturated heterocyclic group is optionally substituted with 1 to 2 of the same or different substituents selected from the group consisting of a fluorine atom, a hydroxyl group, $C_{1-3}$ alkyl optionally substituted with 1 to 2 hydroxyl groups or fluorine atoms, and cyano).

More preferred embodiments of V include a single bond, $C_{3-7}$ cycloalkylene (wherein the cycloalkylene is optionally substituted with 1 to 2 of the same or different substituents selected from the group consisting of a fluorine atom, a hydroxyl group, and $C_{1-3}$ alkyl optionally substituted with 1 to 2 hydroxyl groups or fluorine atoms), and a 3- to 7-membered divalent saturated heterocyclic group (wherein the saturated heterocyclic group is optionally substituted with 1 to 2 of the same or different substituents selected from the group consisting of a fluorine atom, a hydroxyl group, and $C_{1-3}$ alkyl optionally substituted with 1 to 2 hydroxyl groups).

Still more preferred embodiments of V include a single bond, $C_{3-7}$ cycloalkylene (wherein the cycloalkylene is optionally substituted with 1 substituent selected from the group consisting of a hydroxyl group and $C_{1-3}$ alkyl), and a 3- to 7-membered divalent saturated heterocyclic group (wherein the 3- to 7-membered saturated heterocyclic group is optionally substituted with 1 substituent selected from the group consisting of a fluorine atom, cyano, a hydroxyl group, and $C_{1-3}$ alkyl).

Preferred embodiments of W include a single bond and $C_{1-6}$ alkylene (wherein the alkylene is optionally substituted with 1 to 3 of the same or different substituents selected from the group consisting of a fluorine atom, a hydroxyl group, $C_{1-3}$ alkoxy, —$NR^{16}R^{17}$, and cyano).

More preferred embodiments of W include a single bond and $C_{1-3}$ alkylene (wherein the alkylene is optionally substituted with 1 substituent selected from the group consisting of a fluorine atom, a hydroxyl group, and cyano).

More preferred embodiments of W include a single bond and $C_{1-3}$ alkylene (wherein the alkylene is optionally substituted with 1 substituent selected from the group consisting of a fluorine atom and a hydroxyl group).

Still more preferred embodiments of W include a single bond and $C_{1-3}$ alkylene optionally substituted with 1 hydroxyl group.

Preferred embodiments of Q include a hydrogen atom and $NHR^{14}$.

More preferred embodiments of Q include a hydrogen atom, $NH_2$, and NHMe.

More preferred embodiments of Q include a hydrogen atom and $NH_2$.

Still more preferred embodiments of Q include a hydrogen atom.

Still another preferred embodiments of Q include $NH_2$.

One embodiment of the compound represented by formula (1) includes the following (A).

(A)

A compound or a pharmaceutically acceptable salt thereof, wherein $R^1$ is an ethyl group or methyl group optionally substituted with 1 to 3 fluorine atoms, $R^2$ is a hydrogen atom, a halogen atom, cyano, $-OR^8$, $C_{1-6}$ alkyl optionally substituted with 1 to 3 halogen atoms, $C_{3-10}$ cycloalkyl, or a 3- to 10-membered saturated heterocyclic group, $R^3$ is a hydrogen atom or $C_{1-6}$ alkyl, X, Y, and Z each independently represent $CR^8$ or a nitrogen atom, wherein X, Y, and Z are not simultaneously $CR^8$, $R^6$ is a hydrogen atom, a fluorine atom, a chlorine atom, a bromine atom, $C_{1-6}$ alkyl (wherein the alkyl is optionally substituted with 1 to 2 of the same or different substituents selected from the group consisting of a fluorine atom, a hydroxyl group, $C_{1-3}$ alkoxy, $-NR^{16}R^{17}$, and cyano), or 5- to 6-membered heteroaryl (wherein the heteroaryl is optionally substituted with 1 to 2 of the same or different substituents selected from the group consisting of a fluorine atom, a hydroxyl group, $C_{1-3}$ alkyl, $C_{1-3}$ alkoxy, $-NR^{16}R^{17}$, and cyano), L is a single bond or $C_{1-6}$ alkylene (wherein the alkylene is optionally substituted with 1 to 3 of the same or different substituents selected from the group consisting of a fluorine atom, a hydroxyl group, $C_{1-3}$ alkoxy, $-NR^{16}R^{17}$, and cyano), V is a single bond, $C_{3-10}$ cycloalkylene (wherein the cycloalkylene is optionally substituted with 1 to 3 of the same or different substituents selected from the group consisting of a fluorine atom, a hydroxyl group, $C_{1-3}$ alkyl, $C_{1-3}$ alkoxy, $-NR^{16}R^{17}$, and cyano), or a 3- to 10-membered divalent saturated heterocyclic group (wherein the saturated heterocyclic group is optionally substituted with 1 to 3 of the same or different substituents selected from the group consisting of a fluorine atom, a hydroxyl group, $C_{1-3}$ alkyl optionally substituted with 1 to 2 hydroxyl groups or fluorine atoms, $C_{1-3}$ alkoxy, $-NR^{16}R^{17}$, and cyano), W is a single bond or $C_{1-6}$ alkylene (wherein the alkylene is optionally substituted with 1 to 3 of the same or different substituents selected from the group consisting of a fluorine atom, a hydroxyl group, $C_{1-3}$ alkoxy, $-NR^{16}R^{17}$, and cyano), Q is a hydrogen atom or $NHR^{17}$, $R^{14}$ is a hydrogen atom, $C_{1-6}$ alkyl (wherein the alkyl is optionally substituted with 1 to 3 of the same or different substituents selected from the group consisting of a fluorine atom, a hydroxyl group, $C_{1-3}$ alkoxy, $-NR^{16}R^{17}$, and cyano), $C_{3-10}$ cycloalkyl (wherein the cycloalkylene is optionally substituted with 1 to 3 of the same or different substituents selected from the group consisting of a fluorine atom, a hydroxyl group, $C_{1-3}$ alkyl, $C_{1-3}$ alkoxy, $-NR^{16}R^{17}$, and cyano), or a 3- to 10-membered saturated heterocyclic group (wherein the saturated heterocyclic group is optionally substituted with 1 to 3 of the same or different substituents selected from the group consisting of a fluorine atom, a hydroxyl group, $C_{1-3}$ alkyl, $C_{1-3}$ alkoxy, $-NR^{16}R^{17}$, and cyano), and $R^{16}$ and $R^{17}$ are hydrogen atoms or $C_1$ alkyl.

An embodiment of the compound represented by formula (1) includes the following (B).

(B)

A compound or a pharmaceutically acceptable salt thereof, wherein $R^1$ is a methyl group optionally substituted with 1 to 3 fluorine atoms, $R^2$ is a halogen atom, cyano, or C1 alkyl optionally substituted with 1 to 3 halogen atoms, X, Y, and Z each independently represent CRS or a nitrogen atom, wherein X, Y, and Z are not simultaneously $CR^B$, $R^8$ is a hydrogen atom, a fluorine atom, a chlorine atom, a bromine atom, or $C_{1-3}$ alkyl, L is a single bond or $C_{1-6}$ alkylene (wherein the alkylene is optionally substituted with 1 to 3 of the same or different substituents selected from the group consisting of a fluorine atom, a hydroxyl group, $C_{1-3}$ alkoxy, $-NR^{16}R^{17}$, and cyano), V is a single bond, $C_{3-10}$ cycloalkylene (wherein the cycloalkylene is optionally substituted with 1 to 3 of the same or different substituents selected from the group consisting of a fluorine atom, a hydroxyl group, $C_{1-3}$ alkyl, $C_{1-3}$ alkoxy, $-NR^{16}R^{17}$, and cyano), or a 3- to 10-membered divalent saturated heterocyclic group (wherein the saturated heterocyclic group is optionally substituted with 1 to 3 of the same or different substituents selected from the group consisting of a fluorine atom, a hydroxyl group, $C_{1-3}$ alkyl optionally substituted with 1 to 2 hydroxyl groups or fluorine atoms, $C_{1-3}$ alkoxy, $-NR^{16}R^{17}$, and cyano), W is a single bond or $C_{1-6}$ alkylene (wherein the alkylene is optionally substituted with 1 to 3 of the same or different substituents selected from the group consisting of a fluorine atom, a hydroxyl group, $C_{1-3}$ alkoxy, $-NR^{16}R^{17}$, and cyano), Q is a hydrogen atom or $NHR^{14}$, $R^{14}$ is a hydrogen atom, $C_{1-6}$ alkyl (wherein the alkyl is optionally substituted with 1 to 3 of the same or different substituents selected from the group consisting of a fluorine atom, a hydroxyl group, $C_{1-3}$ alkoxy, $-NR^{16}R^{17}$, and cyano), $C_{3-10}$ cycloalkyl (wherein the cycloalkylene is optionally substituted with 1 to 3 of the same or different substituents selected from the group consisting of a fluorine atom, a hydroxyl group, $C_{1-3}$ alkyl, $C_{1-3}$ alkoxy, $-NR^{16}R^{17}$, and cyano), or a 3- to 10-membered saturated heterocyclic group (wherein the saturated heterocyclic group is optionally substituted with 1 to 3 of the same or different substituents selected from the group consisting of a fluorine atom, a hydroxyl group, $C_{1-3}$ alkyl, $C_{1-3}$ alkoxy, $-NR^{16}R^{17}$, and cyano), and $R^{16}$ and $R^{17}$ are hydrogen atoms or $C_{1-6}$ alkyl.

An embodiment of the compound represented by formula (1) includes the following (C).

(C)

A compound or a pharmaceutically acceptable salt thereof, wherein $R^1$ is a methyl group or a fluoromethyl group, $R^2$ is a chlorine atom, cyano, or a trifluoromethyl group, X, Y, and Z each independently represent $CR^8$ or a nitrogen atom, wherein X, Y, and Z are not simultaneously $CR^8$, $R^8$ is a hydrogen atom, a fluorine atom, a chlorine atom, a bromine atom, or $C_{1-3}$ alkyl, L is a single bond or $C_{1-6}$ alkylene (wherein the alkylene is optionally substituted with 1 to 3 of the same or different substituents selected from the group consisting of a fluorine atom, a hydroxyl group, $C_{1-3}$ alkoxy, $-NR^{16}R^{17}$, and cyano), V is a single bond, $C_{3-10}$ cycloalkylene (wherein the cycloalkylene is optionally substituted with 1 to 3 of the same or different substituents selected from the group consisting of a fluorine atom, a hydroxyl group, $C_{1-3}$ alkyl, $C_{1-3}$ alkoxy, $-NR^{16}R^{17}$, and cyano), or a 3- to 10-membered divalent saturated heterocyclic group (wherein the saturated heterocyclic group is optionally substituted with 1 to 3 of the same or different substituents selected from the group consisting of a fluorine atom, a hydroxyl group, $C_{1-3}$ alkyl optionally substituted with 1 to 2 hydroxyl groups or fluorine atoms, $C_{1-3}$ alkoxy, $-NR^{16}R^{17}$, and cyano), W is a single bond or $C_{1-6}$ alkylene (wherein the alkylene is optionally substituted with 1 to 3 of the same or different substituents selected from the group consisting of a fluorine atom, a hydroxyl group, $C_{1-3}$ alkoxy, $-NR^{16}R^{17}$, and cyano), Q is a hydrogen atom or $NHR^{14}$, $R^{14}$ is a hydrogen atom or $C_{1-3}$ alkyl (wherein the alkyl is optionally substituted with 1 substituent selected from the group consisting of a fluorine atom, a hydroxyl group, and cyano), and $R^{16}$ and $R^{17}$ are hydrogen atoms or $C_{1-6}$ alkyl.

An embodiment of the compound represented by formula (1) includes the following (D).

(D)

A compound or a pharmaceutically acceptable salt thereof, wherein $R^1$ is a methyl group, $R^2$ is cyano, X, Y, and Z each independently represent $CR^8$ or a nitrogen atom, wherein X, Y, and Z are not simultaneously $CR^8$, $R^8$ is a hydrogen atom, a fluorine atom, a chlorine atom, a bromine atom, or $C_{1-3}$ alkyl, L is a single bond or $C_{1-6}$ alkylene (wherein the alkylene is optionally substituted with 1 substituent selected from the group consisting of a fluorine atom, a hydroxyl group, and cyano), V is a single bond, $C_{3-7}$ cycloalkylene (wherein the cycloalkylene is optionally substituted with 1 to 2 of the same or different substituents selected from the group consisting of a fluorine atom, a hydroxyl group, $C_{1-3}$ alkyl optionally substituted with 1 to 2 hydroxyl groups, and cyano), or a 3- to 7-membered divalent saturated heterocyclic group (wherein the saturated heterocyclic group is optionally substituted with 1 to 2 of the same or different substituents selected from the group consisting of a fluorine atom, a hydroxyl group, $C_{1-3}$ alkyl optionally substituted with 1 to 2 hydroxyl groups or fluorine atoms), W is a single bond or $C_{1-3}$ alkylene (wherein the alkylene is optionally substituted with 1 substituent selected from the group consisting of a fluorine atom, a hydroxyl group, and cyano), and Q is a hydrogen atom, $NH_2$, or NHMe.

An embodiment of the compound represented by formula (1) or (2) includes the following (E).

(E)

A compound or a pharmaceutically acceptable salt thereof, wherein

X, Y, and Z each independently represent $CR^8$ or a nitrogen atom, wherein X, Y, and Z are not simultaneously $CR^8$, $R^6$ is a hydrogen atom or a chlorine atom, L is a single bond or $C_{1-6}$ alkylene optionally substituted with 1 hydroxyl group or fluorine atom, V is a single bond, $C_{3-7}$ cycloalkylene (wherein the cycloalkylene is optionally substituted with 1 substituent selected from the group consisting of a hydroxyl group and $C_{1-3}$ alkyl), or a 3- to 7-membered divalent saturated heterocyclic group (wherein the saturated heterocyclic group is optionally substituted with 1 substituent selected from the group consisting of a fluorine atom, cyano, a hydroxyl group, and $C_{1-3}$ alkyl optionally substituted with 1 to 2 hydroxyl groups or fluorine atoms), W is a single bond or $C_{1-3}$ alkylene optionally substituted with 1 hydroxyl group, and Q is a hydrogen atom, $NH_2$, or NHMe.

An embodiment of the compound represented by formula (3) includes the following (F).

(F)

A compound or a pharmaceutically acceptable salt thereof, wherein $R^{8a}$ and $R^{8b}$ are each independently a hydrogen atom or a chlorine atom, L is a single bond or $C_{1-3}$ alkylene optionally substituted with 1 hydroxyl group, V is a single bond, $C_{3-7}$ cycloalkylene (wherein the cycloalkylene is optionally substituted with 1 substituent selected from the group consisting of a hydroxyl group and $C_{1-3}$ alkyl), or a 3- to 7-membered divalent saturated heterocyclic group (wherein the saturated heterocyclic group is optionally substituted with 1 substituent selected from the group consisting of a fluorine atom, cyano, a hydroxyl group, and $C_{1-3}$ alkyl), W is a single bond or $C_{1-3}$ alkylene optionally substituted with 1 hydroxyl group, and Q is a hydrogen atom or $NH_2$.

An embodiment of the compound represented by formula (3) includes the following (G).

(G)

A compound or a pharmaceutically acceptable salt thereof, wherein $R^{8a}$ and $R^{8b}$ are each independently a hydrogen atom or a chlorine atom, L is $C_{1-3}$ alkylene optionally substituted with 1 hydroxyl group, V is a single bond, W is a single bond or $C_{1-3}$ alkylene optionally substituted with 1 hydroxyl group, and Q is $NH_2$.

An embodiment of the compound represented by formula (3) includes the following (H).

(H)

A compound or a pharmaceutically acceptable salt thereof, wherein $R^{8a}$ and $R^{8b}$ are each independently a hydrogen atom, L is $C_{1-3}$ alkylene optionally substituted with 1 hydroxyl group, V is $C_{3-7}$ cycloalkylene, W is $C_{1-3}$ alkylene optionally substituted with 1 hydroxyl group, and Q is $NH_2$.

An embodiment of the compound represented by formula (4) includes the following (I).

(I)
A compound or a pharmaceutically acceptable salt thereof, wherein
$R^{8b}$ and $R^{8c}$ are hydrogen atoms,
L is a single bond or $C_{1-3}$ alkylene optionally substituted with 1 hydroxyl group or a fluorine atom,
V is a single bond, $C_{3-7}$ cycloalkylene (wherein the cycloalkylene is optionally substituted with 1 substituent selected from the group consisting of a hydroxyl group and $C_{1-3}$ alkyl), or a 3- to 7-membered divalent saturated heterocyclic group (wherein the saturated heterocyclic group is optionally substituted with 1 substituent selected from the group consisting of a fluorine atom, cyano, a hydroxyl group, and C1-j alkyl optionally substituted with 1 to 3 hydroxyl groups or fluorine atoms),
W is a single bond or $C_{1-3}$ alkylene optionally substituted with 1 hydroxyl group, and
Q is a hydrogen atom, $NH_2$, or NHMe.

An embodiment of the compound represented by formula (4) includes the following (J).

(J)
A compound or a pharmaceutically acceptable salt thereof, wherein
$R^{8b}$ and $R^{8c}$ are each independently a hydrogen atom,
L is $C_{1-3}$ alkylene optionally substituted with 1 hydroxyl group or a fluorine atom,
V is a 3- to 7-membered divalent saturated heterocyclic group (wherein the saturated heterocyclic group is optionally substituted with 1 substituent selected from the group consisting of a fluorine atom, cyano, a hydroxyl group, and $C_{1-3}$ alkyl optionally substituted with 1 to 3 hydroxyl groups and fluorine atoms),
W is a single bond, and
Q is a hydrogen atom.

An embodiment of the compound represented by formula (4) includes the following (K).

(K)
A compound or a pharmaceutically acceptable salt thereof, wherein
$R^{8b}$ and $R^{8c}$ are each independently a hydrogen atom,
L is $C_{1-3}$ alkylene optionally substituted with 1 hydroxyl group or fluorine atom,
V is $C_{3-7}$ cycloalkylene (wherein the cycloalkylene is optionally substituted with 1 substituent selected from the group consisting of a hydroxyl group and $C_{1-3}$ alkyl),
W is $C_{1-3}$ alkylene optionally substituted with 1 hydroxyl group, and
Q is $NH_2$.

An embodiment of the compound represented by formula (4) includes the following (L).

(L)
A compound or a pharmaceutically acceptable salt thereof, wherein
$R^{8b}$ and $R^{8c}$ are each independently a hydrogen atom,
L is a single bond,
V is $C_{3-7}$ cycloalkylene (wherein the cycloalkylene is optionally substituted with 1 substituent selected from the group consisting of a hydroxyl group and $C_{1-3}$ alkyl),
W is a single bond, and
Q is $NH_2$ or NHMe.

An embodiment of the compound represented by formula (4) includes the following (M).

(M)
A compound or a pharmaceutically acceptable salt thereof, wherein
$R^{8b}$ and $R^{8c}$ are each independently a hydrogen atom,
L is $C_{1-3}$ alkylene optionally substituted with 1 hydroxyl group or fluorine atom,
V is a single bond,
W is a single bond or $C_{1-3}$ alkylene optionally substituted with 1 hydroxyl group, and
Q is $NH_2$ or NHMe.

An embodiment of the compound represented by formula (5) includes the following (N).

(N)
A compound or a pharmaceutically acceptable salt thereof, wherein
$R^{8a}$ and $R^{8c}$ are each independently a hydrogen atom,
L is a single bond or $C_{1-3}$ alkylene optionally substituted with 1 hydroxyl group,
V is a single bond, $C_{3-7}$ cycloalkylene (wherein the cycloalkylene is optionally substituted with 1 substituent selected from the group consisting of a hydroxyl group and $C_{1-3}$ alkyl), or a 3- to 7-membered divalent saturated heterocyclic group (wherein the saturated heterocyclic group is optionally substituted with 1 substituent selected from the group consisting of a fluorine atom, cyano, a hydroxyl group, and $C_{1-3}$ alkyl optionally substituted with 1 to 2 hydroxyl groups),
W is a single bond or $C_{1-3}$ alkylene optionally substituted with 1 hydroxyl group, and
Q is a hydrogen atom or $NH_2$.

An embodiment of the compound represented by formula (5) includes the following (O).

(O)
A compound or a pharmaceutically acceptable salt thereof, wherein
$R^{8a}$ and $R^{8c}$ are each independently a hydrogen atom, L is $C_{1-3}$ alkylene optionally substituted with 1 hydroxyl group,
V is a 3- to 7-membered divalent saturated heterocyclic group (wherein the saturated heterocyclic group is optionally substituted with 1 substituent selected from the group consisting of a hydroxyl group and $C_{1-3}$ alkyl optionally substituted with 1 hydroxyl group),
W is a single bond, and
Q is a hydrogen atom.

An embodiment of the compound represented by formula (5) includes the following (P).

(P)
A compound or a pharmaceutically acceptable salt thereof, wherein
$R^{8a}$ and $R^{8c}$ are each independently a hydrogen atom,
L is $C_{1-3}$ alkylene optionally substituted with 1 hydroxyl group,
V is a single bond,
W is a single bond or $C_{1-3}$ alkylene optionally substituted with 1 hydroxyl group, and
Q is $NH_2$.

An embodiment of the compound represented by formula (5) includes the following (Q).

(Q)
A compound or a pharmaceutically acceptable salt thereof, wherein
$R^{8a}$ are each independently a hydrogen atom,
L is $C_{1-3}$ alkylene optionally substituted with 1 hydroxyl group,
V is $C_{3-7}$ cycloalkylene,
W is $C_{1-3}$ alkylene optionally substituted with 1 hydroxyl group, and
Q is $NH_2$.

An embodiment of the compound represented by formula (6) includes the following (R).

(R)

A compound or a pharmaceutically acceptable salt thereof, wherein
$R^{8a}$ is a hydrogen atom,
L is $C_{1-3}$ alkylene,
V is a single bond or $C_{3-7}$ cycloalkylene,
W is a single bond or $C_{1-3}$ alkylene, and
Q is $NH_2$.

Another embodiment of the invention includes 5-({5-[2-(3-aminopropoxy)-4-methoxypyridin-3-yl]-1H-pyrazol-3-yl}amino)pyrazine-2-carbonitrile hydrochloride, which is a crystalline form (form I) having an X ray powder diffraction pattern having a characteristic peak at at least 7.2°±0.2° in terms of 2θ.

Another embodiment of the invention includes 5-({5-[2-(3-aminopropoxy)-4-methoxypyridin-3-yl]-1H-pyrazol-3-yl}amino)pyrazine-2-carbonitrile hydrochloride, which is a crystalline form (form I) having an X ray powder diffraction pattern having a characteristic peak at at least 8.8°±0.2° in terms of 2θ

Another embodiment of the invention includes 5-({5-[2-(3-aminopropoxy)-4-methoxypyridin-3-yl]-1H-pyrazol-3-yl}amino)pyrazine-2-carbonitrile hydrochloride, which is a crystalline form (form I) having an X ray powder diffraction pattern having characteristic peaks at at least 7.2°±0.2θ and 8.8°±0.2° in terms of 2θ.

Another embodiment of the invention includes 5-({5-[2-(3-aminopropoxy)-4-methoxypyridin-3-yl]-1H-pyrazol-3-yl}amino)pyrazine-2-carbonitrile hydrochloride of a crystalline form of form I, having an X ray powder diffraction pattern having characteristic peaks at 7.2°±0.2°, 8.8°±0.2°, 9.8°±0.2°, 10.2°±0.2°, 10.7°±0.2°, 16.7°±0.2°, 18.5°±0.2°, 26.2°±0.2°, 27.0°±0.2°, and 26.4°±0.2° in terms of 2θ. The crystal is identified by 4 or 5 selected from these 10 peaks.

Another embodiment of the invention includes 5-({5-[2-(3-aminopropoxy)-4-methoxypyridin-3-yl]-1H-pyrazol-3-yl}amino)pyrazine-2-carbonitrile phosphate, which is a crystalline form (form II) having an X ray powder diffraction pattern having a characteristic peak at at least 6.8°±0.2° in terms of 2θ.

Another embodiment of the invention includes 5-({5-[2-(3-aminopropoxy)-4-methoxypyridin-3-yl]-1H-pyrazol-3-yl}amino)pyrazine-2-carbonitrile phosphate, which is a crystalline form (form II) having an X ray powder diffraction pattern having a characteristic peak at at least 13.0°±0.2° in terms of 2θ.

Another embodiment of the invention includes 5-({5-[2-(3-aminopropoxy)-4-methoxypyridin-3-yl]-1H-pyrazol-3-yl}amino)pyrazine-2-carbonitrile phosphate, which is a crystalline form (form II) having an X ray powder diffraction pattern having characteristic peaks at at least 6.8°±0.2° and 13.0°±0.2° in terms of 29.

Another embodiment of the invention includes 5-({5-[2-(3-aminopropoxy)-4-methoxypyridin-3-yl]-1H-pyrazol-3-yl}amino)pyrazine-2-carbonitrile phosphate of a crystalline form of form II, having an X ray powder diffraction pattern having characteristic peaks at 6.8°±0.2°, 7.5°±0.2°, 11.7°±0.2°, 11.9°±0.2°, 13.0°±0.2°, 16.4°±0.2°, 19.3°±0.2°, 20.4°±0.2°, 22.7°±0.2°, and 24.3°±0.2° in terms of 2θ. The crystal is identified by having 4 or 5 selected from these 10 peaks.

Another embodiment of the invention includes 5-({5-[2-(3-aminopropoxy)-4-methoxypyridin-3-yl]-1H-pyrazol-3-yl}amino)pyrazine-2-carbonitrile tosylate, which is a crystalline form (form III) having an X ray powder diffraction pattern having a characteristic peak at at least 6.0°±0.2° in terms of 2θ.

Another embodiment of the invention includes 5-({5-[2-(3-aminopropoxy)-4-methoxypyridin-3-yl]-1H-pyrazol-3-yl}amino)pyrazine-2-carbonitrile tosylate, which is a crystalline form (form III) having an X ray powder diffraction pattern having a characteristic peak at at least 17.0°±0.2° in terms of 2θ.

Another embodiment of the invention includes 5-({5-[2-(3-aminopropoxy)-4-methoxypyridin-3-yl]-1H-pyrazol-3-yl}amino)pyrazine-2-carbonitrile tosylate, which is a crystalline form (form III) having an X ray powder diffraction pattern having characteristic peaks at at least 6.0°±0.2° and 17.0°±0.2° in terms of 2θ.

Another embodiment of the invention includes 5-({5-[2-(3-aminopropoxy)-4-methoxypyridin-3-yl]-1H-pyrazol-3-yl}amino)pyrazine-2-carbonitrile tosylate of a crystalline form of form III, having an X ray powder diffraction pattern having characteristic peaks at 6.0°±0.2°, 9.0°±0.2°, 12.1°±0.2°, 14.4°±0.2°, 16.2°±0.2°, 17.0°±0.2°, 22.8°±0.2°, and 26.3°±0.2° in terms of 2θ. The crystal is identified by having 4 or 5 selected from these 10 peaks.

Another embodiment of the invention includes 5-({5-[2-(3-aminopropoxy)-4-methoxypyridin-3-yl]-1H-pyrazol-3-yl}amino)pyrazine-2-carbonitrile, which is a crystalline form (form IV) having an X ray powder diffraction pattern having a characteristic peak at at least 9.3°±0.2° in terms of 2θ.

Another embodiment of the invention includes 5-({5-[2-(3-aminopropoxy)-4-methoxypyridin-3-yl]-1H-pyrazol-3-yl}amino)pyrazine-2-carbonitrile, which is a crystalline form (form IV) having an X ray powder diffraction pattern having a characteristic peak at at least 10.2°±0.2° in terms of 2θ.

Another embodiment of the invention includes 5-({5-[2-(3-aminopropoxy)-4-methoxypyridin-3-yl]-1H-pyrazol-3-yl}amino)pyrazine-2-carbonitrile, which is a crystalline form (form IV) having an X ray powder diffraction pattern having characteristic peaks at at least 9.3°±0.2° and 10.2°±0.2° in terms of 2θ.

Another embodiment of the invention includes 5-({5-[2-(3-aminopropoxy)-4-methoxypyridin-3-yl]-1H-pyrazol-3-yl}amino)pyrazine-2-carbonitrile of a crystalline form of form IV, having an X ray powder diffraction pattern having characteristic peaks at 9.3°±0.2°, 10.2°±0.2°, 10.7°±0.2°, 13.6°±0.2°, 16.7°±0.2°, 17.1°±0.2°, 17.8°±0.2°, 18.6°±0.2°, 26.1°±0.2°, and 26.4° 0.2° in terms of 2θ. The crystal is identified by having 4 or 5 selected from these 10 peaks.

Another embodiment of the invention includes 5-({5-[2-(3-aminopropoxy)-4-methoxypyridin-3-yl]-1H-pyrazol-3-yl}amino)pyrazine-2-carbonitrile, which is a crystalline form (form V) having an X ray powder diffraction pattern having a characteristic peak at at least 7.9°±0.2° in terms of 2θ.

Another embodiment of the invention includes 5-({5-[2-(3-aminopropoxy)-4-methoxypyridin-3-yl]-1H-pyrazol-3-yl}amino)pyrazine-2-carbonitrile, which is a crystalline form (form V) having an X ray powder diffraction pattern having a characteristic peak at at least 8.7°±0.2° in terms of 2θ.

Another embodiment of the invention includes 5-({5-[2-(3-aminopropoxy)-4-methoxypyridin-3-yl]-1H-pyrazol-3-yl}amino)pyrazine-2-carbonitrile, which is a crystalline form (form V) having an X ray powder diffraction pattern having characteristic peaks at at least 7.9°±0.2° and 8.7°±0.2° in terms of 2θ.

Another embodiment of the invention includes 5-({5-[2-(3-aminopropoxy)-4-methoxypyridin-3-yl]-1H-pyrazol-3-yl}amino)pyrazine-2-carbonitrile of a crystalline form of form V, having an X ray powder diffraction pattern having characteristic peaks at 7.9°±0.2°, 8.7°±0.2°, 12.2°±0.2°, 13.1°±0.2°, 15.9°±0.2°, 17.6°±0.2°, 19.9°±0.2°, 21.9°±0.2°, 22.8°±0.2°, and 26.6°±0.2° in terms of 2θ. The crystal is identified by having 4 or 5 selected from these 10 peaks.

Another embodiment of the invention includes 5-({5-[2-(3-aminopropoxy)-4-methoxypyridin-3-yl]-1H-pyrazol-3-yl}amino)pyrazine-2-carbonitrile, which is a crystalline form (form VI) having an X ray powder diffraction pattern having a characteristic peak at at least 5.3°±0.2° in terms of 2θ.

Another embodiment of the invention includes 5-({5-[2-(3-aminopropoxy)-4-methoxypyridin-3-yl]-1H-pyrazol-3-yl}amino)pyrazine-2-carbonitrile, which is a crystalline form (form VI) having an X ray powder diffraction pattern having a characteristic peak at at least 5.7°±0.2° in terms of 2θ.

Another embodiment of the invention includes 5-({5-[2-(3-aminopropoxy)-4-methoxypyridin-3-yl]-1H-pyrazol-3-yl}amino)pyrazine-2-carbonitrile, which is a crystalline form (form VI) having an X ray powder diffraction pattern having characteristic peaks at at least 5.3°±0.2° and 5.7°±0.2° in terms of 2θ.

Another embodiment of the invention includes 5-({5-[2-(3-aminopropoxy)-4-methoxypyridin-3-yl]-1H-pyrazol-3-yl}amino)pyrazine-2-carbonitrile of a crystalline form of form VI, having an X ray powder diffraction pattern having characteristic peaks at 5.3°±0.2°, 5.7°±0.2°, 7.0°±0.2°, 7.3°±0.2°, 7.8°±0.2°, 8.4°±0.2°, 9.3°±0.2°, 10.5°±0.2°, 11.5°±0.2°, and 14.1°±0.2° in terms of 2θ. The crystal is identified by having 4 or 5 selected from these 10 peaks.

When the compound of the present disclosure is administered, the amount used varies depending on the symptom, age, dosing method, or the like. For example for intravenous administration, an effect is expected by administering 0.01 mg (preferably 0.1 mg) as a lower limit and 1000 mg (preferably 100 mg) as an upper limit, once or several times daily depending on the symptoms to adults. Examples of dosing schedules include a single dose administration, once daily administration for 3 consecutive days, twice daily administration for 7 consecutive days, and the like. Each dosing method described above can also be repeated with an interval of about 1 day to about 60 days.

The compound of the present disclosure can be administered through parenteral administration or oral administration, preferably through a parenteral method and more preferably through an intravenous injection. The compound of the present disclosure is preferably formulated as a pharmaceutically acceptable carrier such as a liposome and administered.

A liposome encapsulating the compound of the present disclosure comprises at least one type of phospholipid. Examples of phospholipid include phosphatidylcholine, phosphatidylglycerol, phosphatidic acid, phosphatidylethanolamine, phosphatidylserine, phosphatidylinositol, sphingomyelin, and the like.

A fatty acid residue in a phospholipid is not particularly limited. Examples thereof include saturated or unsaturated fatty acid residues with 14 to 18 carbons. Specific examples thereof include myristic acid, palmitic acid, stearic acid, oleic acid, linoleic acid, and other fatty acid derived acyl groups. Egg yolk lecithins, soybean lecithins, and other naturally derived phospholipids, and hydrogenated egg yolk lecithin, hydrogenated soybean lecithin (also known as hydrogenated soybean phospholipid or hydrogenated soybean phosphatidylcholine), and the like from hydrogenating an unsaturated fatty acid residue thereof can also be used.

Although the amount (molar fraction) of phospholipid added with respect to the entire liposomal membrane components is not particularly limited, the amount is preferably 30 to 80% and more preferably 40 to 70%.

A liposome encapsulating the compound of the present disclosure can comprise sterols. Examples of sterols include cholesterol, β-sitosterol, stigmasterol, campesterol, brassicasterol, ergosterol, fucosterol, and the like. Preferred sterols include cholesterol. Although the amount (molar fraction) of sterols added with respect to the entire liposomal membrane components is not particularly limited, the amount is preferably 0 to 60%, more preferably 10 to 50%, and still more preferably 30 to 50%.

A liposome encapsulating the compound of the invention can comprise a polymer-modified lipid to improve residency in vivo. Although the amount (molar fraction) of polymer-modified lipid added with respect to the entire liposomal membrane components is not particularly limited, the amount is preferably 0 to 20%, and more preferably 1 to 10%. The polymer moiety of a polymer-modified lipid is preferably a hydrophilic polymer, and more preferably a hydrophilic polymer having an end that is not bound to a lipid which is alkoxylated. Specific examples of a polymer moiety of a polymer-modified lipid include, but are not particularly limited to, polyethylene glycol, polypropylene glycol, polyvinyl alcohol, polyvinylpyrrolidone, methoxypolyethylene glycol, methoxypolypropylene glycol, methoxypolyvinyl alcohol, methoxypolyvinylpyrrolidone, ethoxypolyethylene glycol, ethoxypolypropylene glycol, ethoxypolyvinyl alcohol, ethoxypolyvinylpyrrolidone, propoxypolyethylene glycol, propoxypolypropylene glycol, propoxypolyvinyl alcohol, and propoxypolyvinylpyrrolidone. Preferred examples of a polymer moiety of a polymer-modified lipid include polyethylene glycol, methoxypolyethylene glycol, methoxypolypropylene glycol, ethoxypolyethylene glycol, ethoxypolypropylene glycol, propoxypolyethylene glycol, and propoxypolypropylene glycol. More preferred examples of a polymer moiety of a polymer-modified lipid include polyethylene glycol, methoxypolyethylene glycol, ethoxypolyethylene glycol, ethoxypolypropylene glycol, and propoxypolyethylene glycol. Still more preferred examples of a polymer moiety of a polymer-modified lipid include polyethylene glycol and methoxypolyethylene glycol. The most preferred examples of a polymer moiety of a polymer-modified lipid include methoxypolyethylene glycol. The molecular weight of the polymer moiety of a polymer-modified lipid is not particularly limited, but is, for example, 100 to 10000 daltons, preferably 1000 to 7000 daltons, more preferably 1500 to 5000 daltons, and most preferably 1500 to 3000 daltons.

The specific lipid moiety of a polymer-modified lipid is not particularly limited. Examples thereof include phosphatidylethanolamine and diacylglycerol. The lipid moiety of a polymer-modified lipid is preferably phosphatidylethanolamine having a saturated or unsaturated fatty acid residue with 14 to 18 carbons or diacylglycerol having a saturated or unsaturated fatty acid residue with 14 to 18 carbons, more preferably phosphatidylethanolamine having a saturated fatty acid residue with 14 to 18 carbons or diacylglycerol having a saturated fatty acid residue with 14 to 18 carbons, still more preferably phosphatidylethanolamine with a palmitoyl group or stearoyl group or diacylglycerol with a palmitoyl group or stearoyl group. The lipid moiety of a polymer-modified lipid is most preferably distearoylphosphatidylethanolamine.

A liposome encapsulating the compound of the present disclosure can comprise a pharmaceutically acceptable additive. Examples of additives include inorganic acids, inorganic acid salts, organic acids, organic acid salts, saccharides, buffer, antioxidants, and polymers.

Examples of the inorganic acids include phosphoric acid, hydrochloric acid, and sulfuric acid.

Examples of the inorganic acid salts include sodium hydrogen phosphate, sodium chloride, ammonium sulfate, and magnesium sulfate.

Examples of the organic acids include citric acid, acetic acid, succinic acid, and tartaric acid.

Examples of the organic acid salts include sodium citrate, sodium acetate, disodium succinate, and sodium tartrate.

Examples of the saccharides include glucose, sucrose, mannitol, sorbitol, and trehalose.

Examples of the buffer include L-arginine, L-histidine, trometamol (trishydroxymethylaminomethane, Tris), and salts thereof.

Examples of the antioxidants include sodium sulfite, L-cysteine, sodium thioglycolate, sodium thiosulfate, ascorbic acid, and tocopherol.

Examples of the polymers include polyvinyl alcohol, polyvinylpyrrolidone, carboxyvinyl polymer, and carboxymethylcellulose sodium.

The manufacturing method of the compound of the present disclosure represented by formula (1) is exemplified hereinafter with examples, but the manufacturing method of the compound of the present disclosure is not limited thereto. A compound used in the following manufacturing method may form a salt, as long as the reaction is not affected.

The compound of the present disclosure can be manufactured using a known compound as the starting material by, for example, Manufacturing Method A, B, C, D, E, F, G, H, I, J, K, L, M, N, O, P, Q, or R described below, a method in accordance therewith, or an appropriate combination of synthetic methods that are well known to those skilled in the art. The compound of the present disclosure other than formula (a2) can also be manufactured by a method in accordance therewith or an appropriate combination of synthetic methods that are well known to those skilled in the art.

Manufacturing Method A

The compound of the present disclosure represented by formula (a2) can be manufactured by, for example, the following method.

[Chemical Formula 18]

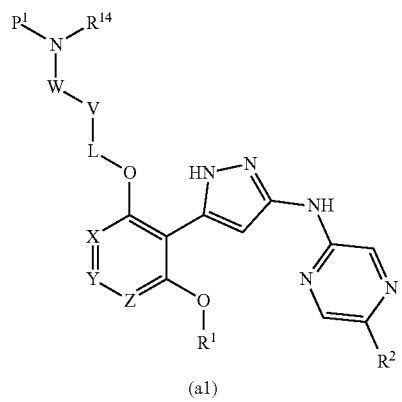

(a1)

-continued

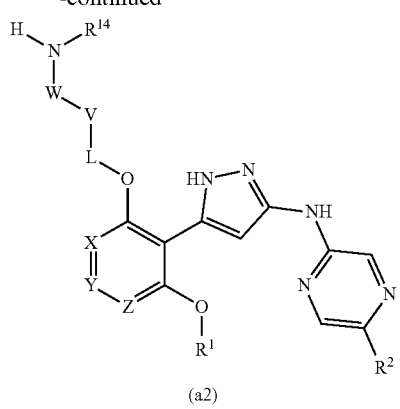

(a2)

wherein $R^1$, $R^2$, $R^{14}$, X, Y, Z, L, V, and W are defined the same as the description in item 1, and $P^1$ refers to an amino protecting group. Examples of $P^1$ include the amino protecting groups described in Protective Groups in Organic Synthesis (authors: Theodora W. Greene, Peter G. M. Wuts, publisher: John Wiley & Sons, Inc., 1999) and the like.

[Step 1]

Compound (a2) can be manufactured by removing protecting group $P^1$ of compound (a1) obtained by the following manufacturing method. This step can be performed in accordance with, for example, the method described in Protective Groups in Organic Synthesis (authors: Theodora W. Greene, Peter G. M. Wuts, publisher: John Wiley & Sons, Inc., 1999) or the like.

Manufacturing Method B

The compound of the present disclosure represented by formula (a1) can be manufactured, for example, by the following method.

[Chemical Formula 19]

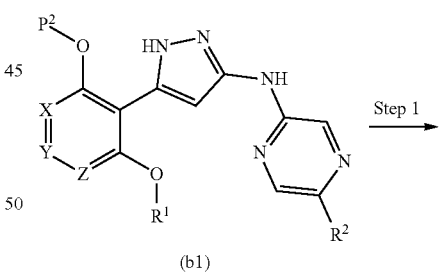

(b1)

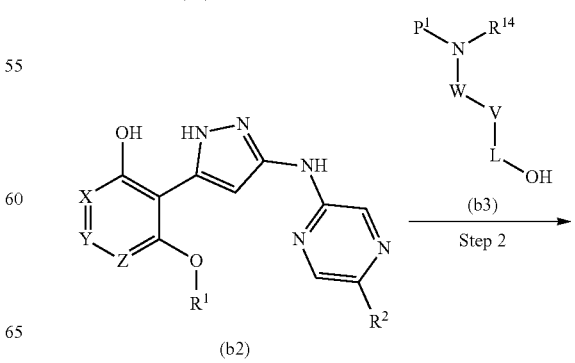

(b2)

-continued

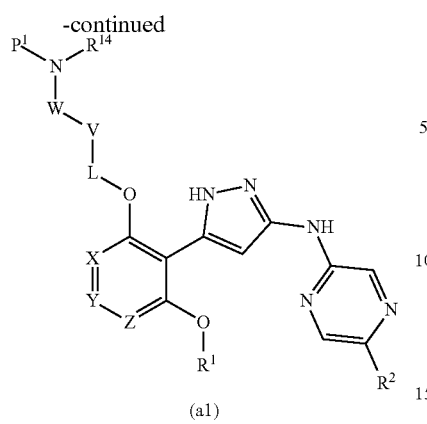

(a1)

wherein $R^1$, $R^2$, $R^{14}$, X, Y, Z, L, V, and W are defined the same as the description in item 1, $P^1$ refers to an amino protecting group, and $P^2$ refers to a phenol protecting group. Examples of $P^1$ include the amino protecting groups described in Protective Groups in Organic Synthesis (authors: Theodora W. Greene, Peter G. M. Wuts, publisher: John Wiley & Sons, Inc., 1999) and the like, and examples of $P^2$ include the phenol protecting groups described in Protective Groups in Organic Synthesis (authors: Theodora W. Greene, Peter G. M. Wuts, publisher: John Wiley & Sons, Inc., 1999) and the like.

Compound (b3) is available as a commercial product.

[Step 1]

Compound (b2) can be manufactured by removing the protecting group $P^2$ of compound (b1) obtained by the following manufacturing method. This step can be performed in accordance with, for example, the method described in Protective Groups in Organic Synthesis (authors: Theodora W. Greene, Peter G. M. Wuts, publisher: John Wiley & Sons, Inc., 1999) or the like.

[Step 2]

Compound (a1) can be manufactured by a Mitsunobu reaction between compound (b2) and compound (b3) in a suitable solvent in the presence of a Mitsunobu reaction.

Examples of Mitsunobu reagents include diethyl azodicarboxylate (DEAD), diisopropyl azodicarboxylate (DIAD), N,N,N',N'-tetraisopropyl azodicarboxamide (TIPA), 1,1'-(azodicarbonyl)dipiperidine (ADDP), N,N,N',N'-tetramethylazodicarboxamide (TMAD), triphenylphosphine, tributylphosphine, and the like. Cyanomethylene trimethylphosphorane (CMMP) and cyanomethylene tributylphosphorane (CMBP) can also be used.

A solvent is not particularly limited as long as it is a solvent that does not react under the reaction conditions of this step. Examples thereof include ether solvents such as diethyl ether, diisopropyl ether, tetrahydrofuran, methylcyclopentyl ether, anisole, and 1,4-dioxane; aromatic hydrocarbon solvents such as benzene, toluene, chlorobenzene, and xylene; ester solvents such as ethyl acetate and methyl acetate; aprotic solvents such as N,N-dimethylformamide, N,N-dimethylacetamide, N-methyl-2-pyrrolidinone, 1,3-dimethyl-2-imidazolidinone, and dimethyl sulfoxide; mixtures thereof, and the like. Preferred examples of solvents include toluene, benzene, THF, 1,4-dioxane, mixtures thereof, and the like.

The reaction time is generally 5 minutes to 72 hours, and preferably 12 hours to 24 hours.

The reaction temperature is generally 0° C. to 100° C. and preferably 0° C. to 50° C.

Manufacturing Method C

The compound of the present disclosure represented by formula (b1) can be manufactured, for example, by the following method.

[Chemical Formula 20]

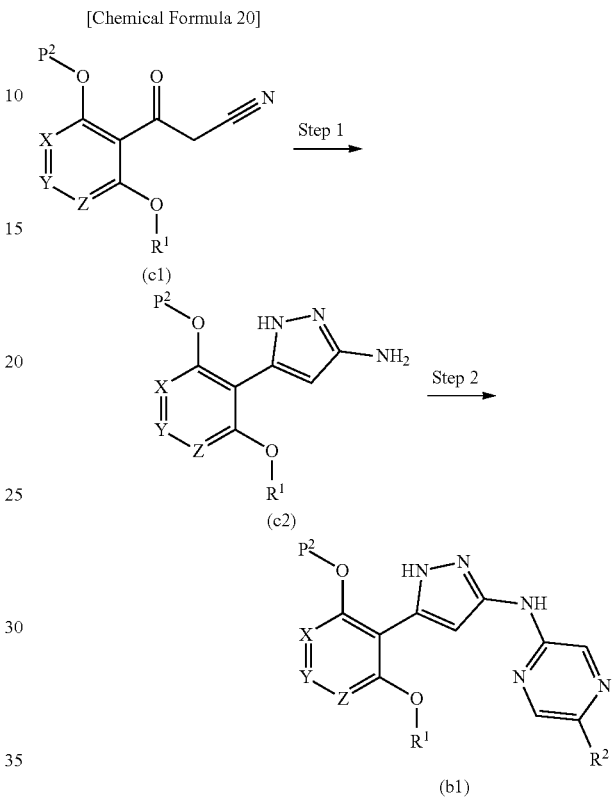

wherein $R^1$, $R^2$, X, Y, and Z are defined the same as the description in item 1, and $P^2$ refers to a phenol protecting group. Examples of $P^2$ include the phenol protecting groups described in Protective Groups in Organic Synthesis (authors: Theodora W. Greene, Peter G. M. Wuts, publisher: John Wiley & Sons, Inc., 1999) and the like.

[Step 1]

Compound (c2) can be manufactured by reacting compound (c1) with hydrazine monohydrate in the presence or absence of a suitable acid in a suitable solvent.

Examples of acids include acetic acid, propionic acid, p-toluenesulfonic acid, methanesulfonic acid, ethanesulfonic acid, hydrochloric acid, sulfuric acid, camphorsulfonic acid, and the like. An acid is preferably acetic acid, p-toluenesulfonic acid, or the like.

A solvent is not particularly limited as long as it is a solvent that does not react under the reaction conditions of this step. Examples thereof include ether solvents such as diethyl ether, diisopropyl ether, tetrahydrofuran, methylcyclopentyl ether, anisole, and 1,4-dioxane; aromatic hydrocarbon solvents such as benzene, toluene, chlorobenzene, and xylene; ester solvents such as ethyl acetate and methyl acetate; aprotic solvents such as N,N-dimethylformamide, N,N-dimethylacetamide, N-methyl-2-pyrrolidinone, 1,3-dimethyl-2-imidazolidinone, and dimethyl sulfoxide; alcohol solvents such as methanol, ethanol, isopropyl alcohol, and butanol; and mixtures thereof. Preferred solvents include 1,4-dioxane, toluene, ethanol, and the like.

The reaction time is generally 5 minutes to 72 hours, and preferably 12 hours to 24 hours.

The reaction temperature is generally 0° C. to 200° C., and preferably 50° C. to 100° C.

[Step 2]

Compound (b1) can be manufactured by reacting compound (c2) with a 5-chloropyrazine derivative in the presence of a suitable base in a suitable solvent. Compound (b1) can also be manufactured by reacting compound (c2) with a 5-chloropyrazine derivative in the presence of a suitable palladium catalyst, ligand, and base in a suitable solvent.

Examples of the base include organic bases such as triethylamine, diisopropylethylamine, tributylamine, 1,5-diazabicyclo[4.3.0]non-5-ene (DBN), 1,8-diazabicyclo[5.4.0]undec-7-ene (DBU), pyridine, dimethylaminopyridine, picoline, N-methylmorpholine (NMM), and N-ethylmorpholine, and inorganic bases such as sodium bicarbonate, potassium bicarbonate, sodium carbonate, potassium carbonate, cesium carbonate, sodium hydroxide, and potassium hydroxide. Preferred examples of bases include triethylamine, diisopropylethylamine, N-ethylmorpholine, potassium carbonate, cesium carbonate, and the like.

Examples of palladium catalysts include salts of palladium chloride or palladium acetate, zerovalent palladium complexes such as tris(dibenzylideneacetone)dipalladium (0) chloroform adduct, and the like.

Examples of ligands include 4,5-bis(diphenylphosphino)-9,9-dimethylxanthene (xantphos), 2,2'-bis(diphenylphosphino)-1,1'-binaphthyl (BINAP), 2-dicyclohexylphosphino-2',6'-dimethoxybiphenyl (SPhos), 2-dicyclohexylphosphino-2',4',6'-triisopropylbiphenyl (XPhos), and other phosphine ligands. Preferred examples of ligands include 4,5-bis(diphenylphosphino)-9,9-dimethylxanthene (xantphos).

A solvent is not particularly limited as long as it is a solvent that does not react under the reaction conditions of this step. Examples thereof include ether solvents such as diethyl ether, diisopropyl ether, tetrahydrofuran, methylcyclopentyl ether, anisole, and 1,4-dioxane; aromatic hydrocarbon solvents such as benzene, toluene, chlorobenzene, and xylene; ester solvents such as ethyl acetate and methyl acetate; aprotic solvents such as N,N-dimethylformamide, N,N-dimethylacetamide, N-methyl-2-pyrrolidinone, 1,3-dimethyl-2-imidazolidinone, and dimethyl sulfoxide; and mixtures thereof. Preferred examples of solvents include tetrahydrofuran, 1,4-dioxane, toluene, dimethyl sulfoxide, and the like.

The reaction time is generally 5 minutes to 48 hours, and preferably 1 hour to 6 hours.

The reaction temperature is generally 0° C. to 200° C., and preferably 50° C. to 100° C.

Manufacturing Method D

The compound of the present disclosure represented by formula (c1) can be manufactured, for example, by the following method.

[Chemical Formula 21]

wherein $R^1$, X, Y, and Z are defined the same as the description in item 1, and $P^2$ refers to a phenol protecting group. Examples of $P^2$ include the phenol protecting groups described in Protective Groups in Organic Synthesis (authors: Theodora W. Greene, Peter G. M. Wuts, publisher: John Wiley & Sons, Inc., 1999) and the like.

[Step 1]

Compound (c1) can be manufactured by reacting compound (d1) with acetonitrile in the presence of a suitable base in a suitable solvent.

An inorganic base can be used as the base. Examples of the inorganic base include hydrides such as sodium hydride, halogenated alkali such as potassium fluoride, alkali hydroxides such as sodium hydroxide and potassium hydroxide, alkali carbonates such as sodium carbonate, potassium carbonate, cesium carbonate, and sodium bicarbonate, alkali alkoxides such as sodium ethoxide, sodium tert-butoxide, and potassium tert-butoxide, and alkali metals such as n-butyllithium, methyllithium, and isopropylmagnesium bromide. Preferred examples of bases include sodium ethoxide, sodium tert-butoxide, potassium tert-butoxide, n-butyllithium, and the like.

A solvent is not particularly limited as long as it is a solvent that does not react under the reaction conditions of this step. Examples thereof include ether solvents such as diethyl ether, diisopropyl ether, tetrahydrofuran, methylcyclopentyl ether, anisole, and 1,4-dioxane; aromatic hydrocarbon solvents such as benzene, toluene, chlorobenzene, and xylene; ester solvents such as ethyl acetate and methyl acetate; aprotic solvents such as N,N-dimethylformamide, N,N-dimethylacetamide, N-methyl-2-pyrrolidinone, 1,3-dimethyl-2-imidazolidinone, and dimethyl sulfoxide; alcohol solvents such as methanol, ethanol, isopropyl alcohol, and butanol; and mixtures thereof. Preferred solvents include tetrahydrofuran, toluene, and the like.

The reaction time is generally 5 minutes to 72 hours, and preferably 12 hours to 24 hours.

The reaction temperature is generally 0° C. to 200° C., and preferably 50° C. to 100° C.

Manufacturing Method E

The compound of the present disclosure represented by formula (b1) can be manufactured, for example, by the following method.

[Chemical Formula 22]

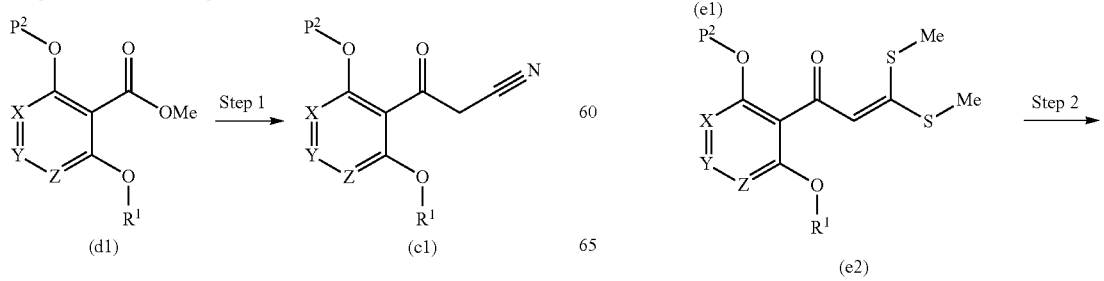

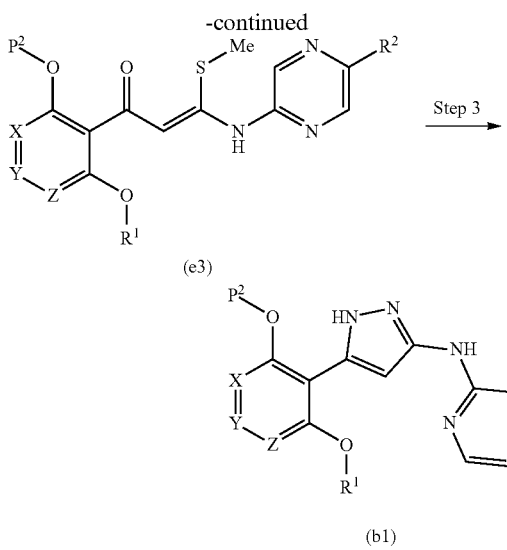

(e3)

(b1)

wherein $R^1$, $R^2$, X, Y, and Z are defined the same as the description in item 1, and $P^2$ refers to a phenol protecting group. Examples of $P^2$ include the phenol protecting groups described in Protective Groups in Organic Synthesis (authors: Theodora W. Greene, Peter G. M. Wuts, publisher: John Wiley & Sons, Inc., 1999) and the like.

[Step 1]

Compound (e2) can be manufactured by reacting compound (e1) with carbon disulfide and iodomethane in the presence of a suitable base in a suitable solvent.

An inorganic base can be used as the base. Examples of the inorganic base include hydrides such as sodium hydride, alkali halides such as potassium fluoride, alkali hydroxides such as sodium hydroxide and potassium hydroxide, alkali carbonates such as sodium carbonate, potassium carbonate, cesium carbonate, and sodium bicarbonate, alkali alkoxides such as sodium ethoxide, sodium tert-butoxide, and potassium tert-butoxide, and alkali metals such as n-butyllithium, methyllithium, and isopropylmagnesium bromide. Preferred examples of bases include sodium hydride, potassium tert-butoxide, and the like.

A solvent is not particularly limited as long as it is a solvent that does not react under the reaction conditions of this step. Examples thereof include ether solvents such as diethyl ether, diisopropyl ether, tetrahydrofuran, methylcyclopentyl ether, anisole, and 1,4-dioxane; aromatic hydrocarbon solvents such as benzene, toluene, chlorobenzene, and xylene; ester solvents such as ethyl acetate and methyl acetate; aprotic solvents such as N,N-dimethylformamide, N,N-dimethylacetamide, N-methyl-2-pyrrolidinone, 1,3-dimethyl-2-imidazolidinone, and dimethyl sulfoxide; alcohol solvents such as methanol, ethanol, isopropyl alcohol, and butanol; and mixtures thereof. Preferred examples of solvents include tetrahydrofuran, toluene, N,N-dimethylformamide, and the like.

The reaction time is generally 5 minutes to 72 hours, and preferably 30 minutes to 2 hours.

The reaction temperature is generally −78° C. to 200° C., and preferably 0° C. to 25° C.

[Step 2]

Compound (e3) can be manufactured by reacting compound (e2) with a 5-aminopyrazine derivative in the presence of a suitable base in a suitable solvent.

Examples of the base include organic bases such as triethylamine, diisopropylethylamine, tributylamine, 1,5-diazabicyclo[4.3.0]non-5-ene (DBN), 1,8-diazabicyclo[5.4.0]undec-7-ene (DBU), pyridine, dimethylaminopyridine, picoline, N-methylmorpholine (NMM), and N-ethylmorpholine, and inorganic bases such as sodium bicarbonate, potassium bicarbonate, sodium carbonate, potassium carbonate, sodium hydroxide, and potassium hydroxide. Preferred examples of bases include triethylamine, diisopropylethylamine, and the like.

A solvent is not particularly limited as long as it is a solvent that does not react under the reaction conditions of this step. Examples thereof include ether solvents such as diethyl ether, diisopropyl ether, tetrahydrofuran, methylcyclopentyl ether, anisole, and 1,4-dioxane; aromatic hydrocarbon solvents such as benzene, toluene, chlorobenzene, and xylene; ester solvents such as ethyl acetate and methyl acetate; aprotic solvents such as N,N-dimethylformamide, N,N-dimethylacetamide, N-methyl-2-pyrrolidinone, 1,3-dimethyl-2-imidazolidinone, and dimethyl sulfoxide; and mixtures thereof. Preferred examples of solvents include tetrahydrofuran, toluene, dimethyl sulfoxide, and the like.

The reaction time is generally 5 minutes to 48 hours, and preferably 2 hours to 8 hours.

The reaction temperature is generally 0° C. to 200° C., and preferably 50° C. to 100° C.

[Step 3]

Compound (b1) can be manufactured by reacting compound (e3) with a hydrazine monohydrate in the presence or absence of a suitable acid in a suitable solvent.

Examples of acids include acetic acid, propionic acid, p-toluenesulfonic acid, methanesulfonic acid, ethanesulfonic acid, hydrochloric acid, sulfuric acid, camphorsulfonic acid, and the like. An acid is preferably acetic acid.

A solvent is not particularly limited as long as it is a solvent that does not react under the reaction conditions of this step. Examples thereof include ether solvents such as diethyl ether, diisopropyl ether, tetrahydrofuran, methylcyclopentyl ether, anisole, and 1,4-dioxane; aromatic hydrocarbon solvents such as benzene, toluene, chlorobenzene, and xylene; ester solvents such as ethyl acetate and methyl acetate; aprotic solvents such as N,N-dimethylformamide, N,N-dimethylacetamide, N-methyl-2-pyrrolidinone, 1,3-dimethyl-2-imidazolidinone, and dimethyl sulfoxide; alcohol solvents such as methanol, ethanol, isopropyl alcohol, and butanol; and mixtures thereof. Preferred examples of solvents include 1,4-dioxane, ethanol, and the like.

The reaction time is generally 5 minutes to 72 hours, and preferably 12 hours to 24 hours.

The reaction temperature is generally 0° C. to 200° C., and preferably 50° C. to 100° C.

Manufacturing Method F

The compound of the present disclosure represented by formula (c1) can be manufactured, for example, by the following method.

[Chemical Formula 23]

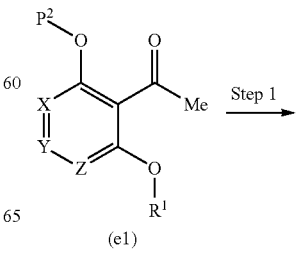

(e1)

-continued

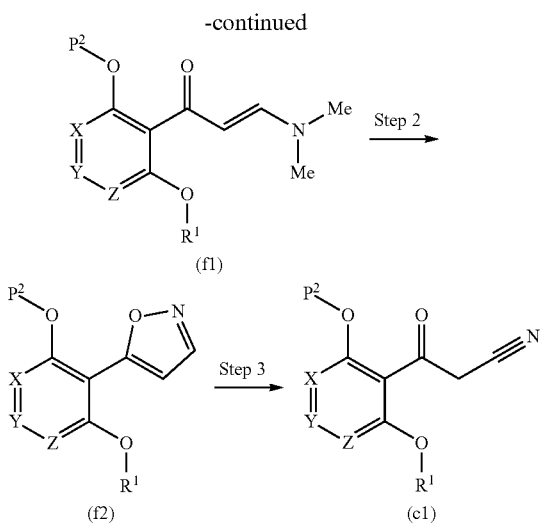

wherein $R^1$, X, Y, and Z are defined the same as the description in item 1, and $P^2$ refers to a phenol protecting group. Examples of $P^2$ include the phenol protecting groups described in Protective Groups in Organic Synthesis (authors: Theodora W. Greene, Peter G. M. Wuts, publisher: John Wiley & Sons, Inc., 1999) and the like.

[Step 1]

Compound (f1) can be manufactured by reacting compound (e1) with dimethylformamide dimethyl acetal in a suitable solvent.

A solvent is not particularly limited as long as it is a solvent that does not react under the reaction conditions of this step. Examples thereof include ether solvents such as diethyl ether, diisopropyl ether, tetrahydrofuran, methylcyclopentyl ether, anisole, and 1,4-dioxane; aromatic hydrocarbon solvents such as benzene, toluene, chlorobenzene, and xylene; ester solvents such as ethyl acetate and methyl acetate; aprotic solvents such as N,N-dimethylformamide, N,N-dimethylacetamide, N-methyl-2-pyrrolidinone, 1,3-dimethyl-2-imidazolidinone, and dimethyl sulfoxide; and mixtures thereof. Preferred examples of solvents include N,N-dimethylformamide and the like.

The reaction time is generally 5 minutes to 48 hours, and preferably 24 hours to 48 hours.

The reaction temperature is generally 0° C. to 200° C., and preferably 60° C. to 120° C.

[Step 2]

Compound (f2) can be manufactured by reacting compound (f1) with hydroxyamine hydrochloride in a suitable solvent.

A solvent is not particularly limited as long as it is a solvent that does not react under the reaction conditions of this step. Examples thereof include ether solvents such as diethyl ether, diisopropyl ether, tetrahydrofuran, methylcyclopentyl ether, anisole, and 1,4-dioxane; aromatic hydrocarbon solvents such as benzene, toluene, chlorobenzene, and xylene; ester solvents such as ethyl acetate and methyl acetate; aprotic solvents such as N,N-dimethylformamide, N,N-dimethylacetamide, N-methyl-2-pyrrolidinone, 1,3-dimethyl-2-imidazolidinone, and dimethyl sulfoxide; alcohol solvents such as methanol, ethanol, isopropyl alcohol, and butanol; and mixtures thereof. Preferred examples of solvents include ethanol, isopropyl alcohol, and the like.

The reaction time is generally 5 minutes to 48 hours, and preferably 6 hours to 12 hours.

The reaction temperature is generally 0° C. to 200° C., and preferably 40° C. to 80° C.

[Step 3]

Compound (c1) can be manufactured by reacting compound (f2) with a base in a suitable solvent.

Examples of the base include inorganic bases such as sodium bicarbonate, potassium bicarbonate, sodium carbonate, potassium carbonate, sodium hydroxide, and potassium hydroxide. Preferred examples of the base include sodium hydroxide, potassium hydroxide, and the like.

A solvent is not particularly limited as long as it is a solvent that does not react under the reaction conditions of this step. Examples thereof include ether solvents such as diethyl ether, diisopropyl ether, tetrahydrofuran, methylcyclopentyl ether, anisole, and 1,4-dioxane; aromatic hydrocarbon solvents such as benzene, toluene, chlorobenzene, and xylene; ester solvents such as ethyl acetate and methyl acetate; aprotic solvents such as N,N-dimethylformamide, N,N-dimethylacetamide, N-methyl-2-pyrrolidinone, 1,3-dimethyl-2-imidazolidinone, and dimethyl sulfoxide; protic solvents such as water, methanol, ethanol, isopropyl alcohol, and butanol; and mixtures thereof. Preferred examples of solvents include mixtures of water and ethanol, etc.

The reaction time is generally 5 minutes to 48 hours, and preferably 1 hour to 6 hours.

The reaction temperature is generally 0° C. to 200° C., and preferably 20° C. to 50° C.

Manufacturing Method G

The compound of the present disclosure represented by formula (a1) can be manufactured, for example, by the following method.

[Chemical Formula 24]

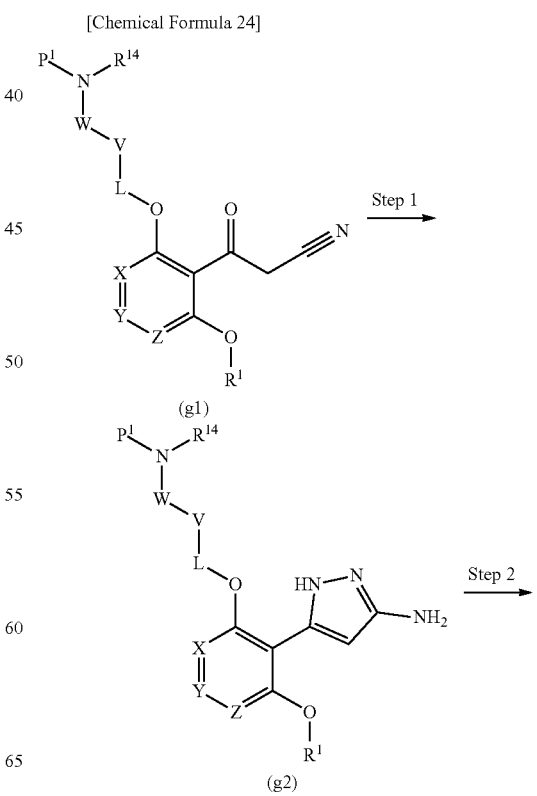

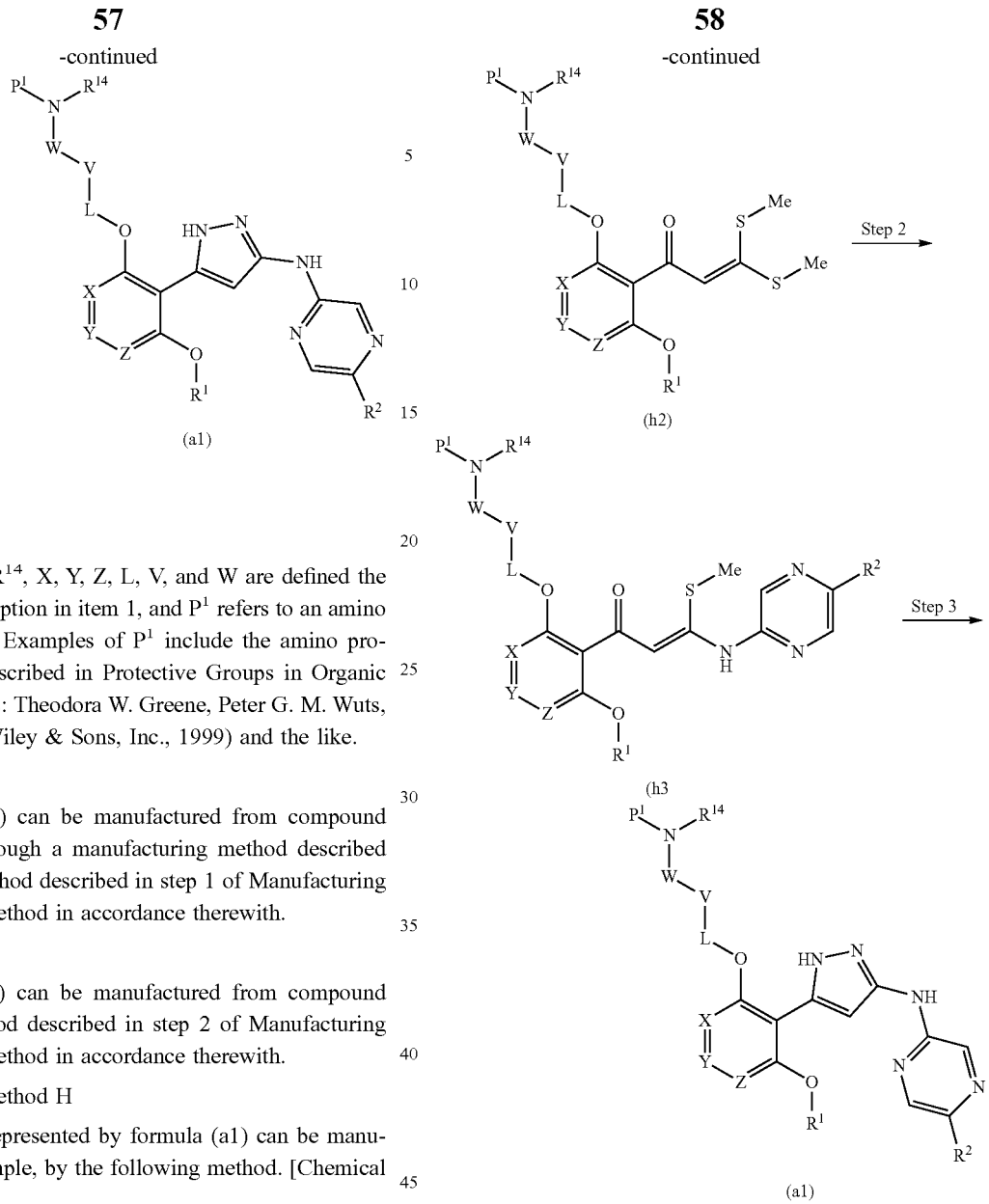

wherein $R^1$, $R^2$, $R^{14}$, X, Y, Z, L, V, and W are defined the same as the description in item 1, and $P^1$ refers to an amino protecting group. Examples of $P^1$ include the amino protecting groups described in Protective Groups in Organic Synthesis (authors: Theodora W. Greene, Peter G. M. Wuts, publisher: John Wiley & Sons, Inc., 1999) and the like.

[Step 1]

Compound (g2) can be manufactured from compound (g1) obtained through a manufacturing method described below, by the method described in step 1 of Manufacturing Method C or a method in accordance therewith.

[Step 2]

Compound (a1) can be manufactured from compound (g2) by the method described in step 2 of Manufacturing Method C or a method in accordance therewith.

Manufacturing Method H

A compound represented by formula (a1) can be manufactured, for example, by the following method. [Chemical Formula 25]

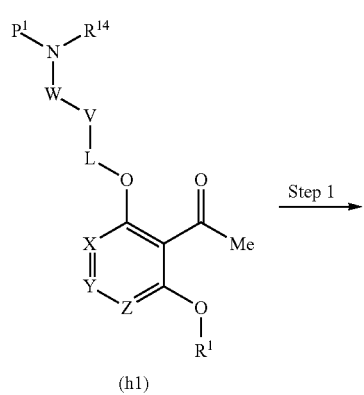

wherein $R^1$, $R^2$, $R^{14}$, X, Y, Z, L, V, and W are defined the same as the description in item 1, and P refers to an amino protecting group. Examples of $P^1$ include the amino protecting groups described in Protective Groups in Organic Synthesis (authors: Theodora W. Greene, Peter G. M. Wuts, publisher: John Wiley & Sons, Inc., 1999) and the like.

[Step 1]

Compound (h2) can be manufactured from compound (h1) obtained through the following method, by the method described in step 1 of Manufacturing Method E or a method in accordance therewith.

[Step 2]

Compound (h3) can be manufactured from compound (h2) by the method described in step 2 of Manufacturing Method E or a method in accordance therewith. [Step 3]

Compound (a1) can be manufactured from compound (h3) by the method described in step 3 of Manufacturing Method E or a method in accordance therewith.

Manufacturing Method I

A compound represented by formula (g1) can be manufactured, for example, by the following method.

[Chemical Formula 26]

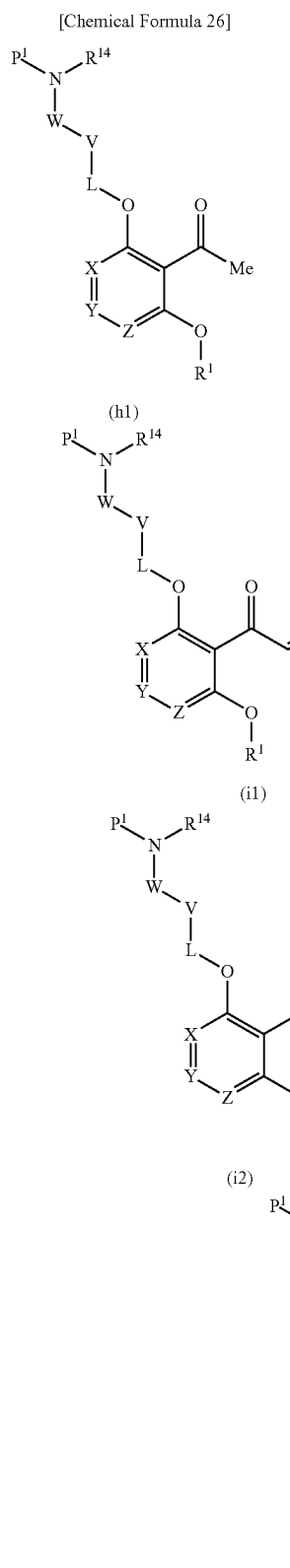

Synthesis (authors: Theodora W. Greene, Peter G. M. Wuts, publisher: John Wiley & Sons, Inc., 1999) and the like.

[Step 1]

Compound (i1) can be manufactured from compound (h1) obtained through the following manufacturing method, by the method described in step 1 of Manufacturing Method F or a method in accordance therewith.

[Step 2]

Compound (i2) can be manufactured from compound (i1) by the method described in step 2 of Manufacturing Method F or a method in accordance therewith.

[Step 3]

Compound (g1) can be manufactured from compound (i2) by the method described in step 3 of Manufacturing Method F or a method in accordance therewith.

Manufacturing Method J

A compound represented by formula (g1) can also be manufactured by, for example, the following method.

[Chemical Formula 27]

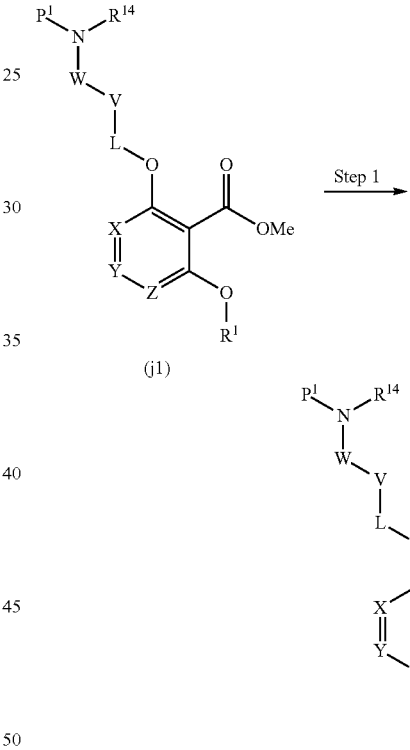

wherein $R^1$, $R^{14}$, X, Y, Z, L, V, and W are defined the same as the description in item 1, and $P^1$ refers to an amino protecting group. Examples of $P^1$ include the amino protecting groups described in Protective Groups in Organic Synthesis (authors: Theodora W. Greene, Peter G. M. Wuts, publisher: John Wiley & Sons, Inc., 1999) and the like.

[Step 1]

Compound (g1) can be manufactured from compound (j1) obtained through a manufacturing method described below, by the method described in step 1 of Manufacturing Method D or a method in accordance therewith.

Manufacturing Method K

The compound of the present disclosure represented by formula (d1) can be manufactured, for example, by the following method.

wherein $R^1$, $R^{14}$, X, Y, Z, L, V, and W are defined the same as the description in item 1, and $P^1$ refers to an amino protecting group. Examples of $P^1$ include the amino protecting groups described in Protective Groups in Organic

[Chemical Formula 28]

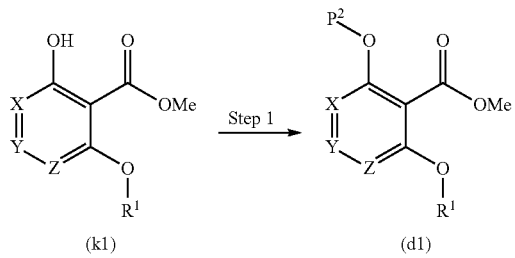

(k1) → (d1)

wherein $R^1$, X, Y, and Z are defined the same as the description in item 1, and $P^2$ refers to a phenol protecting group. Examples of $P^2$ include the phenol protecting groups described in Protective Groups in Organic Synthesis (authors: Theodora W. Greene, Peter G. M. Wuts, publisher: John Wiley & Sons, Inc., 1999) and the like.

Compound (k1) is available as a commercial product.

[Step 1]

Compound (d1) can be manufactured from compound (k1) by, for example, the method described in Protective Groups in Organic Synthesis (authors: Theodora W. Greene, Peter G. M. Wuts, publisher: John Wiley & Sons, Inc., 1999).

Manufacturing Method L

The compound of the present disclosure represented by formula (e1) can be manufactured, for example, by the following method.

[Chemical Formula 29]

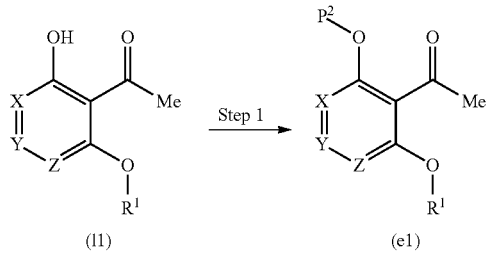

(l1) → (e1)

wherein $R^1$, X, Y, and Z are defined the same as the description in item 1, and $P^2$ refers to a phenol protecting group. Examples of $P^2$ include the phenol protecting groups described in Protective Groups in Organic Synthesis (authors: Theodora W. Greene, Peter G. M. Wuts, publisher: John Wiley & Sons, Inc., 1999) and the like.

Compound (l1) is available as a commercial product.

[Step 1]

Compound (e1) can be manufactured from compound (l1) by the method described in step 1 of Manufacturing Method K or a method in accordance therewith.

Manufacturing Method M

The compound of the present disclosure represented by formula (j1) can be manufactured, for example, by the following method.

[Chemical Formula 30]

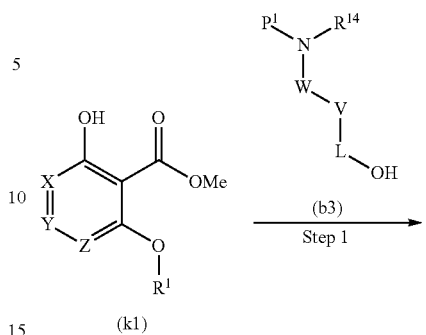

(k1) → (j1)

wherein $R^1$, $R^{14}$, X, Y, Z, L, V, and W are defined the same as the description in item 1, and $P^1$ refers to an amino protecting group. Examples of $P^1$ include the amino protecting groups described in Protective Groups in Organic Synthesis (authors: Theodora W. Greene, Peter G. M. Wuts, publisher: John Wiley & Sons, Inc., 1999) and the like.

Compound (k1) and compound (b3) are available as commercial products.

[Step 1]

Compound (j1) can be manufactured from compound (k1) and compound (b3) by the method described in step 2 of Manufacturing Method B or a method in accordance therewith.

Manufacturing Method N

The compound of the present disclosure represented by formula (j1) can be manufactured, for example, by the following method.

[Chemical Formula 31]

(k1)

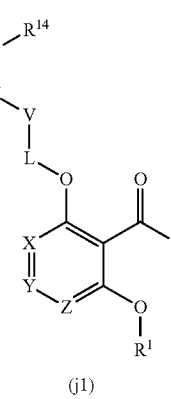

(j1)

[Chemical Formula 32]

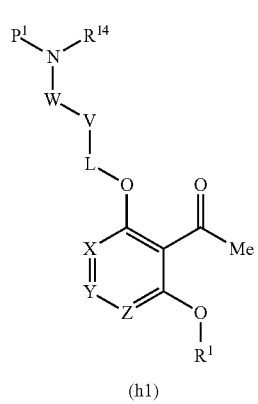

wherein $R^1$, $R^{14}$, X, Y, Z, L, V, and W are defined the same as the description in item 1, $P^1$ refers to an amino protecting group, and LG refers to a leaving group. Examples of $P^1$ include the amino protecting groups described in Protective Groups in Organic Synthesis (authors: Theodora W. Greene, Peter G. M. Wuts, publisher: John Wiley & Sons, Inc., 1999) and the like. Examples of LG include halogen, methanesulfonyloxy, p-toluenesulfonyloxy, trifluoromethanesulfonyloxy, and the like.

Compound (k1) and compound (n1) are available as commercial products.

[Step 1]

Compound (j1) can be manufactured by reacting compound (k1) and compound (n1) in the presence or absence of a suitable base in a suitable solvent.

Examples of the base include organic bases such as triethylamine, diisopropylethylamine, tributylamine, 1,5-diazabicyclo[4.3.0]non-5-ene (DBN), 1,8-diazabicyclo[5.4.0]undec-7-ene (DBU), pyridine, 4-dimethylaminopyridine, picoline, and N-methylmorpholine (NMM) and inorganic bases such as sodium bicarbonate, potassium bicarbonate, sodium carbonate, potassium carbonate, sodium hydroxide, and potassium hydroxide. Preferred examples of the base include triethylamine, diisopropylethylamine, potassium carbonate, sodium hydroxide, and the like.

A solvent is not particularly limited as long as it is a solvent that does not react under the reaction conditions of this step. Examples thereof include alcohol solvents such as methanol, ethanol, 2-propanol (isopropyl alcohol), and tert-butanol; ether solvents such as diethyl ether, diisopropyl ether, tetrahydrofuran, methylcyclopentyl ether, and 1,4-dioxane; aromatic hydrocarbon solvents such as benzene, toluene, chlorobenzene, anisole, and xylene; ester solvents such as ethyl acetate and methyl acetate; aprotic solvents such as acetonitrile, N,N-dimethylformamide, N,N-dimethylacetamide, N-methyl-2-pyrrolidinone, 1,3-dimethyl-2-imidazolidinone, and dimethyl sulfoxide; and mixtures thereof. Preferred examples of solvents include 2-propanol, tetrahydrofuran, toluene, acetonitrile, N,N-dimethylformamide, and the like.

The reaction temperature is generally −80° C. to heating under reflux, and preferably 25° C. to 90° C.

The reaction time is generally 30 minutes to 48 hours, and preferably 6 to 12 hours.

Manufacturing Method O

The compound of the present disclosure represented by formula (h1) can be manufactured, for example, by the following method.

wherein $R^1$, $R^{14}$, X, Y, Z, L, V, and W are defined the same as the description in item 1, and $P^1$ refers to an amino protecting group. Examples of $P^1$ include the amino protecting groups described in Protective Groups in Organic Synthesis (authors: Theodora W. Greene, Peter G. M. Wuts, publisher: John Wiley & Sons, Inc., 1999) and the like.

Compound (l1) and compound (b3) are available as commercial products.

[Step 1]

Compound (h1) can be manufactured from compound (l1) and compound (b3) by the method described in step 2 of Manufacturing Method B or a method in accordance therewith.

Manufacturing Method P

The compound of the present disclosure represented by formula (h1) can be manufactured, for example, by the following method.

[Chemical Formula 33]

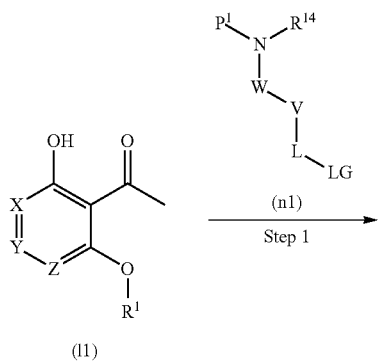

(l1)

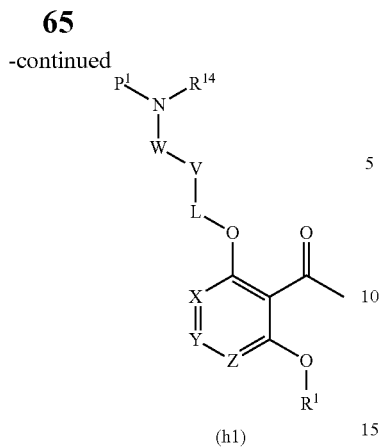

(h1)

wherein $R^1$, $R^{14}$, X, Y, Z, L, V, and W are defined the same as the description in item 1, $P^1$ refers to an amino protecting group, and LG refers to a leaving group. Examples of $P^1$ include the amino protecting groups described in Protective Groups in Organic Synthesis (authors: Theodora W. Greene, Peter G. M. Wuts, publisher: John Wiley & Sons, Inc., 1999) and the like. Examples of LG include halogen, methanesulfonyloxy, p-toluenesulfonyloxy, trifluoromethanesulfonyloxy, and the like.

Compound (l1) and compound (n1) are available as commercial products.

[Step 1]

Compound (h1) can be manufactured from compound (l1) and compound (n1) by the method described in step 2 of Manufacturing Method B or a method in accordance therewith.

Manufacturing Method Q

The compound of the present disclosure represented by formula (h1) can be manufactured, for example, by the following method.

[Chemical Formula 34]

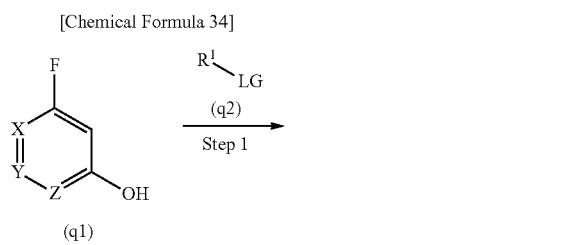

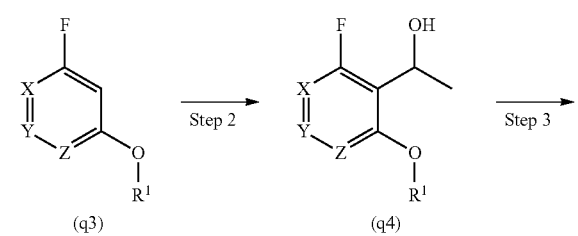

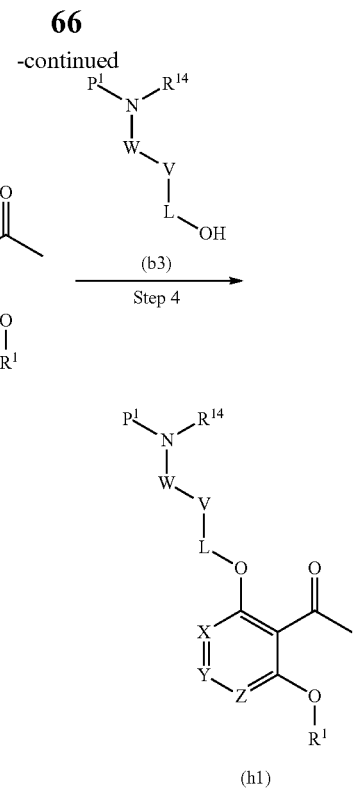

(h1)

wherein $R^1$, $R^{14}$, X, Y, Z, L, V, and W are defined the same as the description in item 1, $P^1$ refers to an amino protecting group, and LG refers to a leaving group. Examples of $P^1$ include the amino protecting groups described in Protective Groups in Organic Synthesis (authors: Theodora W. Greene, Peter G. M. Wuts, publisher: John Wiley & Sons, Inc., 1999) and the like. Examples of LG include halogen, methanesulfonyloxy, p-toluenesulfonyloxy, trifluoromethanesulfonyloxy, and the like.

Compound (q1), compound (q2) and compound (b3) are available as commercial products.

[Step 1]

Compound (q3) can be manufactured from compound (q1) and compound (q2) by the method described in step 1 of Manufacturing Method N or a method in accordance therewith.

[Step 2]

Compound (q4) can be manufactured by reacting compound (q3) with acetaldehyde in the presence of a suitable base in a suitable solvent.

Examples of the base include n-butyllithium, sec-butyllithium, tert-butyllithium, lithium diisopropylamide, lithium tetramethylpiperidide, lithium hexamethyldisilazide, sodium hexamethyldisilazide, potassium hexamethyldisilazide, isopropylmagnesium chloride-lithium chloride complex, and the like.

A solvent is not particularly limited as long as it is a solvent that does not react under the reaction conditions of this step. Examples thereof include ether solvents such as diethyl ether, diisopropyl ether, tetrahydrofuran, methylcyclopentyl ether, and 1,4-dioxane; aromatic hydrocarbon solvents such as benzene, toluene, chlorobenzene, anisole, and xylene; halogen solvents such as methylene chloride, chloroform, and 1,2-dichloroethane; aprotic solvents such as acetonitrile, N,N-dimethylformamide, N,N-dimethylacetamide, N-methyl-2-pyrrolidinone, 1,3-dimethyl-2-imidazolidinone, and dimethyl sulfoxide; and mixtures thereof. Preferred examples of solvents include tetrahydrofuran.

The reaction temperature is generally −80° C. to heating under reflux, and preferably −80° C. to 25° C.

The reaction time is generally 30 minutes to 48 hours, and preferably 6 to 12 hours.

[Step 3]

Compound (q5) can be manufactured by reacting compound (q4) with a suitable oxidizing agent in the presence or absence of a suitable base in a suitable solvent.

Examples of the oxidizing agent include manganese dioxide, Dess-Martin reagents, dimethyl sulfoxide-oxalyl chloride, dimethyl sulfoxide-trifluoroacetic acid anhydride, sulfur trioxide-pyridine complex, 2,2,6,6-tetramethylpiperidin-1-oxy radical-sodium hypochlorite, and the like.

Examples of the base include organic bases such as triethylamine, diisopropylethylamine, tributylamine, 1,5-diazabicyclo[4.3.0]non-5-ene (DBN), 1,8-diazabicyclo[5.4.0]undec-7-ene (DBU), pyridine, 4-dimethylaminopyridine, picoline, and N-methylmorpholine (NMM) and inorganic bases such as sodium bicarbonate, potassium bicarbonate, sodium carbonate, potassium carbonate, sodium hydroxide, and potassium hydroxide.

A solvent is not particularly limited as long as it is a solvent that does not react under the reaction conditions of this step. Examples thereof include halogen solvents such as methylene chloride, chloroform, and 1,2-dichloroethane; ether solvents such as diethyl ether, diisopropyl ether, tetrahydrofuran, methylcyclopentyl ether, and 1,4-dioxane; aromatic hydrocarbon solvents such as benzene, toluene, chlorobenzene, anisole, and xylene; ester solvents such as ethyl acetate and methyl acetate; aprotic solvents such as acetonitrile, N,N-dimethylformamide, N,N-dimethylacetamide, N-methyl-2-pyrrolidinone, 1,3-dimethyl-2-imidazolidinone, and dimethyl sulfoxide; and mixtures thereof. Preferred examples of solvents include methylene chloride, tetrahydrofuran, toluene, acetonitrile, N,N-dimethylformamide, and the like.

The reaction temperature is generally −80° C. to heating under reflux, and preferably −80° C. to 25° C.

The reaction time is generally 30 minutes to 48 hours, and preferably 6 to 12 hours.

[Step 4]

Compound (h1) can be manufactured from compound (q5) and compound (b3) by the method described in step 2 of Manufacturing Method B or a method in accordance therewith.

Manufacturing Method R

The compound of the present disclosure represented by formula (i2) can be manufactured, for example, by the following method.

[Chemical Formula 35]

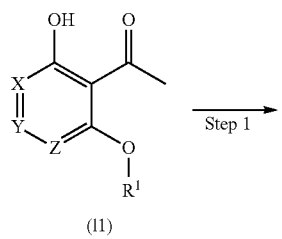

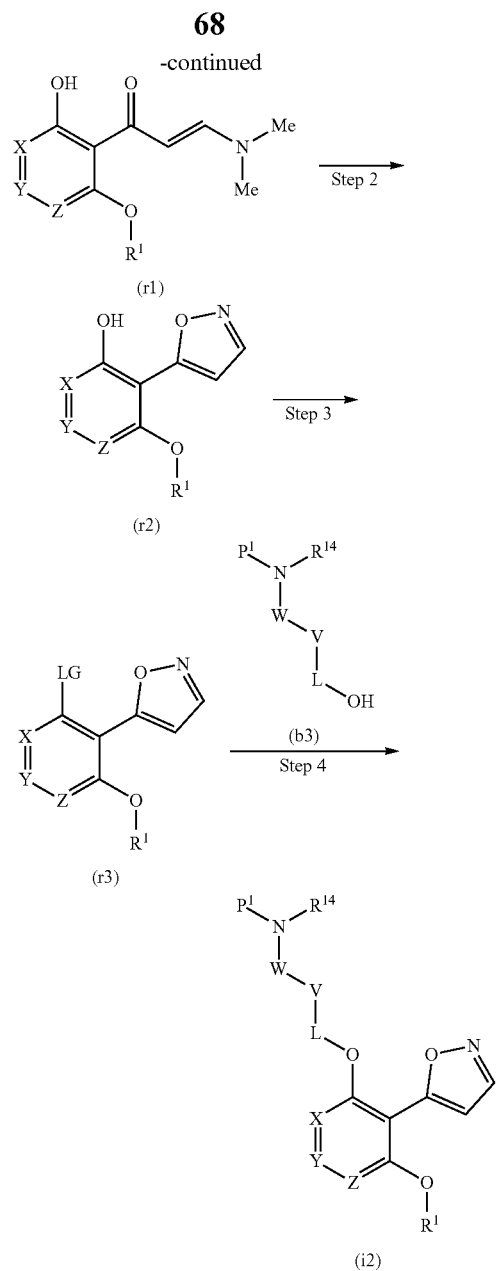

wherein $R^1$, $R^{14}$, X, Y, Z, L, V, and W are defined the same as the description in item 1, $P^1$ refers to an amino protecting group, and LG refers to a leaving group. Examples of $P^1$ include the amino protecting groups described in Protective Groups in Organic Synthesis (authors: Theodora W. Greene, Peter G. M. Wuts, publisher: John Wiley & Sons, Inc., 1999) and the like.

Examples of LG include halogen, methanesulfonyloxy, p-toluenesulfonyloxy, trifluoromethanesulfonyloxy, and the like.

Compound (l1) and compound (b3) are available as commercial products.

[Step 1]

Compound (r1) can be manufactured from compound (l1) by the method described in step 1 of Manufacturing Method F or a method in accordance therewith.

[Step 2]

Compound (r2) can be manufactured from compound (r1) by the method described in step 2 of Manufacturing Method F or a method in accordance therewith.

[Step 3]

Compound (r3) can be manufactured by reacting compound (r2) with a suitable halogenating agent or sulfonylating agent in the presence or absence of a suitable base in a suitable solvent or without a solvent.

Examples of the halogenating agent or sulfonylating agent include thionyl chloride, phosphorus oxychloride, oxalyl chloride, phosphorus tribromide, methanesulfonyl chloride, N-phenylbis(trifluoromethane sulfonimide), trifluoromethanesulfonic anhydride, and the like.

Examples of the base include organic bases such as triethylamine, diisopropylethylamine, tributylamine, 1,5-diazabicyclo[4.3.0]non-5-ene (DBN), 1,8-diazabicyclo[5.4.0] undec-7-ene (DBU), pyridine, 4-dimethylaminopyridine, picoline, and N-methylmorpholine (NMM) and inorganic bases such as sodium bicarbonate, potassium bicarbonate, sodium carbonate, potassium carbonate, sodium hydroxide, and potassium hydroxide.

A solvent is not particularly limited as long as it is a solvent that does not react under the reaction conditions of this step. Examples thereof include halogen solvents such as methylene chloride, chloroform, and 1,2-dichloroethane; ether solvents such as diethyl ether, diisopropyl ether, tetrahydrofuran, methylcyclopentyl ether, and 1,4-dioxane; aromatic hydrocarbon solvents such as benzene, toluene, chlorobenzene, anisole, and xylene; ester solvents such as ethyl acetate and methyl acetate; aprotic solvents such as acetonitrile, N,N-dimethylformamide, N,N-dimethylacetamide, N-methyl-2-pyrrolidinone, 1,3-dimethyl-2-imidazolidinone, and dimethyl sulfoxide; and mixtures thereof. Preferred examples of solvents include methylene chloride, tetrahydrofuran, toluene, acetonitrile, N,N-dimethylformamide, and the like.

The reaction temperature is generally −80° C. to heating under reflux, and preferably 0° C. to heating under reflux.

The reaction time is generally 30 minutes to 48 hours, and preferably 30 minutes to 12 hours.

[Step 4]

Compound (i2) can be manufactured by a reaction of compound (r3) and compound (b3) catalyzed by a suitable palladium source and a ligand in the presence of a suitable base in a suitable solvent.

Examples of the base include organic bases such as triethylamine, diisopropylethylamine, tributylamine, pyridine, 4-dimethylaminopyridine, picoline, and N-methylmorpholine (NMM) and inorganic bases such as sodium carbonate, potassium carbonate, cesium carbonate, sodium hydroxide, and potassium hydroxide. Preferred examples of the base include diisopropylethylamine, cesium carbonate, and the like.

Examples of the palladium source include salts of palladium chloride or palladium acetate, zerovalent palladium complexes such as tris(dibenzylideneacetone)dipalladium (0) chloroform adduct and the like.

Examples of ligands include phosphine ligands such as 4,5-bis(diphenylphosphino)-9,9-dimethylxanthene (xantphos), 2,2'-bis (diphenylphosphino)-1,1'-binaphthyl (BINAP), 2-dicyclohexylphosphino-2',6'-dimethoxybiphenyl (SPhos), and 2-dicyclohexylphosphino-2',4',6'-triisopropylbiphenyl (XPhos). Preferred examples of ligands include 4,5-bis(diphenylphosphino)-9,9-dimethylxanthene (xantphos).

A solvent is not particularly limited as long as it is a solvent that does not react under the reaction conditions of this step. Examples thereof include halogen solvents such as methylene chloride, chloroform, and 1,2-dichloroethane; ether solvents such as diethyl ether, diisopropyl ether, tetrahydrofuran, methylcyclopentyl ether, and 1,4-dioxane; aromatic hydrocarbon solvents such as benzene, toluene, chlorobenzene, anisole, and xylene; ester solvents such as ethyl acetate and methyl acetate; aprotic solvents such as acetonitrile, N,N-dimethylformamide, N,N-dimethylacetamide, N-methyl-2-pyrrolidinone, 1,3-dimethyl-2-imidazolidinone, and dimethyl sulfoazide; and mixtures thereof. Preferred examples of solvents include tetrahydrofuran, 1,4-dioxane, toluene, acetonitrile, N,N-dimethylformamide, and the like.

The reaction temperature is generally 0° C. to heating under reflux, and preferably 50° C. to heating under reflux.

The reaction time is generally 5 minutes to 72 hours, and preferably 2 to 12 hours.

In the manufacturing method described above, the starting material and intermediates for which the manufacturing method is not described are available as commercial products, or can be synthesized from a commercially available product by a method known to those skilled in the art or a method in accordance therewith.

Even without an explicit description of a specific use of a protecting group in each reaction of the manufacturing methods described above, a protecting group can be used as needed. A compound of interest can be obtained by protecting a portion other than the reaction point and deprotecting the portion after the completion of a reaction or a series of reactions as needed if one of the functional groups other than the reaction point is altered under the described reaction condition or if the absence of a protecting group is unsuitable for performing the described method.

As the protecting group, the protecting group described in Protective Groups in Organic Synthesis (authors: Theodora W. Greene, Peter G. M. Wuts, publisher: John Wiley & Sons, Inc., 1999) or the like can be used. Specific examples of amino protecting group include benzyloxylcarbonyl, tert-butoxycarbonyl, acetyl, benzyl, and the like. Specific examples of a protecting group of a hydroxyl group include trialkylsilyl such as trimethylsilyl and tert-butyldimethylsilyl, acetyl, benzyl, and the like.

A method that is commonly used in synthetic organic chemistry (see, for example, the aforementioned Protective Groups in Organic Synthesis) or a method in accordance therewith can be used for the introduction or removal of a protecting group.

As used herein, protecting groups, condensing agents, or the like may be denoted by the nomenclature of IUPAC-IUB (Biochemical Nomenclature Committees) that is commonly used in the art. It should be noted that compound names used herein do not necessarily follow the IUPAC nomenclature.

The intermediates or compounds of interest in the manufacturing methods described above can be guided into another compound in the present disclosure by appropriately converting its functional group (e.g., various conversions using amino, hydroxyl group, carbonyl, halogen, or the like while protecting or deprotecting a functional group as needed). A functional group can be converted by a common method that is routinely used (see, for example, Comprehensive Organic Transformations, R. C. Larock, John Wiley & Sons Inc. (1999), etc.).

The intermediates or compounds of interest in the manufacturing methods described above can be isolated and purified by a purification method that is commonly used in organic synthetic chemistry (e.g., neutralization, filtration, extraction, washing, drying, concentration, recrystallization, various chromatographies). Intermediates can also be used in the subsequent reaction without any particular purification.

Examples of "pharmaceutically acceptable salt" include acid addition salts and base addition salts. Examples of acid addition salts include inorganic acid salts such as hydrochloric acid salt, hydrobromic acid salt, sulfuric acid salt, hydroiodic acid salt, nitric acid salt, and phosphoric acid salt, and organic acid salts such as citric acid salt, oxalic acid salt, phthalic acid salt, fumaric acid salt, maleic acid salt, succinic acid salt, malic acid salt, acetic acid salt, formic acid salt, propionic acid salt, benzoic acid salt, trifluoroacetic acid salt, methanesulfonic acid salt, benzenesulfonic acid salt, p-toluenesulfonic acid salt, and camphorsulfonic acid salt. Examples of base addition salts include inorganic base salts such as sodium salt, potassium salt, calcium salt, magnesium salt, barium salt, and aluminum salt, and organic base salts such as trimethylamine, triethylamine, pyridine, picoline, 2,6-lutidine, ethanolamine, diethanolamine, triethanolamine, tromethamine [tris (hydroxymethyl)methylamine], tert-butylamine, cyclohexylamine, dicyclohexylamine, and N—N-dibenzylethylamine, and the like. Furthermore, examples of "pharmaceutically acceptable salt" include amino acid salts of a basic or acidic amino acid such as arginine, lysine, ornithine, aspartic acid, and glutamic acid.

Salts that are suitable for a staring material and intermediate and salts that are acceptable as a raw material of a pharmaceutical product are conventionally used non-toxic salts. Such salts can be, for example, acid addition salts such as organic acid salts (e.g., acetic acid salt, trifluoroacetic acid salt, maleic acid salt, furamic acid salt, citric acid salt, tartaric acid salt, methanesulfonic acid salt, benzenesulfonic acid salt, formic acid salt, toluenesulfonic acid salt, etc.) and inorganic acid salts (e.g., hydrochloric acid salt, hydrobromic acid salt, hydroiodic acid salt, sulfuric acid salt, nitric acid salt, phosphoric acid salt, etc.), salts of amino acid (e.g., arginine, asparaginic acid, glutamic acid, etc.), metal salts such as alkali metal salts (e.g., sodium salt, potassium salt, etc.) and alkali earth metal salts (e.g., calcium salt, magnesium salt, etc.), ammonium salts, organic base salts (e.g., trimethylamine salt, triethylamine salt, pyridine salt, picoline salt, dicyclohexylamine salt, N,N'-dibenzylethylenediamine salt, etc.), and the like. Those skilled in the art can also appropriately select other salts.

Deuterated compounds prepared by converting any one or more of $^1$H of compounds represented by formulas (1) to (5) to $^2$H(D) are also encompassed by the compounds represented by formulas (1) to (5) in the present disclosure.

The present disclosure encompasses the compounds represented by formulas (1) to (5) and pharmaceutically acceptable salts thereof. The compound of the present disclosure can also be in a form of a hydrate and/or solvate of various solvents (ethanolate, etc.) Thus, such hydrates and/or solvates are also encompassed by the compound of the present disclosure.

The compound of the present disclosure also encompasses enantiomers based on an optically-active center, atropisomers based on axial or planar chirality resulting from restriction of intramolecular rotation, other stereoisomers, tautomers, geometric isomers, all other possible isomers, crystalline forms in any form, and mixtures thereof.

In particular, an enantiomer and an atropisomer can be obtained as a racemate and an optically-active form if an optically-active starting material or intermediate is used, respectively. If necessary, a corresponding raw material, intermediate, or final product racemate can be physically or chemically resolved, during an appropriate step of the manufacturing method described above, into their optical enantiomers by a known separation method, such as a method using an optically active column or a fractional crystallization method. Examples of the resolution method include a diastereomer method for reacting a racemate with an optically-active resolving agent to synthesize two types of diastereomers, and utilizing the difference in physical properties for resolving through a method such as a fractional crystallization method.

If it is desirable to obtain a pharmaceutically acceptable salt of the compound of the present disclosure, a compound represented by formula (1) to (5), when obtained in a form of a pharmaceutically acceptable salt, can be directly purified, or when obtained in a free form, a salt may be formed through a common method by dissolving or suspending the compound in a suitable organic solvent and adding an acid or a base.

A liposome encapsulating the compound of the present disclosure can be manufactured, for example, by the following method.

[Step 1]

A membrane constituting component such as a phospholipid or cholesterol is dissolved in an organic solvent such as chloroform, and the organic solvent is evaporated within a flask to form a thin film of a lipid mixture on the inner wall of the flask. Alternatively, a lipid mixture can be obtained as a lyophilized product by dissolving the component in t-butyl alcohol or the like and then lyophilizing the solution. A membrane constituting component such as phospholipid or cholesterol can also be dissolved in an organic solvent and then a powderized lipid mixture can be obtained using an instantaneous vacuum dryer CRUX (Hosokawa Micron Corporation), or this can be obtained from Nippon Fine Chemical Co., Ltd. under the name Presome®.

[Step 2]

A crude liposome dispersion is obtained by adding and dispersing an internal aqueous phase such as an aqueous ammonium sulfate solution to the lipid mixture obtained in step 1.

[Step 3]

The crude liposome dispersion obtained in step 2 is passed through a filter to attain a desired particle size by using an extruder. Alternatively, the crude liposome dispersion obtained in step 2 is discharged from a nozzle at a high pressure by using a high pressure homogenizer to attain a desire particle size. While the particle size of liposomes is not particularly limited, the particle size is, for example, 10 nm to 200 nm, preferably 30 nm to 150 nm, more preferably 40 nm to 140 nm, still more preferably 50 to 120 nm, and most preferably 60 to 100 nm. The particle size of liposomes is a mean value measured by dynamic light scattering, and can be measured using, for example, Zetasizer Nano ZS (Malvern Instruments).

[Step 4]

For the liposome solution obtained in step 3, the outer aqueous phase is replaced by gel filtration, dialysis, tangential flow filtration, ultrafiltration, or the like.

[Step 5]

The liposome solution obtained in step 4 with the outer aqueous phase replaced is incubated with a compound to be encapsulated to encapsulate the compound in the liposome.

[Step 6]

The resulting liposome encapsulating a compound is subjected to gel filtration, dialysis, tangential flow filtration, ultrafiltration, or the like to remove compounds that are not encapsulated. If a desired encapsulation ratio is achieved in step 5, step 6 can be omitted.

The compound of the present disclosure can be used concomitantly with another drug in order to enhance the effect thereof. Specifically, the compound of the present disclosure can be used concomitantly with a drug such as a hormonal therapy agent, a chemotherapeutic agent, an immunotherapeutic agent, or an agent inhibiting a cell growth factor and its receptor action. Hereinafter, a drug that can be concomitantly used with the compound of the present disclosure is abbreviated as the concomitantly used drug.

Although the compound of the present disclosure exhibits excellent anticancer action when used as a single agent, the effect thereof can be further enhanced, or the QOL of a patient can be improved by concomitantly using one or several of the concomitantly used drugs described above (concomitant use of multiple drugs).

Examples of "hormonal therapy agent" include fosfestrol, diethylstilbestrol, chlorotrianisene, medroxyprogesterone acetate, megestrol acetate, chlormadinone acetate, cyproterone acetate, danazol, dienogest, asoprisnil, allylestrenol, gestrinone, nomegestol, tadenan, mepartricin, raloxifene, ormeroxifene, levormeloxifene, antiestrogens (e.g., tamoxifen citrate, toremifene citrate, and the like), pill formulations, mepitiostane, testolactone, aminoglutethimide, LH-RH derivatives (LH-RH agonists (e.g., goserelin acetate, buserelin, leuprorelin, and the like), and LH-RH antagonists), droloxifene, epitiostanol, ethinylestradiol sulfonate, aromatase inhibitors (e.g., fadrozole hydrochloride, anastrozole, letrozole, exemestane, vorozole, formestane, and the like), antiandrogens (e.g., flutamide, enzalutamide, apalutamide, bicalutamide, nilutamide, and the like), adrenocortical hormone agents (e.g., dexamethasone, prednisolone, betamethasone, triamcinolone, and the like), androgen synthesis inhibitors (e.g., abiraterone and the like), retinoids, drugs that slow the metabolism of retinoids (e.g., liarozole and the like), and the like.

For example, an alkylating agent, antimetabolite, anticancer antibiotic, plant derived anticancer agent, molecularly targeted therapy agent, immunomodulator, other chemotherapeutic agent, or the like can be used as a "chemotherapeutic agent". Representative examples thereof are described below.

Examples of "alkylating agents" include nitrogen mustard, nitrogen mustard n-oxide hydrochloride, chlorambucil, cyclophosphamide, ifosfamide, thiotepa, carboquone, improsulfan tosylate, busulfan, nimustine hydrochloride, mitobronitol, melphalan, dacarbazine, ranimustine, estramustine phosphate sodium, triethylenemelamine, carmustine, lomustine, streptozocin, pipobroman, etoglucide, carboplatin, cisplatin, miboplatin, nedaplatin, oxaliplatin, altretamine, ambamustine, dibrospidium chloride, fotemustine, prednimustine, pumitepa, ribomustin, temozolomide, treosulfan, trofosfamide, zinostatin stimalamer, adozelesin, cystemustine, bizelesin, trabectedin, DDS formulations thereof, and the like.

Examples of "antimetabolite" include mercaptopurine, 6-mercaptopurine riboside, thioinosine, methotrexate, pemetrexed, enocitabine, cytarabine, cytarabine ocfosfate, ancitabine hydrochloride, 5-FU based agents (e.g., fluorouracil, tegafur, UFT, doxifluridine, carmofur, galocitabine, emitefur, capecitabine, and the like), aminopterin, nelzarabine, leucovorin calcium, tabloid, butocin, calcium folinate, calcium levofolinate, cladribine, emitefur, fludarabine, gemcitabine, hydroxycarbamide, pentostatin, piritrexim, idoxuridine, mitoguazone, tiazofurin, ambamustine, bendamustine, DDS formulations thereof, and the like.

Examples of "anticancer antibiotic" include actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarkomycin, carzinophilin, mitotane, zorubicin hydrochloride, mitoxantrone hydrochloride, idarubicin hydrochloride, eribulin, DDS formulations thereof, and the like.

Examples of "plant derived anticancer agent" include etoposide, etoposide phosphate, vinblastine sulfate, vincristine sulfate, vindesine sulfate, teniposide, paclitaxel, docetaxel, DJ-927, vinorelbine, irinotecan, topotecan, DDS formulations thereof, and the like.

Examples of "molecularly targeted therapy agent" include imatinib, gefitinib, erlotinib, sorafenib, dasatinib, sunitinib, nilotinib, lapatinib, pazopanib, ruxolitinib, crizotinib, vemurafenib, vandetanib, ponatinib, cabozantinib, tofacitinib regorafenib, bosutinib, axitinib, dabrafenib, trametinib, nintedanib, idelalisib, ceritinib, lenvatinib, palbociclib, alectinib, afatinib, osimertinib, ribociclib, abemaciclib, brigatinib, neratinib, copanlisib, cobimetinib, ibrutinib, acalabrutinib, encorafenib, binimetinib, baricitinib, fostamatinib, lorlatinib, erdafitinib, entrectinib, dacomitinib, sirolimus, everolimus, temsirolimus, olaparib, rucaparib, niraparib, venetoclax, azacitidine, decitabine, vorinostat, panobinostat, romidepsin, bortezomib, carfilzomib, larotrectinib, ixazomib, and the like.

Examples of "immunomodulator" include lenalidomide, pomalidomide, and the like.

Examples of "other chemotherapeutic agent" include sobuzoxane and the like.

Examples of "immunotherapeutic agent (BRM)" include picibanil, krestin, sizofiran, lentinan, ubenimex, interferon, interleukin, macrophage colony stimulating factor, granulocyte-colony stimulating factor, erythropoietin, lymphotoxin, BCG vaccine, *Corynebacterium parvum*, levamisole, polysaccharide K, procodazole, anti-CTLA4 antibody, anti-PD-1 antibody, anti-PD-LI antibody, and Toll-like Receptor agonist (e.g., TLR7 agonist, TLR8 agonist, TLR9 agonist, and the like).

The cell growth factor in an agent inhibiting a cell growth factor and its receptor action can be any substance, as long as it is a substance that promotes cell growth. A cell growth factor is generally a peptide having a molecular weight of 20,000 or less and exerting action at a low concentration by binding with a receptor. Specific examples thereof include EGF (epidermal growth factor) or substances having substantially the same activity as EGF (e.g., TGF-alpha and the like), insulin or substances having substantially the same activity as insulin (e.g., insulin, IGF (insulin-like growth factor)-1, IGF-2, and the like), FGF (fibroblast growth factor) or substances having substantially the same activity as FGF (e.g., acidic FGF, basic FGF, KGK (keratinocyte growth factor), FGF-10, and the like), and other cell growth factors (e.g., CSF (colony stimulating factor), EPO (erythropoietin), IL-2 (interleukin-2), NGF (nerve growth factor), PDGF (platelet-derived growth factor), TGF-beta (transforming growth factor beta), HGF (hepatocyte growth factor), VEGF (vascular endothelial growth factor), heregulin, angiopoietin, and the like).

The dosing period of the compound of the present disclosure and a concomitantly used drug is not limited. They can be administered simultaneously or separately to a target of administration. The compound of the present disclosure and a concomitantly used drug can also be prepared as a combined drug. The amount of concomitantly used drug to be administered can be appropriately selected based on clinically used doses. The blend ratio of the compound of the present disclosure and a concomitantly used drug can be appropriately selected depending on the subject of administration, route of administration, target disease, symptom, combination, or the like. If, for example, the subject of administration is a human, 0.01 to 100 parts by weight of concomitantly used drug can be used with respect to 1 part by weight of the compound of the present disclosure. They can also be used in combination with an agent (concomitantly used drug) such as an antiemetic, sleep inducing agent, or anticonvulsive in order to suppress side effects thereof.

As used herein, "or" is used when "at least one or more" of the listed matters in the sentence can be employed. When explicitly described herein as "within the range of two values", the range also includes the two values themselves.

Reference literatures such as scientific literatures, patents, and patent applications cited herein are incorporated herein by reference to the same extent that the entirety of each document is specifically described.

The present disclosure has been described while showing preferred embodiments to facilitate understanding. While the present disclosure is described hereinafter based on the Examples, the above descriptions and the following Examples are provided for the sole purpose of exemplification, not limitation of the present disclosure. Thus, the scope of the present disclosure is not limited to the embodiments and Examples that are specifically described herein and is limited only by the scope of claims.

EXAMPLES

The present disclosure are described more specifically with the Reference Examples, Examples, and Test Example hereinafter, but the present invention is not limited thereto.

The present specification may use the following abbreviations.
Ts: p-toluenesulfonyl
THF: tetrahydrofuran
TFA: trifluoroacetic acid
DMF: N,N-dimethylformamide
DMSO: dimethyl sulfoxide
MeCN: acetonitrile
Me: methyl
Boc: tert-butoxycarbonyl
Dess-Martin reagent: Dess-Martin periodinane(1,1,1-triacetoxy-1,1-dihydro-1,2-benziodoxol-3-(1H)-one)

NMR (Nuclear Magnetic Resonance) data used for identifying a compound was obtained with JNM-ECS 400 NMR spectrometer (400 MHz) (JEOL Ltd.)

As symbols used in NMR, s refers to singlet, d refers to doublet, dd refers to doublet of doublets, t refers to triplet, td refers to doublet of triplets, q refers to quartet, m refers to multiplet, br refers to broad, brs refers to broad singlet, brm refers to broad multiplet, and J refers to a coupling constant.

LC/MS (Liquid Chromatography-Mass Spectrometry) analysis conditions used in identification of compounds are as follows. Among the observed mass spectrometry values [MS (m/z)], a value corresponding to monoisotopic mass (precise mass consisting of only the primary isotope) is indicated by [M+H]$^+$, [M−H]$^-$, [M+2H]$^{2+}$, or the like, and the time of retention is indicated by Rt (minutes).
Measurement Condition A
Detector: ACQUITY® SQ detector (Waters)
HPLC: ACQUITY UPLC® system
Column: Waters ACQUITY UPLC® BER C18 (1.7 µm, 2.1 mm×30 mm)
Solvent: solution A: 0.06% formic acid/H$_2$0, solution B: 0.06% formic acid/MeCN
Gradient condition: 0.0-1.3 min Linear gradient from B 2% to 96%
Flow rate: 0.8 mL/min
UV: 220 nm and 254 nm
Column temperature: 40° C.
Measurement Condition B
Detector: APCI 6120 Quadrupole LC/MS (Agilent Technologies)
HPLC: Agilent Technologies 1260 Infinity) system
Column: Agilent Technologies® ZORBAX SB-C18 (1.8 µm, 2.1 mm×50 mm)
Solvent: solution A: 0.1% formic acid/H$_2$O, solution B: MeCN
Gradient condition: 0.0-5.0 min Linear gradient from B 5% to 90:%
Flow rate: 0.6 mL/min
UV: 210 nm, 254 nm, and 280 nm
Column temperature: 40° C.
Measurement Condition C
Detector: Shimadzu LCMS-2020
Column: L-column-2 ODS (4.6 mm×35 mm)
Gradient condition: MeCN/H$_2$O/HCO$_2$H=10/90/0.1→100/0/0.1 (0-2 min), 100/0/0.1 (2-4 min)
Flow rate: 2 mL/min
Column temperature: 40° C.

Reference Example 1 tert-butyl 3-{[(4-acetyl-5-methoxypyridin-3-yl)oxy]methyl}-3-fluoroazetidine-1-carboxylate

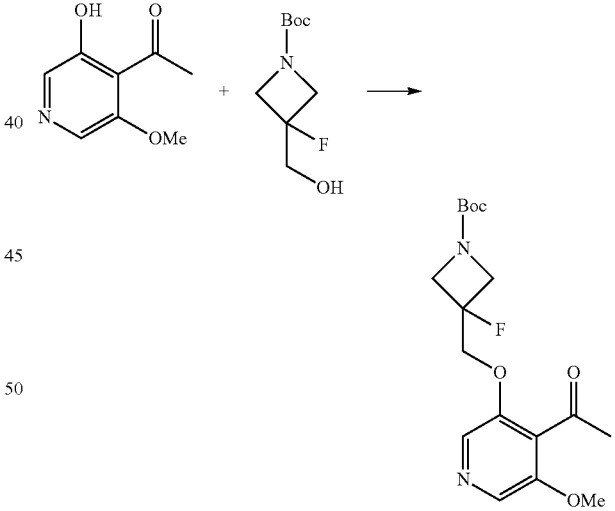

Reference Example 1

Manufacture of tert-butyl 3-{[(4-acetyl-S-methoxypyridin-3-yl)oxy]methyl}-3-fluoroazetidine-1-carboxylate (Reference Example 1)

tert-butyl 3-fluoro-3-(hydroxymethyl)azetidine-1-carboxylate (1.85 g) and triphenylphosphine (3.15 g) were added to a THF (50.0 mL) solution of 1-(3-hydroxy-5-methoxy-4-pyridinyl)ethanone (1.00 g) at room temperature, and the mixture was cooled to 0° C. Diisopropyl azodicarboxylate (2.5 mL) was added and stirred for 12 hours at 0° C. Saturated saline was added to the reaction solution, which was extracted with ethyl acetate. The organic layer was dried with anhydrous sodium sulfate then filtered, and the solvent was evaporated under reduced pressure. The residue was purified by silica gel column chromatography (hexane/ethyl acetate) to obtain Reference Example 1 (720 mg).

LC-MS; [M+H]$^+$ 355.2/Rt (minutes) 0.886 (measurement condition A)

Reference Example 2 tert-butyl 3-{[(3-acetyl-2-methoxypyridin-4-yl)oxy]methyl}-3-(hydroxymethyl)azetidine-1-carboxylate

[Chemical Formula 37]

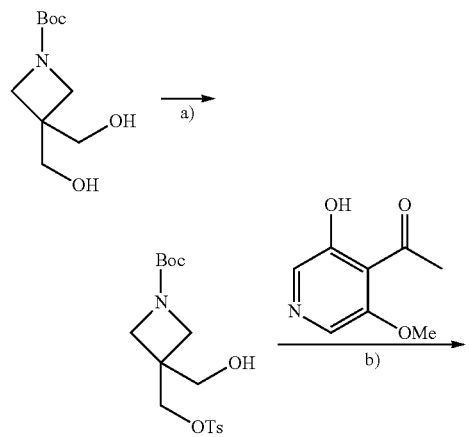

Reference Example 2 a) Manufacture of tert-butyl 3-(hydroxymethyl)-3-{[(4-methylbenzene-1-sulfonyl)oxy]methyl}azetidine-1-carboxylate Pyridine (5.60 mL), trimethylamine hydrochloride (0.13 g), and para-toluenesulfonyl chloride (1.45 g) were added to a methylene chloride (20.0 mL) solution of tert-butyl 3,3-bis(hydroxymethyl) azetidine-1-carboxylate (1.50 g) at 0° C., and the mixture was stirred for 12 hours at room temperature. Saturated saline was added to quench the reaction solution, and the mixture was then extracted with ethyl acetate. The organic layer was dried with anhydrous sodium sulfate and then filtered, and the solvent was evaporated under reduced pressure to obtain the title compound (2.30 g). The resulting residue was used in the subsequent reaction without purification.

LC-MS; [M+H]$^+$ 372.1/Rt (minutes) 0.928 (measurement condition A)

b) Manufacture of tert-butyl 3-{[(3-acetyl-2-methoxypyridin-4-yl)oxy]methyl}-3-(hydroxymethyl)azetidine-1-carboxylate (Reference Example 2)

1-(4-hydroxy-2-methoxy-3-pyridinyl)ethanone (1.00 g) and cesium carbonate (7.80 g) were added to a DMF (10.0 mL) solution of tert-butyl 3-(hydroxymethyl)-3-{[(4-methylbenzene-1-sulfonyl)oxy]methy 1}azetidine-1-carboxylate (2.30 g), and the mixture was stirred for 12 hours at room temperature. Saturated saline was added to the reaction solution, which was extracted with ethyl acetate. The organic layer was dried with anhydrous sodium sulfate and then filtered, and the solvent was evaporated under reduced pressure. The residue was purified by silica gel column chromatography (hexane/ethyl acetate) to obtain Reference Example 2 (1.01 g).

LC-MS; [M+H]$^+$ 367.3/Rt (minutes) 0.796 (measurement condition A)

Reference Example 3 tert-butyl(3-{[3-(3-amino-1H-pyrazol-5-yl)-4-methoxypyridin-2-yl]oxy}propyl) carbamate

[Chemical Formula 38]

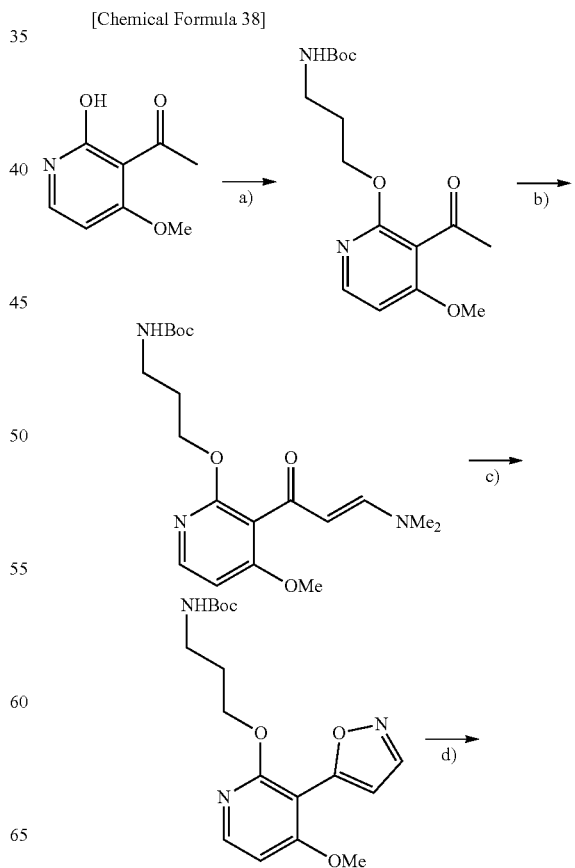

-continued

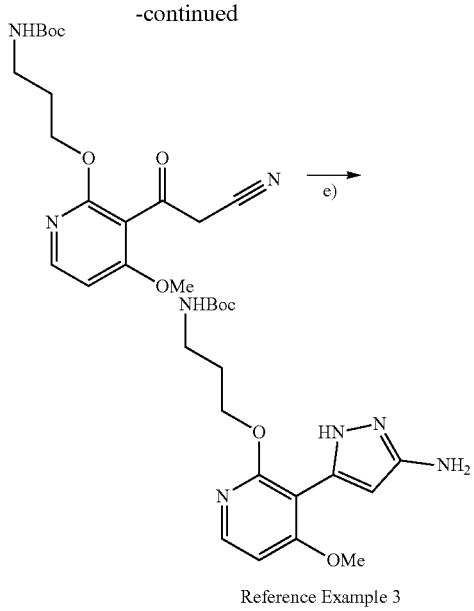

Reference Example 3 a) Manufacture of tert-butyl {3-[(3-acetyl-4-methoxypyridin-2-yl}oxy]propyl)carbamate Cesium carbonate (7.80 g) and 3-(Boc-amino) propylbromide (4.27 g) were added to a DMF (40.0 mL) solution of 1-(2-hydroxy-4-methoxypyridin-3-yl)ethanone (2.00 g) at 0° C., and the mixture was stirred for 12 hours at room temperature. Saturated saline was added to the reaction solution, which was extracted with ethyl acetate. The organic layer was dried with anhydrous sodium sulfate and then filtered, and the solvent was evaporated under reduced pressure. The residue was purified by silica gel column chromatography (hexane/ethyl acetate) to obtain the title compound (2.25 g).

LC-MS; [M+H]$^+$ 325.2/Rt (minutes) 0.959 (measurement condition A)

1H-NMR (CDCl$_3$) δ: 8.06 (1H, d, J=6.0 Hz), 6.55 (1H, d, J=6.0 Hz), 4.97 (1H, brs), 4.40 (2H, t, J=6.4 Hz), 3.86 (3H, s), 3.27-3.24 (2H, m), 2.49 (3H, s), 1.96-1.90 (2H, m), 1.44 (9H, s).

b) Manufacture of tert-butyl [3-({3-[(2E)-3-(dimethylamino)prop-2-enyl]-4-methoxypyridin-2-yl}oxy)propyl]carbamate N,N-dimethylformamide dimethylacetal (10.0 mL) was added to a DMF (10.0 mL) solution of tert-butyl {3-[(3-acetyl-4-methoxypyridin-2-yl)oxy]propyl}carbamate (2.25 g). The mixture was stirred for 24 hours at 115° C. After allowing the reaction solution to cool, the solvent thereof was evaporated under reduced pressure to obtain the title compound (4.30 g) as a crude product.

LC-MS; [M+H]$^+$ 380.3/Rt (minutes) 0.722 (measurement condition A)

c) Manufacture of tert-butyl (3-{[4-methoxy-3-(1,2-oxazol-5-yl)pyridin-2-yl]oxy}propyl)carbamate Hydroxyamine hydrochloride (5.49 g) was added to an ethanol (30.0 mL) solution of tert-butyl [3-({3-[(2E)-3-(dimethylamino)prop-2-enyl]-4-methoxypyridin-2-yl}oxy) propyl]carbamate (4.30 g). The mixture was stirred for 2 hours at 65° C. After allowing the reaction solution to cool, the reaction solution was added to an aqueous saturated sodium bicarbonate solution and quenched. The resulting aqueous solution was extracted twice with ethyl acetate. The resulting organic layer was washed with saturated saline, dried with anhydrous sodium sulfate and then filtered, and the solvent was evaporated under reduced pressure. The residue was purified by silica gel column chromatography (hexane/ethyl acetate) to obtain the title compound (1.63 g).

LC-MS; [M+H]$^+$ 350.2/Rt (minutes) 0.722 (measurement condition A)

1H-NMR (CDCl$_3$) δ: 8.32 (1H, d, J=1.6 Hz), 8.12 (1H, d, J=6.0 Hz), 6.64 (1H, d, J=6.0 Hz), 6.59 (1H, d, J=1.6 Hz), 4.87 (1H, brs), 4.45 (2H, t, J=6.4 Hz), 3.92 (3H, s), 3.28-3.24 (2H, m), 1.99-1.93 (2H, m), 1.44 (9H, s).

d) Manufacture of tert-butyl(3-{[3-(cyanoacetyl)-4-methoxypyridin-2-yl]oxy}propyl)carbamate Potassium hydroxide (0.29 g) was added to a mixture of ethanol (20.0 mL) and water (5.00 mL) of tert-butyl(3-{[4-methoxy-3-(1,2-oxazol-5-yl)pyridin-2-yl]oxy}propyl) carbamate (1.63 g). The mixture was stirred for 5 hours at room temperature. The reaction solution was concentrated under reduced pressure. The residue was added with saturated saline for quenching. The resulting aqueous solution was extracted twice with ethyl acetate. The resulting organic layer was washed with saturated saline, dried with anhydrous sodium sulfate and then filtered, and the solvent was evaporated under reduced pressure. The residue was purified by silica gel column chromatography (hexane/ethyl acetate) to obtain the title compound (1.50 g).

LC-MS; [M+H]$^+$ 350.2/Rt (minutes) 0.872 (measurement condition A)

1H-NMR (CDCl$_3$) δ: 8.14 (1H, d, J=6.0 Hz), 6.59 (1H, d, J=6.0 Hz), 4.94 (1H, brs), 4.44 (2H, t, J=6.0 Hz), 3.92 (3H, s), 3.29-3.23 (2H, m), 1.99-1.93 (2H, m), 1.43 (9H, s).

e) Manufacture of tert-butyl(3-{[3-(3-amino-1H-pyrazol-5-yl)-4-methoxypyridin-2-yl]oxy}propyl) carbamate (Reference Example 3)

Acetic acid (3.28 mL) and hydrazine monohydrate (2.78 mL) were added to an ethanol (20.0 mL) solution of tert-butyl (3-{[3-(cyanoacetyl)-4-methoxypyridin-2-yl]oxy}propyl)carbamate (1.99 g) at 0° C. The mixture was stirred for 24 hours at 90° C. After allowing the reaction solution to cool, the reaction solution was added to an aqueous saturated sodium bicarbonate solution and quenched. The resulting aqueous solution was extracted twice with chloroform. The resulting organic layer was washed with saturated saline, dried with anhydrous sodium sulfate, and then filtered, and the solvent was evaporated under reduced pressure. The residue was purified by silica gel column chromatography (chloroform/methanol) to obtain Reference Example 3 (1.60 g).

LC-MS; [M+H]$^+$ 364.0/Rt (minutes) 0.684 (measurement condition A)

1H-NMR (DMSO-D6) δ: 11.61-10.91 (1H, brs), 8.01 (1H, d, J=12.0 Hz), 6.93-6.89 (1H, m), 6.84 (1H, d, J=6.0 Hz), 5.93 (1H, brs), 4.50 (1H, brs), 4.32 (2H, t, J=6.4 Hz), 3.89 (3H, s), 3.09-3.04 (2H, m), 1.86-1.79 (2H, m), 1.37 (9H, s).

Reference Example 4 tert-butyl(3-{[3-(3-amino-1H-pyrazol-5-yl)-6-chloro-4-methoxypyridin-2-yl]oxy}propyl) carbamate

[Chemical Formula 39]

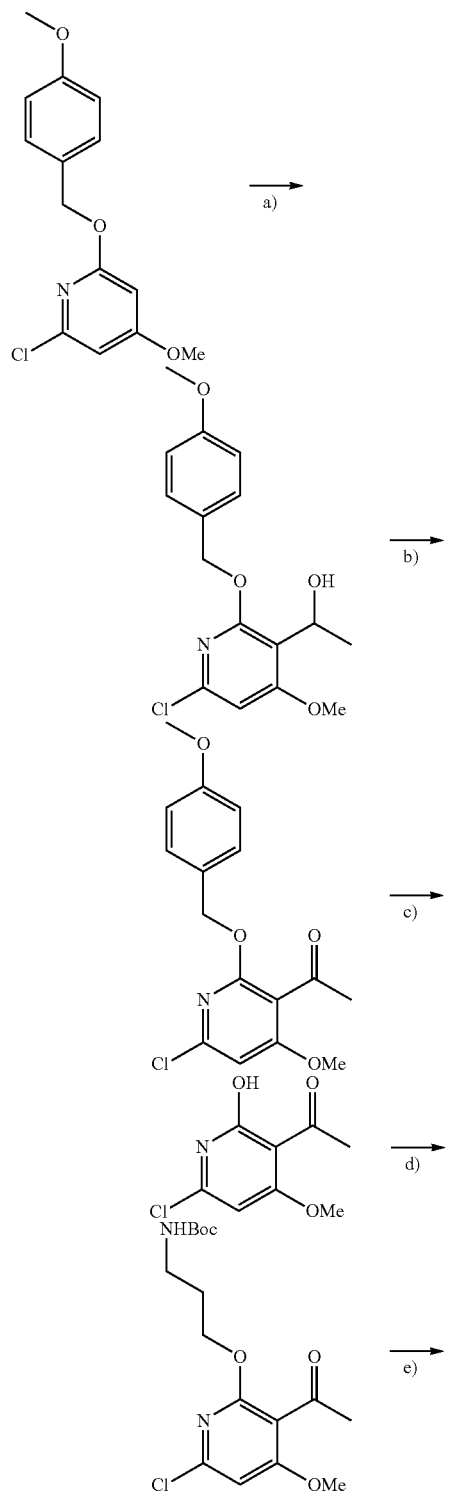

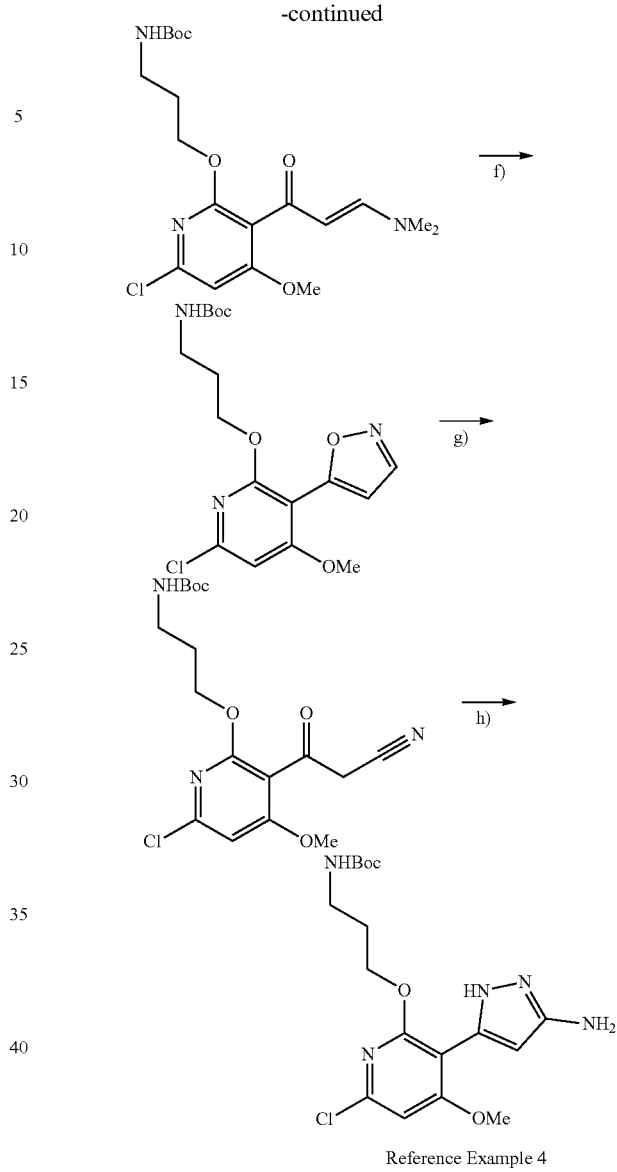

Reference Example 4 a) Manufacture of 1-{6-chloro-4-methoxy-2-[(4-methoxyphenyl)methoxy]pyridin-3-yl}ethan-1-ol A THF (100 mL) solution of 2-chloro-4-methoxy-6-[(4-methoxybenzyl)oxy]pyridine (10.0 g) was cooled to −78° C. 2.8 mol/L n-butyllithium (15.3 mL) was added, and the mixture was stirred for 3 hours at −78° C. Acetamide (6.30 mL) was added, and the mixture was stirred for 6 hours at −78° C. The reaction solution was added with an aqueous saturated sodium bicarbonate solution and quenched, which was extracted with ethyl acetate. The organic layer was dried with anhydrous sodium sulfate and then filtered, and the solvent was evaporated under reduced pressure. The residue was purified by silica gel column chromatography (hexane/ethyl acetate) to obtain the title compound (4.25 g).

LC-MS; [M+H]$^+$ 324.2/Rt (minutes) 1.118 (measurement condition A)

1H-NMR (CDCl$_3$) δ: 7.36 (2H, d, J=8.8 Hz), 6.89 (2H, d, J=8.8 Hz), 6.55 (1H, s), 5.32 (2H, s), 5.16-5.11 (1H, m), 3.85 (0.3H, s), 3.80 (3H, s), 3.30 (1H, s), 1.41 (3H, d, J=6.8 Hz).

13C-NMR (CDCl$_3$) δ: 165.2, 159.6, 147.6, 130.1, 128.6, 114.1, 112.6, 101.8, 68.7, 62.9, 56.3, 55.4, 23.1.

b) Manufacture of 1-{6-chloro-4-methoxy-2-[(4-methoxyphenyl)methoxy]pyridin-3-yl}ethan-1-one A Dess-Martin reagent (6.19 g) was added to a methylene chloride (100 mL) solution of 1-{6-chloro-4-methoxy-2-[(4-methoxyphenyl)methoxy]pyridin-3-yl}ethan-1-ol (3.15 g). The mixture was stirred for 12 hours at room temperature. The reaction solution was added with an aqueous saturated sodium bicarbonate solution and quenched. The resulting aqueous solution was extracted twice with ethyl acetate. The resulting organic layer was washed with saturated saline, dried with anhydrous sodium sulfate, and then filtered, and the solvent was evaporated under reduced pressure. The residue was purified by silica gel column chromatography (hexane/ethyl acetate) to obtain the title compound (2.50 g).

LC-MS; [M+H]$^+$ 322.2/Rt (minutes) 1.081 (measurement condition A)

C) Manufacture of 1-(6-chloro-2-hydroxy-4-methoxypyridin-3-yl)ethan-1-one

TFA (6.00 mL) was added to a methylene chloride (30.0 mL) solution of 1-{6-chloro-4-methoxy-2-[(4-methoxyphenyl)methoxy]pyridin-3-yl}ethan-1-one (2.50 g). The mixture was stirred for 2 hours at room temperature. The solvent was evaporated under reduced pressure, and the residue was purified by amine silica gel column chromatography (chloroform/methanol) to obtain the title compound (2.00 g).

LC-MS; (M+H1V 202.1/Rt (minutes) 0.773 (measurement condition A)

d) Manufacture of tert-butyl {3-[(3-acetyl-6-chloro-4-methoxypyridin-2-yl)oxy]propyl}carbamate Cesium carbonate (9.70 g) and 3-(Boc-amino) propylbromide (5.63 g) were added to a DMF (50.0 mL) solution of 1-(6-chloro-2-hydroxy-4-methoxypyridin-3-yl)ethan-1-one (3.00 g) at 0° C. The mixture was stirred for 12 hours at room temperature. Saturated saline was added to the reaction solution, which was extracted with ethyl acetate. The organic layer was dried with anhydrous sodium sulfate and then filtered, and the solvent was evaporated under reduced pressure. The residue was purified by silica gel column chromatography (hexane/ethyl acetate) to obtain the title compound (1.01 g).

LC-MS; [M+H]$^+$ 359.3/Rt (minutes) 1.123 (measurement condition A)

e) Manufacture of tert-butyl [3-({6-chloro-3-[(2E)-3-(dimethylamino)prop-2-enyl]-4-methoxypyridin-2-yl}oxy)propyl]carbamate N,N-dimethylformamide dimethylacetal (3.00 mL) was added to a DMF (10.0 mL) solution of tert-butyl {3-[(3-acetyl-6-chloro-4-methoxypyridin-2-yl)oxy] propyl}carbamate (840 mg). The mixture was stirred for 24 hours at 115° C. After allowing the reaction solution to cool, the solvent of the reaction solution was evaporated under reduced pressure to obtain the title compound (0.97 g) as a crude product.

LC-MS; [M+H]$^+$ 414.4/Rt (minutes) 0.944 (measurement condition A)

f) Manufacture of tert-butyl(3-{[6-chloro-4-methoxy-3-(1,2-oxazol-5-yl)pyridin-2-yl]oxy}propyl)carbamate Hydroxyamine hydrochloride (1.70 g) was added to an ethanol (30.0 mL) solution of tert-butyl [3-({6-chloro-3-[(2E)-3-(dimethylamino)prop-2-enyl]-4-methoxypyridin-2-yl}oxy)propyl]carbamate (0.97 g). The mixture was stirred for 2 hours at 65° C. After allowing the reaction solution to cool, the reaction solution was added to an aqueous saturated sodium bicarbonate solution and quenched. The resulting aqueous solution was extracted twice with ethyl acetate. The resulting organic layer was washed with saturated saline, dried with anhydrous sodium sulfate, and then filtered, and the solvent was evaporated under reduced pressure. The residue was purified by silica gel column chromatography (hexane/ethyl acetate) to obtain the title compound (677 mg).

LC-MS; [M+H]$^+$ 384.3/Rt (minutes) 1.132 (measurement condition A)

g) Manufacture of tert-butyl (3-{[6-chloro-3-(cyanoacetyl)-4-methoxypyridin-2-yl]oxy}propyl)carbamate Potassium hydroxide (100 mg) was added to a mixture of ethanol (20.0 mL) and water (5.00 mL) of tert-butyl(3-{[6-chloro-4-methoxy-3-(1,2-oxazol-5-yl)pyridin-2-yl]oxy}propyl)carbamate (677 mg). The mixture was stirred for 2 hours at room temperature. The reaction solution was concentrated under reduced pressure. The residue was added to saturated saline and quenched. The resulting aqueous solution was extracted twice with ethyl acetate. The resulting organic layer was washed with saturated saline, dried with anhydrous sodium sulfate, and then filtered, and the solvent was evaporated under reduced pressure. The residue was purified by silica gel column chromatography (hexane/ ethyl acetate) to obtain the title compound (470 mg).

LC-MS; [M+H]$^+$ 384.3/Rt (minutes) 1.064 (measurement condition A)

h) Manufacture of tert-butyl(3-([3-{3-amino-1H-pyrazol-5-yl)-6-chloro-4-methoxypyridin-2-yl] oxy}propyl)carbamate (Reference Example 4)

Acetic acid (0.71 mL) and hydrazine monohydrate (0.77 mL) were added to an ethanol (20.0 mL) solution of tert-butyl (3-{([6-chloro-3-(cyanoacetyl)-4-methoxypyridin-2-yl]oxy}propyl)carbamate (470 mg) at 0° C. The mixture was stirred for 24 hours at 90° C. After allowing the reaction solution to cool, the reaction solution was added to an aqueous saturated sodium bicarbonate solution and quenched. The resulting aqueous solution was extracted twice with chloroform. The resulting organic layer was washed with saturated saline, washed with anhydrous sodium sulfate, and then filtered, and the solvent was evaporated under reduced pressure. The residue was purified by silica gel column chromatography (chloroform/methanol) to obtain Reference Example 4 (350 mg).

LC-MS; [M+H]$^+$ 398.3/Rt (minutes) 0.911 (measurement condition A)

Reference Example 5

1-(4-hydroxy-6-methoxypyrimidin-5-yl)ethan-1-one

[Chemical Formula 40]

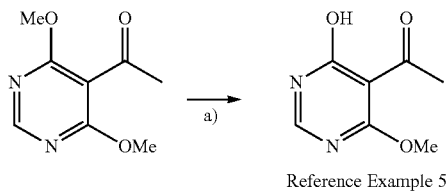

Reference Example 5 a) Manufacture of 1-(4-hydroxy-6-methoxypyrimidin-5-yl)ethan-1-one

A dichloromethane solution (1.0 mol/L, 54.9 mL) of boron tribromide was added to a dichloromethane (30.0 mL) solution of 1-(4,6-dimethoxypyrimidin-5-yl)ethan-1-one (2.00 g) at −60° C. The mixture was stirred for 3 hours at −50° C. or lower. The reaction solution was added with saturated saline and quenched, and then extracted with chloroform. The organic layer was washed with saturated saline, dried with anhydrous sodium sulfate, and then filtered, and the solvent was evaporated under reduced pressure. The residue was purified by silica gel column chromatography (methanol/chloroform) to obtain the title compound (220 mg).

LC-MS; [M+H]$^+$ 169.1/Rt (minutes) 0.367 (measurement condition A)

1H-NMR (CDCl$_3$) δ: 14.31 (1H, brs), 8.36 (1H, s), 4.10 (3H, s), 2.65 (3H, s).

Reference Example 6 tert-butyl(3-{[4-acetyl-5-(fluoromethoxy)pyridin-3-yl]oxy}propyl)carbamate

[Chemical Formula 41]

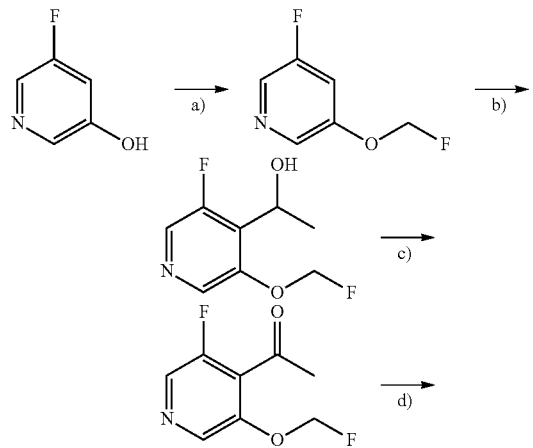

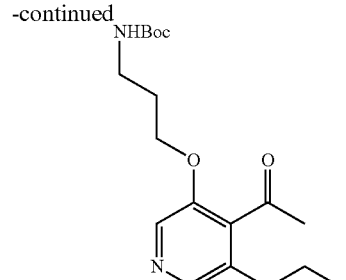

Reference Example 6 a) Manufacture of 3-fluoro-5-(fluoromethoxy)pyridine

Cesium carbonate (4.32 g) and fluoromethyl 4-methylbenzenesulfonate (2.17 g) were added to a DMF (30.0 mL) solution of 5-fluoropyridin-3-ol (1.00 g) at room temperature. The mixture was heated and stirred for 8 hours at 80° C. Water was added to the reaction solution, which was extracted with diethyl ether. The organic layer was dried with anhydrous sodium sulfate and then filtered, and the solvent was evaporated under reduced pressure. The residue was purified by silica gel column chromatography (hexane/ethyl acetate) to obtain the title compound (538 mg).

LC-MS; [M+H]$^+$ 146.0/Rt (minutes) 0.574 (measurement condition A)

b) Manufacture of 1-[3-fluoro-5-(fluoromethoxy)pyridin-4-yl]ethan-1-ol

A THF (15 mL) solution of N,N-diisopropylethylamine (0.687 mL) was cooled to −78° C., and n-butyllithium (1.58 moL/L, 3.05 mL) was added. The mixture was stirred for 15 minutes at 0° C. The reaction solution was cooled again to −78° C., and 3-fluoro-5-(fluoromethoxy)pyridine (538 mg) was added. After stirring for 1 hour, acetaldehyde (0.419 mL) was added. The reaction solution was gradually warmed to room temperature and stirred overnight. Water was then added to the reaction solution, which was extracted with ethyl acetate. The organic layer was dried with anhydrous sodium sulfate and then filtered, and the solvent was evaporated under reduced pressure. The residue was purified by silica gel column chromatography (hexane/ethyl acetate) to obtain the title compound (475 mg).

LC-MS; [M+H]$^+$ 190.1/Rt (minutes) 0.494 (measurement condition A)

1H-NMR (CDCl3) δ: 8.30 (1H, d, J=1.8 Hz), 8.26 (1H, s), 5.85 (1H, dd, J=6.7, 3.1 Hz), 5.71 (1H, dd, J=7.2, 3.2 Hz), 5.31-5.22 (1H, m), 2.60 (1H, dd, J=9.8, 1.8 Hz), 1.59 (3H, d, J=6.7 Hz).

C) Manufacture of 1-[3-fluoro-5-(fluoromethoxy)pyridin-4-yl]ethan-1-one

A dichloromethane (10.0 mL) solution of 1-[3-fluoro-5-(fluoromethoxy)pyridin-4-yl]ethan-1-ol (475 mg) was cooled with ice, and a Dess-Martin reagent (1.60 g) was added. The mixture was stirred overnight at room temperature. An aqueous sodium thiosulfate solution and aqueous saturated sodium bicarbonate solution were added to the reaction solution, which was extracted with chloroform. The resulting organic layer was dried with anhydrous sodium sulfate, and then filtered, and the solvent was evaporated under reduced pressure. The residue was purified by silica gel column chromatography (hexane/ethyl acetate) to obtain the title compound (407 mg).

LC-MS; [M+H]⁺ 188.0/Rt (minutes) 0.618 (measurement condition A)

d) Manufacture of tert-butyl(3-{[4-acetyl-5-(fluoromethoxy)pyridin-3-yl]oxy}propyl)carbamate tert-butyl (3-hydroxypropyl) carbamate (762 mg) was added to a DMF (10.0 mL) solution of 1-[3-fluoro-5-(fluoromethoxy)pyridin-4-yl]ethan-1-one (407 mg) and cesium carbonate (1.42 g), and the mixture was heated and stirred for 8 hours at 80° C. Water was added to the reaction solution, which was extracted with diethyl ether. The organic layer was dried with anhydrous sodium sulfate and then filtered, and the solvent was evaporated under reduced pressure. The residue was purified by silica gel column chromatography (hexane/ethyl acetate) to obtain the title compound (67 mg).

LC-MS; [M+H]⁺ 343.2/Rt (minutes) 0.832 (measurement condition A)

1H-NMR (CDCl3) δ: 8.22 (1H, d, J=1.8 Hz), 8.16 (1H, s), 5.68 (2H, d, J=5.3.6 Hz), 4.70 (1H, brs), 4.15 (2H, t, J=6.1 Hz), 3.32-3.21 (2H, m), 2.50 (3H, s), 2.00-1.93 (2H, m), 1.41 (9H, s).

Reference Example 7 tert-butyl(3-{[4-methoxy-3-(1,2-oxazol-5-yl)pyridin-2-yl]oxy}propyl)carbamate

[Chemical Formula 42]

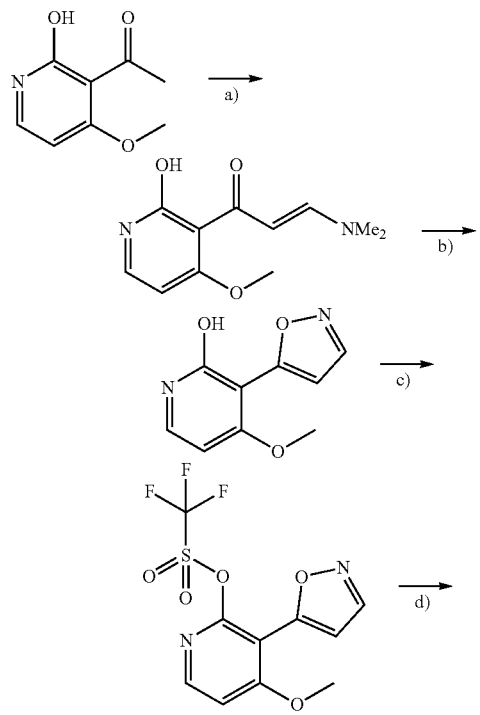

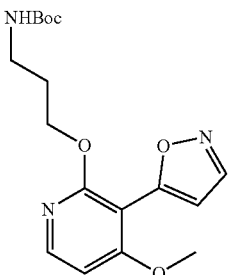

Reference Example 7 a) Manufacture of (2E)-3-(dimethylamino)-1-(2-hydroxy-4-methoxypyridin-3-yl)prop-2-en-1-one tert-butoxybis(dimethylamino)methane (5.21 g) was added to a mixture of 1-(2-hydroxy-4-methoxypyridin-3-yl) ethanone (2.50 g) and toluene (6.23 ml). The mixture was heated and stirred for 6 hours at 55° C. After allowing the mixture to cool, toluene (18.6 ml) was added dropwise. The resulting crystal was collected by filtration and washed with toluene. The crystal was vacuum dried to obtain the title compound (2.87 g). The filtrate was concentrated under reduced pressure. The crystal deposited out from an ethanol/toluene mixture was washed with an ethanol/toluene mixture and vacuum dried to obtain a second crop (0.20 g) of the title compound.

LC-MS; [M+H]⁺ 223.1/Rt (minutes) 1.564

1H-NMR (DMSO-D6) δ: 11.25 (1H, br s), 7.39 (1H, d, J=6.7 Hz), 7.11 (1H, br s), 6.21 (1H, d, J=7.9 Hz), 5.00 (1H, d, J=11.0 Hz), 3.73 (3H, s), 3.00 (3H, br s), 2.75 (3H, br s).

b) Manufacture of 4-methoxy-3-(1,2-oxazol-5-yl)pyridin-2-ol

Hydroxyamine hydrochloride (1.56 g) was added to a mixture of (2E)-3-(dimethylamino)-1-(2-hydroxy-4-methoxypyridin-3-yl)prop-2-en-1-one (2.50 g) and ethanol (37.5 ml). The mixture was stirred for 16 hours at room temperature. Water (37.5 ml) was added to the reaction mixture. The mixture was concentrated under reduced pressure until reaching 28.5 g. Water (9.0 ml) was then further added. The mixture was stirred at 0° C. The resulting crystal was collected by filtration, washed with cold water, and vacuum dried to obtain the title compound (1.53 g).

LC-MS; [M+H]+ 193.1/Rt (minutes) 0.928

1H-NMR (DMSO-D6) δ: 11.83 (1H, br s), 8.51 (1H, d, J=1.8 Hz), 7.61 (1H, d, J=7.3 Hz), 6.83 (1H, d, J=1.8 Hz), 6.38 (1H, d, J=7.3 Hz), 3.93 (3H, s).

c) Manufacture of 4-methoxy-3-(1,2-oxazol-5-yl)pyridin-2-yl trifluoromethanesulfonate Trifluoromethanesulfonic acid anhydride (2.16 g) was added dropwise to a mixture of 4-methoxy-3-(1,2-oxazol-5-yl)pyridin-2-ol (1.23 g) and pyridine (6.1 ml) at 0° C. The reaction mixture was warmed, and stirred for 16 hours at room temperature. The reaction mixture was cooled to 0° C. Water (16 ml) was added dropwise. The mixture was stirred for 1.5 hours at 0° C. The resulting crystal was collected by filtration, washed with a water/pyridine mixture and then water, and vacuum dried to obtain the title compound (1.91 g).

LC-MS; [M+H]⁺ 325.0/Rt (minutes) 4.781

1H-NMR (CDCl3) δ: 8.37 (1H, d, J=1.8 Hz), 8.32 (1H, d, J=6.1 Hz), 7.01 (1H, d, J=6.1 Hz), 6.67 (1H, d, J=1.8 Hz), 4.00 (3H, s).

d) Manufacture of tert-butyl(3-{[4-methoxy-3-(1,2-oxazol-5-yl)pyridin-2-yl]oxy}propyl)carbamate Diisopropylethylamine (72 mg) was added to a mixture of 4-methoxy-3-(1,2-oxazol-5-yl)pyridin-2-yl trifluoromethanesulfonate (50 mg), tert-butyl (3-hydroxypropyl) carbamate (54 mg), 4,5-bis(diphenylphosphino)-9,9-dimethylxanthene (18 mg), tris(dibenzylideneacetone)dipalladium(0) chloroform adduct (16 mg), and toluene (1.5 ml). The mixture was heated and stirred for 4 hours at 100° C. After allowing the reaction mixture to cool, the insoluble matter was filtered out with celite, and the mixture was washed with ethyl acetate. The filtrate was concentrated, and the residue was purified by silica gel column chromatography (hexane/ethyl acetate) to obtain the title compound (30 mg).

LC-MS; [M+H]+ 350.2/Rt (minutes) 4.647

Reference Example 8 to 41

The compounds in Reference Example 8 to 41 shown in the following table were obtained by the similar method to the method described in Reference Examples 1-7 by using a corresponding raw material compound.

TABLE 1-1

| Reference Example | Structural formula | LC-MS; [M + H]+ Time of retention (minutes) | Measurement condition |
|---|---|---|---|
| 8 | | 364.3/0.724 | A |
| 9 | | 364.3/0.722 | A |
| 10 | | 394.3/0.660 | A |
| 11 | | 390.6/0.714 | A |

TABLE 1-2

| | | | |
|---|---|---|---|
| 12 | [structure with Boc-azetidine-OH, CH2O, pyridine-OMe, pyrazole-NH2] | 392.4/ 0.632 | A |
| 13 | [structure with Boc-azetidine-CH2OH, OCH2, pyridine-OMe, pyrazole-NH2] | 406.4/ 0.658 | A |
| 14 | [structure with NHBoc, methyl chiral, propyl-O, pyridine-OMe, pyrazole-NH2] | 378.3/ 0.610 | A |
| 15 | [structure with NHBoc, methyl chiral (opposite), propyl-O, pyridine-OMe, pyrazole-NH2] | 378.3/ 0.616 | A |

TABLE 1-3

| | | | |
|---|---|---|---|
| 16 | [NHBoc-CH2-cyclopropyl-CH2-O-pyridine-OMe-pyrazole-NH2] | 390.3/ 0.633 | A |
| 17 | [Boc-morpholine-CH2O-pyridine-OMe-pyrazole-NH2] | 406.3/ 0.624 | A |
| 18 | [Boc-morpholine (opposite chirality)-CH2O-pyridine-OMe-pyrazole-NH2] | 406.4/ 0.638 | A |
| 19 | [NHBoc-CH2-CH(OTBS)-CH2O-pyridine-OMe-pyrazole-NH2] | 494.5/ 0.981 | A |
| 20 | [NHBoc-propyl-O-pyrimidine-OMe-pyrazole-NH2] | 365.3/ 0.678 | A |

TABLE 1-4

| | | | |
|---|---|---|---|
| 21 | [Boc-azetidine-CH2O-pyridine-OMe-pyrazole-NH2] | 376.3/ 0.611 | A |
| 22 | [Boc-NH-cyclohexyl-O-pyridine-OMe-pyrazole-NH2] | 404.4/ 0.688 | A |

TABLE 1-4-continued

| # | Structure | MS/RT | Method |
|---|---|---|---|
| 23 | Boc-pyrrolidine (3-F) -CH2-O-pyridine(OMe)-pyrazole-NH2 | 408.3/0.687 | A |
| 24 | Boc-pyrrolidine-CH2-O-pyridine(OMe)-pyrazole-NH2 | 390.3/0.674 | A |
| 25 | Boc-pyrrolidine(3-F)-CH2-O-pyridine(OMe)-pyrazole-NH2 | 408.3/0.698 | A |

TABLE 1-5

| # | Structure | MS/RT | Method |
|---|---|---|---|
| 26 | NHBoc-CH2-cyclopropyl-CH2-O-pyrimidine(OMe)-pyrazole-NH2 | 391.3/0.777 | A |
| 27 | NHBoc-(CH2)3-O-pyridine(OCH2F)-pyrazole-NH2 | 382.3/0.660 | A |
| 28 | Boc-azetidine(3-Me)-CH2-O-pyridine(OMe)-pyrazole-NH2 | 390.3/0.660 | A |
| 29 | Boc-azetidine(3-CHF2)-CH2-O-pyridine(OMe)-pyrazole-NH2 | 426.3/0.721 | A |

TABLE 1-6

| # | Structure | MS/RT | Method |
|---|---|---|---|
| 30 | NHBoc-CH2-CH(Me)-CH2-O-pyridine(OMe)-pyrazole-NH2 | 378/1.174 | C |
| 31 | NHBoc-CH2-CH(Me)-CH2-O-pyridine(OMe)-pyrazole-NH2 | 378/1.175 | C |
| 32 | NHBoc-CH2-CHF-CH2-O-pyridine(OMe)-pyrazole-NH2 | 382/1.155 | C |
| 33 | NHBoc-CH2-CHF-CH2-O-pyridine(OMe)-pyrazole-NH2 | 382/1.154 | C |

TABLE 1-7
| 34 | 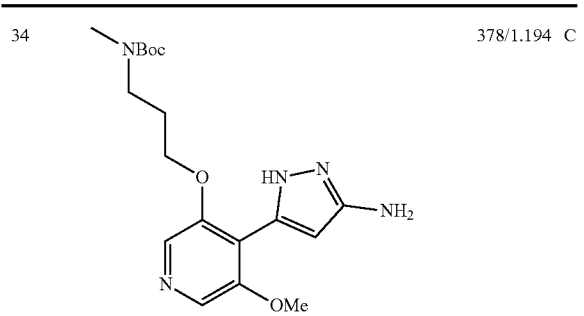 | 378/1.194 C |
| 35 | 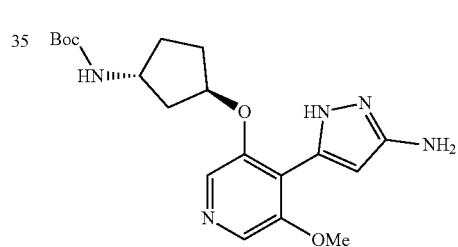 | 390/1.177 C |
| 36 | 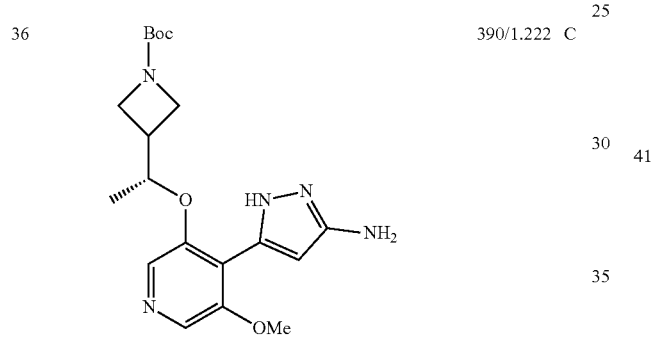 | 390/1.222 C |
| 37 | 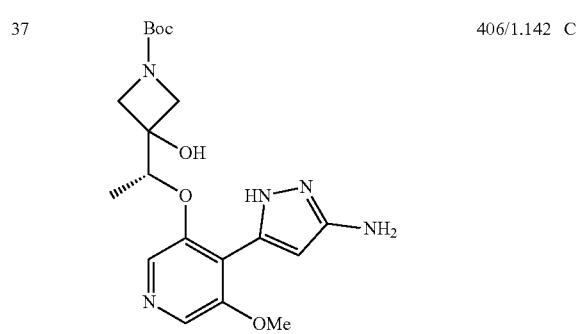 | 406/1.142 C |
TABLE 1-8
| 38 | 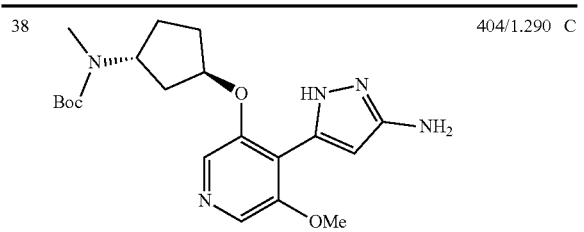 | 404/1.290 C |
TABLE 1-8-continued
| 39 | 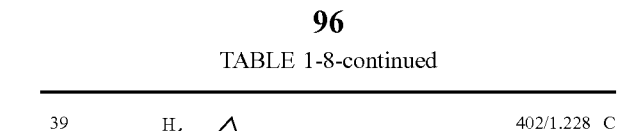 | 402/1.228 C |
| 40 |  | 390/1.344 C |
| 41 |  | 390/1.315 C |
Reference Example 42
tert-butyl {3-[(3-(3-[(5-cyanopyrazin-2-yl)amino]-1H-pyrazol-5-yl}-4-methoxypyridin-2-yl)oxy]propyl)carbamate
[Chemical Formula 43]
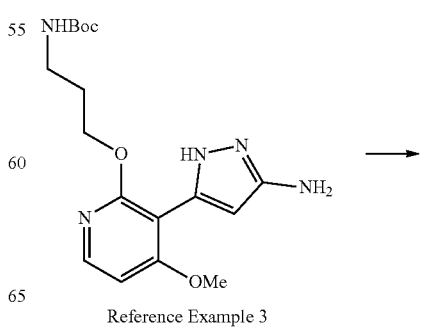
Reference Example 3 →

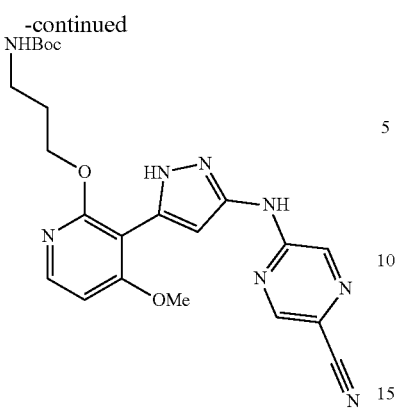

Reference Example 42

4-ethylmorpholine (1.00 mL) and 5-chloropyrazine-2-carbonitrile (461 mg) were added to a DMSO (10.0 mL) solution of tert-butyl(3-{[3-(3-amino-1H-pyrazol-5-yl)-4-methoxypyridin-2-yl]oxy}propyl)carbamate (600 mg) at room temperature. The mixture was stirred for 12 hours at 80° C. Saturated saline was added to the reaction solution, which was extracted with ethyl acetate. The organic layer was dried with anhydrous sodium sulfate and then filtered, and the solvent was evaporated under reduced pressure. The residue was purified by silica gel column chromatography (hexane/ethyl acetate) to obtain the title compound (1.01 g).

LC-MS; [M+H]$^+$ 467.3/Rt (minutes) 0.885 (measurement condition A)

1H-NMR (DMSO-D6) δ: 12.4 (1H, s), 10.7 (1H, s), 8.61 (1H, s), 8.50 (1H, brs), 8.07 (1H, d, J=5.2 Hz), 7.06 (1H, brs), 6.90 (1H, d, J=6.0 Hz), 4.34 (2H, t, J=6.4 Hz), 3.93 (3H, s), 3.14-3.08 (2H, m), 1.87-1.84 (2H, m), 1.35 (9H, s).

Reference Example 43 to 78

The compounds in Reference Examples 43 to 78 shown in the following table were obtained by the similar method to the method described in Reference Example 42 by using a corresponding raw material compound.

TABLE 2-1

| Reference Example | Structural formula | LC-MS: [M + H]$^+$ Time of retention (minutes) | Measurement condition |
|---|---|---|---|
| 43 | | 501.4/1.123 | A |
| 44 | | 467.3/0.898 | A |

TABLE 2-1-continued

| Reference Example | Structural formula | LC-MS: [M + H]+ Time of retention (minutes) | Measurement condition |
|---|---|---|---|
| 45 | (structure) | 467.3/0.885 | A |

TABLE 2-2

| 46 | (structure) | 497.3/0.853 | A |
| 47 | (structure) | 493.4/0.972 | A |

TABLE 2-2-continued

| 48 | (structure) | 495.4/0.849 | A |

TABLE 2-3

| 49 | (structure) | 509.4/0.846 | A |

TABLE 2-3-continued
| 50 | 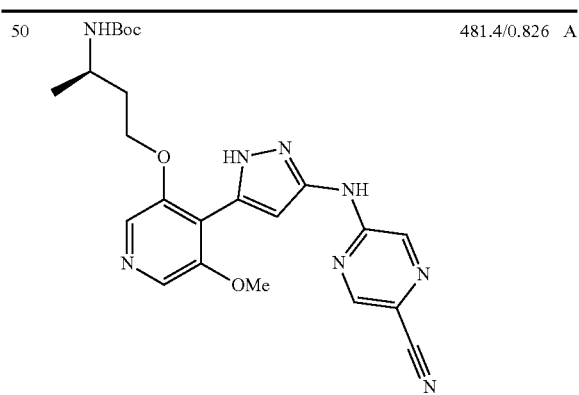 | 481.4/0.826 | A |
|---|---|---|---|
TABLE 2-3-continued
| 51 | 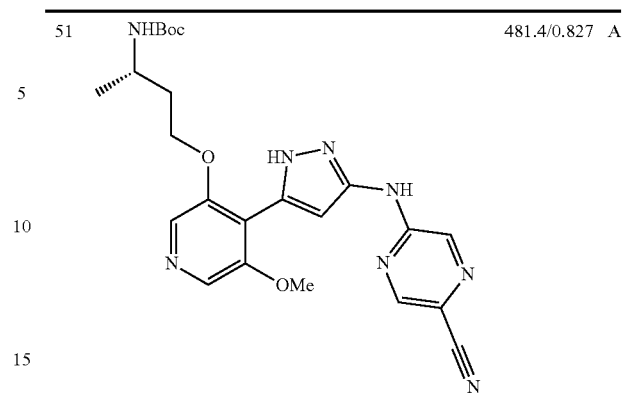 | 481.4/0.827 | A |
|---|---|---|---|
TABLE 2-4
| 52 | 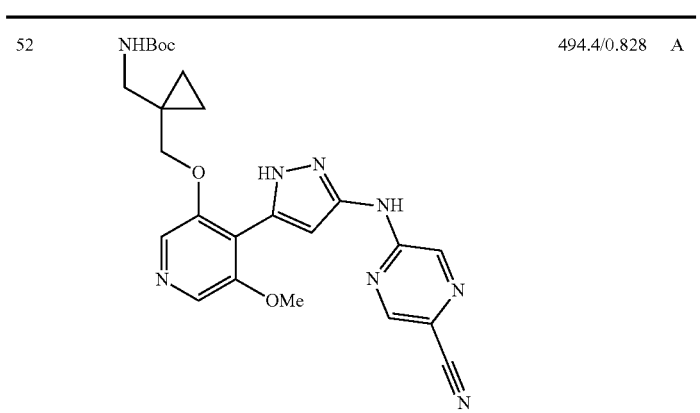 | 494.4/0.828 | A |
|---|---|---|---|
| 53 | 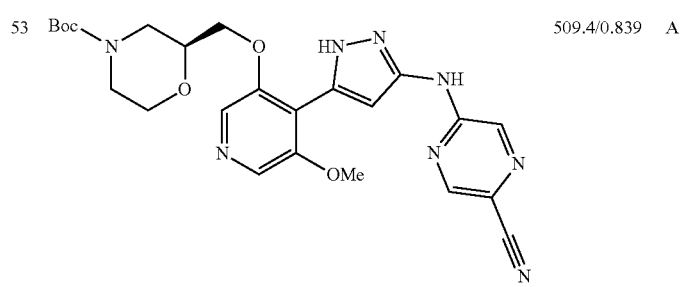 | 509.4/0.839 | A |
| 54 | 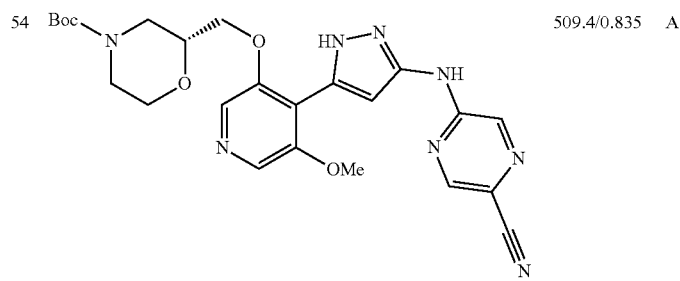 | 509.4/0.835 | A |

TABLE 2-4-continued
| | | |
|---|---|---|
| 55 | 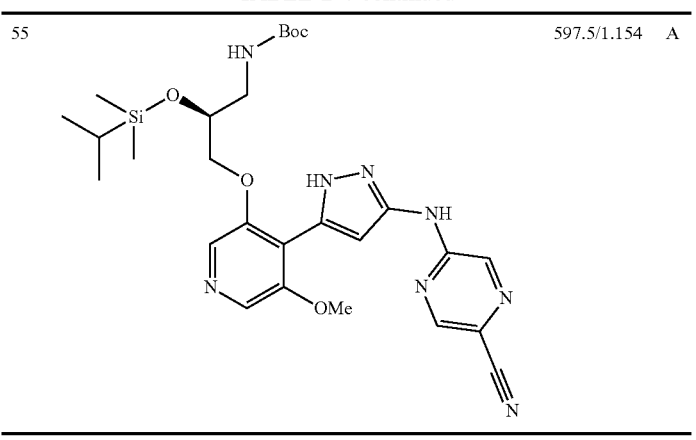 | 597.5/1.154 A |
TABLE 2-5
| | | |
|---|---|---|
| 56 | 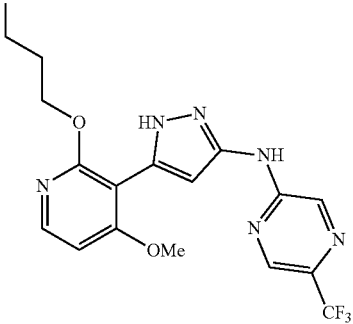 | 510.4/1.017 A |
| 57 | 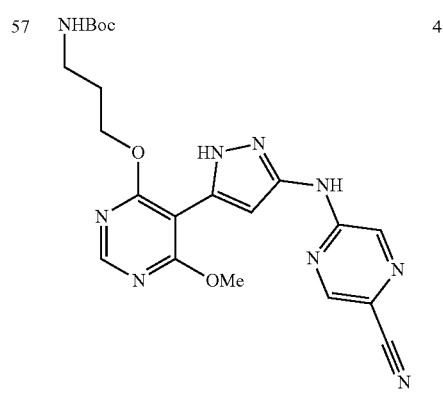 | 468.4/0.927 A |
TABLE 2-5-continued
| | | |
|---|---|---|
| 58 | 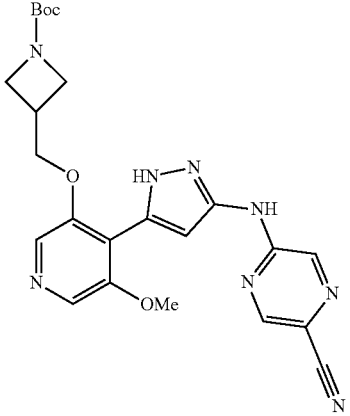 [SMILES: COc1cncc(OCC2CN(C(=O)OC(C)(C)C)C2)c1-c1cc(Nc2cnc(C#N)cn2)n[nH]1] | 479.4/0.819 A |
TABLE 2-6
| | | |
|---|---|---|
| 59 | 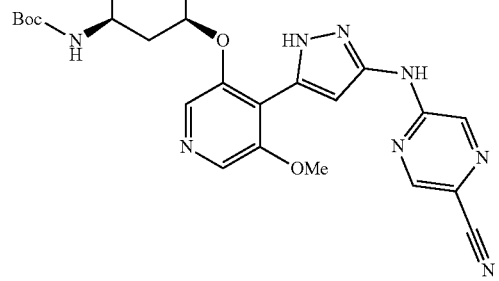 | 507.4/0.872 A |

TABLE 2-6-continued
| 60 | 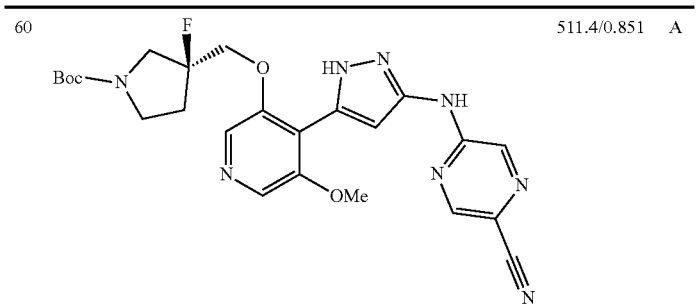 | 511.4/0.851 | A |
| 61 | 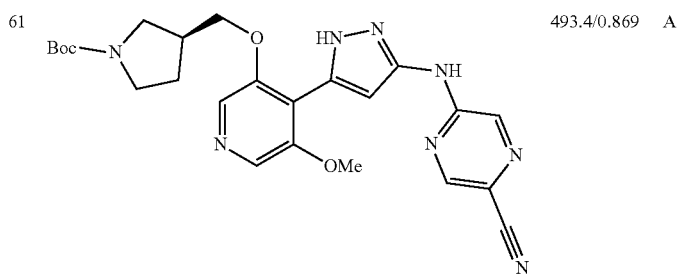 | 493.4/0.869 | A |
| 62 | 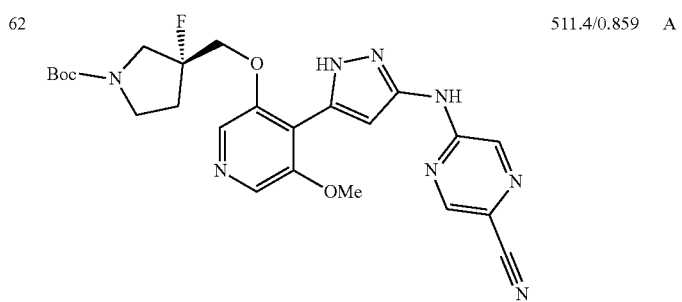 | 511.4/0.859 | A |
TABLE 2-7
| 63 | 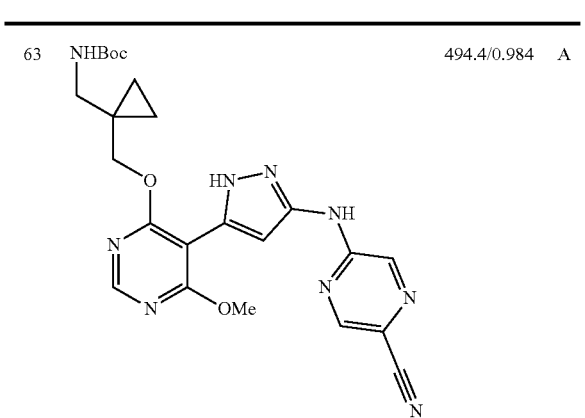 | 494.4/0.984 | A |
| 64 | 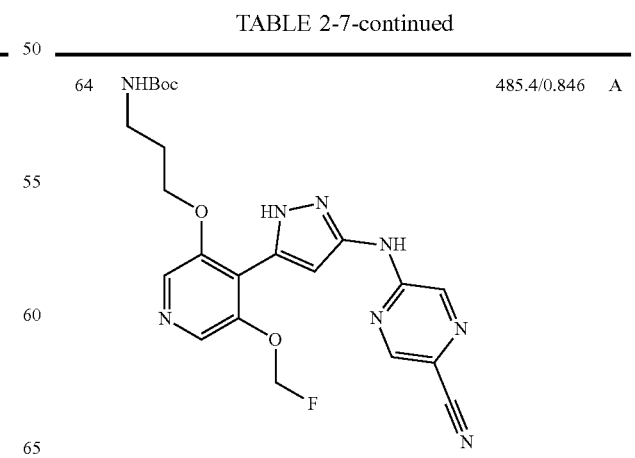 | 485.4/0.846 | A |

TABLE 2-7-continued
| 65 | 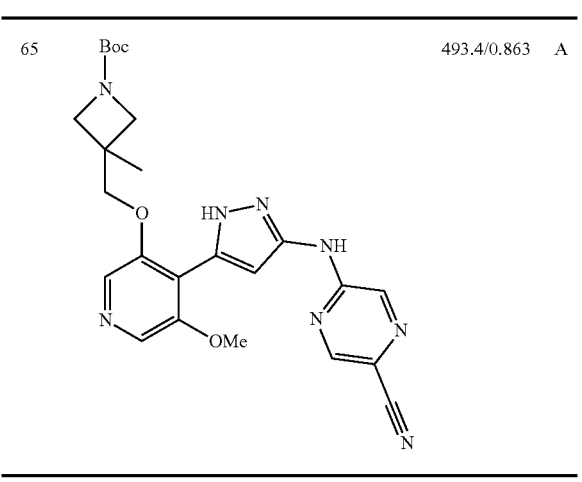 | 493.4/0.863 | A |
TABLE 2-8
| 66 | | 529.4/0.889 | A |
| 67 | | 481.5/0.865 | A |
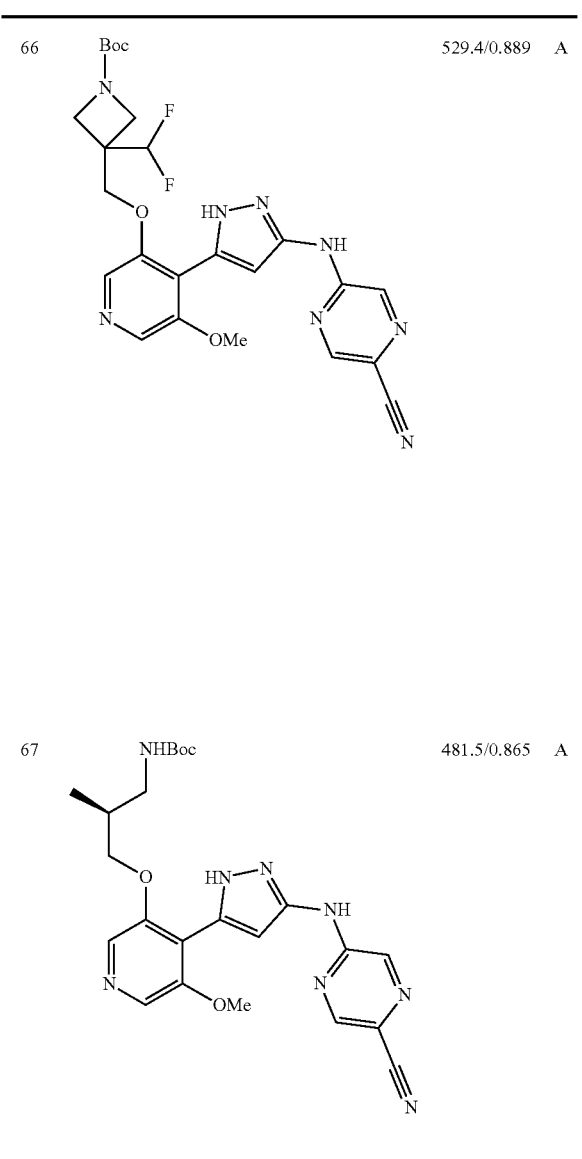
TABLE 2-8-continued
| 68 | 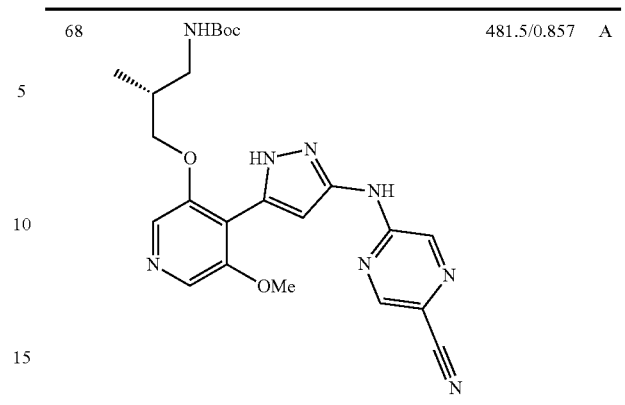 | 481.5/0.857 | A |
TABLE 2-9
| 69 | | 485.4/0.836 | A |
| 70 | | 485.4/0.814 | A |
| 71 | | 481.4/0.848 | A |
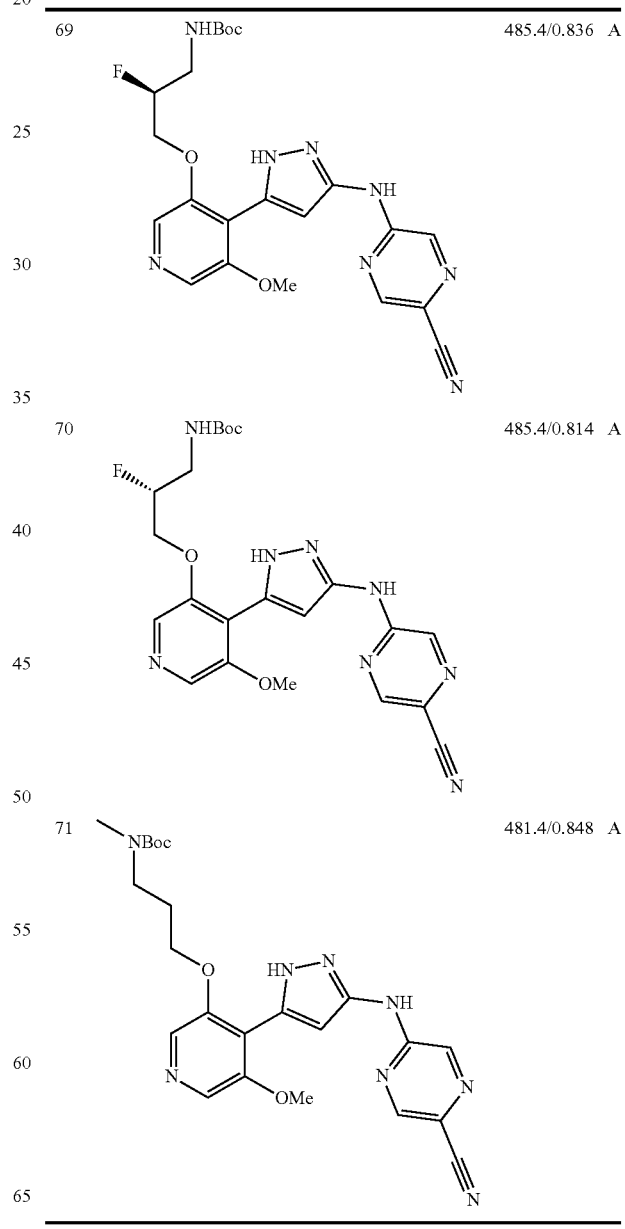

TABLE 2-10

| 72 | [structure] | 493.4/0.850 | A |
| 73 | [structure] | 493.4/0.851 | A |
| 74 | [structure] | 509.4/0.803 | A |

TABLE 2-11

| 75 | [structure] | 507.5/0.928 | A |

TABLE 2-11-continued
| 76 | 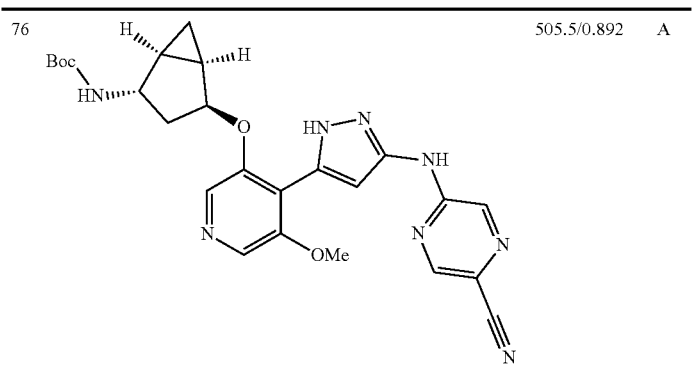 | 505.5/0.892 | A |
|---|---|---|---|
| 77 | | 493.4/0.955 | A |
TABLE 2-12
| 78 | 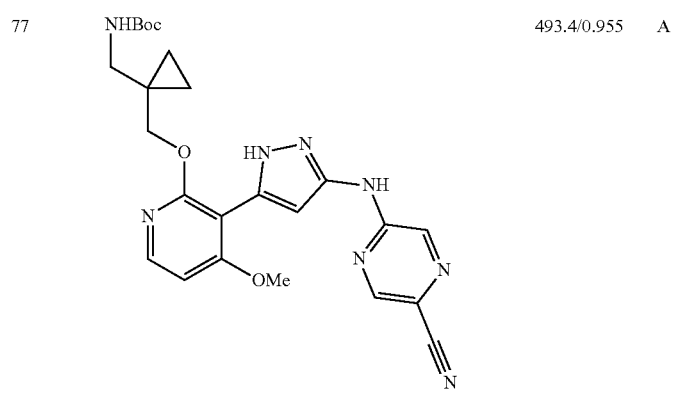 | 493.5/0.943 | A |
Reference Example 79
tert-butyl {3-[(3-{3-[(5-chloropyrazin-2-yl)amino]-1H-pyrazol-5-yl}-4-methoxypyridin-2-yl)oxy]propyl}carbamate
[Chemical Formula 44]
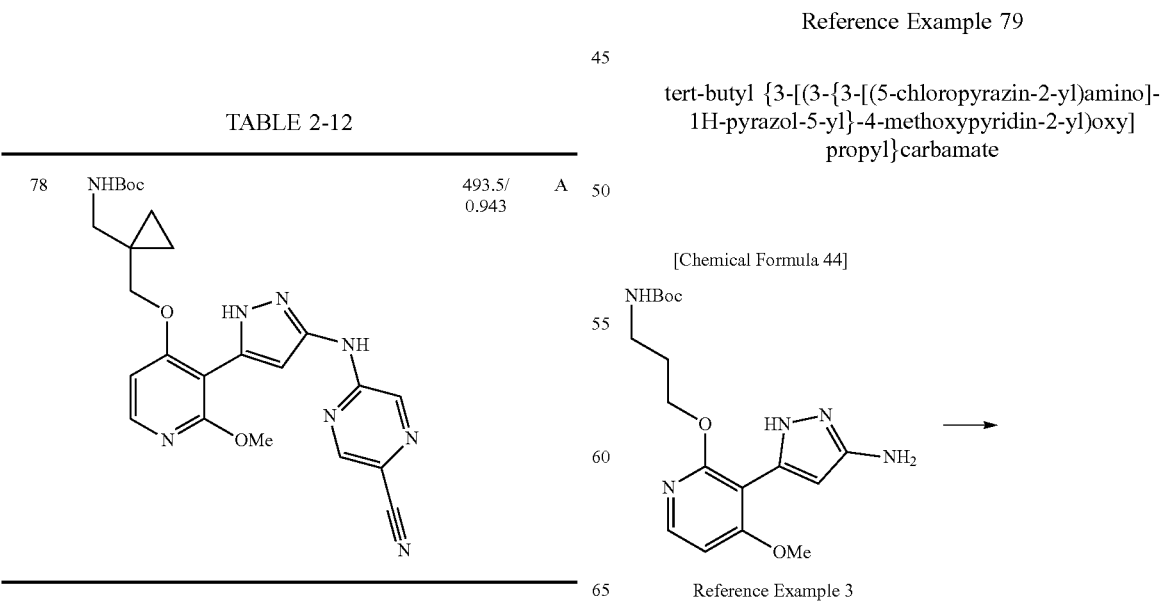
Reference Example 3

-continued

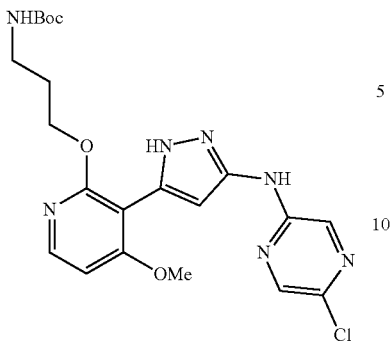

Reference Example 79

2,5-dichloropyrazine (32.9 μL), tris(dibenzylideneacetone)dipalladium(0) (15.1 mg), 4,5-bis(diphenylphosphino)-9,9-dimethylxanthene (19.1 mg), and cesium carbonate (108 mg) were added to a 1,4-dioxane (825 μL) solution of tert-butyl(3-{[3-(3-amino-1H-pyrazol-5-yl)-4-methoxypyridin-2-yl]oxy}propyl)carbamate (60 mg) at room temperature. The mixture was stirred for 2 hours at 150° C. under microwave irradiation. Water was added to the reaction solution, which was extracted with ethyl acetate. The organic layer was washed with saturated saline, dried with anhydrous sodium sulfate, and then filtered, and the solvent was evaporated under reduced pressure. The residue was purified by silica gel column chromatography (hexane/ethyl acetate) to obtain the title compound.

LC-MS; [M+H]$^+$ 476.3/Rt. (minutes) 0.969 (measurement condition A)

Example 1

5-({5-[2-(3-aminopropoxy)-4-methoxypyridin-3-yl]-1H-pyrazol-3-yl}amino))pyrazine-2-carbonitrile

[Chemical Formula 45]

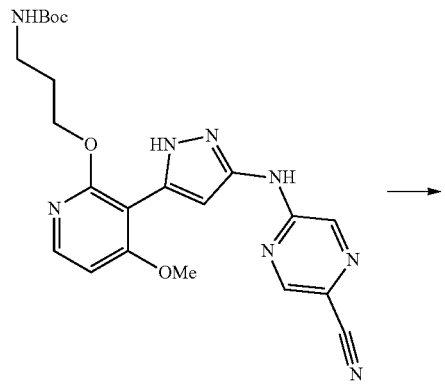

Reference Example 42

-continued

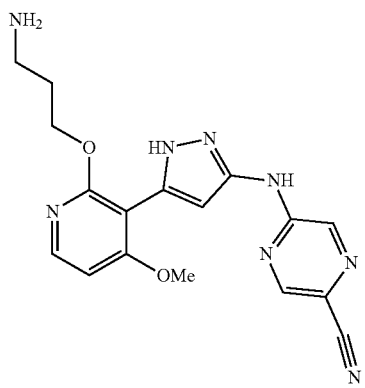

Example 1

TFA (2.00 mL) was added to a methylene chloride (20.0 mL) solution of tert-butyl {3-[(3-{3-[(5-cyanopyrazin-2-yl)amino]-1H-pyrazol-5-yl}-4-methoxypyridin-2-yl)oxy]propyl}carbamate (200 mg) obtained in Reference Example 42 at room temperature. The mixture was stirred for 1 hour at room temperature. The solvent was evaporated under reduced pressure. The residue was purified by amine silica gel column chromatography (ethyl acetate/methanol) to obtain Example 1 (112 mg).

LC-MS; [M+H]$^+$ 367.2/Rt (minutes) 0.671 (measurement condition A)

1H-NMR (DMSO-D6) δ: 8.65 (1H, s), 8.50 (1H, brs), 8.06 (1H, d, J=6.4 Hz), 7.04 (1H, brs), 6.89 (1H, d, J=6.4 Hz), 4.41 (2H, t, J=6.0 Hz), 3.92 (3H, s), 2.75 (1H, t, J=6.8 Hz), 1.85-1.76 (2H, m).

Examples 2 to 38

The compounds in Examples 2 to 38 shown in the following table were obtained by the similar method to Example 1 by using a corresponding raw material compound.

TABLE 3-1

| Example | Structural formula | LC-MS: [M + H]+ Time of retention (minutes) ¹H-NMR |
|---|---|---|
| 2 | (structure with NH₂, propyl-O-, Cl, OMe, pyridine, pyrazole, NH, pyrazine, CN) | 401.3/0.636 (Measurement condition A) ¹H-NMR (DMSO-D6) δ: 8.65 (1H, s), 8.48 (1H, brs), 7.05-6.99 (2H, m), 4.38 (2H, t, J = 6.0 Hz), 3.96 (3H, s), 2.75 (1H, t, J = 6.0 Hz), 1.85-1.78 (2H, m). |
| 3 | (structure with NH₂, propyl-O-, OMe, pyridine, pyrazole, NH, pyrazine, CN) | 367.3/0.673 (Measurement condition A) ¹H-NMR (DMSO-D6) δ: 8.67 (1H, s), 8.48 (1H, brs), 8.19 (2H, d, J = 6.0 Hz), 7.22 (1H, brs), 4.28 (2H, t, J = 6.0 Hz), 3.98 (3H, s), 2.79 (2H, t, J = 6.0 Hz), 1.89-1.85 (2H, m). |
| 4 | (structure with NH₂, propyl-O-, OMe, pyridine, pyrazole, NH, pyrazine, CN) | 367.3/0.610 (Measurement condition A) ¹H-NMR (DMSO-D6) δ: 8.66 (1H, s), 8.49 (1H, brs), 8.05 (1H, d, J = 6.0 Hz), 7.07 (1H, brs), 6.91 (1H, d, J = 5.6 Hz), 4.23 (2H, t, J = 6.0 Hz), 3.93 (3H, s), 3.33 (2H, brs), 2.77 (2H, t, J = 6.0 Hz), 1.88-1.82 (2H, m). |

TABLE 3-2

| 5 | 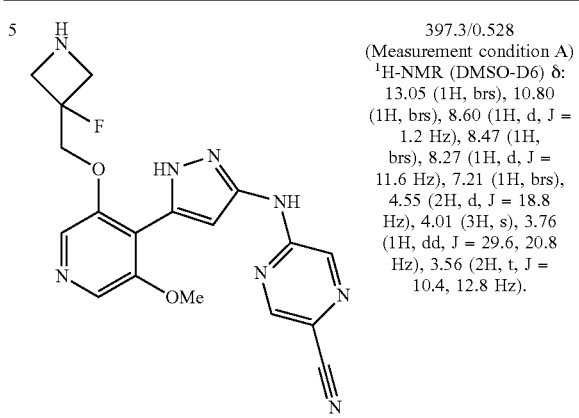 | 397.3/0.528 (Measurement condition A) ¹H-NMR (DMSO-D6) δ: 13.05 (1H, brs), 10.80 (1H, brs), 8.60 (1H, d, J = 1.2 Hz), 8.47 (1H, brs), 8.27 (1H, d, J = 11.6 Hz), 7.21 (1H, brs), 4.55 (2H, d, J = 18.8 Hz), 4.01 (3H, s), 3.76 (1H, dd, J = 29.6, 20.8 Hz), 3.56 (2H, t, J = 10.4, 12.8 Hz). |
| --- | --- | --- |
| 6 | 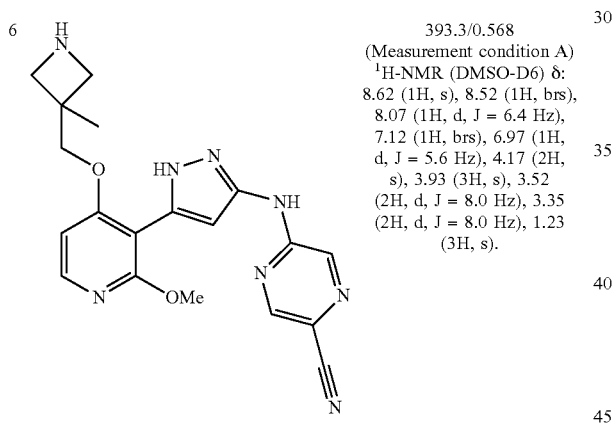 | 393.3/0.568 (Measurement condition A) ¹H-NMR (DMSO-D6) δ: 8.62 (1H, s), 8.52 (1H, brs), 8.07 (1H, d, J = 6.4 Hz), 7.12 (1H, brs), 6.97 (1H, d, J = 5.6 Hz), 4.17 (2H, s), 3.93 (3H, s), 3.52 (2H, d, J = 8.0 Hz), 3.35 (2H, d, J = 8.0 Hz), 1.23 (3H, s). |

TABLE 3-3

| 7 | 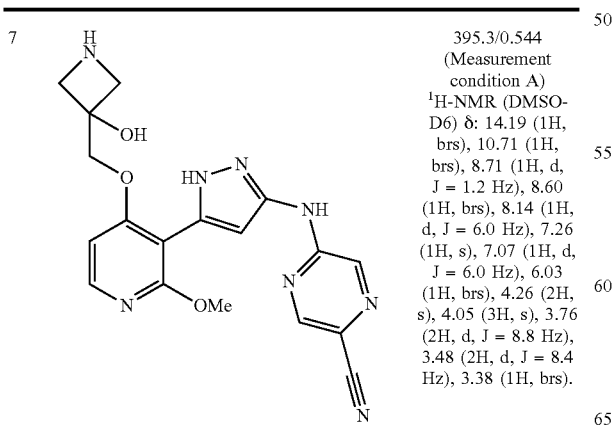 | 395.3/0.544 (Measurement condition A) ¹H-NMR (DMSO-D6) δ: 14.19 (1H, brs), 10.71 (1H, brs), 8.71 (1H, d, J = 1.2 Hz), 8.60 (1H, brs), 8.14 (1H, d, J = 6.0 Hz), 7.26 (1H, s), 7.07 (1H, d, J = 6.0 Hz), 6.03 (1H, brs), 4.26 (2H, s), 4.05 (3H, s), 3.76 (2H, d, J = 8.8 Hz), 3.48 (2H, d, J = 8.4 Hz), 3.38 (1H, brs). |
| --- | --- | --- |

TABLE 3-3-continued

| 8 | 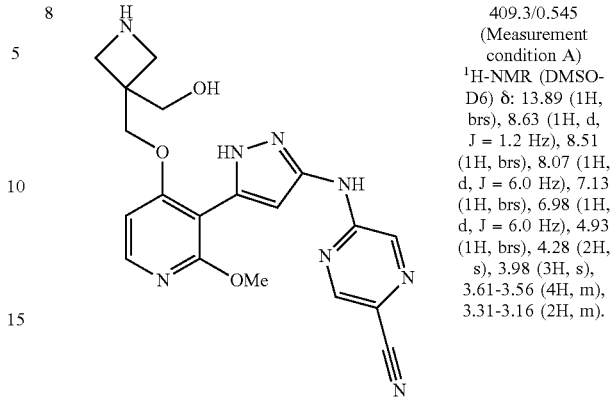 | 409.3/0.545 (Measurement condition A) ¹H-NMR (DMSO-D6) δ: 13.89 (1H, brs), 8.63 (1H, d, J = 1.2 Hz), 8.51 (1H, brs), 8.07 (1H, d, J = 6.0 Hz), 7.13 (1H, brs), 6.98 (1H, d, J = 6.0 Hz), 4.93 (1H, brs), 4.28 (2H, s), 3.98 (3H, s), 3.61-3.56 (4H, m), 3.31-3.16 (2H, m). |
| --- | --- | --- |
| 9 | 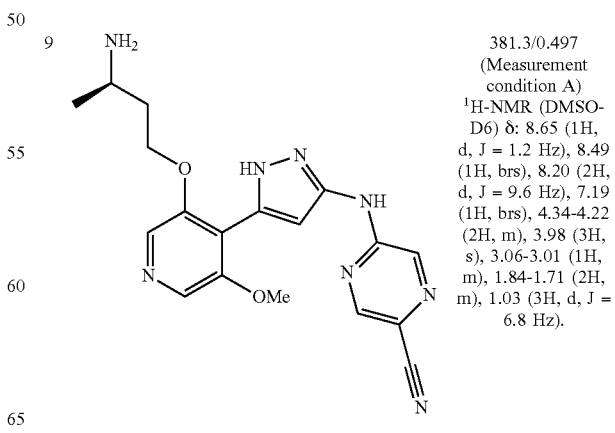 | 381.3/0.497 (Measurement condition A) ¹H-NMR (DMSO-D6) δ: 8.65 (1H, d, J = 1.2 Hz), 8.49 (1H, brs), 8.20 (2H, d, J = 9.6 Hz), 7.19 (1H, brs), 4.34-4.22 (2H, m), 3.98 (3H, s), 3.06-3.01 (1H, m), 1.84-1.71 (2H, m), 1.03 (3H, d, J = 6.8 Hz). |

TABLE 3-4

| 10 | [structure] | 381.3/0.546 (Measurement condition A) ¹H-NMR (DMSO-D6) δ: 8.55 (1H, d, J = 2.0 Hz), 8.39 (1H, brs), 8.10 (2H, d, J = 10.0 Hz), 7.09 (1H, brs), 4.4-4.13 (2H, m), 3.88 (3H, s), 2.96-2.92 (1H, m), 1.88-1.61 (2H, m), 0.94 (3H, d, J = 6.0 Hz) |
|----|----|----|
| 11 | [structure] | 393.3/0.594 (Measurement condition A) ¹H-NMR (DMSO-D6) δ: 8.63 (1H, d, J = 1.2 Hz), 8.49 (1H, brs), 8.17 (2H, d, J = 11.6 Hz), 7.31 (1H, s), 4.13 (2H, s), 3.99 (3H, s), 2.72 (2H, s), 0.57-0.59 (4H, m) |
| 12 | [structure] | 409.3/0.561 (Measurement condition A) ¹H-NMR (DMSO-D6) δ: 12.58 (1H, s), 10.82 (1H, s), 8.71 (1H, d, J = 1.2 Hz), 8.57 (1H, brs), 8.20 (2H, d, J = 3.6 Hz), 7.24 (1H, brs), 4.18 (2H, d, J = 4.8 Hz), 3.99 (3H, s), 3.78-3.75 (2H, m), 3.52-3.46 (1H, m), 2.96-2.93 (1H, m), 2.70-2.56 (4H, m). |

TABLE 3-5

| 13 | [structure] | 409.3/0.497 (Measurement condition A) ¹H-NMR (DMSO-D6) δ: 12.58 (1H, s), 10.82 (1H, s), 8.71 (1H, d, J = 1.2 Hz), 8.46 (1H, brs), 8.20 (2 H, d, J = 3.7 Hz), 7.23 (1H, brs), 4.18 (2H, d, J = 4.9 Hz), 3.99 (3H, s), 3.83-3.76 (2H, m), 3.50 (1H, td, J = 10.8, 2.8 Hz), 2.95 (1H, dd, J = 12.2, 1.8 Hz), 2.70-2.56 (3H, m). |
|----|----|----|

TABLE 3-5-continued

| 14 | [structure] | 383.2/0.452 (Measurement condition A) ¹H-NMR (DMSO-D6) δ: 8.74 (1H, d, J = 1.2 Hz), 8.56 (1H, brs), 8.29 (1H, s), 8.27 (1H, s), 7.30 (1H, brs), 4.30 (1H, dd, Jgem = 9.5, J = 4.6 Hz), 4.22 (1H, dd, Jgem = 9.5, J = 5.8 Hz), 4.05 (3H, s), 3.92-3.87 (1H, m), 2.82 (1H, dd, Jgem = 12.8, J = 5.5 Hz), 2.76 (1H, dd, Jgem = 12.8, J = 6.1 Hz). |
|---|---|---|

TABLE 3-6

| 15 | [structure] | 376/0.578 (Measurement condition A) 1H-NMR (DMSO-D6) δ: 9.99 (1H, s), 8.51 (1H, d, J = 1.2 Hz), 8.31 (1H, d, J = 1.2 Hz), 8.12 (1H, d, J = 6.1 Hz), 6.95 (1H, d, J = 6.1 Hz), 6.91 (1H, s), 4.47 (2H, t, J = 6.1 Hz), 3.99 (3H, s), 2.81 (2H, t, J = 6.7 Hz), 1.92-1.85 (2H, m). |
|---|---|---|
| 16 | [structure] | 410/0.637 (Measurement condition A) 1H-NMR (CD3OD) δ: 8.58 (1H, s), 8.55 (1H, s), 8.13 (1H, d, J = 5.5 Hz), 7.05 (1H, s), 6.94 (1H, d, J = 6.1 Hz), 4.57 (2H, t, J = 6.1 Hz), 4.07 (3H, s), 2.91 (2H, t, J = 6.7 Hz), 2.05 (2H, td, J = 9.6, 5.5 Hz). |
| 17 | [structure] | 368.2/0.558 (Measurement condition A) 1H-NMR (DMSO-D6, 65° C.) δ: 8.61 (1H, s), 8.53 (1H, s), 8.44 (1H, s), 7.06 (1H, s), 4.56 (2H, t, J = 6.1 Hz), 4.05 (3H, s), 2.78 (2H, t, J = 6.4 Hz), 1.90-1.84 (2H, m). |

TABLE 3-7

| 18 | [structure] | 379.2/0.525 (Measurement condition A) ¹H-NMR (DMSO-D6) δ: 14.25 (1H, brs), 8.64 (1H, d, J = 1.2 Hz), 8.50 (1H, brs), 8.24 (1H, s), 8.22 (1H, s), 7.29 (1H, brs), 4.39 (2H, d, J = 3.7 Hz), 4.02 (3H, s), 3.85 (2H, t, J = 7.9 Hz), 3.29 (2H, dd, J = 7.6, 4.0 Hz), 2.98-2.92 (1H, m). |
|---|---|---|

TABLE 3-7-continued

| 19 | [structure] | 407.3/0.597 (Measurement condition A) ¹H-NMR (DMSO-D6) δ: 8.65 (1H, s), 8.51 (1H, brs), 8.23 (1H, s), 8.15 (1H, s), 7.22 (1H, brs), 4.59 (1H, m), 3.97 (3H, s), 2.76 (1H, m), 2.16 (1H, d, J = 11.6 Hz), 1.99 (1H, d, J = 10.4 Hz), 1.79-1.67 (2H, m), 1.41-1.23 (3H, m), 1.11-1.03 (1H, m). |
|---|---|---|
| 20 | [structure] | 411.3/0.562 (Measurement condition A) ¹H-NMR (DMSO-D6) δ: 12.61 (1H, brs), 10.85 (1H, brs), 8.58 (1H, d, J = 1.2 Hz), 8.46 (1H, brs), 8.23 (1H, s), 8.22 (1H, s), 7.27 (1H, brs), 4.54-4.38 (2H, m), 4.00 (3H, s), 3.24-3.15 (1H, m), 3.03-2.93 (2H, m), 2.85-2.79 (1H, m), 2.12-1.87 (2H, m). |

TABLE 3-8

| 21 | [structure] | 393.3/0.603 (Measurement condition A) ¹H-NMR (DMSO-D6) δ: 13.17 (1H, brs), 8.63 (1H, d, J = 1.8 Hz), 8.47 (1H, brs), 8.19 (1H, s), 8.18 (1H, s), 7.26 (1H, brs), 4.20 (1H, dd, J = 9.2, 5.5 Hz), 4.09 (1H, dd, J = 8.9, 6.4 Hz), 3.99 (3H, s), 2.98 (1H, dd, J = 10.4, 7.3 Hz), 2.87 (1H, m), 2.76-2.70 (2H, m), 2.53 (1H, m), 1.92 (1H, m), 1.48 (1H, m). |
|---|---|---|
| 22 | [structure] | 411.3/0.559 (Measurement condition A) ¹H-NMR (DMSO-D6) δ: 12.61 (1H, brs), 10.85 (1H, brs), 8.57 (1H, d, J = 1.2 Hz), 8.45 (1H, brs), 8.23 (1H, s), 8.22 (1H, s), 7.27 (1H, brs), 4.54-4.38 (2H, m), 4.00 (3H, s), 3.24-3.15 (1H, m), 3.03-2.93 (2H, m), 2.85-2.79 (1H, m), 2.12-1.87 (2H, m). |

TABLE 3-9

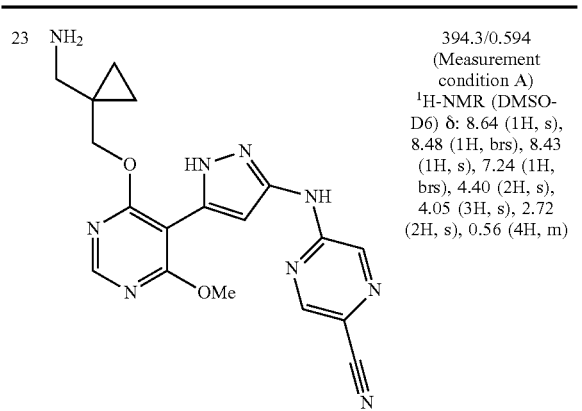

23 | 394.3/0.594 (Measurement condition A) ¹H-NMR (DMSO-D6) δ: 8.64 (1H, s), 8.48 (1H, brs), 8.43 (1H, s), 7.24 (1H, brs), 4.40 (2H, s), 4.05 (3H, s), 2.72 (2H, s), 0.56 (4H, m)

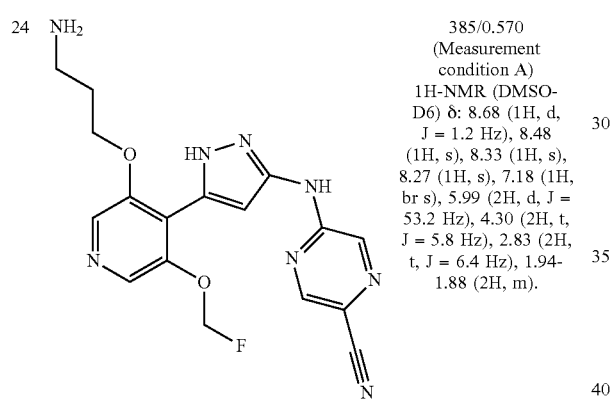

24 | 385/0.570 (Measurement condition A) 1H-NMR (DMSO-D6) δ: 8.68 (1H, d, J = 1.2 Hz), 8.48 (1H, s), 8.33 (1H, s), 8.27 (1H, s), 7.18 (1H, br s), 5.99 (2H, d, J = 53.2 Hz), 4.30 (2H, t, J = 5.8 Hz), 2.83 (2H, t, J = 6.4 Hz), 1.94-1.88 (2H, m).

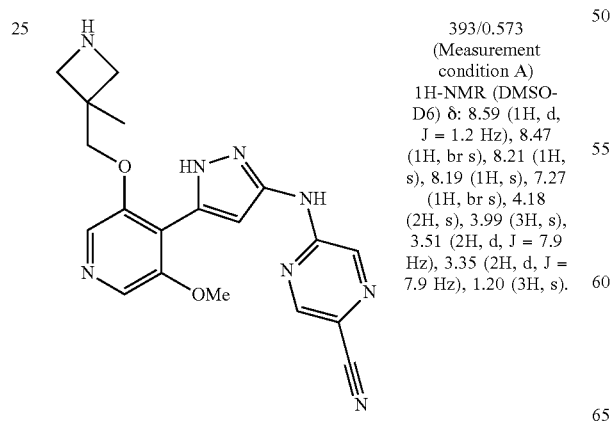

25 | 393/0.573 (Measurement condition A) 1H-NMR (DMSO-D6) δ: 8.59 (1H, d, J = 1.2 Hz), 8.47 (1H, br s), 8.21 (1H, s), 8.19 (1H, s), 7.27 (1H, br s), 4.18 (2H, s), 3.99 (3H, s), 3.51 (2H, d, J = 7.9 Hz), 3.35 (2H, d, J = 7.9 Hz), 1.20 (3H, s).

TABLE 3-10

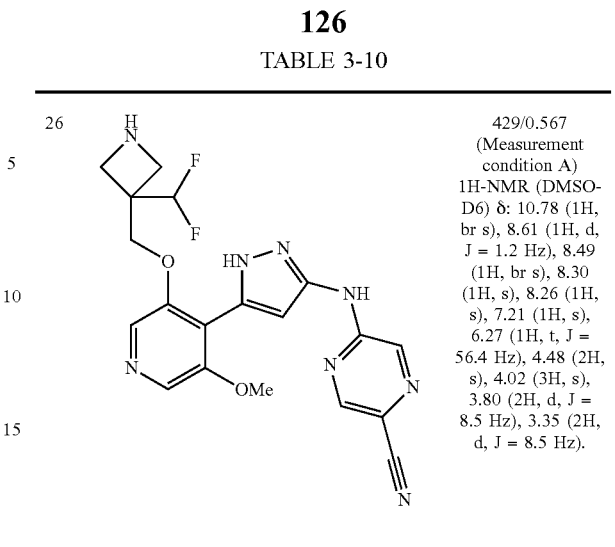

26 | 429/0.567 (Measurement condition A) 1H-NMR (DMSO-D6) δ: 10.78 (1H, br s), 8.61 (1H, d, J = 1.2 Hz), 8.49 (1H, br s), 8.30 (1H, s), 8.26 (1H, s), 7.21 (1H, s), 6.27 (1H, t, J = 56.4 Hz), 4.48 (2H, s), 4.02 (3H, s), 3.80 (2H, d, J = 8.5 Hz), 3.35 (2H, d, J = 8.5 Hz).

27 | 381/0.622 (Measurement condition A) 1H-NMR (DMSO-D6) δ: 8.63 (1H, d, J = 1.2 Hz), 8.46 (1H, br s), 8.21 (1H, s), 8.19 (1H, s), 7.26 (1H, br s), 4.19-4.07 (2H, m), 3.98 (3H, s), 2.67 (2H, d, J = 6.1 Hz), 2.02-1.90 (1H, m), 1.01 (3H, d, J = 6.1 Hz).

28 | 381/0.573 (Measurement condition A) 1H-NMR (DMSO-D6) δ: 8.63 (1H, s), 8.46 (1H, br s), 8.20 (1H, s), 8.19 (1H, s), 7.26 (1H, br s), 4.18-1.07 (2H, m), 3.98 (3H, s), 2.66 (2H, d, J = 6.1 Hz), 2.01-1.91 (1H, m), 1.01 (3H, d, J = 7.3 Hz).

TABLE 3-11

| | | |
|---|---|---|
| 229 | 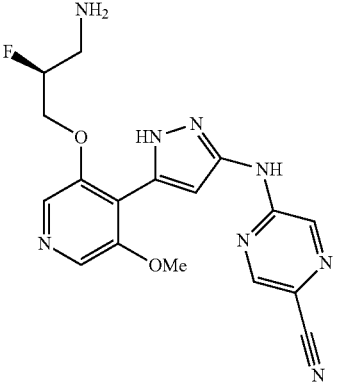 [SMILES: COc1cncc(OC[C@@H](F)CN)c1-c1cc(Nc2cnc(C#N)cn2)n[nH]1] | 385/0.543<br>(Measurement condition A)<br>1H-NMR (DMSO-D6) δ:<br>10.81 (1H, br s), 8.65<br>(1H, d, J = 1.2 Hz), 8.48<br>(1H, br s), 8.22 (2H, s),<br>7.22 (1H, br s), 4.92-<br>4.72 (1H, m), 4.54-4.33<br>(2H, m), 3.99 (3H, s),<br>2.95 (1H, d, J = 6.1 Hz),<br>2.90 (1H, dd, J = 5.8,<br>1.5 Hz). |
| 30 | 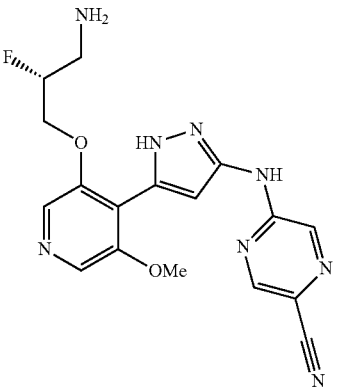 [SMILES: COc1cncc(OC[C@H](F)CN)c1-c1cc(Nc2cnc(C#N)cn2)n[nH]1] | 385/0.548<br>(Measurement condition A)<br>1H-NMR (DMSO-D6) δ: 8.65<br>(1H, d, J = 1.2 Hz), 8.48<br>(1H, br s), 8.22 (2H, s),<br>7.22 (1H, br s), 4.93-<br>4.71 (1H, m), 4.53-4.33<br>(2H, m), 3.99 (3H, s),<br>2.95 (1H, d, J = 6.1 Hz),<br>2.90 (1H, dd, J = 5.8,<br>1.5 Hz). |
| 31 | 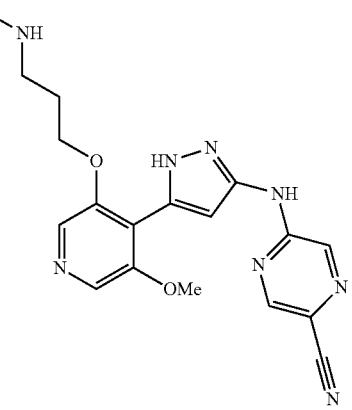 | 381/0.527<br>(Measurement condition A)<br>1H-NMR (DMSO-D6) δ: 8.66<br>(1H, d, J = 1.2 Hz), 8.50<br>(1H, br s), 8.17 (2H, s),<br>7.24 (1H, br s), 4.28<br>(2H, t, J = 5.8 Hz), 3.99<br>(3H, s), 2.69 (2H, t, J =<br>6.1 Hz), 2.31 (3H, s),<br>1.98-1.89 (2H, m). |

TABLE 3-12

| | | |
|---|---|---|
| 32 | 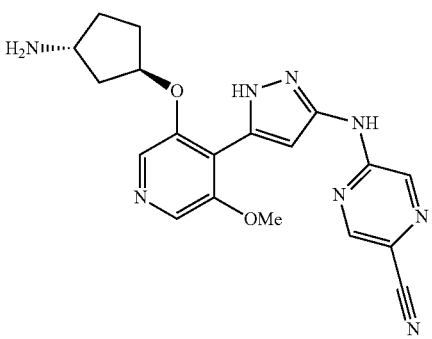 [SMILES: COc1cncc(O[C@@H]2CC[C@@H](N)C2)c1-c1cc(Nc2cnc(C#N)cn2)n[nH]1] | 393/0.576<br>(Measurement condition A)<br>1H-NMR (DMSO-D6) δ:<br>12.52 (1H, br s), 8.66<br>(1H, d, J = 1.2 Hz), 8.47<br>(1H, br s), 8.15 (1H, s),<br>8.13 (1H, s), 7.24 (1H,<br>br s), 5.15-5.07 (1H, m),<br>3.98 (3H, s), 6.56-3.47<br>(1H, m), 2.30-2.18 (1H,<br>m), 2.08-1.90 (2H, m),<br>1.78-1.64 (2H, m), 1.38-<br>1.26 (1H, m). |

TABLE 3-12-continued
| 33 | 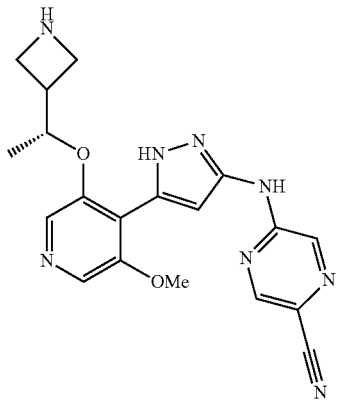 [SMILES: COc1cncc(O[C@H](C)C2CNC2)c1-c1cc(Nc2cnc(C#N)cn2)n[nH]1] | 393/0.608<br>(Measurement condition A)<br>1H-NMR (DMSO-D6) δ: 8.65 (1H, d, J = 1.2 Hz), 8.51 (1H, br s), 8.25 (1H, s), 8.18 (1H, s), 7.18 (1H, br s), 5.02-4.92 (1H, m), 3.99 (3H, s), 3.83-3.77 (2H, m), 3.39-3.35 (1H, m), 3.20-3.14 (1H, m), 2.82-2.72 (1H, m), 1.23 (3H, d, J = 6.1 Hz). |
TABLE 3-13
| 34 | 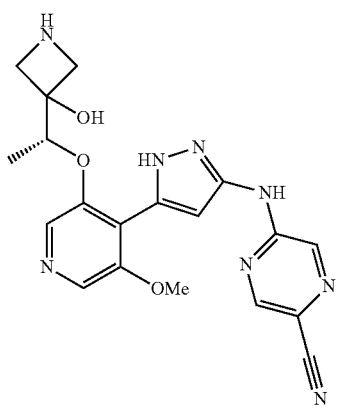 [SMILES: COc1cncc(O[C@H](C)C2(O)CNC2)c1-c1cc(Nc2cnc(C#N)cn2)n[nH]1] | 409/0.626<br>(Measurement condition A)<br>1H-NMR (DMSO-D6) δ: 10.65 (1H, br s), 8.65 (1H, d, J = 1.2 Hz), 8.52 (1H, br s), 8.26 (1H, s), 8.19 (1H, s), 7.20 (1H, br s), 5.98 (1H, br s), 4.80 (1H, d, J = 6.1 Hz), 4.77 (1H, d, J = 6.1 Hz), 4.00 (3H, s), 3.69 (1H, d, J = 7.9 Hz), 3.65 (1H, d, J = 7.9 Hz), 3.52 (1H, d, J = 8.5 Hz), 3.35 (1H, d, J = 8.5 Hz), 1.26 (1H, d, J = 6.1 Hz). |
| 35 | 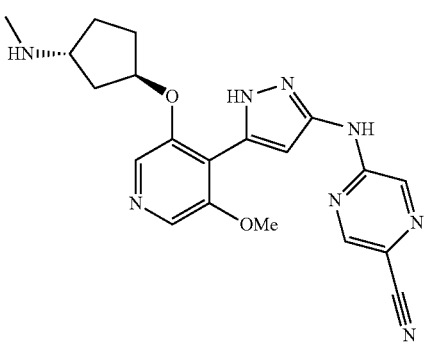 [SMILES: CN[C@@H]1CC[C@@H](Oc2cncc(OC)c2-c2cc(Nc3cnc(C#N)cn3)n[nH]2)C1] | 407/0.642<br>(Measurement condition A)<br>1H-NMR (DMSO-D6) δ: 12.52 (1H, br s), 8.63 (1H, s), 8.48 (1H, br s), 8.15 (1H, s), 8.14 (1H, s), 7.23 (1H, br s), 5.12-5.05 (1H, m), 3.97 (3H, s), 3.19-3.11 (1H, m), 2.20 (3H, s), 2.19-2.09 (1H, m), 2.08-1.99 (1H, m), 1.99-1.89 (1H, m), 1.82-1.71 (2H, m), 1.47-1.36 (1H, m). |

TABLE 3-14

| # | Structure | Data |
|---|---|---|
| 36 | (structure: H₂N-cyclopropyl-pyridine-OMe linked via O to pyrazole-NH-pyrazine-CN) | 405/0.584 (Measurement condition A) 1H-NMR (DMSO-D6) δ: 12.50 (1H, br s), 8.61 (1H, s), 8.50 (1H, br s), 8.28 (1H, s), 8.16 (1H, s), 7.26 (1H, br s), 5.52-5.43 (1H, m), 3.98 (3H, s), 3.35-3.34 (1H, m), 3.33-3.32 (1H, m), 1.87 (1H, dd, J = 13.4, 7.9 Hz), 1.82-1.74 (1H, m), 1.61-1.51 (1H, m), 1.41-1.31 (1H, m), 0.62-0.56 (1H, m), 0.52-0.45 (1H, m). |
| 37 | (structure: NH₂-CH₂-cyclopropyl-CH₂-O-pyridine(OMe)-pyrazole-NH-pyrazine-CN) | 393/0.654 (Measurement condition A) 1H-NMR (DMSO-D6) δ: 8.64 (1H, s), 8.50 (1H, br s), 8.04 (1H, d, J = 5.5 Hz), 7.14 (1H, br s), 6.90 (1H, d, J = 6.1 Hz), 4.27 (2H, s), 3.94 (3H, s), 2.80 (2H, s), 0.63-0.51 (4H, m). |
| 38 | (structure: NH₂-CH₂-cyclopropyl-CH₂-O-pyridine(OMe)-pyrazole-NH-pyrazine-CN isomer) | 393/0.682 (Measurement condition A) 1H-NMR (DMSO-D6) δ: 8.62 (1H, d, J = 1.2 Hz), 8.49 (1H, br s), 8.03 (1H, d, J = 5.5 Hz), 7.18 (1H, br s), 6.87 (1H, d, J = 6.1 Hz), 4.09 (2H, s), 3.95 (3H, s), 2.70 (2H, s), 0.58-0.47 (4H, m). |

X ray powder diffraction in Examples 39 to 44 was measured under the conditions set forth below. The resulting diffraction patterns (XRD spectrum) are shown in FIGS. 1 to 6. Examples 39 to 41 are crystals of various salts of the compound of Example 1, and Examples 42 to 44 are crystalline polymorphisms of the compound of Example 1.

A crystalline form can be identified with a determination based on a characteristic diffraction peak of each crystal shown in the diffraction diagrams of FIGS. 1 to 6.

The primary diffraction peak and characteristic diffraction peak identified from the diffraction patterns in FIGS. 1 to 6 are each listed below. The diffraction peak value in diffraction angle 2θ(°) described in the following Examples can have a slight measurement error depending on the measuring equipment, measurement condition, or the like. Specifically, the measurement error can be within a range of ±0.2, preferably ±0.1.

X-Ray Powder Diffraction Measurement Method:
Detector: Spectris Power X-ray diffraction system Empyrian
X-ray tube: CuKα (wavelength: 1.54 angstroms)
Tube voltage: 45 kV
Tube current: 40 mA
Measurement range: 4 to 40° (2θ)
Step width: 0.013 degrees
Integration time: 100 seconds/step Example 39

5-({5-[2-(3-aminopropoxy)-4-methoxypyridin-3-yl]-1H-pyrazol-3-yl}amino)pyrazine-2-carbonitrile hydrochloride Methanol (0.6 mL) was added to the compound (30.0 mg) of Example 1, and a 5 to 10% (W/V) hydrochloric acid-methanol solution (60 μL) was added. The mixture was stirred for 2 hours at a set temperature of 60° C. After allowing the mixture to cool, the mixture was left standing overnight. The deposited solid was filtered out and dried to obtain the title compound as a crystal (form I).
[Form I] The X ray powder diffraction pattern is shown in FIG. 1.
Primary diffraction peaks: 2θ(°)=7.2, 8.8, 9.8, 10.2, 10.7, 16.7, 18.5, 26.2, 27.0
Characteristic diffraction peaks: 2θ(°)=7.2, 8.8, 9.8, 10.2, 10.7

Example 40

Figure 2:
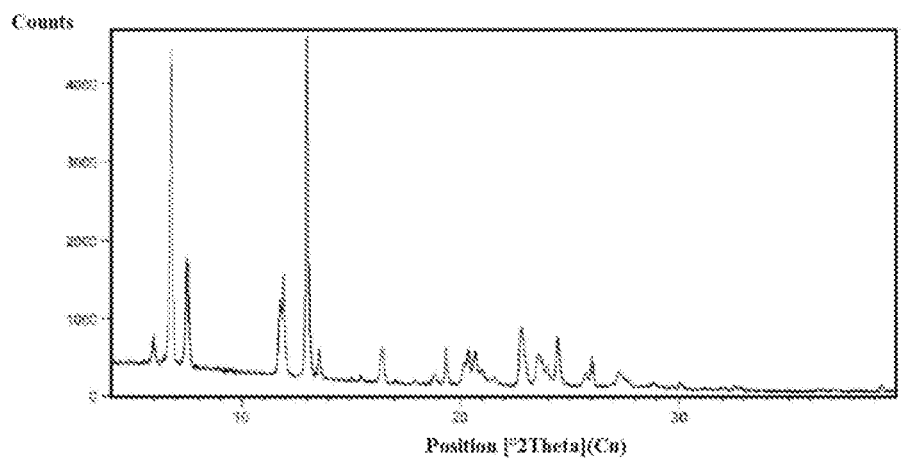
FIG. 2 shows the X ray powder diffraction pattern of form II of a compound of Example 40.

5-({5-[2-(3-aminopropoxy)-4-methoxypyridin-3-yl]-1H-pyrazol-3-yl}amino)pyrazine-2-carbonitrile phosphate 13.4 mg/mL phosphoric acid-methanol solution (1200 μL) was added to the compound (30.0 mg) of Example 1. The mixture was stirred for 4 hours at a set temperature of 60° C. After allowing the mixture to cool, the mixture was left standing overnight. The deposited solid was filtered out and dried to obtain the title compound as a crystal (form II).
[Form II] The X ray powder diffraction pattern is shown in FIG. 2.
Primary diffraction peaks: 2θ(°)=6.8, 7.5, 11.7, 11.9, 13.0, 16.4, 19.3, 20.4, 22.7, 24.3
Characteristic diffraction peaks: 2θ(°)=6.8, 7.5, 11.7, 11.9, 13.0

Example 41

Figure 3:
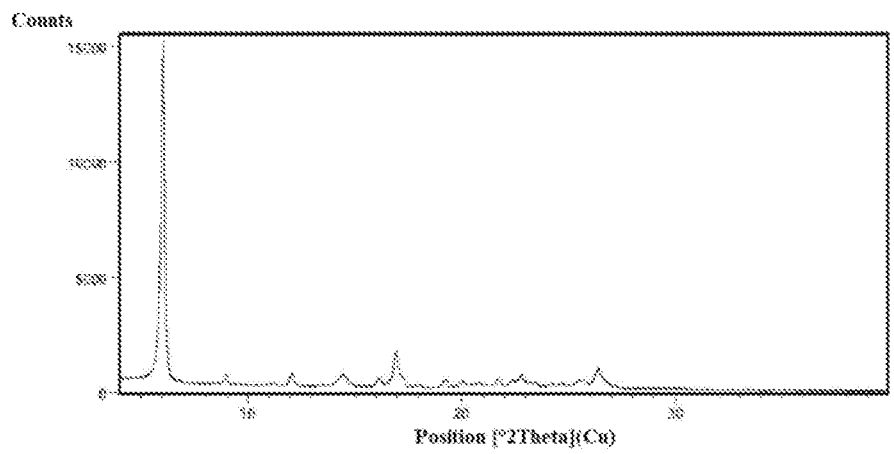
FIG. 3 shows the X ray powder diffraction pattern of form III of a compound of Example 41.

5-((5-[2-(3-aminopropoxy)-4-methoxypyridin-3-yl]-1H-pyrazol-3-yl}amino)pyrazine-2-carbonitrile tosylate Methanol (0.6 mL) was added to the compound (30.0 mg) of Example 1, and 26.0 mg/mL tosic acid-methanol solution (0.6 mL) was further added. The mixture was stirred for 2 hours at a set temperature of 60° C. After allowing the mixture to cool, the mixture was left standing overnight. The deposited solid was filtered out and dried to obtain the title compound as a crystal (form III).
[Form III] The X ray powder diffraction pattern is shown in FIG. 3.
Primary diffraction peaks: 2θ(°)=6.0, 9.0, 12.1, 14.4, 16.2, 17.0, 22.8, 26.3
Characteristic diffraction peaks: 2θ(°)=6.0, 9.0, 12.1, 14.4, 16.2, 17.0

Example 42

5-({5-[2-(3-aminopropoxy)-4-methoxypyridin-3-yl]-1H-pyrazol-3-yl}amino)pyrazine-2-carbonitrile

Figure 4:
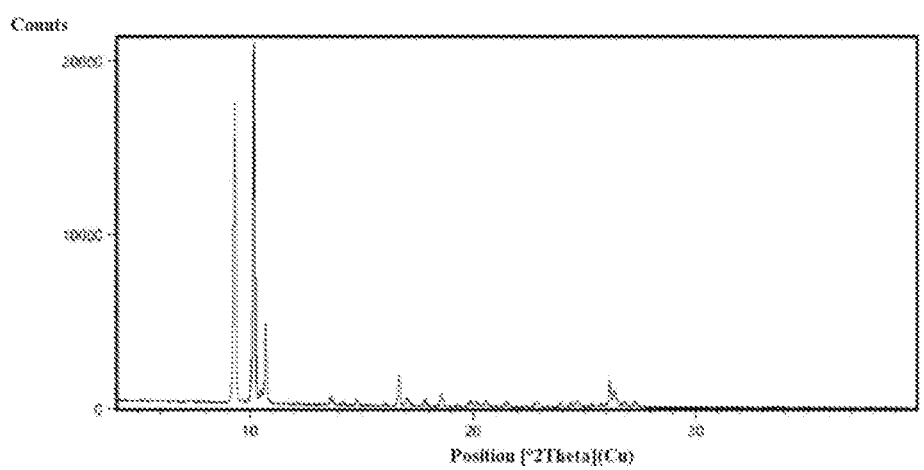
FIG. 4 shows the X ray powder diffraction pattern of form IV of a compound of Example 42.

[Form IV] The X ray powder diffraction pattern is shown in FIG. 4.
From Example 1, the title compound was obtained as a crystal (form IV).
Primary diffraction peaks: 2θ(°)=9.3, 10.2, 10.7, 13.6, 16.7, 17.1, 17.8, 18.6, 26.1, 26.4

Characteristic diffraction peaks: 2θ(°)=9.3, 10.2, 10.7, 16.7, 26.1, 26.4

Example 43

5-({5-[2-(3-aminopropoxy)-4-methoxypyridin-3-yl]-1H-pyrazol-3-yl}amino)pyrazine-2-carbonitrile

Figure 5:
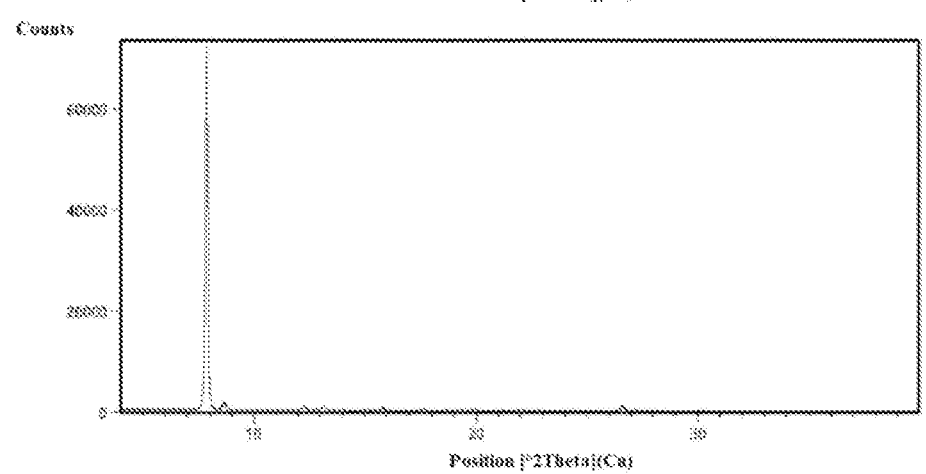
FIG. 5 shows the X ray powder diffraction pattern of form V of a compound of Example 43.

[Form V] The X ray powder diffraction pattern is shown in FIG. 5.
A tetrahydrofuran/water (10/1, 0.5 mL) solution of the compound (5 mg) of Example 1 was added and heated for 1 hour at a set temperature of 105° C. After allowing the mixture to cool, the mixture was sealed and left standing for 4 days, and then opened and left standing for 3 days. The solvent was evaporated. From the deposited solid, the title compound was obtained as a crystal (form V).
Primary diffraction peaks: 2θ(°)=7.9, 8.7, 12.2, 13.1, 15.9, 17.6, 19.9, 21.9, 22.8, 26.6
Characteristic diffraction peaks: 2θ(e)=7.9, 8.7, 12.2, 13.1, 15.9, 26.6

Example 44

5-({5-[2-(3-aminopropoxy)-4-methoxypyridin-3-yl]-1H-pyrazol-3-yl}amino)pyrazine-2-carbonitrile

Figure 6:
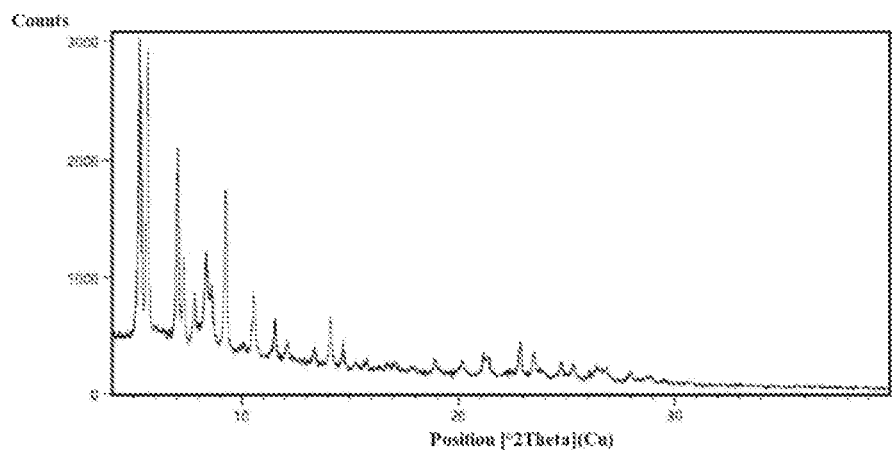
FIG. 6 shows the X ray powder diffraction pattern of form VI of a compound of Example 44.

[Form VI] The X ray powder diffraction pattern is shown in FIG. 6.
An acetone/water (10/1, 0.5 mL) solution of the compound (5 mg) of Example 1 was added. The mixture was heated for 1 hour at a set temperature of 105° C. After allowing the mixture to cool, the mixture was sealed and left standing for 4 days, and then opened and left standing for 3 days. The solvent was evaporated. From the deposited solid, the title compound was obtained as a crystal (form VI).
Primary diffraction peaks: 2θ(°)=5.3, 5.7, 7.0, 7.3, 7.8, 8.4, 9.3, 10.5, 11.5, 14.1
Characteristic diffraction peaks: 2θ(°)=5.3, 5.7, 7.0, 7.3, 8.4, 9.3

Test Example

Test Example 1: CHK1 Inhibitory Activity Test

IMAP TR-FRET Screening Express Kit (R8160) was obtained from Molecular Devices. CHK1 kinase (02-117, Carna Bio), FAM-labeled CHK1tide (R7185, Molecular Devices), and ATP were diluted with an assay buffer so that the final concentration would be 4 μg/mL, 2 μM, and 20 μM, respectively. FAM-PKAtide (R7255, Molecular Devices) and FAM-Phospho-PKAtide (R7304, Molecular Devices) were admixed after dilution, and calibration standard systems for phosphorylation levels from 0 to 100% were created. 5 μL of a compound dissolved in a 0.4% DMSO solution was added to a 384 well plate. A compound study group to which 5 μL of each of CHK1, CHK1tide, and ATP was added, and a standard group to which 20 μL of standard was added were created, and subjected to a kinase reaction for 3 hours at 30° C. Subsequently, 60 μL of Binding Reagent (80% Buffer A, 20% Buffer B, 1:600 Binding Reagent, 1:400 Tb-Donor) was added for a binding reaction for 2 hours at room temperature. SpectraMax Paradigm (Molecular Devices) was used to obtain fluorescence intensity of 520 nm or 490 nm as of 340 nm excitation. The standard was used to compute the phosphorylation level of CHK1tide, and the kinase activity was found by using the equation described below while assuming the phosphorylation level of the DMSO treated group as 100%, and the $IC_{50}$ value corresponding to the concentration of the evaluated compound indicating kinase activity of 50% was calculated.

Kinase inhibition (%)=100−$A/B$×100

A: signal in the presence of evaluated compound
B: signal in negative control (DMSO treated group)

The test shown in Test Example 1 was conducted on the compound obtained in the Examples and prexasertib purchased from MedChemExpress (the supplier is the same in the following Test Examples). The $IC_{50}$ values (nM) for the test results for each tested substance are shown in the following table.

TABLE 4-1

| Example | $IC_{50}$ (nM] | CHK1 inhibition % at 0.1 nM |
|---|---|---|
| Prexasertib | 0.54 | 11 |
| 1 | <0.1 | 55 |
| 2 | 0.22 | 31 |
| 3 | 0.22 | 28 |
| 4 | 0.23 | 25 |
| 5 | 0.33 | 15 |
| 6 | 0.27 | 15 |
| 7 | 0.21 | 29 |
| 8 | <0.1 | 51 |
| 9 | 0.24 | 24 |
| 10 | 0.30 | 20 |
| 11 | 0.18 | 35 |
| 12 | 0.34 | 21 |
| 13 | 0.74 | 6 |
| 14 | 0.22 | 30 |
| 15 | 0.26 | 29 |
| 16 | 3.04 | <5 |
| 17 | 0.30 | 24 |
| 18 | 0.51 | <5 |
| 19 | 0.26 | 20 |
| 20 | 0.34 | 6 |
| 21 | 0.29 | 15 |
| 22 | 0.24 | 22 |
| 23 | 0.79 | <5 |
| 24 | 0.30 | 23 |
| 25 | 0.74 | <5 |
| 26 | 0.14 | 42 |
| 27 | 3.46 | <5 |
| 28 | 0.80 | <5 |
| 20 | 0.60 | <5 |
| 30 | 0.26 | 28 |
| 31 | 0.75 | <5 |
| 32 | 0.76 | <5 |

TABLE 4-2

| 33 | 0.69 | <5 |
|---|---|---|
| 34 | 1.82 | <5 |
| 35 | 0.62 | <5 |
| 36 | 0.73 | <5 |
| 37 | 0.32 | 18 |
| 38 | 0.70 | <5 |

As shown in the above table, the compounds of Examples 1, 2, 3, 4, 5, 6, 7, 8, 9, 10, 11, 12, 14, 15, 17, 18, 19, 20, 21, 22, 24, 26, 28, 30, and 37 exhibited a more potent effect of suppressing CHK1 activity than prexasertib. In particular, the compounds of Examples 1 and 8 have a significant effect of especially potently suppressing CHK1 activity.

Test Example 2: Cell Growth Suppression Experiment

ES-2 cells were obtained from the American Type Culture Collection (ATCC). These cells were cultured at 37° C. in the presence of 5% $CO_2$ in a 10% fetal bovine serum, 11 penicillin/streptomycin containing McCoy's 5a medium.

500 cells were seeded for each well in a 384-well plate, and the evaluated compound was added so that the final concentration of DMSO would be 0.1% to culture the cells for 2 days. After completion of the culture, the cell viability rate was calculated using CellTiter-Glo® 3D Reagent (Promega, G968B). The $IC_{50}$ values corresponding to the concentration of the evaluated compound indicating cell growth suppression ratio of 50% was calculated from the viability rate curve. ES-2 cells are known to exhibit cisplatin resistance.

The test shown in Test Example 2 was conducted on the compounds obtained in Examples and prexasertib. The concentrations at which 50% of cell growth is suppressed of each test compound ($IC_{50}$ value; nM) are shown in the following table. The results of cell growth suppression test on representative compounds of the present disclosure are listed in the following table based on the ranking of I, II, III, IV, and V (1000 nM<I, 1000 nM>II>300 nM, 300 nM>III>100 nM, 100 nM>IV>30 nM, 30 nM>V).

TABLE 5

| Examples | $IC_{50}$ (nM) |
|---|---|
| Prexasertib | V |
| 1 | V |
| 2 | IV |
| 3 | V |
| 4 | V |
| 5 | V |
| 6 | V |
| 7 | IV |
| 8 | IV |
| 9 | IV |
| 10 | IV |
| 11 | V |
| 12 | III |
| 13 | II |
| 14 | II |
| 15 | V |
| 16 | II |
| 17 | V |
| 18 | IV |
| 19 | V |
| 20 | V |
| 21 | V |
| 22 | V |
| 23 | V |
| 24 | II |
| 25 | V |
| 26 | V |
| 27 | V |
| 28 | V |
| 29 | V |
| 30 | V |
| 31 | V |
| 32 | V |
| 33 | V |
| 34 | I |
| 35 | V |
| 36 | V |
| 37 | V |
| 38 | V |

The compounds of Examples 1, 3, 4, 5, 6, 11, 15, 17, 19, 20, 21, 22, 23, 25, 26, 27, 28, 29, 30, 31, 32, 33, 35, 36, 37, and 38 exhibited an excellent cell growth suppression effect that is equivalent to that of prexasertib as shown in the above table.

Test Example 3: hERG Current Blocking Test

The test compounds were added to cultured hERG (human Ether-a-go-go Related Gene) gene stably expressing CHO cell line cells to achieve 0.27 to 100 μM. The hERG current under electric potential stimulation was measured using Qube384 (Sophion Bioscience) to calculate the concentration at which each test compound suppresses 50% hERG current ($IC_{50}$ value; μM).

A test shown in Test Example 3 was conducted on the compounds obtained in the Examples and prexasertib. A value from dividing $IC_{50}$ of hERG obtained in Test Example 3 by My) of CHK1 inhibition obtained in Test Example 1 was calculated as hERG/CHK1 for the compound of each Example. The results are shown in the following table.

TABLE 6-1

| Examples | hERG inhibition $IC_{50}$ (μM) | hERG/CHK1 |
|---|---|---|
| Prexasertib | 3.3 | 6111 |
| 1 | 11.5 | >115000 |
| 2 | 10.7 | 48636 |
| 3 | 87.4 | 397273 |
| 4 | 13.6 | 59130 |
| 5 | 2.7 | 8182 |
| 6 | 0.4 | 1481 |
| 7 | 72.8 | 346667 |
| 8 | >100 | >1000000 |
| 9 | 18.7 | 77917 |
| 10 | 21.6 | 72000 |
| 11 | 5.1 | 38333 |
| 12 | 3.1 | 9118 |
| 13 | <2.7 | <3649 |
| 14 | >100 | >454545 |
| 15 | <2.7 | <10385 |
| 16 | <2.7 | <888 |
| 17 | 12.6 | 42000 |
| 18 | 18.9 | 37059 |
| 19 | 11.3 | 43462 |
| 20 | 3.8 | 11176 |
| 21 | 10.3 | 35517 |
| 22 | 3.0 | 12500 |
| 23 | <2.7 | <6923 |
| 24 | 34.5 | 115000 |
| 25 | 4.7 | 6351 |
| 26 | <2.7 | 19286 |
| 27 | 13.9 | 4017 |
| 28 | 16.7 | 33400 |
| 29 | 11.2 | 18667 |
| 30 | 10.4 | 40000 |
| 31 | 6.9 | 9200 |

TABLE 6-2

| 32 | 56.4 | 74211 |
|---|---|---|
| 33 | 14.5 | 21014 |
| 34 | >100 | >54945 |
| 35 | 8.7 | 14032 |
| 36 | 22.0 | 30137 |
| 37 | <2.7 | <8438 |
| 38 | <2.7 | <4500 |

As shown in the above table, the compounds of Examples 1, 3, 4, 7 to 10, 14, 24, 32, and 34 were demonstrated as having a deviation of 50000-fold or greater between $IC_{50}$ of CHK1 inhibition and $IC_{50}$ of hERG. In particular, the compounds of Examples 1, 3, 7, 8, 14, and 24 were demonstrated as having a deviation of 100000-fold or greater between $IC_{50}$ of CHK1 inhibition and $TC_{50}$ of hERG.

These six compounds exhibit a deviation of 18-fold or greater relative to prexasertib and have a different effect of having high safety.

Test Example 4: CYP3A4 MBI and Enzyme Inactivation Clearance Evaluation

Cytochrome P450 (hereinafter CYP) is the most important group of enzymes associated with drug metabolism. Many of the pharmacokinetic interactions are based on inhibition of CYP activity. CYP includes a plurality of molecular species. In particular, CYP3A4 has the highest ratio of involvement in the metabolism of a drug in an oxidation reaction by CYP and accounts for the majority of CYP in the liver.

The mode of CYP inhibition is roughly divided into "reversible inhibition" and "irreversible inhibition (mechanism-based inhibition: MBI)". It is known that CYP inhibition based on MBI in particular has the possibility of inducing not only drug interactions but also a severe side effect (hepatotoxicity, etc.) (Curr Opin Drug Discov Devel. 2010 January, 13(1), 66-77, Therapeutics and Clinical Risk Management, 2005, 1 (1), 3-13).

CYP3A4 MBI and enzyme inactivation clearance were evaluated using the compound of the Example and prexasertib.

The effect and mode of inhibition of the test compound on CYP3A4 were evaluated using a human liver microsome as an enzyme source and midazolam or testosterone as a substrate. A substrate-derived metabolite of the test compound added groups (4 concentrations) and a substrate-derived metabolite of a no addition group were measured by LC-MS/MS after 30 minutes of metabolic reaction at 37° C., and the inhibition rate was calculated from the ratio thereof. The $IC_{50}$ value was calculated from a concentration plot. When an MBI action was found in a test compound, since it is known that $IC_{50}$ decreases by starting a reaction from adding a substance after pre-incubation in the presence of NADPH (cofactor) (Xenobiotica, 2009, 39(2), 99-112), the compound was determined as having an MBI action when the change in the $IC_{50}$ value due to pre-incubation was 2-fold or greater.

When an MBI action was found, $k_{inact}$ (maximum enzyme inactivation rate constant) and K; (concentration of inhibitor resulting in 50% of maximum enzyme inactivation rate) were calculated by nonlinear least squares method. Furthermore, enzyme inactivation clearance was calculated in accordance with the method described in Drug Metabolism and Disposition, 2011, 39(7), 1247-1254 ($CL_{int}$–$k_{inact}$/$K_I$ (ml/min/mmol)×CYP contents (pmol/mg protein)).

The enzyme inactivation clearance and the factor of change in the $IC_{50}$ value by pre-incubation that can be an indicator of MRI action of the compound of each Example and prexasertib on CYP3A4 are shown in the following table.

TABLE 7-1

| Example | Factor of change in $IC_{50}$ value | Enzyme inactivation clearance (μl/min/mg protein) |
|---|---|---|
| Prexasertib | 2.6 | 0.019 |
| 1 | Not Detected | — |
| 2 | Not Detected | — |
| 3 | 3.1 | 0.036 |
| 4 | Not Detected | — |
| 5 | 2.9 | 0.717 |
| 6 | Not Detected | — |
| 7 | Not Detected | — |
| 8 | Not Detected | — |
| 9 | 4.5 | 0.150 |

TABLE 7-1-continued

| Example | Factor of change in IC$_{50}$ value | Enzyme inactivation clearance (μl/min/mg protein) |
|---|---|---|
| 10 | 3.3 | 0.091 |
| 11 | 3.5 | 1.040 |
| 12 | 2.7 | 0.287 |
| 13 | 3.6 | 0.484 |
| 14 | Not Detected | — |
| 17 | 10.9 | 0.766 |
| 18 | 3.9 | 0.352 |
| 19 | 8.4 | 1.157 |
| 20 | 3.7 | 1.112 |
| 21 | 2.5 | 0.074 |
| 22 | 2.1 | 0.349 |
| 23 | 2.4 | 0.433 |
| 25 | 2.6 | 0.722 |
| 26 | 2.2 | >100 |
| 27 | 3.6 | 0.679 |
| 28 | 3.5 | 0.188 |
| 29 | Not Detected | 0.054 |
| 30 | Not Detected | — |

TABLE 7-2

| 31 | Not Detected | — |
|---|---|---|
| 32 | 3.4 | 3.831 |
| 33 | 2.3 | 0.887 |
| 34 | Not Detected | 0.002 |
| 35 | 2.9 | 0.192 |
| 36 | 3.9 | 0.430 |
| 37 | Not Detected | — |
| 38 | Not Detected | — |

The inventors newly found that prexasertib has a risk of inducing a severe side effect such as hepatotoxicity by inhibiting CYP3A4 based on MBI.

As shown in the above table, it was revealed that, although prexasertib exhibits inhibition of CYP3A4 based on MBI, the compounds of Examples 1, 2, 4, 6 to 8, 14, 29 to 31, 34, 37, and 38 do not exhibit inhibition of CYP3A4 based on MBI. In view of this result, the compounds of Examples 1, 2, 4, 6 to 8, 14, 29 to 31, 34, 37, and 38 have a different effect of inducing not only drug interactions but also having high safety with reduced risk of severe side effect such as hepatotoxicity. In particular, the compound represented by formula (3) exhibits a particularly high safety and having a different effect.

Test Example 5. Human Bone Marrow Cell Colony Formation Test (Hemotoxicological Evaluation Test)

Human bone marrow CD34 positive hematopoietic stem cells were obtained from Lonza K. K. The frozen cells were thawed in a medium prepared by mixing a Methocult Express medium and a 10% fetal bovine serum with 1% penicillin/streptomycin containing RPMI 1640 medium at 9:1. 5000 cells were seeded per well in a 6 well plate and cultured overnight at 0.37° C. in the presence of 5% CO$_2$. The evaluated compound was added so that the final concentration of DMSO would be 0.1% and 100 nM, and the cells were cultured for 48 hours. The cells were retrieved and washed with PBS. ⅙ of the amount of cells was seeded in a 12 well plate and cultured for about. 2 weeks at 37° C. in the presence of 5% CO$_2$. After completion of culture, the number of colonies formed was calculated using Thiazolyl blue tetrazolium bromide (MTT).

The test shown in Test Example 5 was conducted for a representative compound obtained in the Examples and prexasertib. The results are shown in the following table.

TABLE 8

| Compound | concentration (nM) | Colony count(/well) mean | S.D. |
|---|---|---|---|
| DMSO | — | 34 | 17 |
| Prexasertib | 100 | 19 | 9 |
| Example 1 | 100 | 34 | 24 |

As shown in the above table, it was revealed that, although 100 nM of prexasertib exhibits an effect of suppressing human bone marrow cell colony formation, 100 nM of Example 1 does not exhibit an effect of suppressing human bone marrow colony formation. In view of the results, the compound of Example 1 has a different effect of having high safety with respect to hemotoxicity.

Test Example 6. Liposome Encapsulation Test

Liposome encapsulation tests were conducted for representative Example compounds and prexasertib.

6.48 g of hydrogenated soybean phosphatidylcholine (COATSOME NC-21E, NOF Corporation), 2.32 g of cholesterol (Sigma) and 2.06 g of distearoylphosphatidylethanolamine-methoxypolyethylene glycol 2000 (SUNBRIGHT DSPE-020CN, NOF Corporation) were dissolved in 560 mL of t-butyl alcohol heated to 65° C. The solution was frozen with dry ice/acetone bath and t-butyl alcohol was then removed by evaporation under reduced pressure to obtain a lipid mixture.

200 mL of 250 mM ammonium sulfate solution was added to the lipid mixture. The resulting mixture was heated to 65° C. and dispersed with a homogenizer (ULTRA-TURRAX, IKA) to obtain a crude liposome dispersion. The crude liposome dispersion was further dispersed with a high pressure homogenizer (Nano-Mizer NM2, Yoshida Kikai) at a pressure of 100 MPa to obtain a liposome with a mean particle size (Z-average) of about 80 nm. A dialysis cassette (Slide-A-Lyzer G2 Dialysis Cassettes 20K MWCO, Thermo Scientific) was used to replace the outer aqueous phase of liposome with 10 mM L-histidine buffer/10% sucrose solution (pH 6.5) to obtain an empty liposome solution. The solution was filtered through a 0.22 μm membrane filter, and 10 mM L-histidine buffer/101 sucrose solution (pH 6.5) was added to adjust the total lipid concentration to be 75 mM (75 μmol/mL) or 50 mM (50 μmol/mL). The prepared amount was increased or decreased appropriately.

2 to 3 mg of the test compound was weighed out. 1 mL of empty liposome solution with a total lipid concentration of 50 mM was added. An aqueous 1 mol/L hydrochloric acid or 1 mol/L sodium hydroxide solution was added to adjust the pH to 5.5 to 7. The mixture was heated for 10 to 30 minutes in a 65° C. water bath and then cooled with ice. Insolubles, when present, were removed by centrifugation for 5 minutes at 15,000×g.

The liposome encapsulation ratio was calculated as follows.

100 μL of liposome solution was passed through an ultrafiltration filter (Amicon Ultra, 100K, 0.5 mL, Merck), and centrifuged at 4° C. at 15,000×g for 10 minutes. The concentration of the compound in the filtrate after ultrafiltration was measured by HPLC as the unencapsulated compound concentration.

The liposome solution was diluted with a trifluoroacetic acid/water/methanol mixture (0.1/25/75) and was left standing for 10 minutes or longer at 5° C. The solution was centrifuged for 5 minutes at 15,000×g to remove insolubles. The compound concentration in the supernatant was measured by HPLC as the compound concentration in the liposome solution.

The encapsulation ratio and the encapsulation efficiency were calculated by the following equations.

Encapsulation ratio (%)=(compound concentration in liposome solution−unencapsulated compound concentration)×100/compound concentration in liposome solution Encapsulation efficiency (%)=(compound concentration in liposome solution−unencapsulated compound concentration)×100/concentration upon compound introduction HPLC measurement conditions are the following.
HPLC Conditions
Column: Acquity UPLC BEH C18, 1.7 μm, 50×2.1 mm
Column temperature: 40° C.
Mobile phase: A: 0.1% trifluoroacetic acid containing water
B: acetonitrile
A/B (min): 95/5 (0)→0/100 (3.5)→0/100 (4)→95/5 (4.01)→95/5 (5)
Flow rate: 0.8 mL/min
Detection: UV visible detector, measured wavelength 254 nm
Injected volume: 3 μL or 5 μL homogenizer (ULTRA-TURRAX, IKA) to obtain a crude liposome dispersion. The crude liposome dispersion was further dispersed with a high pressure homogenizer (Nano-Mizer NM2, Yoshida Kikai) at a pressure of 100 MPa to obtain a liposome with a mean particle size (Z-average) of about 80 nm. A dialysis cassette (Slide-A-Lyzer G2 Dialysis Cassettes 20K MWCO, Thermo Scientific) was used to replace the outer aqueous phase of liposome with 10 mM L-histidine buffer/10% sucrose solution (pH 6.5). The mixture was filtered through a 0.22 μm membrane filter to obtain an empty liposome solution with a total lipid concentration of 75 mM (75 μmol/mL).

The compound of Example 1 was weighed out. About 0.4 mL of 10 mM L-histidine buffer/10% sucrose solution (pH 6.5), about 0.1 mL of 0.1 mol/L hydrochloric acid, and 1 mL of the empty liposome solution were added, and the pH was adjusted to 6 to 6.5 by adding 1 mol/L hydrochloric acid. The mixture was heated for 30 minutes in a 65° C. water bath and then cooled with ice. The mixture was then filtered through a 0.22 μm membrane filter.

The liposome encapsulation ratio was calculated as follows. Unencapsulated compound concentration: The compound concentration was measured by HPLC for a solution prepared by adding 100 μL of aqueous 4% phosphoric acid solution to 100 μL of liposome solution. HPLC measurement conditions are the following.
HPLC Conditions
Column: MonoSelect nPEC (GL Sciences Inc.)
Column temperature: 30° C.

TABLE 9

| Compound | Concentration upon compound introduction (mg/mL) | Compound concentration in liposome solution (mg/mL) | Encapsulation ratio (%) | Encapsulation efficiency (%) |
|---|---|---|---|---|
| Prexasertib | 2 | 2.16 | 99.8 | 107.7 |
| Example 1 | 3 | 2.70 | 97.1 | 87.4 |
| Example 3 | 2 | 1.86 | 99.3 | 92.3 |
| Example 4 | 2 | 1.73 | 99.9 | 86.6 |
| Example 5 | 3 | 2.97 | 100.0 | 99.1 |
| Example 6 | 3 | 3.01 | 99.9 | 100.3 |

It was confirmed that prexasertib and Examples 1, 3, 4, 5, and 6 can achieve a high encapsulation efficiency of 80% or higher. A significant increase in the liquid viscosity was found when pH was adjusted by adding 1 mol/L hydrochloric acid during the liposome encapsulation procedure in Example 4. The increase in viscosity can be an issue in large-scale liposome manufacture. Meanwhile, an increase in viscosity was not found during the liposome encapsulation procedure in Examples 1, 3, 5, and 6. Thus, the compounds represented by formulas (3) and (4) exhibited a particularly superb liposome encapsulation operability.

Test Example 6A. Liposome Encapsulation Test of Example 1

A liposome encapsulation test was conducted on the compound of Example 1.

11.08 g of Presome ACD-1 (pre-prepared mixture consisting of hydrogenated soybean phosphatidylcholine, cholesterol, and distearoylphosphatidylethanolamine-methoxypolyethylene glycol 2000 at a mass ratio of 3:1:1, Nippon Fine Chemical Co., Ltd.) was weighed out, and 200 mL of 250 mM ammonium sulfate solution was added. The resulting mixture was heated to 65° C. and dispersed with a Mobile phase: A: 0.1% trifluoroacetic acid containing water
B: acetonitrile
A/B (min): 95/5 (0)→95/5 (1)→70/30 (6)→70/30 (7)→95/5 (7.01)→95/5 (10)
Flow rate: 1 mL/min
Detection: UV visible detector, measured wavelength 254 nm
Injected volume: 2 μL
Compound concentration in liposome solution: The liposome solution was diluted with a trifluoroacetic acid/water/methanol mixture (0.1/25/75) and was left standing for 10 minutes or longer at 5° C. The mixture was centrifuged for 5 minutes at 15,000×g to remove insolubles. The compound concentration in the supernatant was measured by HPLC.
HPLC measurement conditions are the following.
HPLC Conditions
Column: Acquity UPLC BEH C18, 1.7 μm, 50×2.1 mm
Column temperature: 40° C.
Mobile phase: A: 0.1% trifluoroacetic acid containing water
B: acetonitrile
A/B (min): 95/5 (0)→0/100 (3.5)→0/100 (4)→95/5 (4.01)→95/5 (5)
Flow rate: 0.8 mL/min Detection: UV visible detector, measured wavelength 254 nm injected volume: 5 μL The encapsulation ratio and encapsulation efficiency were calculated by the following equations.

Encapsulation ratio (%)=(compound concentration in liposome solution−unencapsulated compound concentration)×100/compound concentration in liposome solution Encapsulation efficiency (%)=(compound concentration in liposome solution−unencapsulated compound concentration)−100/concentration upon compound introduction

TABLE 10

| Compound | Concentration upon compound introduction (mg/mL) | Compound concentration in liposome solution (mg/mL) | Encapsulation ratio (%) | Encapsulation efficiency (%) |
|---|---|---|---|---|
| Example 1 | 2 | 1.94 | 94.1 | 91.3 |
|  | 3 | 2.84 | 96.6 | 91.6 |
|  | 4 | 3.78 | 97.5 | 92.2 |

It was confirmed that Example 1 can achieve high liposome encapsulation efficiency of 90% or higher.

Test Example 6B. Liposome Encapsulation Test of Example 1

A liposome encapsulation test was conducted on the compound of Example 1.

11.08 g of Presome ACD-1 (pre-prepared mixture consisting of hydrogenated soybean phosphatidylcholine, cholesterol, and distearoylphosphatidylethanolamine-methoxy-polyethylene glycol 2000 at a mass ratio of 3:1:1, Nippon Fine Chemical Co., Ltd.) was weighed out, and 200 mL of 250 mM ammonium sulfate solution was added. The resulting mixture was heated to 65° C. and dispersed with a homogenizer (ULTRA-TURRAX, IKA) to obtain a crude liposome dispersion. The crude liposome dispersion was further dispersed with a high pressure homogenizer (Nano-Mizer NM2, Yoshida Kikai) at a pressure of 100 MPa to obtain a liposome with a mean particle size (Z-average) of about 81 nm. A dialysis cassette (Slide-A-Lyzer G2 Dialysis Cassettes 20K MWCO, Thermo Scientific) was used to replace the outer aqueous phase of liposome with 10 mM L-histidine buffer/9.4% sucrose solution (pH 6.5). The mixture was filtered through a 0.22 μm membrane filter to obtain an empty liposome solution with a total lipid concentration of 53.1 mg/mL.

120 mg of the compound of Example 1 was weighed out. 18.3 mL of 10 mM L-histidine buffer/9.4% sucrose solution (pH 6.5), 0.3 mL of 1 mol/L hydrochloric acid, and 41.7 mL of the empty liposome solution were added, and the pH was adjusted to 6.5 with 1 mol/L hydrochloric acid or 1 mol/L sodium hydroxide. The solution was heated for 30 minutes in a 50° C. water bath and then cooled with ice. The mixture was filtered through a 0.22 μm membrane filter. The compound concentration in the liposome solution of Example 1 was 2.00 mg/mL, the encapsulation ratio was 98.0%, and the mean particle size (Z-average) was 84 nm.

The liposome encapsulation ratio was calculated as follows.

Unencapsulated compound concentration: 100 μL of liposome solution, 100 μL of aqueous 4% phosphoric acid solution, and 300 μL of saline were mixed. The mixture was centrifuged for 60 minutes at 100,000×g to remove insolubles. The compound concentration in the supernatant was measured by HPLC.

Compound concentration in liposome solution: The liposome solution was diluted with a trifluoroacetic acid/water/methanol mixture (0.1/25/75) and was left standing for 10 minutes or longer at 5° C. The mixture was centrifuged for 5 minutes at 15,000×g to remove the insolubles. The compound concentration in the supernatant was measured by HPLC.

HPLC measurement conditions are the following.

HPLC Conditions

Column: Acquity UPLC BEH C18, 1.7 μm, 50×2.1 mm

Column temperature: 40° C.

Mobile phase: A: 0.1% trifluoroacetic acid containing water

B: acetonitrile

A/B (min): 95/5 (0)→0/100 (3.5)→0/100 (4)→95/5 (4.01)→95/5 (5)

Flow rate: 0.8 mL/min

Detection: UV visible detector, measured wavelength 254 nm

Injected volume: 5 μL

The encapsulation ratio was calculated by the following equation.

Encapsulation ratio (%)=(compound concentration in liposome solution−unencapsulated compound concentration)×100/compound concentration in liposome solution A liposome encapsulating the compound of Example 1 was stored at 5° C. to study the change in the compound concentration, encapsulation ratio, and mean particle size. As shown in Table 11, a significant change in the compound concentration, encapsulation ratio, and mean particle size was not found for a liposome encapsulating Example 1, thus revealing that the liposome has excellent storage stability.

TABLE 11

| Compound | Storage period | Compound concnetration (mg/mL) | Encapsulation ratio (%) | Mean particle size (Z-average) |
|---|---|---|---|---|
| Example 1 | Initial value | 2.00 | 98.0 | 84 |
|  | 1 W | 2.07 | 98.5 | — |
|  | 2 W | 2.00 | 98.7 | — |
|  | 4 W | 1.90 | 98.9 | — |
|  | 2 M | 2.10 | 99.3 | — |
|  | 3 M | 1.94 | 99.0 | — |
|  | 6 M | 2.06 | 99.5 | 89 |

Test Example 7. Pharmacokinetic Test

A prexasertib solution formulation and liposome formulations of Examples 1, 3, and 6 and prexasertib were intravenously administrated to mice to measure the concentration of the test compound in blood.

The test used a solution formulation, which was dissolved in a 10 mM glycine/5% mannitol solution (pH2) or 20% sulfobutylether-N-cyclodextrin containing 10 mM glycine/5% mannitol solution (pH2) and then filtered through a 0.22 μm membrane filter.

The test used a liposome formulation, which was produced from preparing a liposome encapsulating a test compound by the similar method to Test Example 6, replacing an outer aqueous phase of a liposome with 10 mM L-histidine buffer/10% sucrose solution (pH 6.5) by using gel filtration column PD-10 (GE Healthcare), then filtering the liposome through a 0.22 μm membrane filter, and adding a 10 mM L-histidine buffer/10% sucrose solution (pH 6.5) to adjust the concentration.

<Administration Test>

The solution formulation or liposome formulation was instantaneously and intradermally administered into 7 week old female BALB/c mice. Blood was collected over time up to 72 hours after administration from the jugular vein under no anesthesia. Blood immediate after collection, to which 4 times the volume of methanol was added, was centrifuged, and the concentration of the test compound in the supernatant that was obtained was quantified by LC-MS/MS. LC-MS/MS measurement conditions are the following.
HPLC: Prominence system (Shimazu Corporation)
MS/MS: 4000 QTRAP (SCIEX)
Column: Cadenza CD-C18, 3 μm, 50×2 mm (Imtakt Corporation)
Column temperature: 40° C.
Mobile phase: A: 0.1% formic acid containing water
B: 0.1% formic acid containing acetonitrile
A/B (min): 90/10 (0)→10/90 (2.5)→10/90 (3.5)→90/10 (3.6)→90/10 (5.0)
Flow rate: 0.4 mL/min
Detection: ESI (positive mode)
Injected volume: 0.1 to 5 μL The test results are shown in the following table. In the table, "mean" refers to the mean, and "S.D." refers to the standard deviation. Tables 12, 13, 14, 15, and 16 show the plasma test compound concentrations from 0 hours to 72 hours after administration.

TABLE 12

| Solution formulation of prexasertib | Plasma compound concentration (ng/mL) | | | | |
|---|---|---|---|---|---|
| 1.0 mg/kg (i.v.) | 1 | 2 | 3 | mean | S.D. |
| 0.08 hr | 245 | 277 | 160 | 227 | 61 |
| 0.25 hr | 138 | 112 | 140 | 130 | 16 |
| 0.5 hr | 93.6 | 139 | 90 | 108 | 27 |
| 1.0 hr | 51.2 | 44.3 | 64.9 | 53.5 | 11 |
| 6.0 hr | N.D. | 9.95 | 5.46 | 5.14 | 5.0 |
| 24.0 hr | N.D. | N.D. | N.D. | N.D. | N.A. |
| 48.0 hr | N.D. | N.D. | N.D. | N.D. | N.A. |
| 72.0 hr | N.D. | N.D. | N.D. | N.D. | N.A. |

TABLE 13

| Liposome formulation of prexasertib | Plasma compound concentration (ng/mL) | | | | |
|---|---|---|---|---|---|
| 1.0 mg/kg (i.v.) | 1 | 2 | 3 | mean | S.D. |
| 0.08 hr | 28200 | 24800 | 27400 | 26800 | 1778 |
| 0.25 hr | 23200 | 26600 | 25200 | 25000 | 1709 |
| 0.5 hr | 26200 | 26100 | 23800 | 25367 | 1358 |
| 1.0 hr | 20200 | 24600 | 21000 | 21933 | 2344 |
| 6.0 hr | 12600 | 13000 | 11200 | 12267 | 945 |
| 24.0 hr | 1610 | 2290 | 3630 | 2510 | 1028 |
| 48.0 hr | 211 | 320 | 232 | 254 | 58 |
| 72.0 hr | 7.98 | 11.3 | 21.8 | 13.7 | 7.2 |

TABLE 14

| | Liposome formulation of Example 1 | | | | |
|---|---|---|---|---|---|
| | Plasma compound concentration (ng/mL) | | | | |
| 1.0 mg/kg (i.v.) | 1 | 2 | 3 | mean | S.D. |
| 0.08 hr | 30400 | 31100 | 30800 | 30767 | 351 |
| 0.25 hr | 30500 | 29600 | 33300 | 31133 | 1930 |
| 0.5 hr | 28700 | 27600 | 27800 | 28033 | 586 |
| 1.0 hr | 24800 | 25500 | 24600 | 24967 | 473 |
| 6.0 hr | 18300 | 19000 | 16900 | 18067 | 1069 |
| 24.0 hr | 7200 | 5940 | 6810 | 6650 | 645 |
| 48.0 hr | 2000 | 2000 | 1580 | 1860 | 242.5 |
| 72.0 hr | 159 | 22.6 | 194 | 125.2 | 90.6 |

TABLE 15

Liposome formulation of Example 3

| 1.0 mg/kg (i.v.) | Plasma compound concentration (ng/mL) | | | | |
|---|---|---|---|---|---|
| | 1 | 2 | 3 | mean | S.D. |
| 0.08 hr | 31000 | 29100 | 37000 | 32363 | 4124 |
| 0.25 hr | 33700 | 34200 | 30900 | 32933 | 1779 |
| 0.5 hr | 25400 | 24500 | 30800 | 25867 | 3258 |
| 1.0 hr | 23600 | 24700 | 26900 | 26733 | 1955 |
| 6.0 hr | 15600 | 14800 | 17300 | 15900 | 1277 |
| 24.0 hr | 9780 | 8730 | 8710 | 9073 | 612 |
| 48.0 hr | 3520 | 2960 | 4940 | 3807 | 1021 |
| 72.0 hr | 1340 | 1442 | 1020 | 1267 | 219 |

TABLE 16

Liposome formulation of Example 6

| 1.0 mg/kg (i.v.) | Plasma compound concentration (ng/mL) | | | | |
|---|---|---|---|---|---|
| | 1 | 2 | 3 | mean | S.D. |
| 0.08 hr | 24700 | 23500 | 28800 | 25667 | 2779 |
| 0.25 hr | 25800 | 28100 | 25400 | 26433 | 1457 |
| 0.5 hr | 20700 | 31400 | 24700 | 22267 | 2136 |
| 1.0 hr | 23300 | 20100 | 21900 | 21787 | 1804 |
| 5.0 hr | 11100 | 10100 | 12700 | 11300 | 1311 |
| 24.0 hr | 1050 | 1050 | 926 | 1009 | 71.6 |
| 48.0 hr | 50.1 | 31.4 | 24.8 | 35.4 | 13.1 |
| 72.0 hr | N.D. | N.D. | N.D. | N.D. | N.A. |

Table 17 shows the AUC calculated by the trapezoidal method from 0 hours after administration to a point in time (t) at which the plasma test compound concentration was able to be quantified for AUC associated with liposome formulations of Examples 1, 3, 6 and prexasertib.

TABLE 17

| Example | $AUC_{0-t}$ (ng · hr/mL) |
|---|---|
| Prexasertib | 236309 |
| 1 | 447473 |
| 3 | 583953 |
| 6 | 186225 |

The above results confirmed high blood retention upon intravenous administration of the liposome formulations prepared by liposome encapsulation of Example 1 and Example 3. This result shows that 72 hours of sustained exposure was achieved, which is important for maximizing the efficacy of prexasertib reported in a non-clinical trial. Therefore, Example 1 and Example 3 have an excellent pharmacokinetic profile and are very useful as an anticancer agent. It was demonstrated that a nitrogen atom on a pyridine ring, which is a feature of a compound set forth in formula (3), is present at a specific position.

Test Example 8. Drug Efficacy Evaluation Test Using Tumor-Bearing Mice Transplanted with ES-2 Cells Antitumor effect was evaluated by using prexasertib, a liposome formulation encapsulating prexasertib, and a liposome formulation encapsulating Example 1.

The test used a solution formulation of prexasertib, which was prepared by dissolving prexasertib in a 10 mM glycine/5% mannitol solution (pH2) containing 20% sulfobutyle-ther-β-cyclodextrin and then filtering the mixture through a 0.22 μm membrane filter.

A liposome formulation was prepared by the similar method to Test Example 6. The test compound was weighed out. An empty liposome solution with a total lipid concentration of 50 mM was added so that the compound concentration would be 2 mg/mL, and 1 mol/L hydrochloric acid was added to adjust the pH to 6 to 7. Alternatively, 10 mM L-histidine buffer/10% sucrose solution (pH 6.5) and hydrochloric acid were added to the test compound to dissolve or disperse the compound, and an empty liposome solution with a total lipid concentration of 75 mM was added so that the compound concentration would be 2 mg/mL, and the pH was adjusted to 6 to 7. The mixture was heated for 10 to 30 minutes in a 65° C. water bath, and then cooled with ice. The mixture was left standing overnight or longer in a 5° C. refrigerator and then filtered with a 0.22 μm membrane filter. The liposome encapsulation ratio calculated by the method described in Test Example 6 was 99% or higher.

ES-2 cells (ATCC) were intradermally transplanted at $1\times10^6$ cells/mouse into the flank region in 4 to 7 week old BALB/c-nu/nu mice (CAnN.Cg-Foxn1nu/CrlCrlj, female, Charles River Laboratories Japan). After confirming engraftment of the ES-2 cells 5 to 14 days post-transplantation, a solution formulation was intravenously administered at a dose of 30 mg/kg or a liposome formulation was intravenously administered at a dose of 3 mg/kg, 7.5 mg/kg, or 20 mg/kg once a week, or the same was subcutaneously administered twice a day for 3 consecutive days (total of 6 administration in a week). The tumor volume was measured over time from the start of administration to evaluate the tumor volume reduction from administration of the compound. The tumor volume was calculated by the following equation by using the minor axis and major axis of tumor measured with an electronic caliper (Mitutoyo).

Tumor volume [mm$^3$]=0.5×(minor axis [mm])$^2$×major axis [mm]

A control administration group administered with only a solvent and a compound of the present disclosure administration group were compared. T/C was calculated from the following equation to evaluate the antitumor effect. The complete tumor regression (CR) individual ratio as of the completion of administration due to administration of a solution formulation or liposome formulation was also recorded. For the control administration group, an empty liposome solution prepared by the similar method to Test Example 6 was used.

T/C (%)=(tumor volume as of completion of administration of the compound of the present disclosure administration group–tumor volume as of the start of administration of the compound of the present disclosure administration group/ (tumor volume as of completion of administration of the control administration group–tumor volume as of the start of administration of the control administration group)×100

Table 18 shows the T/C (%) and CR individual ratio for tumor-bearing mice transplanted with ES-2 cells at each dosage and dosing period for the test compound.

TABLE 18

| Test | Route of administration | Dosage (mg/kg) | Dosage period (days) | Schedule (times/week) | T/C (%) | CR (%) |
|---|---|---|---|---|---|---|
| Solution formulation of prexasertib | Intravenous | 30 (maximum tolerable dose) | 14 | 1 | 73 | 0 |
| Solution formulation of prexasertib | Subcutaneous | 10 (maximum tolerable dose) | 14 | 6 | −5 | 0 |
| Liposome formulation of prexasertib | Intravenous | 3 | 10 | 1 | 64 | 0 |
| Liposome formulation of prexasertib | Intravenous | 7.5 | 10 | 1 | −4 | 0 |
| Liposome formulation of prexasertib | Intravenous | 20 | 14 | 1 | −17 | 33 |
| Liposome formulation of Example 1 | Intravenous | 3 | 10 | 1 | 61 | 0 |
| Liposome formulation of Example 1 | Intravenous | 7.5 | 10 | 1 | 6 | 0 |
| Liposome formulation of Example 1 | Intravenous | 20 | 14 | 1 | −18 | 33 |

The drug efficacy evaluation test using tumor-bearing mice revealed that Example 1 prepared as a liposome formulation, at any of the dosages, exhibited an excellent antitumor effect in the same manner as prexasertib prepared as a liposome formulation. These liposome formulations achieved tumor regression, which cannot be achieved by prexasertib prepared as a solution formulation, in an evaluation test using the dosage of 20 mg/kg. In view of the test results, Example 1 is a promising compound exhibiting an excellent antitumor effect, which is a significant effect.

Test Example 9. Measurement of Neutrophil Count Using Tumor-Bearing Mice Transplanted with ES-2 Cells ES-2 cells (ATCC) were intradermally transplanted at $1 \times 10^6$ cells/mouse into the flank region in 4 to 7 week old BALB/c-nu/nu mice (CAnN.Cg-Foxn1nu/CrlCrlj, female, Charles River Laboratories Japan). After confirming survival of the ES-2 cells 5 to 14 days post-transplantation, a liposome formulation encapsulating prexasertib and a liposome formulation encapsulating Example 1 were intravenously administered once at each dose. Blood was collected 72 hours after administration to measure the neutrophil count. An empty liposome solution prepared by the similar method to Test Example 6 was used for comparison in this test.

A control administration group administered with an empty liposome solution and administration groups administered with Example 1 prepared as a liposome formulation or prexasertib prepared as a liposome formulation were compared. The ratio of residual neutrophils was calculated from the following equation to evaluate the safety of each formulation.

Ratio of residual neutrophils (%)=(neutrophil count 72 hours after administration in administration group)/(neutrophil count 72 hours after administration in control administration group)×100

Table 19 shows the ratio of residual neutrophils for tumor-bearing mice transplanted with ES-2 cells.

TABLE 19

| Test | Dosage (mg/kg) | Ratio of residual neutrophils (%) |
|---|---|---|
| Empty liposome | — | — |
| Liposome formulation of prexasertib | 3 | 15 |
| Liposome formulation of prexasertib | 7.5 | 4 |
| Liposome formulation of Example 1 | 3 | 61 |
| Liposome formulation of Example 1 | 7.5 | 20 |
| Liposome formulation of Example 1 | 20 | 11 |

Example 1 prepared as a liposome formulation exhibits the same antitumor effect at the same dosage as prexasertib prepared as a liposome formulation. The ratio of residual neutrophils was 15% at the minimum effective dose of 3 mg/kg for the prexasertib prepared as a liposome formulation, with both an antitumor effect and hemotoxicity being simultaneously observed. Meanwhile, the ratio of residual neutrophils was 61% at the minimum effective dose of 3 mg/kg for Example 1 prepared as a liposome formulation, with less hemotoxic side effects. Furthermore, as shown in Test Example 8, Example 1 prepared as a liposome formulation exhibited a higher ratio of residual neutrophils at a dosage of 20 mg/kg, where tumor regression is observed, than administration of prexasertib prepared as a liposome formulation at 7.5 mg/kg. In view of the above, Example 1 is an excellent compound having a significant effect, with both higher safety and efficacy than prexasertib. Likewise, a liposome formulation of Example 1 is an excellent compound having a significant effect, with both high safety and efficacy.

Test Example 10. Human Bone Marrow Cell Myeloid Lineage Differentiation Induction Test (Hemotoxicological Evaluation Test)

Human bone marrow CD34 positive hematopoietic stem cells were obtained from Lonza K. K. The frozen cells were thawed in a 11 fetal bovine serum containing IMDM medium and suspended in a Complete hemaTox® Myeloid Medium. 1000 cells were seeded per well in a 96-well plate. The evaluated compound was added so that the final concentration of DMSO would be 0.11 and 3 nM, and the cells were cultured for 7 days at 37° C. in the presence of 5% $CO_2$. After completion of culture, half of the amount of cell suspension was retrieved from each well. The luminescence was measured using CellTiter-Glo® 3D Reagent (Promega, G968B) to calculate the cell survival percentage by the following equation.

Cell survival percentage (%)=(measurement value of luminescence after 7 days of evaluated compound)/(measurement value of luminescence after 7 days of control group)×100

The test shown in Test Example 10 was conducted on a representative compound obtained in the Examples and prexasertib.

TABLE 20

| Compound | concentration (nM) | Viable cell ratio (%) mean | S.D. |
|---|---|---|---|
| DMSO | — | 100 | 2 |
| Prexasertib | 3 | 26 | 3 |
| Example 1 | 3 | 82 | 1 |

As shown in the above table, it was revealed that 3 nM of prexasertib exhibited an effect of suppressing myeloid cells induced to differentiate from human bone marrow cells, but 3 nM of Example 1 does not exhibit an effect of suppressing myeloid cells induced to differentiate from human bone marrow cells. In view of the results, Example 1 is a compound with a significant and different effect, having high safety with respect to homotoxicity, compared to prexasertib.

Test Example 11. Tumor PD Test Using Tumor-Bearing Mice Transplanted with ES-2 Cells Pharmaco Dynamic (PD) responses in tumor were evaluated using prexasertib, liposome formulation encapsulating prexasertib, and liposome formulation encapsulating Example 1.

The test used a solution formulation of prexasertib, which was prepared by dissolving prexasertib in a 10 mM glycine/5% mannitol solution (pH2) containing 20% sulfobutyle-ther-β-cyclodextrin and then filtering the mixture through a 0.22 μm membrane filter.

A liposome formulation was prepared by the similar method to Test Example 6. The test compound was weighed out. An empty liposome solution with a total lipid concentration of 50 mM was added so that the compound concentration would be 2 mg/mL, and 1 mol/L hydrochloric acid was added to adjust the pH to 6 to 7. Alternatively, 10 mM L-histidine buffer/10%: sucrose solution (pH 6.5) and hydrochloric acid were added to the test compound to dissolve or disperse the compound, and an empty liposome solution with a total lipid concentration of 75 mM was added so that the compound concentration would be 2 mg/mL, and the pH was adjusted to 6 to 7. The solution was heated for 10 to 30 minutes in a 65° C. water bath, and then cooled with ice. The solution was left standing overnight or longer in a 5° C. refrigerator and then filtered with a 0.22 μm membrane filter. The liposome encapsulation ratio calculated by the method described in Test Example 6 was 99% or higher.

Ovarian cancer ES-2 cells (ATCC) were intradermally transplanted at 1×10$^6$ cells/mouse into the flank region in 4 to 7 week old BALB/c-nu/nu mice (CAnN.Cg-Foxn1nu/CrlCrlj, female, Charles River Laboratories Japan). After confirming engraftment of the ES-2 cells 5 to 14 days post-transplantation, a formulation was administered under the following conditions for each test:

Test A: a solution formulation was intravenously administered at a single dose of 30 mg/kg or a liposome formulation was intravenously administered at a single dose of 7.5 mg/kg, 3 mg/kg, 1 mg/kg, or 0.3 mg/kg. Test B: a solution formulation was intravenously administered at a single dose of 30 mg/kg or a Liposome formulation was intravenously administered at a single dose of 7.5 mg/kg, 3 mg/kg, 1 mg/kg, or 0.3 mg/kg. Test C: a liposome formulation was intravenously administered at a single dose of 20 mg/kg, 7.5 mg/kg, 3 mg/kg, 1 mg/kg, or 0.3 mg/kg. After administration, tumor was harvested after 1, 3, or 6 days to evaluate PD responses of tumor due to compound administration.

PD responses in tumor were evaluated by Western blotting. Each band intensity detected with an anti-γH2AX antibody (05-636, Merck) and anti-Tubulin antibody (3673, Cell Signaling Technology) was calculated using the ImageJ software.

A control administration group administered with only a solvent and a compound of the present disclosure administration group were compared. The relative value of each band intensity was calculated with the following equation to evaluate the PD response in tumor. For the control administration group, an empty liposome solution prepared by the similar method to Test Example 6 was used.

Intensity of γH2AX={(band intensity of γH2AX in tumor of the compound of the present disclosure administration group)/(band intensity of tubulin in tumor of the compound of the present disclosure administration group)}/{(band intensity of γH2AX in tumor of the control administration group/band intensity of tubulin in tumor of the control administration group)}×100

Figure 7:
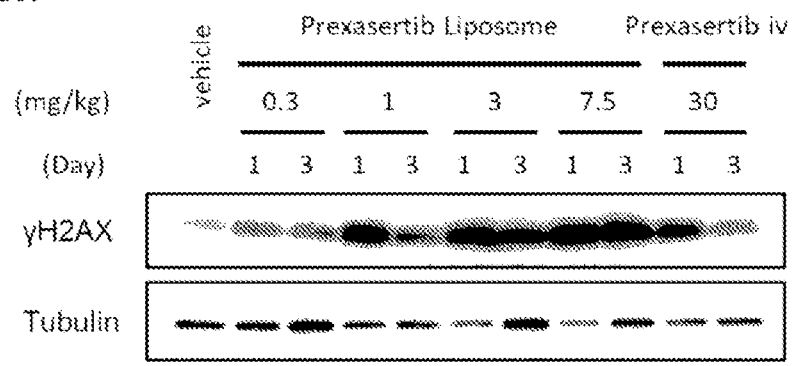
FIG. 7 is a diagram showing tumor PD responses using ES-2 bearing mice for Test A of Test Example 11, prexasertib solution formulation or liposome formulation. PD responses were evaluated by detecting the expression levels of γH2AX and Tubulin by Western blotting, quantifying each band intensity with ImageJ software, and computing the relative value of the expression level of γH2AX with the expression level of Tubulin. The vertical axis indicates the relative value of γH2AX.
Figure 7:
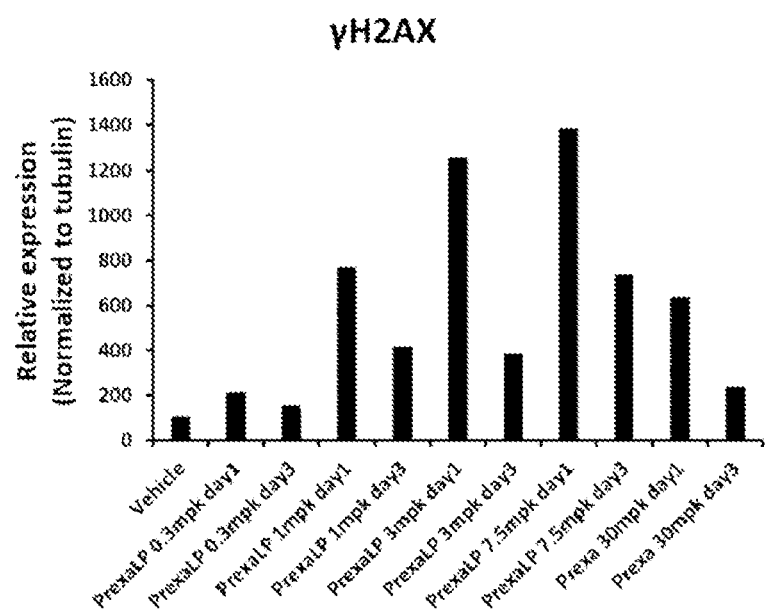
Figure 8:
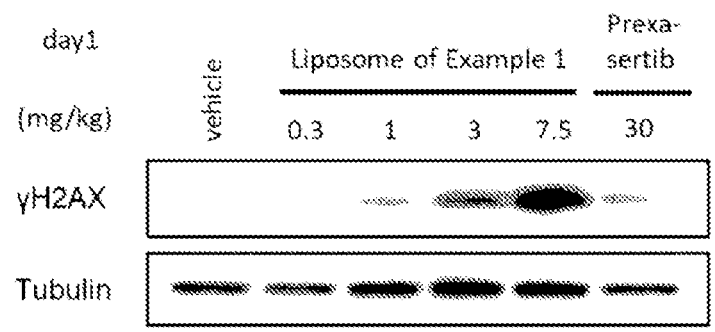
FIG. 8 is a diagram showing antitumor PD responses using ES-2 bearing mice for Test B of Test Example 11, prexasertib solution formulation or liposome formulation of Example 1. PD responses were evaluated by detecting the expression levels of γH2AX and Tubulin by Western blotting, quantifying each band intensity with ImageJ software, and computing the relative value of the expression level of γH2AX with the expression level of Tubulin. The vertical axis indicates the relative value of γH2AX.
Figure 8:
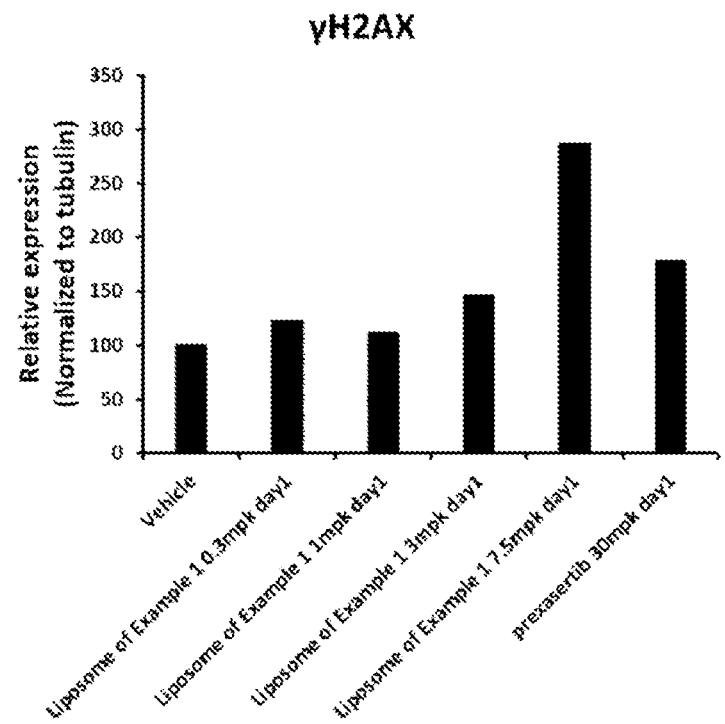
Figure 9:
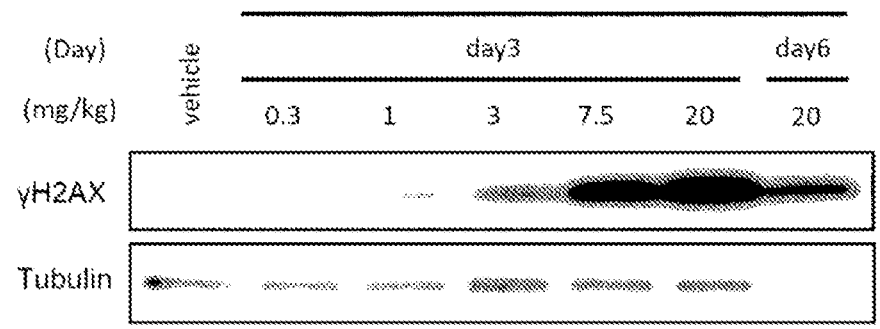
FIG. 9 is a diagram showing antitumor PD responses using ES-2 bearing mice for Test C of. Test Example 11 or liposome formulation of Example 1. PD responses were evaluated by detecting the expression levels of γH2AX and Tubulin by Western blotting, quantifying each band intensity with ImageJ software, and computing the relative value of the expression level of γH2AX with the expression level of Tubulin. The vertical axis indicates the relative value of γH2AX.
Figure 9:
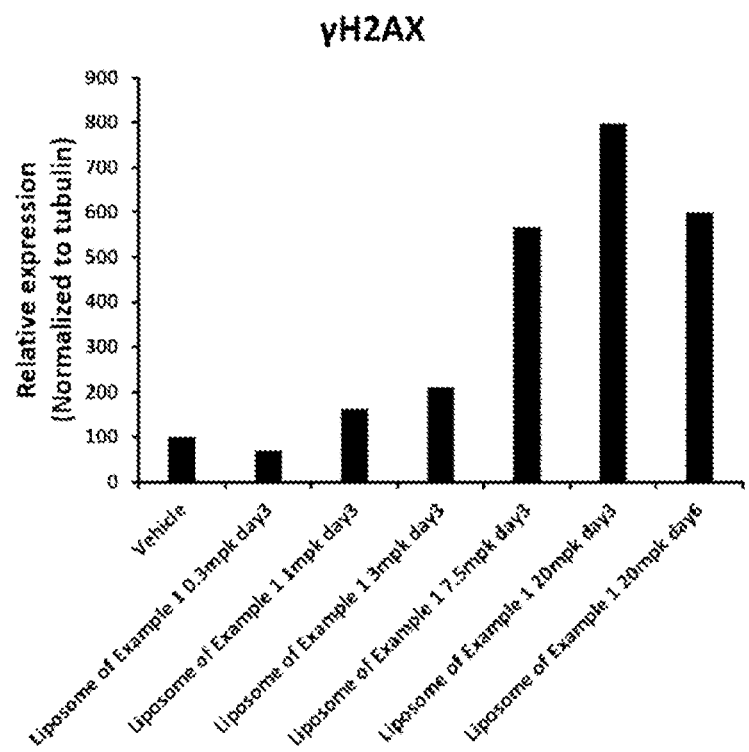

FIG. 7 to 9 show the intensity of γH2AX for tumor-bearing mice transplanted with ES-2 cells at each dosage and dosing period for the test compound.

In view of the above results, a potent PD response was observed at a dosage of 7.5 mg/kg 3 days after administration, and a PD response that could not be achieved with prexasertib prepared as a solution formulation was achieved from administration of prexasertib prepared as a liposome formulation, as shown in test A of Test Example 11. A potent PD response was observed at a dosage of 7.5 mg/kg 1 day after administration, and a PD response that could not be achieved with prexasertib prepared as a solution formulation was achieved from administration of Example 1 prepared as a liposome formulation, as shown in test B of Test Example 11. A potent PD response was observed at dosages of 7.5 mg/kg and 20 mg/kg 3 days and 6 days after administration from administration of Example 1 prepared as a liposome formulation, as shown in test C of Test Example 11. It was shown that these liposome formulations achieve 72 hours of sustained exposure, which is important for maximizing the efficacy of prexasertib reported in a non-clinical trial as shown in Test Example 7. Therefore, Example 1 has an excellent pharmacokinetic and pharmacodynamic profiles and are very useful as an anticancer agent.

Test Example 12. Drug Efficacy Evaluation Test Using Peritoneal Dissemination Tumor-Bearing Mice Transplanted with ES-2 Cells Antitumor effects were evaluated using prexasertib, liposome formulation encapsulating prexasertib, and liposome formulation encapsulating Example 1.

The test used a solution formulation of prexasertib, which was prepared by dissolving prexasertib in a 10 mM glycine/5% mannitol solution (pH2) containing 20% sulfobutyle-ther-β-cyclodextrin and then filtering the mixture through a 0.22 μm membrane filter.

A liposome formulation was prepared by the similar method to Test Example 6.

A cell line from Luciferase expressing ovarian cancer ES-2 cells (ATCC) was intraperitoneally transplanted at 1×10$^6$ cells/mouse in 5 week old BALB/c-nu/nu mice (CAnN.Cg-Foxn1nu/CrlCrlj, female, Charles River Laboratories Japan). After confirming engraftment of the ES-2 cells 5 to 14 days post-transplantation with an IVIS Imaging System (PerkinElmer), a solution formulation was intravenously administered once a week at a dose of 30 mg/kg or a liposome formulation was intravenously administered once a week at a dose of 4.5 mg/kg or 20 mg/kg. Luminescence due to luciferase was measured over time from the start of administration to evaluate the tumor regression action due to compound administration. The mice were observed based on the change in body weight, systemic symptoms, and the tumor size estimated from luminescence due to luciferase. The survival period was measured for mice exhibiting a healthy state without severe diagnosis.

The median survival period was calculated for a control administration group administered with only a solvent and a compound of the present disclosure administration group to evaluate the antitumor effect. For the control administration group, an empty liposome solution prepared by the similar method to Test Example 6 was used.

Table 21 shows the median survival period for peritoneal dissemination tumor-bearing mice transplanted with ES-2 cells at each dosage and dosing period of test compound.

TABLE 21

| Test | Dosage (mg/kg) | Dosing period (days) | Schedule (times/week) | Median survival period (days) |
| --- | --- | --- | --- | --- |
| Empty liposome | — | 35 | 1 | 18.5 |
| Solution formulation of prexasertib | 30 (maximum tolerable dose) | 35 | 1 | 27 |
| Liposome formulation of prexasertib | 20 | 35 | 1 | 33.5 |
| Liposome formulation of Example 1 | 4.5 | 35 | 1 | 24 |
| Liposome formulation of Example 1 | 20 | 35 | 1 | 32 |

It was revealed by the drug efficacy evaluation test using peritoneal dissemination tumor-bearing mice that Example 1 prepared as a liposome formulation exhibits an excellent antitumor effect in the same manner as prexasertib prepared as a liposome formulation at a dosage of 20 mg/kg. These liposome formulations achieved prolongation of survival period, which cannot be achieved with prexasertib prepared as a solution formulation in an evaluation test using a dosage of 20 mg/kg. In view of the test results, Example 1 is a promising compound exhibiting an excellent antitumor effect, which is a significant effect.

Test Example 13. Drug Efficacy Evaluation Test Using Orthotopic Ovarian Tumor-Bearing Mice Transplanted with ES-2 Cells Antitumor effects were evaluated using prexasertib, a liposome formulation encapsulating prexasertib, and a liposome formulation encapsulating Example 1.

The test used a solution formulation of prexasertib, which was prepared by dissolving prexasertib in a 10 mM glycine/5% mannitol solution (pH2) containing 20% sulfobutyl-ether-β-cyclodextrin and then filtering the mixture through a 0.22 μm membrane filter.

A liposome formulation was prepared by the similar method to Test Example 6.

A cell line from Luciferase expressing ovarian cancer ES-2 cells (ATCC) was transplanted within the right ovary at 1×10⁶ cells/mouse in 5 week old BALB/c-nu/nu mice (CAnN.Cg-Foxn1nu/CrlCrlj, female, Charles River Laboratories Japan). After confirming engraftment of the ES-2 cells 5 to 14 days post-transplantation with an IVIS Imaging System (PerkinElmer), a solution formulation was intravenously administered once a week at a dose of 30 mg/kg or a liposome formulation was intravenously administered once a week at a dose of 4.5 mg/kg or 20 mg/kg. Luminescence due to luciferase was measured over time from the start of administration to evaluate the tumor regression action due to compound administration. The mice were observed based on the tumor size estimated from luminescence due to the change in body weight, systemic symptoms, and luciferase. The survival period was measured for mice exhibiting a healthy state without severe diagnosis.

The median survival period was calculated for a control administration group administered with only a solvent and a compound of the present disclosure administration group to evaluate the antitumor effect. For the control administration group, an empty liposome solution prepared by the similar method to Test Example 6 was used.

Table 22 shows the median survival period for orthotopic ovarian tumor-bearing mice transplanted with ES-2 cells at each dosage and dosing period for test compound.

TABLE 22

| Test | Dosage (mg/kg) | Dosing period (days) | Schedule (times/week) | Median survival period (days) |
| --- | --- | --- | --- | --- |
| Empty liposome | | 56 | 1 | 31.5 |
| Solution formulation of prexasertib | 30 (maximum tolerable dose) | 56 | 1 | 36 |
| Liposome formulation of prexasertib | 20 | 56 | 1 | 48.5 |
| Liposome formulation of Example 1 | 4.5 | 56 | 1 | 39.5 |
| Liposome formulation of Example 1 | 20 | 56 | 1 | 46 |

It was revealed by the drug efficacy evaluation test using orthotopic ovarian tumor-bearing mice that Example 1 prepared as a liposome formulation exhibits an excellent antitumor effect in the same manner as prexasertib prepared as a liposome formulation at a dosage of 20 mg/kg. These liposome formulations achieved prolongation of survival period, which cannot be achieved with prexasertib prepared as a solution formulation, in an evaluation test using a dosage of 20 mg/kg. In view of the test results, Example 1 is a promising compound exhibiting an excellent antitumor effect, which is a significant effect.

Test Example 14. Drug Efficacy Evaluation Test Using Tumor-Bearing Mice Transplanted with Various Cancer Cells Antitumor effects were evaluated using a liposome formulation encapsulating Example 1.

A liposome formulation was prepared by the similar method to Test Example 6.

Ovarian cancer SKOV-3 cells (ATCC) or sarcoma SJCRH30 cells (ATCC) or sarcoma HT-1080 cells (ATCC) or pancreatic cancer AsPC-1 cells (ATCC) or pancreatic cancer BxPC-3 cells (ATCC) or lung cancer Calu-6 cells (ATCC) or ovarian cancer OV5304 cells (Crown Bioscience) were intradermally transplanted at $5\times10^5$ cells/mouse or $1\times10^6$ cells/mouse or $3\times10^6$ cells/mouse or $5\times10^5$ cells/mouse or 8 mm$^3$ to 27 mm$^3$ tumor mass/mouse into the flank region in 4 to 7 week old BALB/c-nu/nu mice (CAnN.Cg-Foxn1nu/CrlCrlj, female, Charles River Laboratories Japan) or NOD SCID mice (NOD.CB17-Prkdc$^{scid}$/J, female, Charles River Laboratories Japan). After confirming engraftment of the various cancer cells 5 to 27 days post-transplantation, a liposome formulation was intravenously administered once a week at a dose of 4.5 mg/kg or 10 mg/kg or 20 mg/kg. The tumor volume was measured over time from the start of administration to evaluate the tumor volume reduction from administration of the compound. The tumor volume was calculated by the following equation by using the minor axis and major axis of tumor measured with an electronic caliper (Mitutoyo). It is known that BxPC-3 cells exhibit gemcitabine resistance, and OV5304 exhibits PARP inhibitor resistance.

Tumor volume [mm$^3$]=0.5×(minor axis [mm])$^2$×major axis [mm]

A control administration group administered with only a solvent and a compound of the present disclosure administration group were compared. T/C was calculated from the following equation to evaluate the antitumor effect. For the control administration group, an empty liposome solution prepared by the similar method to Test Example 6 was used.

T/C (%)=(tumor volume as of the end of administration of the compound of the present disclosure administration group−tumor volume as of the start of administration of the compound of the present disclosure administration group)/(tumor volume as of the end of administration of the control administration group−tumor volume as of the start of administration of the control administration group)×100

Table 23 shows T/C (%) for tumor-bearing mice transplanted with various cancer cells at each dosage and dosing period for the test compound.

TABLE 23

| Cancer cell Line | Cancer type | Test | Dosage (mg/kg) | Dosing period (days) | Schedule (times/week) | T/C (%) |
|---|---|---|---|---|---|---|
| SKOV-3 | Ovarian cancer | Liposome formulation of Example 1 | 20 | 21 | 1 | 10 |
| SJCRH30 | Sarcoma | Liposome formulation of Example 1 | 10 | 14 | 1 | 3 |
| HT-1080 | Sarcoma | Liposome formulation of Example 1 | 20 | 14 | 1 | 5 |
| AsPC-1 | Pancreatic cancer | Liposome formulation of Example 1 | 4.5 | 21 | 1 | 73 |
| AsPC-1 | Pancreatic cancer | Liposome formulation of Example 1 | 20 | 21 | 1 | 27 |
| BxPC-3 | Pancreatic cancer | Liposome formulation of Example 1 | 4.5 | 21 | 1 | 45 |
| BxPC-3 | Pancreatic cancer | Liposome formulation of Example 1 | 20 | 21 | 1 | 21 |
| Calu-6 | Lung cancer | Liposome formulation of Example 1 | 10 | 14 | 1 | 2 |
| OV5304 | Ovarian cancer | Liposome formulation of Example 1 | 20 | 25 | 1 | 83 |

It was revealed by the concomitantly used drug efficacy evaluation test using tumor-bearing mice that Example 1 prepared as a liposome formulation exhibits an excellent antitumor effect on various cancer cell lines. In view of the test results, Example 1 is a promising compound exhibiting an excellent antitumor effect, which is a significant effect.

Test Example 15. Concomitantly Used Drug Efficacy Evaluation Test Using Tumor-Bearing Mice Transplanted with PA-1 Cells Antitumor effects were evaluated using a liposome formulation encapsulating Example 1 and cisplatin.

Cisplatin (Randa Injection 50 mg/100 mL, Nippon Kayaku) was used.

A liposome formulation was prepared by the similar a method to Test Example 6.

Ovarian cancer PA-1 cells (ATCC) were intradermally transplanted at $5\times10^6$ cells/mouse into the flank region in 4 to 7 week old BALB/c-nu/nu mice (CAnN.Cg-Foxn1nu/CrlCrlj, female, Charles River Laboratories Japan). After confirming engraftment of the PA-1 cells 5 to 14 days post-transplantation, a liposome formulation was administered at 20 mg/kg, cisplatin was administered at 2.5 mg/kg, or they were administered at a combined dose, intravenously once a week, peritoneally twice a week, or combined. The tumor volume was measured over time from the start of administration to evaluate the tumor volume reduction from administration of the compound. The tumor volume was calculated by the following equation by using the minor axis and major axis of tumor measured with an electronic caliper (Mitutoyo).

Tumor volume [mm$^3$]=0.5×(minor axis [mm])$^2$×major axis [mm]

A control administration group administered with only a solvent and a compound of the present disclosure administration group were compared. T/C was calculated from the following equation to evaluate the antitumor effect. The complete tumor regression (CR) individual ratio as of the end of administration due to a liposome formulation, cisplatin, or concomitant administration was also recorded. For the control administration group, an empty liposome solution prepared by the similar method to Test Example 6 was used.

T/C (%)=(tumor volume as of the end of administration of the compound of the present disclosure administration group−tumor volume as of the start of administration of the compound of the present disclosure administration group)/(tumor volume as of the end of administration of the control administration group−tumor volume as of the start of administration of the control administration group)×100

Table 24 shows the T/C (%) and CR individual ratio for tumor-bearing mice transplanted with PA-1 cells at each dosage and dosing period for the test compound.

TABLE 24

| Test | Route of administration | Dosage (mg/kg) | Dosing period (days) | Schedule (times/ week) | T/C (%) | CR (%) |
|---|---|---|---|---|---|---|
| Liposome formulation of Example 1 | Intravenous | 20 | 21 | 1 | −5 | 0 |
| Cisplatin | Peritoneal | 2.5 | 21 | 2 | 52 | 0 |
| Liposome formulation of Example 1 and cisplatin | Intravenous and peritoneal | 20 and 2.5 | 21 | 1 and 2 | −11 | 50 |

It was revealed by the concomitantly used drug efficacy evaluation test using tumor-bearing mice that Example 1 prepared as a liposome formulation exhibits an excellent antitumor effect in concomitant use with cisplatin. In view of the test results, Example 1 is a promising compound exhibiting an excellent antitumor effect, which is a significant effect.

Test Example 16. Concomitantly Used Drug Efficacy Evaluation Test Using Tumor-Bearing Mice Transplanted with ES-2 Cells Antitumor effects were evaluated using a liposome formulation encapsulating Example 1 and gemcitabine.

Gemcitabine (Gemzar Injection 200 mg, Eli Lilly Japan) dissolved in saline (Otsuka Normal Saline, Otsuka Pharmaceutical Factory) was used.

A liposome formulation was prepared by the similar method to Test Example 6. The test compound was weighed out. An empty liposome solution with a total lipid concentration of 50 mM was added so that the compound concentration would be 2 mg/mL, and 1 mol/L hydrochloric acid was added to adjust the pH to 6 to 7. Alternatively, 10 mM L-histidine buffer/10% sucrose solution (pH 6.5) and hydrochloric acid were added to the test compound to dissolve or disperse the compound, and an empty liposome solution with a total lipid concentration of 75 mM was added so that the compound concentration would be 2 mg/mL, and the pH was adjusted to 6 to 7. The solution was heated for 10 to 30 minutes in a 65° C. water bath, and then cooled with ice. The solution was left standing overnight or longer in a 5° C. refrigerator and then filtered with a 0.22 μm membrane filter. The liposome encapsulation ratio calculated by the method described in Test Example 6 was 99% or higher.

Ovarian cancer ES-2 cells (ATCC) were intradermally transplanted at $1\times10^6$ cells/mouse into the flank region in 4 to 7 week old BALB/c-nu/nu mice (CAnN.Cg-Foxn1nu/CrlCrlj, female, Charles River Laboratories Japan). After confirming engraftment of the ES-2 cells 5 to 14 days post-transplantation, a liposome formulation was administered at 4.5 mg/kg, gemcitabine was administered at 30 mg/kg, or they were administered at a combined dose, intravenously once a week, peritoneally twice a week, or concomitantly. The tumor volume was measured over time from the start of administration to evaluate the tumor volume reduction due to compound administration. The tumor volume was calculated by the following equation by using the minor axis and major axis of tumor measured with an electronic caliper (Mitutoyo).

Tumor volume $[mm^3]=0.5\times(\text{minor axis } [mm])^2 \times \text{major axis } [mm]$ A control administration group administered with only a solvent and a compound of the present disclosure administration group were compared. T/C was calculated from the following equation to evaluate the antitumor effect. The complete tumor regression (CR) individual ratio as of the end of administration due to a liposome formulation, gemcitabine, or concomitant administration was also recorded. For the control administration group, an empty liposome solution prepared by the similar method to Test Example 6 was used.

T/C (%)=(tumor volume as of the end of administration of the compound of the present disclosure administration group−tumor volume as of the start of administration of the compound of the present disclosure administration group)/(tumor volume as of the end of administration of the control administration group−tumor volume as of the start of administration of the control administration group)×100

Table 25 shows the T/C (%) and CR individual ratio for tumor-bearing mice transplanted with ES-2 cells at each dosage and dosing period for the test compound.

TABLE 25

| Test | Route of administration | Dosage (mg/kg) | Dosing period (days) | Schedule (times/ week) | T/C (%) | CR (%) |
|---|---|---|---|---|---|---|
| Liposome formulation of Example 1 | Intravenous | 4.5 | 14 | 1 | 58 | 0 |
| Gemcitabine | Peritoneal | 30 | 14 | 2 | 9 | 0 |
| Liposome formulation of Example 1 and gemcitabine | Intravenous and peritoneal | 4.5 and 30 | 14 | 1 and 2 | −15 | 100 |

It was revealed by the concomitantly used drug efficacy evaluation test using tumor-bearing mice that Example 1 prepared as a liposome formulation exhibits an excellent antitumor effect in concomitant use with gemcitabine. In view of the test results, Example 1 is a promising compound exhibiting an excellent antitumor effect, which is a significant effect.

Test Example 17. Measurement of Neutrophil Count Using Tumor-Bearing Mice Transplanted with ES-2 Cells Ovarian cancer ES-2 cells (ATCC) were intradermally transplanted at 1×10" cells/mouse into the flank region in 4 to 7 week old BALB/c-nu/nu mice (CAnN.Cg-Foxn1nu/CrlCrlj, female, Charles River Laboratories Japan). After confirming engraftment of the ES-2 cells 5 to 14 days post-transplantation, a liposome formulation was administered at 4.5 mg/kg, gemcitabine was administered at 30 mg/kg, or they were administered at a combined dose, intravenously once a week, peritoneally twice a week, or combined. Blood was collected 96 hours after the final administration to measure the neutrophil count. For comparison in this test, an empty liposome solution prepared by the similar method to Test Example 6 was used.

A control administration group administered with an empty liposome solution was compared with each of administration groups administered with Example 1 prepared as a liposome formulation, gemcitabine, and a combination thereof. The ratio of residual neutrophils was calculated from the following equation to evaluate the safety of each formulation.

Ratio of residual neutrophils (%)=(neutrophil count of administration group 96 hours after administration)/(neutrophil count of control administration group 96 hours after administration)×100

Table 26 shows the ratio of residual neutrophils for tumor-bearing mice transplanted with ES-2 cells.

TABLE 26

| Test | Dosage (mg/kg) | Dosing period (days) | Schedule (times/week) | Ratio of residual neutrophils (%) |
|---|---|---|---|---|
| Empty liposome | — | 14 | 1 | — |
| Liposome formulation of Example 1 | 4.5 | 14 | 1 | 87 |
| Gemcitabine | 30 | 14 | 2 | 39 |
| Liposome formulation of Example 1 and gemcitabine | 4.5 and 30 | 14 | 1 and 2 | 38 |

The ratio of residual neutrophils for Example 1 prepared as a liposome formulation is 87% at 4.5 mg/kg. As shown in Test Example 17, Example 1 prepared as a liposome formulation exhibits an antitumor effect while not exhibiting hemotoxic side effects. Furthermore, Example 1 prepared as a liposome formulation in concomitant administration with gemcitabine exhibits a high ratio of residual neutrophils for which tumor regression is observed as shown in Test Example 17, without exacerbating a hemotoxic side effect due to gemcitabine. In view of the above, Example 1 prepared as a liposome formulation is an excellent compound having a significant effect, with both high safety and efficacy.

Test Example 18. Drug Efficacy Evaluation Test Regarding the Order of Concomitant Administration Using Tumor-Bearing Mice Transplanted with ES-2 Cells Antitumor effects were evaluated using a liposome formulation encapsulating Example 1 and gemcitabine.

Gemcitabine (Gemzar Injection 200 mg, Eli Lilly Japan) dissolved in saline (Otsuka Normal Saline, Otsuka Pharmaceutical Factory) was used.

A liposome formulation was prepared by the similar method to Test Example 6.

Ovarian cancer ES-2 cells (ATCC) were intradermally transplanted at $1\times10^6$ cells/mouse into the flank region in 4 to 7 week old BALB/c-nu/nu mice (CAnN.Cg-Foxn1nu/CrlCrlj, female, Charles River Laboratories Japan). After confirming engraftment of the ES-2 cells 5 to 14 days post-transplantation, a liposome formulation was administered at 4.5 mg/kg and gemcitabine was administered at 30 mg/kg, intravenously once or peritoneally once. The tumor volume was measured over time from the start of administration to evaluate the tumor volume reduction due to compound administration. The tumor volume was calculated by the following equation by using the minor axis and major axis of tumor measured with an electronic caliper (Mitutoyo).

Tumor volume [mm³]=0.5×(minor axis [mm])²×major axis [mm]

A control administration group administered with only a solvent and a compound of the present disclosure administration group were compared, T/C was calculated from the following equation to evaluate the antitumor effect. The complete tumor regression (CR) individual ratio as of the end of administration due to liposome formulation or gemcitabine or concomitant administration was also recorded. For the control administration group, an empty liposome solution prepared by the similar method to Test Example 6 was used.

T/C (%)=(tumor volume as of the end of administration of the compound of the present disclosure administration group−tumor volume as of the start of administration of the compound of the present disclosure administration group)/(tumor volume as of the end of administration of the control administration group−tumor volume as of the start of administration of the control administration group)×100

Table 27 shows the T/C (%) and CR individual ratio for tumor-bearing mice transplanted with ES-2 cells at each dosage and dosing period of the test compound.

TABLE 27

| Test | T/C (%) |
|---|---|
| Liposome formulation of Example 1 (Day 1) and gemcitabine (Day 1) | 22 |
| Liposome formulation of Example 1 (Day 2) and gemcitabine (Day 1) | 7 |
| Liposome formulation of Example 1 (Day 5) and gemcitabine (Day 1) | 66 |
| Liposome formulation of Example 1 (Day 1) and gemcitabine (Day 2) | 21 |
| Liposome formulation of Example 1 (Day 1) and gemcitabine (Day 5) | 34 |

It was revealed by the concomitantly used drug efficacy evaluation test using tumor-bearing mice that Example 1 prepared as a liposome formulation exhibits an excellent antitumor effect in concomitant use with gemcitabine. As shown in Test Example 18, an antitumor effect through concomitant use of Example 1 prepared as a liposome formulation and gemcitabine has the most potent effect from the order of administering a liposome formulation of Example 1 on the day after administration of gemcitabine, and next most potent effect was exhibited from simultaneous administration or administration of gemcitabine on the day after administration of a liposome formulation of Example 1. In view of the test results, Example 1 is a promising compound exhibiting an excellent antitumor effect, which is a significant effect.

Test Example 19. Concomitantly Used Drug Efficacy Evaluation Test Using Tumor-Bearing Mice Transplanted with MC38 Cells Antitumor effects were evaluated using a liposome formulation encapsulating Example 1 and anti-PD-1 antibody.

An anti-PD-1 antibody (114116, Biolegend) diluted with PBS (Invitrogen) was used.

A liposome formulation was prepared by the similar method to Test Example 6. The test compound was weighed out. An empty liposome solution with a total lipid concentration of 50 mM was added so that the compound concentration would be 2 mg/mL, and 1 mol/L hydrochloric acid was added to adjust the pH to 6 to 7. Alternatively, 10 mM L-histidine buffer/103 sucrose solution (pH 6.5) and hydrochloric acid were added to the test compound to dissolve or disperse the compound, and an empty liposome solution with a total lipid concentration of 75 mM was added so that the compound concentration would be 2 mg/mL, and the pH was adjusted to 6 to 7. The solution was heated for 10 to 30 minutes in a 65° C. water bath, and then cooled with ice. The solution was left standing overnight or longer in a 5° C. refrigerator and then filtered with a 0.22 μm membrane filter. The liposome encapsulation ratio calculated by the method described in Test Example 6 was 99% or higher.

Mouse colon cancer MC38 cells (Kerafast) were intradermally transplanted at $5 \times 10^5$ cells/mouse into the flank region in 4 to 7 week old c57BL/6J mice (C57BL/6J, female, Charles River Laboratories Japan). After confirming engraftment of the MC38 cells 5 to 14 days post-transplantation, a liposome formulation was administered at 10 mg/kg, anti-PD-1 antibody was administered at 200 μg/head, or they were administered at a combined dose, intravenously once a week, peritoneally twice a week, or concomitantly. The tumor volume was measured over time from the start of administration to evaluate the tumor volume reduction due to compound administration. The tumor volume was calculated by the following equation by using the minor axis and major axis of tumor measured with an electronic caliper (Mitutoyo).

Tumor volume $[mm^3] = 0.5 \times (\text{minor axis } [mm])^2 \times \text{major axis } [mm]$ A control administration group administered with only a solvent and a compound of the present disclosure administration group were compared. T/C was calculated from the following equation to evaluate the antitumor effect. The complete tumor regression (CR) individual ratio as of the end of administration due to liposome formulation or anti-PD-1 antibody or concomitant administration was also recorded. For the control administration group, an empty liposome solution prepared by the similar method to Test Example 6 was used.

T/C (%)=(tumor volume as of the end of administration of the compound of the present disclosure administration group–tumor volume as of the start of administration of the compound of the present disclosure administration group)/(tumor volume as of the end of administration of the control administration group–tumor volume as of the start of administration of the control administration group)×100

Table 28 shows the T/C(%) and CR individual ratio for tumor-bearing mice transplanted with MC38 cells at each dosage and dosing period for the test compound.

TABLE 28

| Test | Route of administration | Dosage (mg/kg) | Dosing period (days) | Schedule (times/week) | T/C (%) | CR (%) |
|---|---|---|---|---|---|---|
| Liposome formulation of Example 1 | Intravenous | 10 mg/kg | 14 | 1 | 43 | 0 |
| Anti-PD-1 antibody | Peritoneal | 200 μg/head | 14 | 2 | 23 | 0 |
| Liposome formulation of Example 1 and anti-PD-1 antibody | Intravenous and peritoneal | 10 mg/kg and 200 μg/head | 14 | 1 and 2 | 5 | 60 |

It was revealed by the concomitantly used drug efficacy evaluation test using tumor-bearing mice that Example 1 prepared as a liposome formulation exhibits an excellent antitumor effect in concomitant use with an anti-PD-1 antibody. As shown in Test Example 19, tumor-bearing mice transplanted with MC38 cells are models in which an anti-PD-1 antibody exhibits an antitumor effect. In view of the test results, Example 1 is a promising compound exhibiting an excellent antitumor effect on a model in which an anti-PD-1 antibody exhibits an antitumor effect, which is a significant effect.

Test Example 20. Concomitantly Used Drug Efficacy Evaluation Test Using Tumor-Bearing Mice Transplanted with EMT6 Cells Antitumor effects were evaluated using a liposome formulation encapsulating Example 1 and an anti-PD-1 antibody.

An anti-PD-1 antibody (114116, Biolegend) diluted with PBS (Invitrogen) was used.

A liposome formulation was prepared by the similar method to Test Example 6.

Mouse breast cancer EMT6 cells (ATCC) were intradermally transplanted at $5 \times 10^5$ cells/mouse into the flank region in 4 to 7 week old BALB/c mice (BALB/cAnNCrlCrlj, female, Charles River Laboratories Japan). After confirming engraftment of the EMT6 cells 5 to 14 days post-transplantation, a liposome formulation was administered at 10 mg/kg, anti-PD-1 antibody was administered at 200 μg/head, or they were administered at a combined dose, intravenously once a week, peritoneally twice a week, or concomitantly. The tumor volume was measured over time from the start of administration to evaluate the tumor volume reduction due to compound administration. The tumor volume was calculated by the following equation by using the minor axis and major axis of tumor measured with an electronic caliper (Mitutoyo).

Tumor volume $[mm^3] = 0.5 \times (\text{minor axis } [mm])^2 \times \text{major axis } [mm]$ A control administration group administered with only a solvent and a compound of the present disclosure administration group were compared. T/C was calculated from the following equation to evaluate the antitumor effect. The complete tumor regression (CR) individual ratio as of the end of administration due to liposome formulation or anti-PD-1 antibody or concomitant administration was also recorded. For the control administration group, an empty liposome solution prepared by the similar method to Test Example 6 was used.

T/C (%)=(tumor volume as of the end of administration of the compound of the present disclosure administration group–tumor volume as of the start of administration of the compound of the present disclosure administration group)/(tumor volume as of the end of administration of the control administration group−tumor volume as of the start of administration of the control administration group)×100

Table 29 shows the T/C(%) and CR individual ratio for tumor-bearing mice transplanted with EMT6 cells at each dosage and dosing period for the test compound.

TABLE 29

| Test | Route of administration | Dosage | Dosing period (days) | Schedule (times/ week) | T/C (%) | CR (%) |
|---|---|---|---|---|---|---|
| Liposome formulation of Example 1 | Intravenous | 10 mg/kg | 14 | 1 | 36 | 20 |
| Anti-PD-1 antibody | Peritoneal | 200 μg/head | 14 | 2 | 102 | 20 |
| Liposome formulation of Example 1 and anti-PD-1 antibody | Intravenous and peritoneal | 10 mg/kg and 200 μg/head | 14 | 1 and 2 | −6 | 100 |

It was revealed by the concomitantly used drug efficacy evaluation test using tumor-bearing mice that Example 1 prepared as a liposome formulation exhibits an excellent antitumor effect in concomitant use with an anti-PD-1 antibody. As shown in Test Example 20, tumor-bearing mice transplanted with EMT6 cells are models in which an anti-PD-1 antibody exhibits an antitumor effect. In view of the test results, Example 1 is a promising compound exhibiting an excellent antitumor effect in concomitant use of Example 1 prepared as a liposome formulation and anti-PD-1 antibody on a model in which an anti-PD-1 antibody does not exhibit an antitumor effect, which is a significant effect.

Test Example 21. Drug Efficacy Evaluation Test Regarding the Order of Concomitant Administration Using Tumor-Bearing Mice Transplanted with EMT6 Cells Antitumor effects were evaluated using a liposome formulation encapsulating Example 1 and anti-PD-1 antibody. An anti-PD-1 antibody (114116, Biolegend) diluted with PBS (Invitrogen) was used.
A liposome formulation was prepared by the similar method to Test Example 6.
Mouse breast cancer EMT6 cells (ATCC) were intradenually transplanted at 5×10$^5$ cells/mouse into the flank region in 5 week old BALB/c mice (BALB/cAnNCrlCrlj, female, Charles River Laboratories Japan). After confirming engraftment of the EMT6 cells 5 days post-transplantation, a liposome formulation was administered at 6 mg/kg and anti-PD-1 antibody was administered at 200 μg/head intravenously once a week and peritoneally once a week. The tumor volume was measured over time from the start of administration to evaluate the tumor volume reduction due to compound administration. The tumor volume was calculated by the following equation by using the minor axis and major axis of tumor measured with an electronic caliper (Mitutoyo).

Tumor volume [mm$^3$]=0.5×(minor axis [mm])$^2$×major axis [mm]

A control administration group administered with only a solvent and a compound of the present disclosure administration group were compared. T/C was calculated from the following equation to evaluate the antitumor effect. The complete tumor regression (CR) individual ratio as of the end of administration due to a liposome formulation or anti-PD-1 antibody was also recorded. For the control administration group, an empty liposome solution prepared by the similar method to Test Example 6 was used.

T/C (%)=(tumor volume as of the end of administration of the compound of the present disclosure administration group−tumor volume as of the start of administration of the compound of the present disclosure administration group)/(tumor volume as of the end of administration of the control administration group−tumor volume as of the start of administration of the control administration group)×100

Table 30 shows the T/C (%) and CR individual ratio for tumor-bearing mice transplanted with EMT6 cells at each dosage and dosing period of the test compound.

TABLE 30

| Test | T/C (%) | CR (%) |
|---|---|---|
| Liposome formulation of Example 1 (Days 1 and 8 and 15) and anti-PD-1 antibody (Days 1 and 8 and 15) | 19 | 40 |
| Liposome formulation of Example 1 (Days 1 and 8 and 15) and anti-PD-1 antibody (Days 4 and 11 and 18) | 33 | 0 |
| Liposome formulation of Example 1 (Days 4 and 11 and 18) and anti-PD-1 antibody (Days 1 and 8 and 15) | 46 | 0 |

It was revealed by the concomitantly used drug efficacy evaluation test using tumor-bearing mice that Example 1 prepared as a liposome formulation exhibits an excellent antitumor effect in concomitant use with an anti-PD-1 antibody. As shown in Test Example 21, an antitumor effect from concomitant use of Example 1 prepared as a liposome formulation and anti-PD-1 antibody exhibits the most potent effect with simultaneous administration and next most potent effect was exhibited from the order of concomitant administration of administering an anti-PD-1 antibody after administration of a liposome formulation of Example 1. In view of the test results, Example 1 is a promising compound exhibiting an excellent antitumor effect, which is a significant effect.

Test Example 22. Kinase Selectivity Test

The selectivity for 370 wild-type kinases of prexasertib, Example 1, and Example 3 was evaluated by HotSpot Full Panel Kinase profiling (Reaction Biology).
Buffer: 20 mM HEPES, pH 7.5, 10 mM MgCl$_2$, 2 mM MrCl$_2$ (as needed), 1 mM EGTA, 0.02% Brij35, 0.02 mg/mL BSA, 0.1 mM Na$_3$VO$_4$, 2 mM DTT, 1% DMSO
ATP concentration: 10 μm
Reaction time: 2 hours
ATP conversion rate in 2 hours: 5 to 20%
Compound concentration: 100 nM
The names of the kinase and residual activity (%) at 100 nM are shown in Table 31 to Table 33 for 370 wild-type kinases with residual activity at 100 nM of less than 25% for prexasertib, Example 1, and Example 3.

TABLE 31

| Kinase | Residual activity (%) after adding prexasertib (100 nM) |
|---|---|
| RSK2 | 0.98 |
| RSK3 | 1.69 |
| CHK1 | 1.97 |
| RSK1 | 2.23 |
| CAMK2A | 2.52 |
| SIK2 | 2.62 |
| RSK4 | 4.78 |
| CAMK2D | 6.07 |
| LOK/STK10 | 6.15 |
| CHK2 | 6.41 |
| RET | 7.12 |
| TNIK | 7.76 |
| MARK4 | 10.22 |
| MEK5 | 10.72 |
| MELK | 11.40 |
| SIK1 | 11.93 |
| MARK3 | 12.64 |
| TRKC | 12.67 |
| MARK1 | 14.10 |
| MARK2/PAR-1BA | 14.26 |
| BRSK2 | 14.44 |
| ARK5/NUAK1 | 17.88 |
| CDK8/CYCLIN C | 18.06 |
| CDK19/CYCLIN C | 19.87 |
| GLK/MAP4K3 | 20.81 |
| BRSK1 | 21.69 |
| LRRK2 | 23.54 |

TABLE 32

| Kinase | Residual activity (%) after adding Example 1 (100 nM) |
|---|---|
| CHK1 | 2.87 |
| RSK3 | 3.91 |
| RSK2 | 4.32 |
| RSK1 | 8.51 |
| RSK4 | 9.05 |
| CAMK2A | 13.90 |
| SIK2 | 14.12 |
| MELK | 17.18 |
| TRKC | 17.43 |
| TNIK | 17.81 |
| RET | 19.04 |
| MARK4 | 24.10 |

TABLE 33

| Kinase | Residual activity (%) after adding Example 3 (100 nM) |
|---|---|
| RSK2 | 2.22 |
| CHK1 | 2.24 |
| RSK3 | 3.13 |
| RSK1 | 4.74 |
| SIK2 | 4.85 |
| RSK4 | 6.11 |
| CAMK2A | 7.18 |
| MELK | 11.28 |
| MARK4 | 11.52 |
| MARK2/PAR-1BA | 13.37 |
| MARK1 | 13.99 |
| MARK3 | 14.18 |
| TNIK | 15.11 |
| CAMK2D | 15.60 |
| BRSK2 | 17.03 |
| TRKC | 19.27 |
| CHK2 | 19.41 |
| RET | 20.57 |
| LOK/STK10 | 22.15 |
| ARK5/NUAK1 | 22.68 |
| CDK8/CYCLIN C | 23.71 |
| BRSK1 | 24.80 |

As shown in the above table, the compounds of Examples 1 and 3 exhibited higher CHK1 selectivity than prexasertib. In particular, Example 1 has a significant effect of selectively inhibiting CHK1 activity, so that an excellent antitumor effect due to CHK1 inhibition was exhibited while avoiding expression of toxicity due to non-selective kinase inhibition.

Test Example 23. CHK1/CHK2 Selectivity Test

A test compound was dissolved in dimethylsulfoxide (DMSO) and further diluted with DMSO to prepare a solution with a concentration that is 100-fold of the test concentration. The solution was further diluted 25-fold with an assay buffer as a test compound solution. A positive control was similarly processed to prepare a positive control solution. A 4-fold concentration test compound solution was prepared with an assay buffer (20 mM HEPES, 0.01% Triton X-100, 1 mM DTT, pH 7.5). A 4-fold concentration substrate/ATP/metal solution was prepared with a kit buffer (20 mM HEPES, 0.01% Triton X-100, 5 mM DTT, pH 7.5). A 2-fold concentration kinase solution was prepared with an assay buffer. 5 µL of the 4-fold concentration test compound solution, 5 µL of the 4-fold concentration substrate/ATP/metal solution, and 10 µL of the 2-fold concentration kinase solution were mixed in a well of a 384-well polypropylene plate and reacted for 1 hour at room temperature. 70 µL of Termination Buffer (QuickScout Screening Assist MSA; Carna Biosciences) was added to terminate the reaction. Substrate peptides and phosphorylated peptides in the reaction solution were separated and quantified using a LabChip™ system (Perkin Elmer). The kinase reaction was evaluated by the product ratio (P/(P+S)) calculated from the substrate peptide peak height (S) and phosphorylated peptide peak height (P). The inhibition ratio was calculated from the mean signal of each test compound test well, with the mean signal of a control well comprising all reaction components as 0% inhibition, and the mean signal of a background well (with no enzyme added) as 100% inhibition. The $IC_{50}$ value was found by approximating a plot of test substance concentration and inhibition ratio to a four parameter logistic curve by a non-linear least square method.

Table 34 shows the $IC_{50}$ value with respect to CHK1 and CHK2 for prexasertib and Example 1.

TABLE 34

| Kinase | Prexasertib | Example 1 |
|---|---|---|
| CHK1 | $<3.0 \times 10^{-10}$M | $<3.0 \times 10^{-10}$M |
| CHK2 | $1.03 \times 10^{-8}$M | $5.66 \times 10^{-8}$M |

As shown in the above table, the compound of Example 1 exhibited higher CHK1 selectivity compared to prexasertib. Therefore, Example 1 exhibited an excellent antitumor effect due to CHK1 inhibition while avoiding expression of toxicity due to CHK2 inhibition.

In view of the results of Test Examples 1 to 1.3, the compounds of the invention exhibited high CHK1 inhibitory activity (Test Example 1) and a high cancer cell growth suppressing effect (Test Example 2). Furthermore, the compounds of the invention are characterized by low risk of cardiotoxicity (Test Example 3) and efficient encapsulation into a liposome (Test Examples 6, 6A, and 6B).

The inventors newly found a problem to be solved of having a risk of hepatotoxicity from prexasertib, and the compound represented by formula (3) (pyridine derivative with a nitrogen atom at a specific position) in particular, overcomes the problem with high safety (Test Example 4). In addition, the compound represented by formula (3) in particular, has excellent pharmacokinetics (Test Example 7).

The compound of Example 1, which is a representative compound encompassed by formula (3), has a 5-fold or greater CHK1 inhibitory activity relative to prexasertib (Test Example 1), and has a significant effect of exhibiting a potent cell growth suppression effect (Test Example 2). In addition, it was found that the compound of Example 1 has a much lower cardiotoxicity than prexasertib (Test Example 3) with no risk of hepatotoxicity, which is the new problem of prexasertib (Test Example 4), and has a different effect of significantly reduced risk of hemotoxicity relative to prexasertib (Test Example 5 and Test Example 10). Furthermore, the compound of Example 1 exhibits excellent pharmacokinetics (Test Example 7), is efficiently encapsulated into a liposome, and exhibits excellent liposome encapsulation operability (Test Examples 6, 6A, and 6B).

Furthermore, the compound of Example 1 prepared as a liposome formulation has a significant effect of exhibiting an excellent antitumor effect in vitro and in vivo, while having a different effect of high safety (Test Example 8, Test Example 9, and Test Example 11 to Test Example 14). Concomitant use of an existing anticancer agent with a compound of Example 1 has a feature of both excellent antitumor effect and high safety (Test Example 15 to Test Example 21). Since the compound of Example 1 has a more significant effect of selectively inhibiting CHK1 compared to prexasertib, the compound exhibits an excellent antitumor effect from CHK1 inhibition while avoiding expression of toxicity due to non-selective kinase inhibition (Test Example 22 to Test Example 23).

In view of the above, the compound of Example 1 has an unexpected effect from having a significant effect of higher efficacy as well as a different effect of exhibiting higher safety compared to prexasertib. The liposome formulation of Example 1 is an excellent agent having an unexpected effect with excellent blood retention, antitumor effect, and high safety.

The present disclosure relates to a CHK1 inhibitor, which is an antitumor agent with a high therapeutic effect while reducing side effects. As a result of diligent study, the inventors found that the compound represented by formula (1) has a potent inhibitory action against CHK1 and an excellent antitumor action. In particular, a series of compounds having a pyridine ring with a nitrogen atom at a specific position, represented by formula (3), was confirmed to exhibit a significant and different effect to complete the present invention.

Specifically, the inventors created the series of compounds of Examples 1 to 38, which exhibits a very high CHK1 inhibitory activity (Test Example 1), high cancer cell toxicity (Test Example 2), as well as a different effect of high safety in view of weak hERG inhibitor (Test Example 3). Furthermore, the inventors have found the problem to be solved of having a risk of hepatotoxicity from prexasertib, and found that the compound of the invention has a different effect of overcoming the problem (Test Example 4). In particular, "compound represented by formula (3) having a pyridine ring with a nitrogen atom at a specific substitution position" represented by Example 1 and the like has a very significant and different effect.

The compounds of Example 1 and the like represented by formula (3) exhibit high safety with respect to hemotoxicity without suppressing human bone marrow cell colony formation, unlike prexasertib (Test Example 5), with a very high liposome encapsulation efficiency and excellent liposome encapsulation operability (Test Examples 6, 6A, and 6B), and high blood retention due to preparation into a liposome formulation (Test Example 7). Such a liposome formulation, despite having a tumor regression effect that cannot be achieved by prexasertib in a tumor-bearing model (Test Example 8), has very high safety (Test Examples 9 and 10). Example 1 itself has excellent pharmacokinetic and pharmacodynamic profiles (Test Example 11), and the liposome formulation exhibited an effect of prolonging survival period that cannot be achieved by prexasertib (Test Examples 12 and 13) and broad efficacy against various cancers (Test Example 14). Concomitant use of Example 1 prepared as a liposome formulation and various anticancer agents (cisplatin, gemcitabine, or PD-1 antibody) exhibited a significant effect (Test Examples 15 to 21). The compound of Example 1, since it has a more significant effect of selectively suppressing CHK1 activity compared to prexasertib, exhibits an excellent antitumor effect due to CHK1 inhibition while avoiding expression of toxicity due to non-selective kinase inhibition (Test Examples 22 to 23).

As described above, the present disclosure is exemplified by the use of its preferred embodiments. It is understood that the scope of the present disclosure should be interpreted solely based on the Claims. The present application claims priority to Japanese Patent Application No. 2020-198648 (filed on Nov. 30, 2020). It is understood that the entire content thereof is incorporated herein by reference. It is also understood that any patent, any patent application, and any references cited herein should be incorporated herein by reference in the same manner as the contents are specifically described herein.

INDUSTRIAL APPLICABILITY

The compounds of the present disclosure potently inhibit Checkpoint Kinase 1 (CHK1). These liposome formulations exhibit a potent antitumor effect based on CHK1 inhibitory action by achieving sustained drug exposure due to the controlled release effect thereof. Therefore, the compound of the present disclosure and pharmaceutically acceptable salt thereof, a pharmaceutical composition comprising the same, and liposome formulation comprising the same are useful as a therapeutic agent or prophylactic agent for a pathological condition associated with CHK1.

The invention claimed is:

1. A compound or a pharmaceutically acceptable salt thereof, selected from 5-({5-[2-(3-aminopropoxy)-4-methoxypyridin-3-yl]-1H-pyrazol-3-yl}amino)pyrazine-2-carbonitrile, 5-({5-[3-(3-aminopropoxy)-5-methoxypyridin-4-yl]-1H-pyrazol-3-yl}amino)pyrazine-2-carbonitrile, or 5-({5-[4-(3-aminopropoxy)-2-methoxypyridin-3-yl]-1H-pyrazol-3-yl}amino)pyrazine-2-carbonitrile.

2. The compound or pharmaceutically acceptable salt thereof of claim 1, which is 5-({5-[2-(3-aminopropoxy)-4-methoxypyridin-3-yl]-1H-pyrazol-3-yl}amino)pyrazine-2-carbonitrile or pharmaceutically acceptable salt thereof.

3. The compound or pharmaceutically acceptable salt thereof of claim 1, which is 5-({5-[3-(3-aminopropoxy)-5-methoxypyridin-4-yl]-1H-pyrazol-3-yl}amino)pyrazine-2-carbonitrile or pharmaceutically acceptable salt thereof.

4. The compound or pharmaceutically acceptable salt thereof of claim 1, which is
5-({S-[4-(3-aminopropoxy)-2-methoxypyridin-3-yl]-1H-pyrazol-3-yl}amino)pyrazine-2-carbonitrile or pharmaceutically acceptable salt thereof.

5. A liposome comprising the compound or pharmaceutically acceptable salt thereof of claim 1.

6. A pharmaceutical composition comprising the compound or pharmaceutically acceptable salt thereof of claim 1 as an active ingredient.

7. The pharmaceutical composition of claim 6, further comprising a liposome encapsulating at least one compound or pharmaceutically acceptable salt thereof selected from the group consisting of
5-({5-[2-(3-aminopropoxy)-4-methoxypyridin-3-yl]-1H-pyrazol-3-yl}amino)pyrazine-2-carbonitrile,
5-({5-[3-(3-aminopropoxy)-5-methoxypyridin-4-yl]-1H-pyrazol-3-yl}amino)pyrazine-2-carbonitrile, and
5-({5-[4-(3-aminopropoxy)-2-methoxypyridin-3-yl]-1H-pyrazol-3-yl}amino)pyrazine-2-carbonitrile.

8. The pharmaceutical composition of claim 7, wherein the liposome further comprises a phospholipid.

9. The pharmaceutical composition of claim 7, wherein the liposome comprises
(1) at least one compound or pharmaceutically acceptable salt thereof selected from the group consisting of
5-({5-[2-(3-aminopropoxy)-4-methoxypyridin-3-yl]-1H-pyrazol-3-yl}amino)pyrazine-2-carbonitrile,
5-({5-[3-(3-aminopropoxy)-5-methoxypyridin-4-yl]-1H-pyrazol-3-yl}amino)pyrazine-2-carbonitrile, and
5-({5-[4-(3-aminopropoxy)-2-methoxypyridin-3-yl]-1H-pyrazol-3-yl)amino)pyrazine-2-carbonitrile, and
(2) a phospholipid.

10. The pharmaceutical composition of claim 8, wherein the phospholipid is one selected from the group consisting of phosphatidylcholine, phosphatidylglycerol, phosphatidic acid, phosphatidylethanolamine, phosphatidylserine, phosphatidylinositol, sphingomyelin, soybean lecithin, egg yolk lecithin, hydrogenated egg yolk lecithin, and hydrogenated soybean lecithin or a combination of two or more thereof.

11. The pharmaceutical composition of claim 9, wherein the phospholipid is one selected from the group consisting of phosphatidylcholine, phosphatidylglycerol, phosphatidic acid, phosphatidylethanolamine, phosphatidylserine, phosphatidylinositol, sphingomyelin, soybean lecithin, egg yolk lecithin, hydrogenated egg yolk lecithin, and hydrogenated soybean lecithin or a combination of two or more thereof.

12. The pharmaceutical composition of claim 7, wherein the liposome further comprises sterol.

13. The pharmaceutical composition of claim 12, wherein the sterol is cholesterol.

14. The pharmaceutical composition of claim 7, wherein the liposome further comprises a polymer modified lipid.

15. The pharmaceutical composition of claim 14, wherein a polymer moiety of the polymer-modified lipid is polyethylene glycol, polypropylene glycol, polyvinyl alcohol, polyvinylpyrrolidone, methoxypolyethylene glycol, methoxypolypropylene glycol, methoxypolyvinyl alcohol, methoxypolyvinylpyrrolidone, ethoxypolyethylene glycol, ethoxypolypropylene glycol, ethoxypolyvinyl alcohol, ethoxypolyvinylpyrrolidone, propoxypolyethylene glycol, propoxypolypropylene glycol, propoxypolyvinyl alcohol, or propoxypolyvinylpyrrolidone.

16. The pharmaceutical composition of claim 15, wherein a lipid moiety of the polymer-modified lipid is phosphatidylethanolamine or diacylglycerol.

17. The pharmaceutical composition of claim 7, wherein the liposome comprises
(1) at least one compound or pharmaceutically acceptable salt thereof selected from the group consisting of
5-({5-[2-(3-aminopropoxy)-4-methoxypyridin-3-yl]-1H-pyrazol-3-yl}amino)pyrazine-2-carbonitrile,
5-({5-[3-(3-aminopropoxy)-5-methoxypyridin-4-yl]-1H-pyrazol-3-yl}amino)pyrazine-2-carbonitrile, and
5-({5-[4-(3-aminopropoxy)-2-methoxypyridin-3-yl]-1H-pyrazol-3-yl}amino)pyrazine-2-carbonitrile,
(2) 40 to 70 mol % of phospholipid,
(3) 30 to 50 mol % of cholesterol, and
(4) 1 to 10 mol % of polymer-modified lipid.

18. The pharmaceutical composition of claim 7, wherein the liposome further comprises an additive selected from the group consisting of inorganic acids, inorganic acid salts, organic acids, organic acid salts, saccharides, buffer, antioxidants, and polymers.

* * * * *